(12) United States Patent
Narain et al.

(10) Patent No.: US 10,023,864 B2
(45) Date of Patent: Jul. 17, 2018

(54) METHODS OF TREATING A METABOLIC SYNDROME BY MODULATING HEAT SHOCK PROTEIN (HSP) 90-BETA

(71) Applicant: Berg LLC, Nashville, TN (US)

(72) Inventors: Niven Rajin Narain, Cambridge, MA (US); Rangaprasad Sarangarajan, Boylston, MA (US); Vivek Kannoth Vishnudas, Bedford, MA (US); Enxuan Jing, West Roxbury, MA (US)

(73) Assignee: Berg LLC, Nashville, TN (US)

( * ) Notice: Subject to any disclaimer, the term of this patent is extended or adjusted under 35 U.S.C. 154(b) by 0 days.

(21) Appl. No.: 14/733,845

(22) Filed: Jun. 8, 2015

(65) Prior Publication Data

US 2015/0353930 A1    Dec. 10, 2015

Related U.S. Application Data

(60) Provisional application No. 62/009,116, filed on Jun. 6, 2014, provisional application No. 62/096,649, filed on Dec. 24, 2014, provisional application No. 62/108,530, filed on Jan. 27, 2015.

(51) Int. Cl.
| | | |
|---|---|---|
| *C07H 21/02* | (2006.01) | |
| *C07H 21/04* | (2006.01) | |
| *A61K 48/00* | (2006.01) | |
| *C12N 15/113* | (2010.01) | |
| *A61K 31/198* | (2006.01) | |
| *A61K 31/7088* | (2006.01) | |
| *A61K 38/08* | (2006.01) | |

(52) U.S. Cl.
CPC .......... *C12N 15/113* (2013.01); *A61K 31/198* (2013.01); *A61K 31/7088* (2013.01); *A61K 38/08* (2013.01); *C12N 2310/11* (2013.01); *C12N 2310/111* (2013.01); *C12N 2310/14* (2013.01); *C12N 2310/315* (2013.01); *C12N 2310/321* (2013.01); *C12N 2310/322* (2013.01); *C12N 2310/353* (2013.01); *C12N 2310/3513* (2013.01); *C12N 2310/3521* (2013.01); *C12N 2310/3531* (2013.01); *C12N 2320/31* (2013.01); *C12N 2320/32* (2013.01)

(58) Field of Classification Search
CPC .......................... C12N 2310/11; C12N 15/113; A61K 31/713; A61K 48/00
See application file for complete search history.

(56) References Cited

U.S. PATENT DOCUMENTS

| | | | |
|---|---|---|---|
| 7,189,723 B2 | 3/2007 | Mitchell et al. | |
| 7,531,323 B2 | 5/2009 | Larsen et al. | |
| 7,674,795 B2 | 3/2010 | Mailliet et al. | |
| 7,678,803 B2 | 3/2010 | Huang et al. | |
| 7,820,658 B2 | 10/2010 | Dymock et al. | |
| 7,855,192 B2 | 12/2010 | Ashley et al. | |
| 8,183,279 B2 | 5/2012 | Eggenweiler et al. | |
| 8,217,050 B2 | 7/2012 | Moffat et al. | |
| 8,277,807 B2 | 10/2012 | Gallagher et al. | |
| 8,318,790 B2 | 11/2012 | Ying et al. | |
| 8,324,240 B2 | 12/2012 | Cai et al. | |
| 9,533,002 B2 | 1/2017 | Narain et al. | |
| 2006/0094682 A1 | 5/2006 | Westwick et al. | |
| 2007/0003555 A1 | 1/2007 | LeClair | |
| 2007/0191917 A1 | 8/2007 | Poulaki et al. | |
| 2007/0249540 A1 | 10/2007 | Papathanassiu | |
| 2008/0070930 A1 | 3/2008 | Huang et al. | |
| 2008/0193928 A1* | 8/2008 | Castro | C07K 16/18 435/6.12 |
| 2009/0076006 A1 | 3/2009 | Qian et al. | |
| 2009/0298818 A1 | 12/2009 | Lyons et al. | |
| 2010/0015126 A1 | 1/2010 | Gebbink et al. | |
| 2010/0022635 A1 | 1/2010 | Rajewski | |
| 2010/0048482 A1 | 2/2010 | Mochly-Rosen et al. | |
| 2010/0279311 A1 | 11/2010 | Kimura | |
| 2010/0292169 A1 | 11/2010 | Yao et al. | |
| 2010/0298280 A1 | 11/2010 | Kioschis-Schneider et al. | |
| 2011/0046155 A1 | 2/2011 | Frederickson et al. | |
| 2011/0065734 A1 | 3/2011 | Bar et al. | |
| 2011/0118258 A1 | 5/2011 | Courtney et al. | |
| 2011/0160175 A1 | 6/2011 | Martin et al. | |
| 2011/0201587 A1 | 8/2011 | Shapiro | |
| 2011/0201643 A1 | 8/2011 | Maier et al. | |
| 2011/0218143 A1 | 9/2011 | Kaushal et al. | |
| 2011/0230444 A1 | 9/2011 | Garcia-Echeverria et al. | |

(Continued)

FOREIGN PATENT DOCUMENTS

| | | |
|---|---|---|
| CN | 102112478 | 6/2011 |
| CN | 102227221 | 10/2011 |

(Continued)

OTHER PUBLICATIONS

U.S. Appl. No. 13/902,354, filed May 24, 2013, US2014/0154266, Pending.

Calamia, et al., "Hsp90β Inhibition Modulates Nitric Oxide Production and Nitric Oxide-Induced Apoptosis in Human Chondrocytes", 2011, BMC Musculoskeletal Disorders 12: 989-995.

Imamura et al., "Involvement of Heat Shock Protein 90 in the Degradation of Mutant Insulin Receptors by the Proteasome", 1998, JBC 273 (18): 11183-11188.

Urban et al., "Heat Shock Response and Insulin-Associated Neurodegeneration", 2012, Trends in Pharmacological Sciences 33(3): 129-137.

Hirosumi et al., "A Central Role for JNK in Obesity and Insulin Resistance", 2002, Nature 420 (6913): 333-336.

(Continued)

*Primary Examiner* — Amy H Bowman
(74) *Attorney, Agent, or Firm* — McCarter & English, LLP; Elizabeth A. Hanley, Esq.; Jill Mello

(57) ABSTRACT

The invention provides HSP90β inhibitors comprising an antisense oligonucleotide targeting HSP90β, pharmaceutical compositions comprising said inhibitors and methods of treatment of a metabolic syndrome by administering said HSP90β inhibitors to a subject in need thereof. The antisense oligonucleotides may be targeted to skeletal muscle.

37 Claims, 51 Drawing Sheets

(56) References Cited

U.S. PATENT DOCUMENTS

| | | |
|---|---|---|
| 2011/0230551 A1 | 9/2011 | Gunatilaka et al. |
| 2011/0237560 A1 | 9/2011 | Di Noia et al. |
| 2011/0262449 A1 | 10/2011 | Petrilli et al. |
| 2011/0281902 A1 | 11/2011 | Manley et al. |
| 2012/0196815 A1 | 8/2012 | Timmermann et al. |
| 2012/0252745 A1 | 10/2012 | Blagg et al. |
| 2012/0289430 A1* | 11/2012 | Yamka ................. A23K 1/1631 506/9 |
| 2012/0309684 A1* | 12/2012 | Wood ............... A61K 47/48276 514/16.4 |
| 2012/0309750 A1 | 12/2012 | Kang et al. |
| 2017/0166891 A1 | 6/2017 | Narain et al. |

FOREIGN PATENT DOCUMENTS

| | | | |
|---|---|---|---|
| CN | 102 772 399 A | 11/2012 | |
| WO | WO 98/53804 * | 12/1998 | ........... C12N 15/113 |
| WO | WO-2003/023001 | 3/2003 | |
| WO | WO-2004/096212 A1 | 11/2004 | |
| WO | WO 2005/113571 A2 * | 12/2005 | ......... C12N 2310/11 |
| WO | WO-2006/020269 A2 | 2/2006 | |
| WO | WO-2007/137237 A2 | 11/2007 | |
| WO | 2008/044034 A1 | 4/2008 | |
| WO | WO-2009/010957 A2 | 1/2009 | |
| WO | WO-2009/109616 A2 | 9/2009 | |
| WO | WO-2009/114470 A2 | 9/2009 | |
| WO | WO-2009/142618 A1 | 11/2009 | |
| WO | WO-2010/015617 A1 | 2/2010 | |
| WO | WO-2010/117425 A1 | 10/2010 | |
| WO | WO-2011/083150 A2 | 7/2011 | |
| WO | WO-2011/133659 A2 | 10/2011 | |
| WO | WO-2012/106343 A2 | 8/2012 | |
| WO | WO-2012/139010 A1 | 10/2012 | |
| WO | WO-2013/015661 A2 | 1/2013 | |
| WO | WO-2013/177535 A2 | 11/2013 | |

OTHER PUBLICATIONS

Lee et al., "Biochemical and Biophysical Research Communications", on-line Dec. 19, 2012, Biochemical and Biophysical Research Communications 430(3): 1109-1113.

Neckers et al., "Hsp90 Molecular Chaperone Inhibitors: Are We There Yet?", 2012, Clinical Cancer Research 18 (1): 64-76.

Genbank Accession No. DQ147989.1.

Genbank Accession No. AK146809.1.

International Search Report for International Application No. PCT/US2013/042692, dated Oct. 29, 2013.

International Search Report for International Application No. PCT/US2015/034750, dated Jan. 12, 2016.

Didelot C., et al., "Interaction of heat-shock protein 90β isoform (HSP90β) with cellular inhibitor of apoptosis 1 (c-IAP1) is required for cell differentiation", Cell Death and Differentiation (2008), 15, 859-866.

Alberti et al., The metabolic syndrome—a new worldwide definition. Lancet. Sep. 24-30, 2005;366(9491):1059-62.

Chen et al., Caspase-10-mediated heat shock protein 90 beta cleavage promotes UVB irradiation-induced cell apoptosis. Mol Cell Biol. Jul. 2009;29(13):3657-64.

Desarzens et al., Hsp90 blockers inhibit adipocyte differentiation and fat mass accumulation. PLoS One. Apr. 4, 2014;9(4):e94127. 11 pages.

Jing et al., Heat Shock Protein 90 Beta (Hsp90 Beta) Isoform Represents a Novel 1st in Class Target Regulating Systemic Energy Metabolism for Treatment of Metabolic Diseases. American Diabetes Association. May 31, 2014;63 (Suppl 1):A480. Poster 1867-P.

* cited by examiner

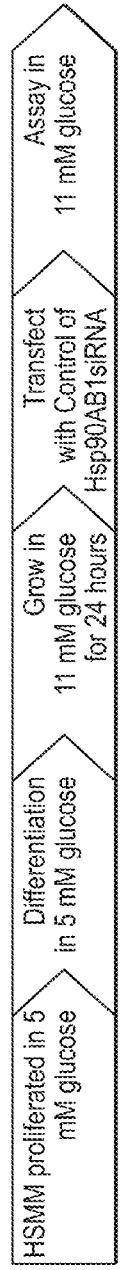
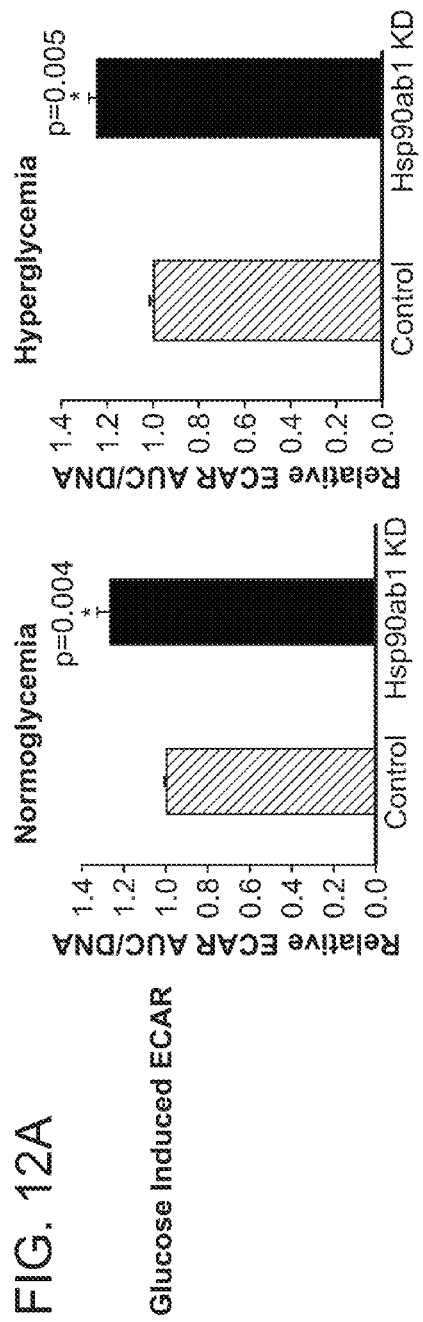
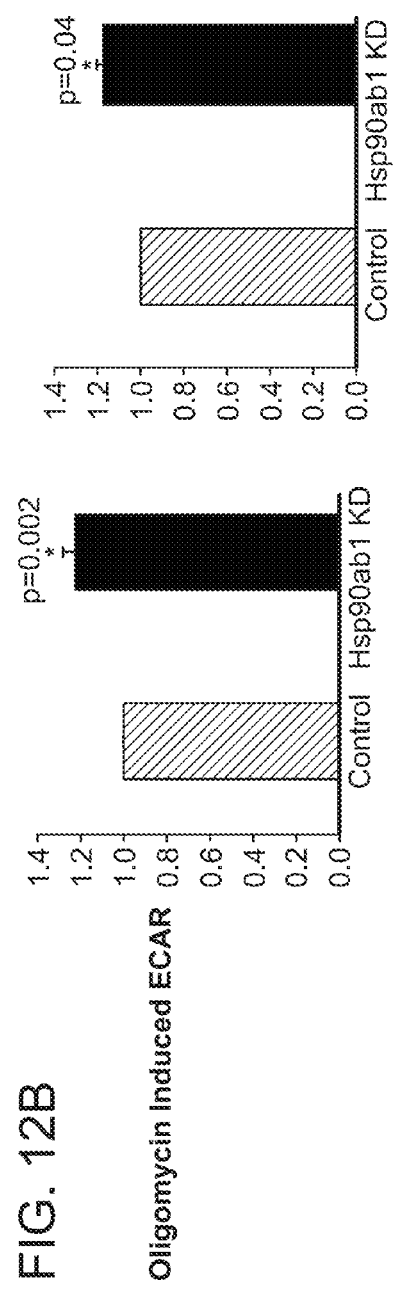
FIG. 12A
FIG. 12B

FIG. 13B
Normoglycemia
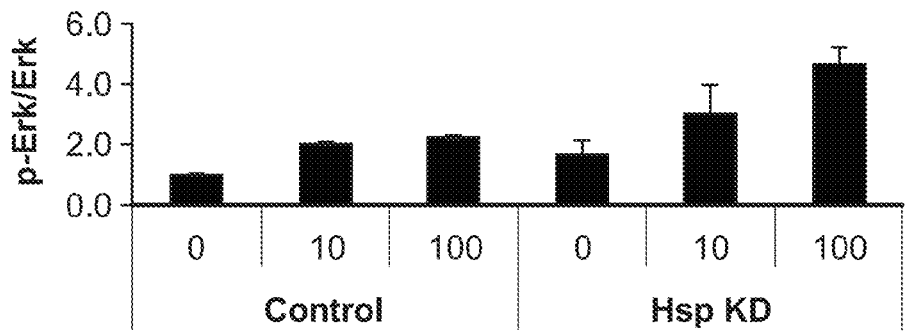
Hyperglycemia
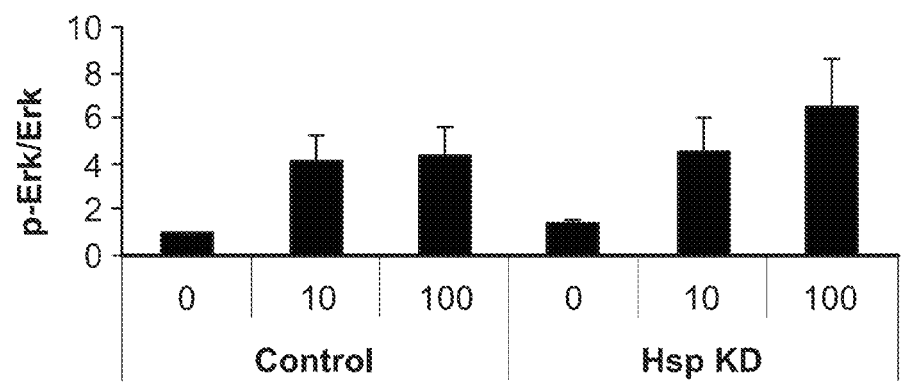
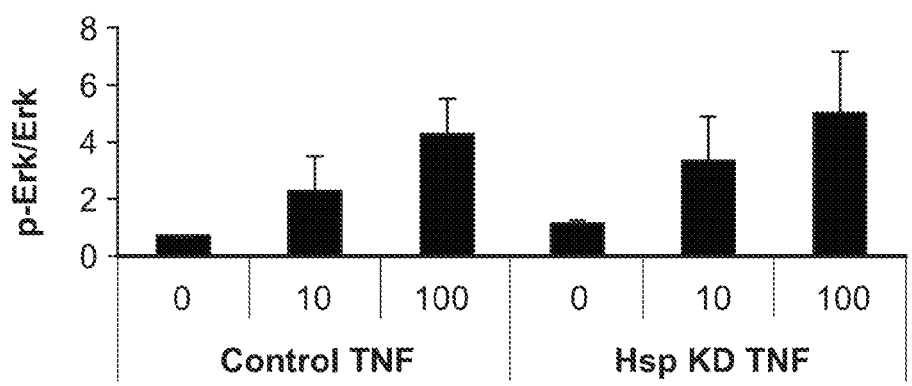

FIG. 15

Homo sapiens heat shock 90kDa protein 1, alpha (HSPCA) gene, complete cds.
ACCESSION   DQ314871
VERSION     DQ314871.1  GI:83699648

```
   1 atgccccgt gttcgggcgg ggacggctcc accctcctg ggccctccct tcgggacagg
  61 gactgtccg cccagagtgc tgaatacccg cgcgaccgtc tggatcccg cccaggaagc
 121 ccctctgaag cctcctcgcc gccgtttctg agaagcaggg cacctgttaa ctggtaccaa
 181 gaaaaggccc aagtgtttct ctggcatctg ttggtgtctg gatccaccac tctactctgt
 241 ctctggaaac agcccttcca cgtctctgca ttccctgtca ctgcgtcact ggccttcaga
 301 cagagccaag gtgcagggca acacctctac aaggatctgc agccatttat attgcttagg
 361 ctactgatgc ctgaggaaac ccagacccaa gaccaaccga tggaggagga ggaggttgag
 421 acgttcgcct ttcaggcaga aattgcccag ttgatgtcat tgatcatcaa tactttctac
 481 tcgaacaaag agatctttct gagagagctc atttcaaatt catcagatgc attggacaaa
 541 atccggtatg aaagcttgac agatcccagt aaattagact ctgggaaaga gctgcatatt
 601 aaccttatac cgaacaaaca agatcgaact ctcactattg tggatactgg aattggaatg
 661 accaaggctg acttgatcaa taaccttggt actatcgcca agtctgggac aaaagcgttc
 721 atggaagctt gcaggctggt gcagatatc tctatgattg gccagttcgg tgttggtttt
 781 tattctgctt atttggttgc tgagaaagta actgtgatca ccaaacataa cgatgatgag
 841 cagtacgctt gggagtcctc agcagggga tcattcacag tgaggacaga cacaggtgaa
 901 cctatgggtc gtggaacaaa agttatccta cacctgaaag aagaccaaac tgagtacttg
 961 gaggaacgaa gaataaagga gattgtgaag aaacattctc agtttattgg atatcccatt
1021 actctttttg tggagaagga acgtgataaa gaagtaagcg atgatgaggc tgaagaaaag
1081 gaagacaaag aagaagaaaa agaaaagaa gagaaagagt cggaagacaa acctgaaatt
1141 gaagatgttg gttctgatga ggaagaagaa aagaaggatg gtgacaagaa gaagaagaag
1201 aagattaagg aaaagtacat cgatcaagaa gagctcaaca aaacaaagcc catctggacc
1261 agaaatcccg acgatattac taatgaggag tacggagaat ctataagag cttgaccaat
1321 gactgggaag atcacttggc agtgaagcat ttttcagttg aaggacagtt ggaattcaga
1381 gcccttctat ttgtcccacg acgtgctcct tttgatctgt ttgaaaacag aaagaaaaag
1441 aacaatatca aattgtatgt acgcagagtt ttcatcatgg ataactgtga ggagctaatc
1501 cctgaatatc tgaacttcat tagagggtg gtagactcgg aggatctccc tctaaacata
1561 tcccgtgaga tgttgcaaca aagcaaaatt ttgaaagtta tcaggaagaa tttggtcaaa
1621 aaatgcttag aactctttac tgaactggcg gaagataaag agaactacaa gaaattctat
1681 gagcagttct ctaaaaacat aaagcttgga atacacgaag actctcaaaa tcggaagaag
1741 ctttcagagc tgttaaggta ctacacatct gcctctggtg atgagatggt ttctctcaag
1801 gactactgca ccagaatgaa ggagaaccag aaacatatct attatatcac aggtgagacc
1861 aaggaccagg tagctaactc agcctttgtg aacgtcttc ggaaacatgg cttagaagtg
1921 atctatatga ttgagcccat tgatgagtac tgtgtccaac agctgaagga atttgagggg
1981 aagcttttag tgtcagtcac caaagaaggc ctggaacttc cagaggatga agaagagaaa
2041 aagaagcagg aagagaaaaa acaaagttt gagaacctct gcaaaatcat gaaagacata
2101 ttggagaaaa agttgaaaa ggtggttgtg tcaaaccgat ggtgacatc tccatgctgt
2161 attgtcacaa gcacatatgg ctggacagca acatggaga gaatcatgaa agctcaagcc
2221 ctaagagaca actcaacaat gggttacatg gcagcaaaga acacctgga gataaaccct
2281 gaccattcca ttattgagac cttaaggcaa aaggcagagg ctgataagaa cgacaagtct
2341 gtgaaggatc tggtcatctt gctttatgaa actgcgctcc tgtcttctgg cttcagtctg
2401 gaagatcccc agacacatgc taacaggatc tacaggatga tcaaacttgg tctgggtatt
2461 gatgaagatg accctactgc tgatgatacc agtgctgctg taactgaaga aatgccaccc
2521 cttgaaggag atgacgacac atcacgcatg gaagaagtag actaa (SEQ ID NO: 7)
```

FIG. 15 (continued)

TRANSLATION

DEFINITION  heat shock 90kDa protein 1, alpha [Homo sapiens].
ACCESSION   ABC40730
VERSION     ABC40730.1  GI:83699649

```
  1 mppcsggdgs tppgpslrdr dcpaqsaeyp rdrldprpgs pseassppfl rsrapvnwyq
 61 ekaqvflwhl lvsgsttllc lwkqpfhvsa fpvtaslafr qsqgagqhly kdlqpfillr
121 llmpeetqtq dqpmeeeeve tfafqaeiaq lmsliintfy snkeiflrel isnssdaldk
181 iryesltdps kldsgkelhi nlipnkqdrt ltivdtgigm tkadlinnlg tiaksgtkaf
241 mealqagadi smigqfgvgf ysaylvaekv tvitkhndde qyawessagg sftvrtdtge
301 pmgrgtkvil hlkedqteyl eerrikeivk khsqfigypi tlfvekerdk evsddeaeek
361 edkeeekeke ekesedkpei edvgsdeeee kkdgdkkkkk kikekyidqe elnktkpiwt
421 rnpdditnee ygefyksltn dwedhlavkh fsvegqlefr allfvprrap fdlfenrkkk
481 nniklyvrrv fimdnceeli peylnfirgv vdsedlplni sremlqqski ikvirknlvk
541 kclelftela edkenykkfy eqfskniklg ihedsqnrkk lsellryyts asgdemvslk
601 dyctrmkenq khiyyitget kdqvansafv erlrkhglev iymiepidey cvqqlkefeg
661 ktlvsvtkeg lelpedeeek kkqeekktkf enlckimkdi lekkvekvvv snrlvtspcc
721 ivtstygwta nmerimkaqa lrdnstmgym aakkhleinp dhsiietlrq kaeadkndks
781 vkdlvillye tallssqfsl edpqthanri yrmiklglgi deddptaddt saavteempp
841 legdddtsrm eevd (SEQ ID NO: 8)
```

FIG. 16

Homo sapiens heat shock protein 90kDa alpha (cytosolic), class B member 1 (HSP90AB1), mRNA
ACCESSION   NM_007355 XR_108652 XR_112882 XR_113895
VERSION   NM_007355.2  GI:20149593

```
   1 ctccggcgca gtgttgggac tgtctgggta tcggaaagca agcctacgtt gctcactatt
  61 acgtataatc ctttctttt caagatgcct gaggaagtgc accatggaga ggaggaggtg
 121 gagacttttg cctttcaggc agaaattgcc caactcatgt ccctcatcat caataccttc
 181 tattccaaca aggagatttt ccttcgggag ttgatctcta atgcttctga tgccttggac
 241 aagattcgct atgagagcct gacagaccct tcgaagttgg acagtggtaa agagctgaaa
 301 attgacatca tccccaaccc tcaggaacgt accctgactt ggtagacac aggcattggc
 361 atgaccaaag ctgatctcat aaataatttg ggaaccattg ccaagtctgg tactaaagca
 421 ttcatggagg ctcttcaggc tggtgcagac atctccatga ttgggcagtt tggtgttggc
 481 ttttattctg cctacttggt ggcagagaaa gtggttgtga tcacaaagca aacgatgat
 541 gaacagtatg cttgggagtc ttctgctgga ggttccttca ctgtgcgtgc tgaccatggt
 601 gagcccattg cagggtac caaagtgatc ctccatctta agaagatca gacagagtac
 661 ctagaagaga ggcgggtcaa agaagtagtg aagaagcatt ctcagttcat aggctatccc
 721 atcacccttt atttggagaa ggaacgagag aaggaaatta gtgatgatga ggcagaggaa
 781 gagaaaggtg agaagaaga ggaagataaa gatgatgaag aaaaacccaa gatcgaagat
 841 gtgggttcag atgaggagga tgacagcggt aaggataaga agaagaaaac taagaagatc
 901 aaagagaaat acattgatca ggaagaacta aacaagacca gcctatttg accagaaac
 961 cctgatgaca tcacccaaga ggagtatgga gaattctaca agagcctcac taatgactgg
1021 gaagaccact tggcagtcaa gcacttttct gtagaaggtc agttggaatt cagggcattg
1081 ctatttattc ctcgtcgggc tccctttgac cttttgaga acaagaagaa aaagaacaac
1141 atcaaactct atgtccgccg tgtgttcatc atggacagct gtgatgagtt gataccagag
1201 tatctcaatt ttatccgtgg tgtggttgac tctgaggatc tgccctgaa catctcccga
1261 gaaatgctcc agcagagcaa atcttgaaa gtcattcgca aaacattgt taagaagtgc
1321 cttgagctct tctctgagct ggcagaagac aaggagaatt acaagaaatt ctatgaggca
1381 ttctctaaaa atctcaagct tggaatccac gaagactcca ctaaccgccg ccgcctgtct
1441 gagctgctgc gctatcatac ctcccagtct ggagatgaga tgacatctct gtcagagtat
1501 gtttctcgca tgaaggagac acagaagtcc atctattaca tcactggtga gagcaaagag
1561 caggtggcca actcagcttt tgtggagcga gtgcggaaac ggggcttcga ggtggtatat
1621 atgaccgagc ccattgacga gtactgtgtg cagcagctca aggaatttga tgggaagagc
1681 ctggtctcag ttaccaagga gggtctggag ctgcctgagg atgaggagga gaagaagaag
1741 atggaagaga gcaaggcaaa gtttgagaac ctctgcaagc tcatgaaaga atcttagat
1801 aagaaggttg agaaggtgac aatctccaat agacttgtgt cttcaccttg ctgcattgtg
1861 accagcacct acggctggac agccaatatg gagcggatca tgaaagccca ggcacttcgg
1921 gacaactcca ccatgggcta tatgatggcc aaaaagcacc tggagatcaa ccctgaccac
1981 cccattgtgg agacgctgcg gcagaaggct gaggccgaca gaatgataa ggcagttaag
2041 gacctggtgg tgctgctgtt tgaaaccgcc ctgctatctt ctggctttc ccttgaggat
2101 ccccagaccc actccaaccg catctatcgc atgatcaagc taggtctagg tattgatgaa
2161 gatgaagtgg cagcagagga acccaatgct gcagttcctg atgagatccc ccctctcgag
2221 ggcgatgagg atgcgtctcg catggaagaa gtcgattagg ttaggagttc atagttggaa
2281 aacttgtgcc cttgtatagt gtcccatgg gctcccactg cagcctcgag tgccctgtc
2341 ccacctggct cccctgctg gtgtctagtg ttttttccc tctcctgtcc ttgtgttgaa
2401 ggcagtaaac taagggtgtc aagccccatt ccctctctac tcttgacagc aggattggat
2461 gttgtgtatt gtggtttatt ttatttctt cattttgttc tgaaattaaa gtatgcaaaa
2521 taaagaatat gccgttttaa aaaaaaaaaa aaaaaaaaaa aaaaaaa (SEQ ID NO: 9)
```

FIG. 16 (continued)

TRANSLATION

```
  1 mpeevhhgee evetfafqae iaqlmsliin tfysnkeifl relisnasda ldkiryeslt
 61 dpskldsgke lkidiipnpq ertltlvdtg igmtkadlin nlgtiaksgt kafmealqag
121 adismigqfg vgfysaylva ekvvvitkhn ddeqyawess aggsftvrad hgepigrgtk
181 vilhlkedqt eyleerrvke vvkkhsqfig ypitlyleke rekeisddea eeekgekeee
241 dkddeekpki edvgsdeedd sgkdkkkktk kikekyidqe elnktkpiwt rnpdditqee
301 ygefyksltn dwedhlavkh fsvegqlefr allfiprrap fdlfenkkkk nniklyvrrv
361 fimdscdeli peylnfirgv vdsedlplni sremlqqski lkvirknivk kclelfsela
421 edkenykkfy eafsknlklg ihedstnrrr lsellryhts qsgdemtsls eyvsrmketq
481 ksiyyitges keqvansafv ervrkrgfev vymtepidey cvqqlkefdg kslvsvtkeg
541 lelpedeeek kkmeeskakf enlcklmkei ldkkvekvti snrlvsspcc ivtstygwta
601 nmerimkaqa lrdnstmgym makkhleinp dhpivetlrq kaeadkndka vkdlvvilfe
661 tallssqfsl edpqthsnri yrmiklglgi dedevaaeep naavpdeipp legdedasrm
721 eevd (SEQ ID NO: 10)
```

FIG. 17

Nucleic acid sequence alignment

```
HSP90-alpha   ATGCCCCCGTGTTCGGGCGGGGACGGCTCCACCCCTCCTGGGCCCTCCCTTCGGGACAGG  60
HSP90-beta    ------------------------------------------------CTCCGG------   6

HSP90-alpha   GACTGTCCCGCCCAGAGTGCTGAATACCCGCGCGACCGTCTGGATCCCCGCCCAGGAAGC  120
HSP90-beta    ---------CGC----AGTGTTGG----------GACTGTCTGGGTATC-----GGAAAGC  39
                       ***    **** **          *** ****** *  *    * ****

HSP90-alpha   CCCTCTGAAGCCTCCTCGCCGCCGTTTCTGAGAAGCAGGGCACCTGTTAACTGGTACCAA  180
HSP90-beta    -------AAGCCTAC---------GTT---------------------------------  50
                     ****** *         ***

HSP90-alpha   GAAAAGGCCCAAGTGTTTCTCTGGCATCTGTTGGTGTCTGGATCCACCACTCTACTCTGT  240
HSP90-beta    ------GCTCA----------------------------------------CTATTACGT  64
                    ** **                                          *** *  **

HSP90-alpha   CTCTGGAAACAGCCCTTCCACGTCTCTGCATTCCCTGTCACTGCGTCACTGGCCTTCAGA  300
HSP90-beta    --------ATAATCCTTTT-----------------------------------------  75
                      * *  ****

HSP90-alpha   CAGAGCCAAGGTGCAGGGCAACACCTCTACAAGGATCTGCAGCCATTTATATTGCTTAGG  360
HSP90-beta    -----------------------CTTTTCAAG----------------------------  84
                                    ** * ****

HSP90-alpha   CTACTGATGCCTGAGGAAACCCAGACCCAAGACCAACCGATGGAGGAGGAGGAGGTTGAG  420
HSP90-beta    ------ATGCCTGAGGAAGTGCA--------------CCATGGAG-AGGAGGCAGGTGGAG  123
                    ***********  **               * ****** ********** ***

HSP90-alpha   ACGTTCGCCTTTCAGGCAGAAATTGCCCAGTTGATGTCATTGATCATCAATACTTTCTAC  480
HSP90-beta    ACTTTTGCCTTTCAGGCAGAAATTGCCCAACTCATGTCCCTCATCATCAATACCTTCTAT  183
              ** ** ***********************  * ***** * ********** *****

HSP90-alpha   TCGAACAAAGAGATCTTTCTGAGAGAGCTCATTTCAAATTCATCAGATGCATTGGACAAA  540
HSP90-beta    TCCAACAAGGAGATTTTTCCTTCGGGAGTTGATCTCTAATGCTTCTGATGCCTTGGACAAG  243
              ** ***** ***** ****  *    * * * *  *  *  ** ***** ********

HSP90-alpha   ATCCGGTATGAAAGCTTGACAGATCCCAGTAAATTAGACTCTGGGAAAGAGCTGCATATT  600
HSP90-beta    ATTCGCTATGAGAGCCTGACAGACCCTTCGAAGTTGGACAGTGGTAAAGAGCTGAAAATT  303
              ** ** ***** *** ******* **   *   ** *** *** ********* * ***

HSP90-alpha   AACCTTATACCGAACAAACAAGATCGAACTCTCACTATTGTGGATACTGGAATTGGAATG  660
HSP90-beta    GACATCATCCCCAACCCTCAGGAACGTACCCTGACTTTGGTAGACACAGGCATTGGCATG  363
               * * ** ** **  **  ** ** ** ** *** * ** ** ** ** ***** ***

HSP90-alpha   ACCAAGGCTGACTTGATCAATAACCTTGGTACTATCGCCAAGTCTGGGACCAAAGCGTTC  720
HSP90-beta    ACCAAAGCTGATCTCATAAATAATTTGGGAACCATTGCCAAGTCTGGTACTAAAGCATTC  423
              ***** ***** * ** ***** ** *** ** ** ********** ** ***** ***

HSP90-alpha   ATGGAAGCTTTGCAGGCTGGTGCAGATATATCTCTATGATTGGCCAGTTCGGTGTTGGTTTT  780
HSP90-beta    ATGGAGGCTCTTCAGGCTGGTGCAGACATCTCCATGATTGGGCAGTTTGGTGTTGGCTTT  483
              ***** ***  * ************* ** ** ******** ***** ******* ***

HSP90-alpha   TATTCTGCTTATTTGGTTGCTGAGAAAGTAACTGTGATCACCAAACATAACGATGATGAG  840
HSP90-beta    TATTCTGCCTACTTGGTGGCAGAGAAAGTGGTTGTGATCACAAAGCACAACGATGATGAA  543
              ******** **  ***** ** ********   *******   ** ***********
```

FIG. 17 (continued)

```
HSP90-alpha    CAGTACGCTTGGGAGTCCTCAGCAGGGGGATCATTCACAGTGAGGACAGACACAGGTGAA 900
HSP90-beta     CAGTATGCTTGGGAGTCTTCTGCTGGAGGTTCCTTCACTGTGCGTGCTGACCATGGTGAG 603
               ***** ********** ** ** ** ** ** ***** *** *   * *   *****

HSP90-alpha    CCTATGGGTCGTGGAACAAAAGTTATCCTACACCTGAAAGAAGACCAAACTGAGTACTTG 960
HSP90-beta     CCCATTGGCAGGGGTACCAAAGTGATCCTCCATCTTAAAGAAGATCAGACAGAGTACCTA 663
               ** ** **  * ** ** ***** ***** ** ** ******** ** ** ****** *

HSP90-alpha    GAGGAACGAAGAATAAAGGAGATTGTGAAGAAACATTCTCAGTTTATTGGAGATCCCATT 1020
HSP90-beta     GAAGAGAGGCGGGTCAAAGAAGTAGTGAAGAAGCATTCTCAGTTCATAGGCTATCCCATC 723
               ** **  *  *   *  *** ** ** ** ** ********** **  ** ********

HSP90-alpha    ACTCTTTTTGTGGAGAAGGAACGTGATAAAGAAGTAAGCGATGATGAGGCTGAAGAAAAG 1080
HSP90-beta     ACCCTTTATTTGGAGAAGGAACGAGAGAAGGAAATTAGTGATGATGAGGCAGAGGAAGAG 783
               ** **** * ************ ** ** ** ** ** ************ ** ** **

HSP90-alpha    GAAGACAAAGAAGAAGAAAAAGAAAAAGAAGAGAAAGAGTCGGAAGACAAACCTGAAATT 1140
HSP90-beta     AAAGGTGAGAAAGAAGAGGAAGATAAAGATGA---------TGAAGAAAAACCCAAGATC 834
                **    * *******  **** ***** **         ***** *****  **  **

HSP90-alpha    GAAGATGTTGGTTCTGATGAGGAAGAAGAAAAGAAGGATGGTGACAAGAAGAAGAAGAAG 1200
HSP90-beta     GAAGATGTGGGTTCAGATGAGGAGGATGACAGCGGTAAGGATAAGAAGAAGAAAACTAAG 894
               ******** ***** ******* **  **     *     *  ********  *  ***

HSP90-alpha    AAGATTAAGGAAAAGTACATCGATCAAGAAGAGCTCAACAAAACAAAGCCCATCTGGACC 1260
HSP90-beta     AAGATCAAAGAGAAATACATTGATCAGGAAGAACTAAACAAGACCAAGCCTATTTGGACC 954
               ***** ** ** ** ***** ***** ***** **  ****  * ***** ** *****

HSP90-alpha    AGAAATCCCGACGATATTACTAATGAGGAGTACGGAGAATTCTATAAGAGCTTGACCAAT 1320
HSP90-beta     AGAAACCCTGATGACATCACCCAAGAGGAGTATGGAGAATTCTACAAGAGCCTCACTAAT 1014
               ***** ** ** ** ** **  * ******** *********** ****** * ** ***

HSP90-alpha    GACTGGGAAGATCACTTGGCAGTGAAGCATTTTTCAGTTGAAGGACAGTTGGAATTCAGA 1380
HSP90-beta     GACTGGGAAGACCACTTGGCAGTCAAGCACTTTTCTGTAGAAGGTCAGTTGGAATTCAGG 1074
               *********** *********** ***** ***** ** ***** ****************

HSP90-alpha    GCCCTTCTATTTGTCCCACGACGTGCTCCTTTTGATCTGTTTGAAAACAGAAAGAAAAAG 1440
HSP90-beta     GCATTGCTATTTATTCCTCGTCGGGCTCCCTTTGACCTTTTTGAGAACAAGAAGAAAAAG 1134
               **  * ****** * ** ** **  **** ***** **  ** ** ** ** ********

HSP90-alpha    AACAATATCAAATTGTATGTACGCAGAGTTTTCATCATGGATAACTGTGAGGAGCTAATC 1500
HSP90-beta     AACAACATCAAACTCTATGTCCGCCGTGTGTTCATCATGGACAGCTGTGATGAGTTGATA 1194
               ***** ****** * ***** * **  * ************ * ***** *** * **

HSP90-alpha    CCTGAATATCTGAACTTCATTAGAGGGGTGGTAGACTCGGAGGATCTCCCTCTAAACATA 1560
HSP90-beta     CCAGAGTATCTCAATTTTATCCGTGGTGTGGTTGACTCTGAGGATCTGCCCCTGAACATC 1254
               ** ** ***** ** ** **  ** ** ***** ***** ****** *** ** *****

HSP90-alpha    TCCCGTGAGATGTTGCAACAAAGCAAAATTTTGAAAGTTATCAGGAAGAATTTGGTCAAA 1620
HSP90-beta     TCCCGAGAAATGCTCCAGCAGAGCAAAATCTTGAAAGTCATTCGCAAAAACATTGTTAAG 1314
               ***** ** *** * ** ** ******** ******** ** * ** ** * *** **

HSP90-alpha    AAATGCTTAGAACTCTTTACTGAACTGGCGGAAGATAAAGAGAACTACAAGAAATTCTAT 1680
HSP90-beta     AAGTGCCTTGAGCTCTTCTCTGAGCTGGCAGAAGACAAGGAGAATTACAAGAAATTCTAT 1374
               ** *** * ** ***** * *** ***** ***** ** **** **************

HSP90-alpha    GAGCAGTTCTCTAAAAACATAAAGCTTGGAATACACGAAGACTCTCAAAATCGGAAGAAG 1740
HSP90-beta     GAGGCATTCTCTAAAAATCTCAAGCTTGGAATCCACGAAGACTCCACTAACCGCCGCCGC 1434
               ***   *********** *  *********** *********** *  ** **  * *
```

FIG. 17 (continued)

```
HSP90-alpha   CTTTCAGAGCTGTTAAGGTACTACACATCTGCCTCTGGTGATGAGATGGTTTCTCTCAAG 1800
HSP90-beta    CTGTCTGAGCTGCTGCGCTATCATACCTCCCAGTCTGGAGATGAGATGACATCTCTGTCA 1494
              ** ** ****** *   * **  * ** **    ***** ********   *****

HSP90-alpha   GACTACTGCACCAGAATGAAGGAGAACCAGAAACATATCTATTATATCACAGGTGAGACC 1860
HSP90-beta    GAGTATGTTTCTCGCATGAAGGAGACACAGAAGTCCATCTATTACATCACTGGTGAGAGC 1554
              ** **    *  * ********* ****   ******** ***** ******* *

HSP90-alpha   AAGGACCAGGTAGCTAACTCAGCCTTTGTGGAACGTCTTCGGAAACATGGCTTAGAAGTG 1920
HSP90-beta    AAAGAGCAGGTGGCCAACTCAGCTTTTGTGGAGCGAGTGCGGAAACGGGGCTTCGAGGTG 1614
              ** ** ***** ** ******* ******** ** *  * ******     *** ** ***

HSP90-alpha   ATCTATATGATTGAGCCCATTGATGAGTACTGTGTCCAACAGCTGAAGGAATTTGAGGGG 1980
HSP90-beta    GTATATATGACCGAGCCCATTGACGAGTACTGTGTGCAGCAGCTCAAGGAATTTGATGGG 1674
               * *******  ************* ********* ** ***** ***********  ***

HSP90-alpha   AAGACTTTAGTGTCAGTCACCAAAGAAGGCCTGGAACTTCCAGAGGATGAAGAAGAGAAA 2040
HSP90-beta    AAGAGCCTGGTCTCAGTTACCAAGGAGGGTCTGGAGCTGCCTGAGGATGAGGAGGAGAAG 1734
              ****   *  ** ***** *****  ** ** ***** ** ** ******** ** *****

HSP90-alpha   AAGAAGCAGGAAGAGAAAAAAACAAAGTTTGAGAACCTCTGCAAAATCATGAAAGACATA 2100
HSP90-beta    AAGAAGATGGAAGAGAGCAAGGCAAAGTTTGAGAACCTCTGCAAGCTCATGAAAGAAATC 1794
              ******  ********  **  ********************** ** ********** **

HSP90-alpha   TTGGAGAAAAAAGTTGAAAAGGTGGTTGTGTCAAACCGATTGGTGACATCTCCATGCTGT 2160
HSP90-beta    TTAGATAAGAAGGTTGAGAAGGTGACAATCTCCAATAGACTTGTGTCTTCACCTTGCTGC 1854
              ** ** ** ** ***** ******   * ** **  **  ** ** ** ** ** *****

HSP90-alpha   ATTGTCACAAGCACATATGGCTGGACAGCAAACATGGAGAGAATCATGAAAGCTCAAGCC 2220
HSP90-beta    ATTGTGACCAGCACCTACGGCTGGACAGCCAATATGGAGCGGATCATGAAAGCCCAGGCA 1914
              ***** ** ***** ** *********** ** ****** * *********** ** **

HSP90-alpha   CTAAGAGACAACTCAACAATGGGTTACATGGCAGCAAAGAAACACCTGGAGATAAACCCT 2280
HSP90-beta    CTTCGGGACAACTCCACCATGGGCTATATGATGGCCAAAAAGCACCTGGAGATCAACCCT 1974
              **  * ******** **  *****  **  ***  ** ** ** ************ ******

HSP90-alpha   GACCATTCCATTATTGAGACCTTAAGGCAAAAGGCAGAGGCTGATAAGAACGACAAGTCT 2340
HSP90-beta    GACCACCCCATTGTGGAGACGCTGCGGCAGAAGGCTGAGGCCGACAAGAATGATAAGGCA 2034
              *****   ****  * ****  * *****  ***** **** ** ***** ** *** *

HSP90-alpha   GTGAAGGATCTGGTCATCTTGCTTTATGAAACTGCGCTCCTGTCTTCTGGCTTCAGTCTG 2400
HSP90-beta    GTTAAGGACCTGGTGGTGCTGCTGTTTGAAACCGCCCTGCTATCTTCTGGCTTTTCCCTT 2094
              ** ***** *****   *  *****  * **** ** ***  * *********       **

HSP90-alpha   GAAGATCCCCAGACACATGCTAACAGGATCTACAGGATGATCAAACTTGGTCTGGGTATT 2460
HSP90-beta    GAGGATCCCCAGACCCACTCCAACCGCATCTATCGCATGATCAAGCTAGGTCTAGGTATT 2154
              ** *********** **  *  ***  ******  * ******** ** ***** ******

HSP90-alpha   GATGAAGATGACCCTACTGCTGATGATACCAGTGCTGCTGTAACTGAAGAAATGCCACCC 2520
HSP90-beta    GATGAAGATGAAGTGGCAGCAGAGGAACCCAATGCTGCAGTTCCTGATGAGATCCCCCCT 2214
              ***********    * ** ** **   *** ****** **    *** ** ** ** **

HSP90-alpha   CTTGAAGGAGATGACGACACATCACGCATGGAAGAAGTAGACTAA---------------- 2565
HSP90-beta    CTCGAGGGCGATGAGGATGCGTCTCGCATGGAAGAAGTCGATTAGGTTAGGAGTTCATAG 2274
              ** ** ** ***** **  * ** ************** **  **

HSP90-alpha   ------------------------------------------------------------
HSP90-beta    TTGGAAAACTTGTGCCCTTGTATAGTGTCCCCATGGGCTCCCACTGCAGCCTCGAGTGCC 2334
```

FIG. 17 (continued)

```
HSP90-alpha  ------------------------------------------------------------
HSP90-beta   CCTGTCCCACCTGGCTCCCCCTGCTGGTGTCTAGTGTTTTTTTCCCTCTCCTGTCCTTGT 2394

HSP90-alpha  ------------------------------------------------------------
HSP90-beta   GTTGAAGGCAGTAAACTAAGGGTGTCAAGCCCCATTCCCTCTCTACTCTTGACAGCAGGA 2454

HSP90-alpha  ------------------------------------------------------------
HSP90-beta   TTGGATGTTGTGTATTGTGGTTTATTTTATTTTCTTCATTTTGTTCTGAAATTAAAGTAT 2514

HSP90-alpha  ----------------------------------------------------
                                                         (SEQ ID NO: 7)

HSP90-beta   GCAAAATAAAGAATATGCCGTTTTAAAAAAAAAAAAAAAAAAAAAAAAAAA 2567
                                                         (SEQ ID NO: 9)
```

FIG. 17 (continued)

Amino acid sequence alignment

```
HSP90-alpha    MPPCSGGDGSTPPGPSLRDRDCPAQSAEYPRDRLDPRPGSPSEASSPPFLRSRAPVNWYQ  60
HSP90-beta     ------------------------------------------------------------

HSP90-alpha    EKAQVFLWHLLVSGSTTLLCLWKQPFHVSAFPVTASLAFRQSQGAGQHLYKDLQPFILLR 120
HSP90-beta     ------------------------------------------------------------

HSP90-alpha    LLMPEETQTQDQPMEEEEVETFAFQAEIAQLMSLIINTFYSNKEIFLRELISNSSDALDK 180
HSP90-beta     --MPEEVHHG-----EEEVETFAFQAEIAQLMSLIINTFYSNKEIFLRELISNASDALDK  53
                 ****.:     ************************************:******

HSP90-alpha    IRYESLTDPSKLDSGKELHINLIPNKQDRTLTIVDTGIGMTKADLINNLGTIAKSGTKAF 240
HSP90-beta     IRYESLTDPSKLDSGKELKIDIIPNPQERTLTLVDTGIGMTKADLINNLGTIAKSGTKAF 113
               ******************:.*:.***.*:***:***************************

HSP90-alpha    MEALQAGADISMIGQFGVGFYSAYLVAEKVTVITKHNDDEQYAWESSAGGSFTVRTDTGE 300
HSP90-beta     MEALQAGADISMIGQFGVGFYSAYLVAEKVVVITKHNDDEQYAWESSAGGSFTVRADHGE 173
               ****************************** ***********************.* **

HSP90-alpha    PMGRGTKVILHLKEDQTEYLEERRIKEIVKKHSQFIGYPITLFVEKERDKEVSDDEAEEK 360
HSP90-beta     PIGRGTKVILHLKEDQTEYLEERRVKEVVKKHSQFIGYPITLYLEKEREKEISDDEAEEE 233
               *.*********************:.**:***************:.***:**:********.

HSP90-alpha    EDKEEEKEKEEKESEDKPEIEDVGSDEEEEKKDGDKKKKKKIKEKYIDQEELNKTKPIWT 420
HSP90-beta     KG---EKEEEDKDDEEKPKIEDVGSDEEDDSGKDKKKKTKKIKEKYIDQEELNKTKPIWT 290
               :.   **:.*:.* *.***.*********.. ***   *** .****************

HSP90-alpha    RNPDDITNEEYGEFYKSLTNDWEDHLAVKHFSVEGQLEFRALLFVPRRAPFDLFENRKKK 480
HSP90-beta     RNPDDITQEEYGEFYKSLTNDWEDHLAVKHFSVEGQLEFRALLFIPRRAPFDLFENKKKK 350
               *******:************************************:**********.***

HSP90-alpha    NNIKLYVRRVFIMDNCEELIPEYLNFIRGVVDSEDLPLNISREMLQQSKILKVIRKNLVK 540
HSP90-beta     NNIKLYVRRVFIMDSCDELIPEYLNFIRGVVDSEDLPLNISREMLQQSKILKVIRKNIVK 410
               **************.*:***************************************:**

HSP90-alpha    KCLELFTELAEDKENYKKFYEQFSKNIKLGIHEDSQNRKKLSELLRYYTSASGDEMVSLK 600
HSP90-beta     KCLELFSELAEDKENYKKFYEAFSKNLKLGIHEDSTNRRRLSELLRYHTSQSGDEMTSLS 470
               ******:.************* ****:********.**::*******:** *****.**.

HSP90-alpha    DYCTRMKENQKHIYYITGETKDQVANSAFVERLRKHGLEVIYMIEPIDEYCVQQLKEFEG 660
HSP90-beta     EYVSRMKETQKSIYYITGESKEQVANSAFVERVRKRGFEVVYMTEPIDEYCVQQLKEFDG 530
               :*  :****.** *******:*:*********.**:*:**:** *************:*

HSP90-alpha    KTLVSVTKEGLELPEDEEEKKKQEEKKTKFENLCKIMKDILEKKVEKVVVSNRLVTSPCC 720
HSP90-beta     KSLVSVTKEGLELPEDEEEKKKMEESKAKFENLCKLMKEILDKKVEKVTISNRLVSSPCC 590
               *:********************.**.*.*******:**:**:******. ****::****

HSP90-alpha    IVTSTYGWTANMERIMKAQALRDNSTMGYMAAKKHLEINPDHSIIETLRQKAEADKNDKS 780
HSP90-beta     IVTSTYGWTANMERIMKAQALRDNSTMGYMMAKKHLEINPDHPIVETLRQKAEADKNDKA 650
               ****************************** *********.*:************.

HSP90-alpha    VKDLVILLYETALLSSGFSLEDPQTHANRIYRMIKLGLGIDEDDPTADDTSAAVTEEMPP 840
HSP90-beta     VKDLVVLLFETALLSSGFSLEDPQTHSNRIYRMIKLGLGIDEDEVAAEEPNAAVPDEIPP 710
               *****:**:*****************:*****************. :*:. ***.:*:**

HSP90-alpha    LEGDDDTSRMEEVD  854 (SEQ ID NO: 8)
HSP90-beta     LEGDEDASRMEEVD  724 (SEQ ID NO: 10)
               ****:*::*******
```

FIG. 18A

NC1 ASO:
mA*mU*mA* mC*mG*mC* G*T*A* T*T*A* T*A*C* G*C*G* mA*mU*mU* mA*mA*mC mHsp90ab1_ASO1:
mU*mC*mU*mC* mC*mU*T*C*T*C* C*C*A*C* G*T*T*C* C*T*mU*mC*mU*mC*mC*mA mHsp90ab1_ASO2:
mA*mU*mC* mC*mU*mC* T*T*C* T*C*C* C*G*T* T*C*C* mU*mU*mC* mU*mC*mC mHsp90ab1_ASO3:
mA*mC*mU*mU*mC*mC*T*T*G*A*C*C*C*C*T*C*C*T*mU*mC*mC*mU*mC*mC mHsp90ab1_ASO4:
mC*mU*mU* mC*mC*mU* T*G*A* C*C*C* T*C*C* C*C*T* mC*mC*mU* mC*mC*mA mHsp90ab1_ASO5:
mC*mC*mA* mC*mU*mU* C*C*T* T*G*A* C*C*C* T*C*C* mU*mC*mC* mC*mC*mU mHsp90ab1_ASO6:
mU*mC*mC* mU*mC*mC T*C*T T*T*C T*C*A C*C*T mU*mU*mC mU*mC*mU mHsp90ab1_ASO7:
mA*mC*mU* mA*mC*mU* T*C*C* T*T*G* A*C*C* C*T*C* mC*mU*mC* mU*mC*mC mHsp90ab1_ASO8:
mC*mU*mC* mC*mU*mC* C*T*T* G*A*C* C*C*T* C*C*T* mC*mU*mC* mC*mA*mA mHsp90ab1_ASO9:
mC*mA*mC* mU*mU*mC* C*T*T* G*A*C* C*C*T* C*C*T* mC*mU*mC* mC*mU*mC

FIG. 18B mHsp90ab1_ASO1:
mU*mC*mU*mC*mC*mU*T*C*T*C*C*C*G*T*T*C*C*T*mU*mC*mU*mC*mC*mA

```
Query    3    TCCTTCTCCGTTCCTTCTCCA    24
              ||||||||  |||||||||||||
Sbjct  879    TCCTTCTCTCGTTCCTTCTCCA   858
```

Variants:
1mU*m<u>U</u>*mU*mC*mC*mU*T*C*T*C*<u>T</u>*C*G*T*T*C*C*T*mU*mC*mU*mC*mC*mA
2mU*mC*mU*mC*mC*mU*T*C*T*C*<u>T</u>*C*G*T*T*C*C*T*mU*mC*mU*mC*mC*mA
3mU*m<u>U</u>*mU*mC*mC*mU*T*C*T*C*C*C*G*T*T*C*C*T*mU*mC*mU*mC*mC*mA mHsp90ab1_ASO2:
mA*mU*mC* mU*mC*mC* T*T*C* T*C*C* C*G*T* T*C*C* mU*mU*mC* mU*mC*mC

```
Query    4    TCCTTCTCCGTTCCTTCTCC     24
              ||||||||  ||||||||||||
Sbjct  879    TCCTTCTCTCGTTCCTTCTCC    859
```

Variants:
1mA*mU*m<u>U</u>* mU*mC*mC* T*T*C* T*C*<u>T</u>* C*G*T* T*C*C* mU*mU*mC* mU*mC*mC
2mA*mU*mC* mU*mC*mC* T*T*C* T*C*<u>T</u>* C*G*T* T*C*C* mU*mU*mC* mU*mC*mC
3mA*mU*m<u>U</u>* mU*mC*mC* T*T*C* T*C*C* C*G*T* T*C*C* mU*mU*mC* mU*mC*mC mHsp90ab1_ASO6:
mU*mC*mC* mU*mC*mC* T*C*T* T*T*C* T*C*A* C*C*T* mU*mU*mC* mU*mC*mU

```
Query    1    TCCTCCTCTTTCTCACCTTTCTCT   24
              |||||  ||||||||||||||||||
Sbjct  927    TCCTCTTCTTTCTCACCTTTCTCT  904
```

Variant:
1mU*mC*mC* mU*mC*m<u>U</u>* T*C*T* T*T*C* T*C*A* C*C*T* mU*mU*mC* mU*mC*mU mHsp90ab1_ASO8:
mC*mU*mC* mC*mU*mU* C*T*C* C*C*G* T*T*C* C*T*T* mC*mU*mC* mC*mA*mA

```
Query    2    TCCTTCTCCGTTCCTTCTCCAA   24
              ||||||||  |||||||||||||
Sbjct  879    TCCTTCTCTCGTTCCTTCTCCAA  857
```

Variants:
1m<u>U</u>*mU*mC* mC*mU*mU* C*T*C* <u>T</u>*C*G* T*T*C* C*T*T* mC*mU*mC* mC*mA*mA
2mC*mU*mC* mC*mU*mU* C*T*C* <u>T</u>*C*G* T*T*C* C*T*T* mC*mU*mC* mC*mA*mA
3m<u>U</u>*mU*mC* mC*mU*mU* C*T*C* C*C*G* T*T*C* C*T*T* mC*mU*mC* mC*mA*mA

|  | Fold change/NC | SEM | T test paired ASO vs NC |
|---|---|---|---|
| NC | 100% | 0.0000 | |
| ASO1 | 70% | 0.0651 | 0.0431 |
| ASO2 | 67% | 0.0590 | 0.0314 |
| ASO3 | 45% | 0.0399 | 0.0053 |
| ASO4 | 55% | 0.1880 | 0.1373 |
| ASO5 | 37% | 0.0299 | 0.0023 |
| ASO6 | 32% | 0.0657 | 0.0092 |

DNAse target
Human and mouse HSP90ab1 are 96% homologous

FIG. 24
Measurement of heat production in mice treated with ASO for eight weeks
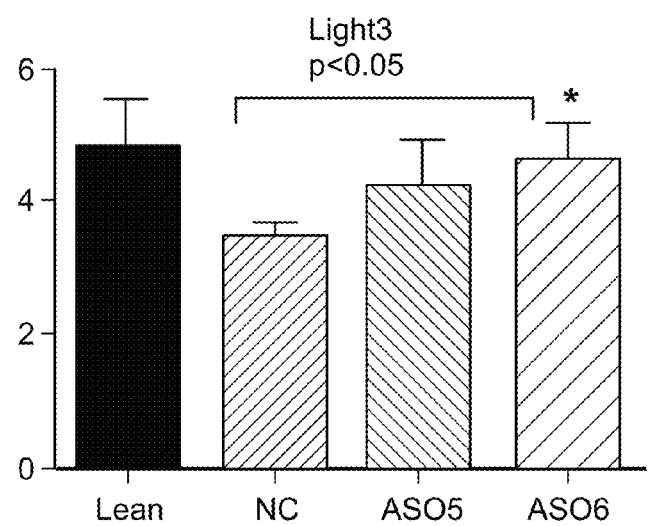
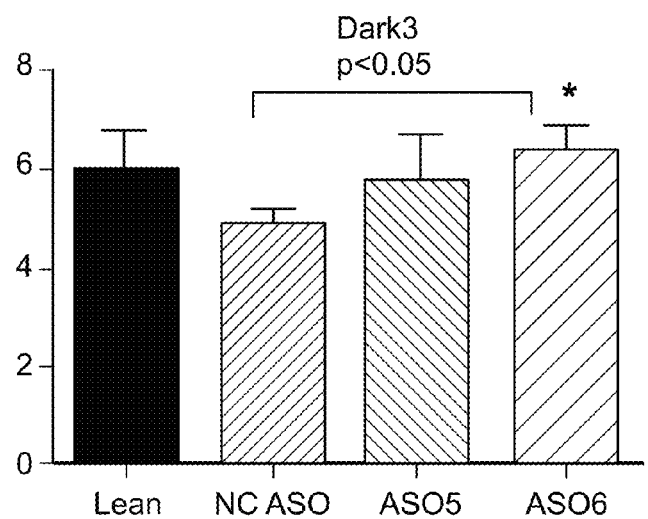

FIG. 31 (continued)

ASO14

5' mU*mC*mU*mU*C*C*T*C*T*G*C*C*T*C*A*T*mC*mA*mU*mC*mA*mC 3'
Length: 24  3' End Position: 1
G + C%: 50  Tm: 44.4
AntiSense MW: 7785.2

```
              930        940        950        960        970
               |          |          |          |          |
Human   TAGTGATGATGAGGCAGAGGAAGAGAGAAAGAAGAGGAAGA
Monkey  TAGTGATGATGAGGCAGAGGAAGAGAGAAAGAAGAGGAAGA
Mouse   CAGTGATGATGAGGCAGAGAGGAAGAGAGAAAGAGGAGGAAGA
                         Target sequence
```

ASO15

5' mU*mU*mC*mU*mC*C*T*C*T*G*C*C*T*C*A*mU*mC*mA*mU*mC*mA 3'
Length: 24  3' End Position: 2
G + C%: 45.8  Tm: 43.5
AntiSense MW: 7786.2

```
              930        940        950        960        970
               |          |          |          |          |
Human   TAGTGATGATGAGGCAGAGGAAGAGAGAAAGAAGAGGAAGA
Monkey  TAGTGATGATGAGGCAGAGGAAGAGAGAAAGAAGAGGAAGA
Mouse   CAGTGATGATGAGGCAGAGAGGAAGAGAGAAAGAGGAGGAAGA
                         Target sequence
                              18
```

FIG. 31 (continued)

ASO16    5' mU*mU*mC*mU*mC*T*T*C*C*T*C*T*G*C*C*T*C*mA*mU*mC*mA*mU*mC 3'
         Length: 24    3' End Position: 3
         G + C%: 45.8  Tm: 42.0
         AntiSense MW: 7777.2

```
               930       940       950       960       970
                |         |         |         |         |
Human   TAGTGATGATGAGGCAGAGGAAGAAAGAGAAAGGTGAGAAAGAGAGGAAGA
Monkey  TAGTGATGATGAGGCAGAGGAAGAAAGAGAAAGGTGAGAAAGAGAGGAAGA
Mouse   CAGTGATGATGAGGCAGAGGAAGAGAGAGAAAGGTGAGAAAGAGGAGGAAGA
                            _____/
                                      Target sequence
```

ASO17    5' mC*mU*mU*mC*mU*C*T*T*C*C*T*C*T*G*C*C*T*mC*mA*mU*mC*mA*mU 3'
         Length: 24    3' End Position: 4
         G + C%: 45.8  Tm: 42.3
         AntiSense MW: 7777.2

```
               930       940       950       960       970
                |         |         |         |         |
Human   TAGTGATGATGAGGCAGAGGAAGAAAGAGAAAGGTGAGAAAGAGAGGAAGA
Monkey  TAGTGATGATGAGGCAGAGGAAGAAAGAGAAAGGTGAGAAAGAGAGGAAGA
Mouse   CAGTGATGATGAGGCAGAGGAAGAGAGAGAAAGGTGAGAAAGAGGAGGAAGA
                             _____/
                                      Target sequence
```

FIG. 31 (continued)

ASO18  5' mA*mU*mG*mC*mC*mC*mC*T*G*A*A*T*T*C*C*A*A*C*T*mG*mA*mC*mC*mU*mU 3'
Length: 24    3' End Position: 7
G + C%: 45.8    Tm: 38.4
AntiSense MW: 7935.4

```
                 1220       1230       1240       1250       1260
                  |          |          |          |          |
Human    TTCTGTAGAAGGTCAGTTGGAATTCAGGGCATTGCTATTTATTCCTTCCTCGTC
Monkey   TTCTGTAGAAGGTCAGTTGGAATTCAGGGCATTGCTATTCATTCCTTCCTCGTC
Mouse    CTCTGTAGAAGGTCAGTTGGAATTCAGGGCATTGCTCTTCATTCCTTCCCCGGC
                                  ╰─────────Target sequence─────────╯
```

ASO19  5' mA*mA*mU*mG*mC*mC*mC*C*T*G*A*A*T*T*C*C*A*A*C*mU*mG*mA*mC*mC*mU 3'
Length: 24    3' End Position: 8
G + C%: 45.8    Tm: 38.9
AntiSense MW: 7944.4

```
                 1220       1230       1240       1250       1260
                  |          |          |          |          |
Human    TTCTGTAGAAGGTCAGTTGGAATTCAGGGCATTGCTATTTATTCCTTCCTCGTC
Monkey   TTCTGTAGAAGGTCAGTTGGAATTCAGGGCATTGCTATTCATTCCTTCCTCGTC
Mouse    CTCTGTAGAAGGTCAGTTGGAATTCAGGGCATTGCTCTTCATTCCTTCCCCGGC
                                        ╰────20────╯
                                     Target sequence
```

FIG. 31 (continued)

ASO22  5' mG*mC*mA*mA*mU*mG*C*C*C*T*G*A*A*T*T*C*C*A*mA*mC*mU*mG*mA*mC 3'
Length: 24    3' End Position: 10
G + C%: 50    Tm: 39.7
AntiSense MW: 7983.4

```
              1220       1230       1240       1250       1260
               |          |          |          |          |
Human    TTCTGTAGAAGGTCAGTTGGAATTCAGGGCATTGCTATTTATTCCTCGTC
Monkey   TTCTGTAGAAGGTCAGTTGGAATTCAGGGCATTGCTATTCATTCCTCGTC
Mouse    CTCTGTAGAAGGTCAGTTGGAATTCAGGGCATTGCTCTTCATTCCCCGGC
                         _____/
                                   Target sequence
```

ASO23  5' mA*mC*mU*mG*mA*C*C*A*G*G*C*T*C*T*T*C*mC*mC*mA*mU*mC*mA 3'
Length: 24    3' End Position: 2
G + C%: 54.2  Tm: 48.2
AntiSense MW: 7959.4

```
              1830       1840       1850       1860       1870
               |          |          |          |          |
Human    GGAATTTGATGGGAAGAGCCTGGTCTCAGTTACCAAGGAGGGTCTG
Monkey   GGAGTTTGATGGGAAGAGCCTGGTCTCAGTTACCAAGGAGGGTCTG
Mouse    GGAGTTTGATGGGAAGAGCCTGGTCTCAGTGACTAAGGAGGGCCTG
                                  _____/
                                          22
                                    Target sequence
```

FIG. 33B
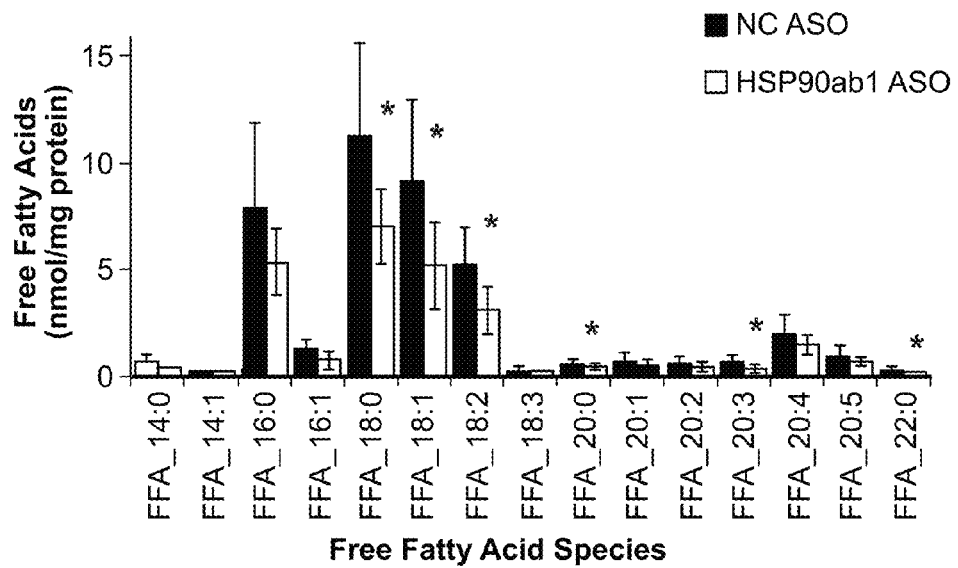
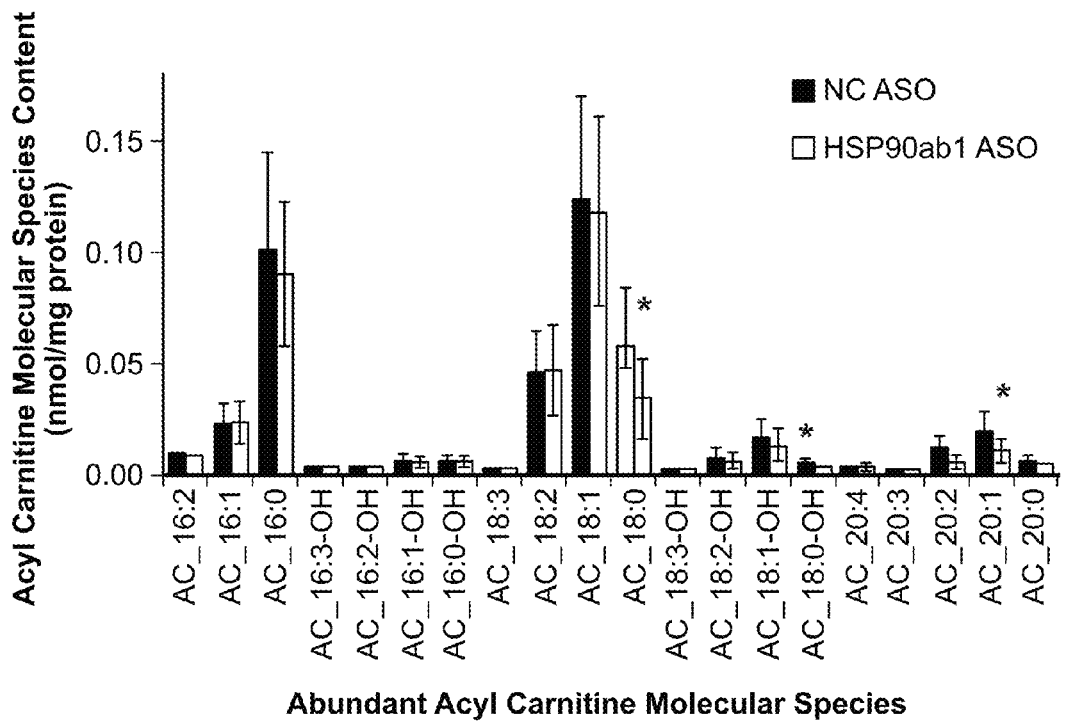

SEQUENCE LISTING

```
<160> NUMBER OF SEQ ID NOS: 107

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1
aggccgacaa gaaugauaag gcagt                                          25

<210> SEQ ID NO 2
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
```
acugccuuau cauucuuguc ggccuca         27

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
caacgaugau gaacaguaug cuugg         25

<210> SEQ ID NO 4
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ccaagcauac uguucaucau cguugug         27

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
cguugcucac uauuacguau aaucc         25

<210> SEQ ID NO 6
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ggauuauacg uaauagugag caacgua         27

<210> SEQ ID NO 7
<211> LENGTH: 2565
<212> TYPE: DNA
<213> ORGANISM: Homo sapiens

<400> SEQUENCE: 7 atgccccgt gttcgggcgg ggacggctcc acccctcctg ggccctccct tcgggacagg     60
gactgtcccg cccagagtgc tgaatacccg cgcgaccgtc tggatccccg cccaggaagc    120
ccctctgaag cctcctcgcc gccgtttctg agaagcaggg cacctgttaa ctggtaccaa    180
gaaaaggccc aagtgttcct ctggcatctg ttggtgtctg gatccaccac tctactctgt    240
ctctggaaac agcccttcca cgtctctgca ttccctgtca ctgcgtcact ggccttcaga    300
cagagccaag gtgcagggca acacctctac aaggatctgc agccatttat attgcttagg    360
ctactgatgc ctgaggaaac ccagacccaa gaccaaccga tggaggagga ggaggttgag    420
acgttcgcct ttcaggcaga aattgcccag ttgatgtcat tgatcatcaa tactttctac    480

```
tcgaacaaag agatctttct gagagagctc atttcaaatt catcagatgc attggacaaa      540
atccggtatg aaagcttgac agatcccagt aaattagact ctgggaaaga gctgcatatt      600
aaccttatac cgaacaaaca agatcgaact ctcactattg tggatactgg aattggaatg      660
accaaggctg acttgatcaa taaccttggt actatcgcca agtctgggac caaagcgttc      720
atggaagctt tgcaggctgg tgcagatatc tctatgattg gccagttcgg tgttggtttt      780
tattctgctt atttggttgc tgagaaagta actgtgatca ccaaacataa cgatgatgag      840
cagtacgctt gggagtcctc agcaggggga tcattcacag tgaggacaga cacaggtgaa      900
cctatgggtc gtggaacaaa agttatccta cacctgaaag aagaccaaac tgagtacttg      960
gaggaacgaa gaataaagga gattgtgaag aaacattctc agtttattgg atatcccatt     1020 actcttttg tggagaagga acgtgataaa gaagtaagcg atgatgaggc tgaagaaaag     1080
gaagacaaag aagaagaaaa agaaaaagaa gagaaagagt cggaagacaa acctgaaatt     1140
gaagatgttg gttctgatga ggaagaagaa aagaaggatg tgacaagaa gaagaagaag     1200 aagattaagg aaaagtacat cgatcaagaa gagctcaaca aaacaaagcc catctggacc     1260
agaaatcccg acgatattac taatgaggag tacggagaat tctataagag cttgaccaat     1320
gactgggaag atcacttggc agtgaagcat ttttcagttg aaggacagtt ggaattcaga     1380
gcccttctat ttgtcccacg acgtgctcct tttgatctgt ttgaaaacag aagaaaaag     1440 aacaatatca aattgtatgt acgcagagtt ttcatcatgg ataactgtga ggagctaatc     1500
cctgaatatc tgaacttcat tagaggggtg gtagactcgg aggatctccc tctaaacata     1560
tcccgtgaga gtgttgcaaca aagcaaaatt ttgaaagtta tcaggaagaa tttggtcaaa     1620
aaatgcttag aactctttac tgaactggcg gaagataaag agaactacaa gaaattctat     1680
gagcagttct ctaaaaacat aaagcttgga atacacgaag actctcaaaa tcggaagaag     1740
ctttcagagc tgttaaggta ctacacatct gcctctggtg atgagatggt ttctctcaag     1800
gactactgca ccagaatgaa ggagaaccag aaacatatct attatatcac aggtgagacc     1860
aaggaccagg tagctaactc agcctttgtg aacgtcttc ggaaacatgg cttagaagtg     1920
atctatatga ttgagcccat tgatgagtac tgtgtccaac agctgaagga atttgagggg     1980
aagactttag tgtcagtcac caaagaaggc ctggaacttc agaggatga agaagagaaa     2040 aagaagcagg aagagaaaaa aacaaagttt gagaacctct gcaaaatcat gaaagacata     2100
ttggagaaaa aagttgaaaa ggtggttgtg tcaaaccgat tggtgacatc tccatgctgt     2160
attgtcacaa gcacatatgg ctggacagca aacatggaga gaatcatgaa agctcaagcc     2220
ctaagagaca actcaacaat gggttacatg gcagcaaaga acacctgga gataaaccct     2280 gaccattcca ttattgagac cttaaggcaa aaggcagagg ctgataagaa cgacaagtct     2340
gtgaaggatc tggtcatctt gctttatgaa actgcgctcc tgtcttctgg cttcagtctg     2400
gaagatcccc agacacatgc taacaggatc tacaggatga tcaaacttgg tctgggtatt     2460
gatgaagatg accctactgc tgatgatacc agtgctgctg taactgaaga aatgccaccc     2520
cttgaaggag atgacgacac atcacgcatg gaagaagtag actaa                     2565
```

<210> SEQ ID NO 8
<211> LENGTH: 854
<212> TYPE: PRT
<213> ORGANISM: Homo sapiens

<400> SEQUENCE: 8

Met Pro Pro Cys Ser Gly Gly Asp Gly Ser Thr Pro Pro Gly Pro Ser

-continued

```
1               5                   10                  15
Leu Arg Asp Arg Asp Cys Pro Ala Gln Ser Ala Glu Tyr Pro Arg Asp
                20                  25                  30
Arg Leu Asp Pro Arg Pro Gly Ser Pro Ser Glu Ala Ser Ser Pro Pro
                35                  40                  45
Phe Leu Arg Ser Arg Ala Pro Val Asn Trp Tyr Gln Glu Lys Ala Gln
                50                  55                  60
Val Phe Leu Trp His Leu Val Ser Gly Ser Thr Thr Leu Leu Cys
 65                 70                  75                  80
Leu Trp Lys Gln Pro Phe His Val Ser Ala Phe Pro Val Thr Ala Ser
                85                  90                  95
Leu Ala Phe Arg Gln Ser Gln Gly Ala Gly Gln His Leu Tyr Lys Asp
                100                 105                 110
Leu Gln Pro Phe Ile Leu Leu Arg Leu Leu Met Pro Glu Glu Thr Gln
                115                 120                 125
Thr Gln Asp Gln Pro Met Glu Glu Glu Val Glu Thr Phe Ala Phe
                130                 135                 140
Gln Ala Glu Ile Ala Gln Leu Met Ser Leu Ile Ile Asn Thr Phe Tyr
145                 150                 155                 160
Ser Asn Lys Glu Ile Phe Leu Arg Glu Leu Ile Ser Asn Ser Ser Asp
                165                 170                 175
Ala Leu Asp Lys Ile Arg Tyr Glu Ser Leu Thr Asp Pro Ser Lys Leu
                180                 185                 190
Asp Ser Gly Lys Glu Leu His Ile Asn Leu Ile Pro Asn Lys Gln Asp
                195                 200                 205
Arg Thr Leu Thr Ile Val Asp Thr Gly Ile Gly Met Thr Lys Ala Asp
                210                 215                 220
Leu Ile Asn Asn Leu Gly Thr Ile Ala Lys Ser Gly Thr Lys Ala Phe
225                 230                 235                 240
Met Glu Ala Leu Gln Ala Gly Ala Asp Ile Ser Met Ile Gly Gln Phe
                245                 250                 255
Gly Val Gly Phe Tyr Ser Ala Tyr Leu Val Ala Glu Lys Val Thr Val
                260                 265                 270
Ile Thr Lys His Asn Asp Asp Glu Gln Tyr Ala Trp Glu Ser Ser Ala
                275                 280                 285
Gly Gly Ser Phe Thr Val Arg Thr Asp Thr Gly Glu Pro Met Gly Arg
                290                 295                 300
Gly Thr Lys Val Ile Leu His Leu Lys Glu Asp Gln Thr Glu Tyr Leu
305                 310                 315                 320
Glu Glu Arg Arg Ile Lys Glu Ile Val Lys Lys His Ser Gln Phe Ile
                325                 330                 335
Gly Tyr Pro Ile Thr Leu Phe Val Glu Lys Glu Arg Asp Lys Glu Val
                340                 345                 350
Ser Asp Asp Glu Ala Glu Glu Lys Glu Asp Lys Glu Glu Glu Lys Glu
                355                 360                 365
Lys Glu Glu Lys Glu Ser Glu Asp Lys Pro Glu Ile Glu Asp Val Gly
                370                 375                 380
Ser Asp Glu Glu Glu Glu Lys Lys Asp Gly Asp Lys Lys Lys Lys Lys
385                 390                 395                 400
Lys Ile Lys Glu Lys Tyr Ile Asp Gln Glu Glu Leu Asn Lys Thr Lys
                405                 410                 415
Pro Ile Trp Thr Arg Asn Pro Asp Asp Ile Thr Asn Glu Glu Tyr Gly
                420                 425                 430
```

```
Glu Phe Tyr Lys Ser Leu Thr Asn Asp Trp Glu Asp His Leu Ala Val
            435                 440                 445
Lys His Phe Ser Val Glu Gly Gln Leu Glu Phe Arg Ala Leu Leu Phe
450                 455                 460
Val Pro Arg Arg Ala Pro Phe Asp Leu Phe Glu Asn Arg Lys Lys Lys
465                 470                 475                 480
Asn Asn Ile Lys Leu Tyr Val Arg Arg Val Phe Ile Met Asp Asn Cys
                485                 490                 495
Glu Glu Leu Ile Pro Glu Tyr Leu Asn Phe Ile Arg Gly Val Val Asp
                500                 505                 510
Ser Glu Asp Leu Pro Leu Asn Ile Ser Arg Glu Met Leu Gln Gln Ser
            515                 520                 525
Lys Ile Leu Lys Val Ile Arg Lys Asn Leu Val Lys Lys Cys Leu Glu
530                 535                 540
Leu Phe Thr Glu Leu Ala Glu Asp Lys Glu Asn Tyr Lys Lys Phe Tyr
545                 550                 555                 560
Glu Gln Phe Ser Lys Asn Ile Lys Leu Gly Ile His Glu Asp Ser Gln
                565                 570                 575
Asn Arg Lys Lys Leu Ser Glu Leu Leu Arg Tyr Tyr Thr Ser Ala Ser
            580                 585                 590
Gly Asp Glu Met Val Ser Leu Lys Asp Tyr Cys Thr Arg Met Lys Glu
            595                 600                 605
Asn Gln Lys His Ile Tyr Tyr Ile Thr Gly Glu Thr Lys Asp Gln Val
            610                 615                 620
Ala Asn Ser Ala Phe Val Glu Arg Leu Arg Lys His Gly Leu Glu Val
625                 630                 635                 640
Ile Tyr Met Ile Glu Pro Ile Asp Glu Tyr Cys Val Gln Gln Leu Lys
                645                 650                 655
Glu Phe Glu Gly Lys Thr Leu Val Ser Val Thr Lys Glu Gly Leu Glu
                660                 665                 670
Leu Pro Glu Asp Glu Glu Lys Lys Gln Glu Glu Lys Lys Thr
            675                 680                 685
Lys Phe Glu Asn Leu Cys Lys Ile Met Lys Asp Ile Leu Glu Lys Lys
            690                 695                 700
Val Glu Lys Val Val Ser Asn Arg Leu Val Thr Ser Pro Cys Cys
705                 710                 715                 720
Ile Val Thr Ser Thr Tyr Gly Trp Thr Ala Asn Met Glu Arg Ile Met
                725                 730                 735
Lys Ala Gln Ala Leu Arg Asp Asn Ser Thr Met Gly Tyr Met Ala Ala
            740                 745                 750
Lys Lys His Leu Glu Ile Asn Pro Asp His Ser Ile Ile Glu Thr Leu
            755                 760                 765
Arg Gln Lys Ala Glu Ala Asp Lys Asn Asp Lys Ser Val Lys Asp Leu
770                 775                 780
Val Ile Leu Leu Tyr Glu Thr Ala Leu Leu Ser Ser Gly Phe Ser Leu
785                 790                 795                 800
Glu Asp Pro Gln Thr His Ala Asn Arg Ile Tyr Arg Met Ile Lys Leu
                805                 810                 815
Gly Leu Gly Ile Asp Glu Asp Pro Thr Ala Asp Asp Thr Ser Ala
                820                 825                 830
Ala Val Thr Glu Glu Met Pro Pro Leu Glu Gly Asp Asp Asp Thr Ser
835                 840                 845
```

Arg Met Glu Glu Val Asp
    850

<210> SEQ ID NO 9
<211> LENGTH: 2567
<212> TYPE: DNA
<213> ORGANISM: Homo sapiens

<400> SEQUENCE: 9

| | | | | | |
|---|---|---|---|---|---|
| ctccggcgca | gtgttgggac | tgtctgggta | tcggaaagca | agcctacgtt gctcactatt | 60 |
| acgtataatc | cttttctttt | caagatgcct | gaggaagtgc | accatggaga ggaggaggtg | 120 |
| gagacttttg | cctttcaggc | agaaattgcc | caactcatgt | ccctcatcat caataccttc | 180 |
| tattccaaca | aggagatttt | ccttcgggag | ttgatctcta | atgcttctga tgccttggac | 240 |
| aagattcgct | atgagagcct | gacagaccct | tcgaagttgg | acagtggtaa agagctgaaa | 300 |
| attgacatca | tccccaaccc | tcaggaacgt | accctgactt | tggtagacac aggcattggc | 360 |
| atgaccaaag | ctgatctcat | aaataatttg | ggaaccattg | ccaagtctgg tactaaagca | 420 |
| ttcatggagg | ctcttcaggc | tggtgcagac | atctccatga | ttgggcagtt tggtgttggc | 480 |
| ttttattctg | cctacttggt | ggcagagaaa | gtggttgtga | tcacaaagca caacgatgat | 540 |
| gaacagtatg | cttgggagtc | ttctgctgga | ggttccttca | ctgtgcgtgc tgaccatggt | 600 |
| gagcccattg | caggggtac | caaagtgatc | ctccatctta | agaagatca gacagagtac | 660 |
| ctagaagaga | ggcgggtcaa | agaagtagtg | aagaagcatt | ctcagttcat aggctatccc | 720 |
| atcacccttt | atttggagaa | ggaacgagag | aaggaaatta | gtgatgatga ggcagaggaa | 780 |
| gagaaaggtg | agaaagaaga | ggaagataaa | gatgatgaag | aaaaacccaa gatcgaagat | 840 |
| gtgggttcag | atgaggagga | tgacagcggt | aaggataaga | agaagaaaac taagaagatc | 900 |
| aaagagaaat | acattgatca | ggaagaacta | aacaagacca | agcctatttg gaccagaaac | 960 |
| cctgatgaca | tcacccaaga | ggagtatgga | gaattctaca | agagcctcac taatgactgg | 1020 |
| gaagaccact | tggcagtcaa | gcactttct | gtagaaggtc | agttggaatt cagggcattg | 1080 |
| ctatttattc | ctcgtcgggc | tccctttgac | cttttgaga | caagaagaa aagaacaac | 1140 |
| atcaaactct | atgtccgccg | tgtgttcatc | atggacagct | gtgatgagtt gataccagag | 1200 |
| tatctcaatt | ttatccgtgg | tgtggttgac | tctgaggatc | tgcccctgaa catctcccga | 1260 |
| gaaatgctcc | agcagagcaa | aatcttgaaa | gtcattcgca | aaacattgt taagaagtgc | 1320 |
| cttgagctct | tctctgagct | ggcagaagac | aaggagaatt | acaagaaatt ctatgaggca | 1380 |
| ttctctaaaa | atctcaagct | tggaatccac | gaagactcca | ctaaccgccg ccgcctgtct | 1440 |
| gagctgctgc | gctatcatac | ctcccagtct | ggagatgaga | tgacatctct gtcagagtat | 1500 |
| gtttctcgca | tgaaggagac | acagaagtcc | atctattaca | tcactggtga gagcaaagag | 1560 |
| caggtggcca | actcagcttt | tgtggagcga | gtgcggaaac | ggggcttcga ggtggtatat | 1620 |
| atgaccgagc | ccattgacga | gtactgtgtg | cagcagctca | aggaatttga tgggaagagc | 1680 |
| ctggtctcag | ttaccaagga | gggtctggag | ctgcctgagg | atgaggagga agaagaagaag | 1740 |
| atggaagaga | gcaaggcaaa | gtttgagaac | ctctgcaagc | tcatgaaaga aatcttagat | 1800 |
| aagaaggttg | agaaggtgac | aatctccaat | agacttgtgt | cttcaccttg ctgcattgtg | 1860 |
| accagcacct | acggctggac | agccaatatg | gagcggatca | tgaaagccca ggcacttcgg | 1920 |
| gacaactcca | ccatgggcta | tatgatggcc | aaaaagcacc | tggagatcaa ccctgaccac | 1980 |
| cccattgtgg | agacgctgcg | gcagaaggct | gaggccgaca | agaatgataa ggcagttaag | 2040 |

-continued

```
gacctggtgg tgctgctgtt tgaaaccgcc ctgctatctt ctggctttc ccttgaggat    2100 ccccagaccc actccaaccg catctatcgc atgatcaagc taggtctagg tattgatgaa    2160
gatgaagtgg cagcagagga acccaatgct gcagttcctg atgagatccc ccctctcgag    2220
ggcgatgagg atgcgtctcg catggaagaa gtcgattagg ttaggagttc atagttggaa    2280
aacttgtgcc cttgtatagt gtccccatgg gctcccactg cagcctcgag tgccctgtc    2340 ccacctggct ccccctgctg gtgtctagtg ttttttttccc tctcctgtcc ttgtgttgaa    2400
ggcagtaaac taagggtgtc aagccccatt ccctctctac tcttgacagc aggattggat    2460
gttgtgtatt gtggtttatt ttattttctt cattttgttc tgaaattaaa gtatgcaaaa    2520 taagaatat gccgttttaa aaaaaaaaaa aaaaaaaaaa aaaaaa              2567
```

<210> SEQ ID NO 10
<211> LENGTH: 724
<212> TYPE: PRT
<213> ORGANISM: Homo sapiens

<400> SEQUENCE: 10

```
Met Pro Glu Glu Val His His Gly Glu Glu Val Glu Thr Phe Ala
1               5                   10                  15

Phe Gln Ala Glu Ile Ala Gln Leu Met Ser Leu Ile Ile Asn Thr Phe
            20                  25                  30

Tyr Ser Asn Lys Glu Ile Phe Leu Arg Glu Leu Ile Ser Asn Ala Ser
        35                  40                  45

Asp Ala Leu Asp Lys Ile Arg Tyr Glu Ser Leu Thr Asp Pro Ser Lys
    50                  55                  60

Leu Asp Ser Gly Lys Glu Leu Lys Ile Asp Ile Ile Pro Asn Pro Gln
65                  70                  75                  80

Glu Arg Thr Leu Thr Leu Val Asp Thr Gly Ile Gly Met Thr Lys Ala
                85                  90                  95

Asp Leu Ile Asn Asn Leu Gly Thr Ile Ala Lys Ser Gly Thr Lys Ala
            100                 105                 110

Phe Met Glu Ala Leu Gln Ala Gly Ala Asp Ile Ser Met Ile Gly Gln
        115                 120                 125

Phe Gly Val Gly Phe Tyr Ser Ala Tyr Leu Val Ala Glu Lys Val Val
    130                 135                 140

Val Ile Thr Lys His Asn Asp Asp Glu Gln Tyr Ala Trp Glu Ser Ser
145                 150                 155                 160

Ala Gly Gly Ser Phe Thr Val Arg Ala Asp His Gly Glu Pro Ile Gly
                165                 170                 175

Arg Gly Thr Lys Val Ile Leu His Leu Lys Glu Asp Gln Thr Glu Tyr
            180                 185                 190

Leu Glu Glu Arg Arg Val Lys Glu Val Val Lys Lys His Ser Gln Phe
        195                 200                 205

Ile Gly Tyr Pro Ile Thr Leu Tyr Leu Glu Lys Glu Arg Glu Lys Glu
    210                 215                 220

Ile Ser Asp Asp Glu Ala Glu Glu Lys Gly Glu Lys Glu Glu Glu
225                 230                 235                 240

Asp Lys Asp Asp Glu Glu Lys Pro Lys Ile Glu Asp Val Gly Ser Asp
                245                 250                 255

Glu Glu Asp Asp Ser Gly Lys Asp Lys Lys Lys Lys Thr Lys Lys Ile
            260                 265                 270

Lys Glu Lys Tyr Ile Asp Gln Glu Glu Leu Asn Lys Thr Lys Pro Ile
        275                 280                 285
```

```
Trp Thr Arg Asn Pro Asp Asp Ile Thr Gln Glu Glu Tyr Gly Glu Phe
    290             295                 300
Tyr Lys Ser Leu Thr Asn Asp Trp Glu Asp His Leu Ala Val Lys His
305             310                 315                 320
Phe Ser Val Glu Gly Gln Leu Glu Phe Arg Ala Leu Leu Phe Ile Pro
                325                 330                 335
Arg Arg Ala Pro Phe Asp Leu Phe Glu Asn Lys Lys Lys Asn Asn
                340                 345                 350
Ile Lys Leu Tyr Val Arg Arg Val Phe Ile Met Asp Ser Cys Asp Glu
            355                 360                 365
Leu Ile Pro Glu Tyr Leu Asn Phe Ile Arg Gly Val Val Asp Ser Glu
        370                 375                 380
Asp Leu Pro Leu Asn Ile Ser Arg Glu Met Leu Gln Gln Ser Lys Ile
385                 390                 395                 400
Leu Lys Val Ile Arg Lys Asn Ile Val Lys Lys Cys Leu Glu Leu Phe
                405                 410                 415
Ser Glu Leu Ala Glu Asp Lys Glu Asn Tyr Lys Lys Phe Tyr Glu Ala
                420                 425                 430
Phe Ser Lys Asn Leu Lys Leu Gly Ile His Glu Asp Ser Thr Asn Arg
            435                 440                 445
Arg Arg Leu Ser Glu Leu Leu Arg Tyr His Thr Ser Gln Ser Gly Asp
450                 455                 460
Glu Met Thr Ser Leu Ser Glu Tyr Val Ser Arg Met Lys Glu Thr Gln
465                 470                 475                 480
Lys Ser Ile Tyr Tyr Ile Thr Gly Glu Ser Lys Glu Gln Val Ala Asn
            485                 490                 495
Ser Ala Phe Val Glu Arg Val Arg Lys Arg Gly Phe Glu Val Val Tyr
                500                 505                 510
Met Thr Glu Pro Ile Asp Glu Tyr Cys Val Gln Gln Leu Lys Glu Phe
            515                 520                 525
Asp Gly Lys Ser Leu Val Ser Val Thr Lys Glu Gly Leu Glu Leu Pro
            530                 535                 540
Glu Asp Glu Glu Glu Lys Lys Lys Met Glu Glu Ser Lys Ala Lys Phe
545                 550                 555                 560
Glu Asn Leu Cys Lys Leu Met Lys Glu Ile Leu Asp Lys Lys Val Glu
                565                 570                 575
Lys Val Thr Ile Ser Asn Arg Leu Val Ser Ser Pro Cys Cys Ile Val
            580                 585                 590
Thr Ser Thr Tyr Gly Trp Thr Ala Asn Met Glu Arg Ile Met Lys Ala
            595                 600                 605
Gln Ala Leu Arg Asp Asn Ser Thr Met Gly Tyr Met Met Ala Lys Lys
        610                 615                 620
His Leu Glu Ile Asn Pro Asp His Pro Ile Val Glu Thr Leu Arg Gln
625                 630                 635                 640
Lys Ala Glu Ala Asp Lys Asn Asp Lys Ala Val Lys Asp Leu Val Val
                645                 650                 655
Leu Leu Phe Glu Thr Ala Leu Leu Ser Ser Gly Phe Ser Leu Glu Asp
            660                 665                 670
Pro Gln Thr His Ser Asn Arg Ile Tyr Arg Met Ile Lys Leu Gly Leu
            675                 680                 685
Gly Ile Asp Glu Asp Glu Val Ala Ala Glu Glu Pro Asn Ala Ala Val
        690                 695                 700
```

Pro Asp Glu Ile Pro Pro Leu Glu Gly Asp Glu Asp Ala Ser Arg Met
705                 710                 715                 720

Glu Glu Val Asp

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 11
auacgcgtat tatacgcgau uaac                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 12
ucuccutctc ccgttcctuc ucca                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)

```
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 13
aucuccttct cccgttccuu cucc                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 14
acuuccttga ccctcctcuc cucc                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 15
cuuccutgac cctcctctcc ucca                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
```

```
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 16
ccacuucctt gaccctccuc uccu                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 17
uccucctctt tctcacctuu cucu                                              24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 18
accacutcct tgaccctccu cucc                                              24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 19
cuccuuctcc cgttccttcu ccaa                                           24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 20
cacuuccttg accctcctcu ccuc                                           24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'-O-methyl nucleotide
<220> FEATURE:
<221> NAME/KEY: modified_base
<222> LOCATION: (16)..(20)
<223> OTHER INFORMATION: 2'-O-methyl nucleotide
<220> FEATURE:
<221> NAME/KEY: misc_feature
<222> LOCATION: (1)..(20)
<223> OTHER INFORMATION: Phosphorothioate linkage

<400> SEQUENCE: 21
ucuccacctc ctcctcucca                                                20

<210> SEQ ID NO 22
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'-O-methyl nucleotide
<220> FEATURE:
<221> NAME/KEY: modified_base
<222> LOCATION: (16)..(20)
<223> OTHER INFORMATION: 2'-O-methyl nucleotide
<220> FEATURE:
<221> NAME/KEY: misc_feature
<222> LOCATION: (1)..(20)
<223> OTHER INFORMATION: Phosphorothioate linkage

<400> SEQUENCE: 22
gucuccacct cctccucucc                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(5)
<223> OTHER INFORMATION: 2'-O-methyl nucleotide
<220> FEATURE:
<221> NAME/KEY: modified_base
<222> LOCATION: (16)..(20)
<223> OTHER INFORMATION: 2'-O-methyl nucleotide
<220> FEATURE:
<221> NAME/KEY: misc_feature
<222> LOCATION: (1)..(20)
<223> OTHER INFORMATION: Phosphorothioate linkage

<400> SEQUENCE: 23
cuccacctcc tcctcuccau                                              20

<210> SEQ ID NO 24
<211> LENGTH: 24
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 24
```
cucuucctct gcctcatcau cacu                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 25
ucucuucctc tgcctcatca ucac                                              24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 26
uucucutcct ctgcctcauc auca                                              24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature

```
<222> LOCATION: (1)..(24)
<223> OTHER INFORMATION: Phosphorothioate linkage

<400> SEQUENCE: 27
uuucucuucc tctgcctcau cauc                                          24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 28
cuuucucuuc ctctgcctca ucau                                          24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 29
augccctgaa ttccaactga ccuu                                          24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
```

```
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 30
aaugcccuga attccaacug accu                                              24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 31
caaugcccug aattccaacu gacc                                              24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 32
ugcccugaat tccaactgac cuuc                                              24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 33
gcaaugcccu gaauuccaac ugac                                          24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 34
acugagacca ggctcttccc auca                                          24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 35
uuuccutctc tcgttcctuc ucca                                          24

<210> SEQ ID NO 36
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 36
ucuccutctc tcgttcctuc ucca                                        24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 37
uuuccutctc ccgttcctuc ucca                                        24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 38
auuuccttct ctcgttccuu cucc                                        24
```

```
<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 39
aucuccttct ctcgttccuu cucc                                           24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 40
auuuccttct cccgttccuu cucc                                           24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage
```

```
<400> SEQUENCE: 41
uccucutctt tctcacctuu cucu                                              24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 42
uuccuuctct cgttccttcu ccaa                                              24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
<220> FEATURE:
<221> NAME/KEY: misc_feature
<222> LOCATION: (1)..(24)
<223> OTHER INFORMATION: Phosphorothioate linkage

<400> SEQUENCE: 43
cuccuuctct cgttccttcu ccaa                                              24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(6)
<223> OTHER INFORMATION: 2'-O-methyl nucleotide
<220> FEATURE:
<221> NAME/KEY: modified_base
<222> LOCATION: (19)..(24)
<223> OTHER INFORMATION: 2'-O-methyl nucleotide
```

```
<220> FEATURE:
<221> NAME/KEY: misc_feature
<222> LOCATION: (1)..(24)
<223> OTHER INFORMATION: Phosphorothioate linkage

<400> SEQUENCE: 44
uuccuuctcc cguuccuucu ccaa                                          24

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tccttctccc gttccttctc ca                                            22

<210> SEQ ID NO 46
<211> LENGTH: 22
<212> TYPE: DNA
<213> ORGANISM: Homo sapiens

<400> SEQUENCE: 46
tccttctctc gttccttctc ca                                            22

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tccttctccc gttccttctc c                                             21

<210> SEQ ID NO 48
<211> LENGTH: 21
<212> TYPE: DNA
<213> ORGANISM: Homo sapiens

<400> SEQUENCE: 48
tccttctctc gttccttctc c                                             21

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tcctcctctt tctcaccttt ctct                                          24

<210> SEQ ID NO 50
<211> LENGTH: 24
<212> TYPE: DNA
<213> ORGANISM: Homo sapiens

<400> SEQUENCE: 50
tcctcttctt tctcaccttt ctct                                          24
```

```
<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
tccttctccc gttccttctc caa                                            23

<210> SEQ ID NO 52
<211> LENGTH: 23
<212> TYPE: DNA
<213> ORGANISM: Homo sapiens

<400> SEQUENCE: 52
tccttctctc gttccttctc caa                                            23

<210> SEQ ID NO 53
<211> LENGTH: 16
<212> TYPE: PRT
<213> ORGANISM: Artificial sequence
<220> FEATURE:
<223> OTHER INFORMATION: Description of Artificial Sequence: Synthetic
      cell penetrating peptide

<400> SEQUENCE: 53

Arg Gln Ile Lys Ile Trp Phe Gln Asn Arg Arg Met Lys Trp Lys Lys
1               5                   10                  15

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 54

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 55
<211> LENGTH: 22
<212> TYPE: PRT
<213> ORGANISM: Artificial Sequence
<220> FEATURE:
<223> OTHER INFORMATION: Description of Artificial Sequence: Synthetic
      cell penetrating peptide

<400> SEQUENCE: 55

Met Val Thr Val Leu Phe Arg Arg Leu Arg Ile Arg Arg Ala Cys Gly
1               5                   10                  15

Pro Pro Arg Val Arg Val
            20

<210> SEQ ID NO 56
<211> LENGTH: 8
<212> TYPE: PRT
<213> ORGANISM: Artificial sequence
<220> FEATURE:
<223> OTHER INFORMATION: Description of Artificial Sequence: Synthetic
      cell penetrating peptide
```

```
<400> SEQUENCE: 56

Tyr Asp Glu Glu Gly Gly Gly Glu
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      targeting peptide

<400> SEQUENCE: 57

Ala Ser Ser Leu Asn Ile Ala
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      targeting peptide

<400> SEQUENCE: 58

Trp Asp Ala Asn Gly Lys Thr
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      targeting peptide

<400> SEQUENCE: 59

Gly Glu Thr Arg Ala Pro Leu
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      targeting peptide

<400> SEQUENCE: 60

Cys Gly His His Pro Val Tyr Ala Cys
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      targeting peptide

<400> SEQUENCE: 61

His Ala Ile Tyr Pro Arg His
1               5

<210> SEQ ID NO 62
<211> LENGTH: 48
<212> TYPE: DNA
```

<213> ORGANISM: Homo sapiens

<400> SEQUENCE: 62
ttcaagatgc ctgaggaagt gcaccatgga gaggaggagg tggagact        48

<210> SEQ ID NO 63
<211> LENGTH: 48
<212> TYPE: DNA
<213> ORGANISM: Macaca nemestrina

<400> SEQUENCE: 63
ttcaagatgc ctgaggaagt gcaccatgga gaggaggagg tggagact        48

<210> SEQ ID NO 64
<211> LENGTH: 48
<212> TYPE: DNA
<213> ORGANISM: Mus musculus

<400> SEQUENCE: 64
gtcaagatgc ctgaggaagt gcaccatgga gaggaggagg tggagacc        48

<210> SEQ ID NO 65
<211> LENGTH: 48
<212> TYPE: DNA
<213> ORGANISM: Homo sapiens

<400> SEQUENCE: 65
tagtgatgat gaggcagagg aagagaaagg tgagaaagaa gaggaaga        48

<210> SEQ ID NO 66
<211> LENGTH: 48
<212> TYPE: DNA
<213> ORGANISM: Macaca nemestrina

<400> SEQUENCE: 66
tagtgatgat gaggcagagg aagagaaagg tgagaaagaa gaggaaga        48

<210> SEQ ID NO 67
<211> LENGTH: 48
<212> TYPE: DNA
<213> ORGANISM: Mus musculus

<400> SEQUENCE: 67
cagtgatgat gaggcagagg aagagaaagg tgagaaagag gaggaaga        48

<210> SEQ ID NO 68
<211> LENGTH: 50
<212> TYPE: DNA
<213> ORGANISM: Homo sapiens

<400> SEQUENCE: 68
ttctgtagaa ggtcagttgg aattcagggc attgctattt attcctcgtc        50

<210> SEQ ID NO 69
<211> LENGTH: 50
<212> TYPE: DNA
<213> ORGANISM: Macaca nemestrina

<400> SEQUENCE: 69
ttctgtagaa ggtcagttgg aattcagggc attgctattc attcctcgtc        50

<210> SEQ ID NO 70
<211> LENGTH: 50

```
<212> TYPE: DNA
<213> ORGANISM: Mus musculus

<400> SEQUENCE: 70
ctctgtagaa ggtcagttgg aattcagggc attgctcttc attccccggc         50

<210> SEQ ID NO 71
<211> LENGTH: 46
<212> TYPE: DNA
<213> ORGANISM: Homo sapiens

<400> SEQUENCE: 71
ggaatttgat gggaagagcc tggtctcagt taccaaggag ggtctg              46

<210> SEQ ID NO 72
<211> LENGTH: 46
<212> TYPE: DNA
<213> ORGANISM: Mus musculus

<400> SEQUENCE: 72
ggagtttgat gggaagagcc tggtctcagt taccaaggag ggtctg              46

<210> SEQ ID NO 73
<211> LENGTH: 46
<212> TYPE: DNA
<213> ORGANISM: Mus musculus

<400> SEQUENCE: 73
ggagtttgat gggaagagcc tggtctcagt gactaaggag ggcctg              46

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
auacgcgtat tatacgcgau uaac                                      24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
ucuccutctc ccgttcctuc ucca                                      24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 76
aucuccttct cccgttccuu cucc                                          24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
acuuccttga ccctcctcuc cucc                                          24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
cuuccutgac cctcctctcc ucca                                          24

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79 ccacuuccتt gaccctccuc uccu                                          24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
uccucctctt tctcacctuu cucu                                          24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 81
accacutcct tgaccctccu cucc                                              24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
cuccuuctcc cgttccttcu ccaa                                              24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
cacuuccttg accctcctcu ccuc                                              24

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
ucuccacctc ctcctcucca                                                   20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
gucuccacct cctccucucc                                                   20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 86
cuccacctcc tcctcuccau                                               20

<210> SEQ ID NO 87
<211> LENGTH: 24
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 87
cucuucctct gcctcatcau cacu                                          24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
ucucuucctc tgcctcatca ucac                                          24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
uucucutcct ctgcctcauc auca                                          24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
uuucucttcc tctgcctcau cauc                                          24

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 91
cuuucucuuc ctctgcctca ucau                                                24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
augccctgaa ttccaactga ccuu                                                24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
aaugccctga attccaacug accu                                                24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
caaugccctg aattccaacu gacc                                                24

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
ugcccugaat tccaactgac cuuc                                                24

<210> SEQ ID NO 96
<211> LENGTH: 24
<212> TYPE: DNA
<213> ORGANISM: Artificial Sequence
<220> FEATURE:

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
gcaaugccct gaattccaac ugac                                           24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
acugagacca ggctcttccc auca                                           24

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
uuuccutctc tcgttcctuc ucca                                           24

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
ucuccutctc tcgttcctuc ucca                                           24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100
uuuccutctc ccgttcctuc ucca                                           24

<210> SEQ ID NO 101
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
auuuccuucu cucguuccuu cucc                                          24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
aucuccuucu cucguuccuu cucc                                          24

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
auuuccuucu cccguuccuu cucc                                          24

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
uccucuucuu ucucaccuuu cucu                                          24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
uuccuucucu cguuccuucu ccaa                                          24

<210> SEQ ID NO 106
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
cuccuuctct cgttccttcu ccaa                                            24

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
uuccuuctcc cgttccttcu ccaa                                            24
```

METHODS OF TREATING A METABOLIC SYNDROME BY MODULATING HEAT SHOCK PROTEIN (HSP) 90-BETA

RELATED APPLICATIONS

This application claims priority to U.S. Provisional Patent Application No. 62/009,116 filed on Jun. 6, 2014, U.S. Provisional Patent Application No. 62/096,649 filed on Dec. 24, 2014, and U.S. Provisional Patent Application No. 62/108,530 filed on Jan. 27, 2015, the contents of each of which are incorporated herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 119992_14701_Sequence_Listing. The size of the text file is 57 KB, and the text file was created on Jun. 8, 2015.

BACKGROUND

As the levels of blood glucose rise postprandially, insulin is secreted and stimulates cells of the peripheral tissues (skeletal muscles and fat) to actively take up glucose from the blood as a source of energy. Loss of glucose homeostasis as a result of dysregulated insulin secretion or action typically results in metabolic disorders such as diabetes, which may be co-triggered or further exacerbated by obesity. Because these conditions are often fatal, strategies to restore adequate glucose clearance from the bloodstream are required.

Although diabetes may arise secondary to any condition that causes extensive damage to the pancreas (e.g., pancreatitis, tumors, administration of certain drugs such as corticosteroids or pentamidine, iron overload (i.e., hemochromatosis), acquired or genetic endocrinopathies, and surgical excision), the most common forms of diabetes typically arise from primary disorders of the insulin signaling system. There are two major types of diabetes, namely type 1 diabetes (also known as insulin dependent diabetes (IDDM)) and type 2 diabetes (also known as insulin independent or non-insulin dependent diabetes (NIDDM)), which share common long-term complications in spite of their different pathogenic mechanisms.

Type 1 diabetes, which accounts for approximately 10% of all cases of primary diabetes, is an organ-specific autoimmune disease characterized by the extensive destruction of the insulin-producing beta cells of the pancreas. The consequent reduction in insulin production inevitably leads to the deregulation of glucose metabolism. While the administration of insulin provides significant benefits to patients suffering from this condition, the short serum half-life of insulin is a major impediment to the maintenance of normoglycemia. An alternative treatment is islet transplantation, but this strategy has been associated with limited success.

Type 2 diabetes, which affects a larger proportion of the population, is characterized by a deregulation in the secretion of insulin and/or a decreased response of peripheral tissues to insulin, i.e., insulin resistance. While the pathogenesis of type 2 diabetes remains unclear, epidemiologic studies suggest that this form of diabetes results from a collection of multiple genetic defects or polymorphisms, each contributing its own predisposing risks and modified by environmental factors, including excess weight, diet, inactivity, drugs, and excess alcohol consumption. Although various therapeutic treatments are available for the management of type 2 diabetes, they are associated with various debilitating side effects. Accordingly, patients diagnosed with or at risk of having type 2 diabetes are often advised to adopt a healthier lifestyle, including loss of weight, change in diet, exercise, and moderate alcohol intake. Such lifestyle changes, however, are not sufficient to reverse the vascular and organ damages caused by diabetes.

SUMMARY OF THE INVENTION

In one aspect the invention relate to a method of treating a metabolic syndrome in a subject, comprising administering to a subject in need thereof an HSP90β specific inhibitor, wherein the inhibitor comprises an antisense oligonucleotide, thereby treating the metabolic syndrome in the subject.

In certain embodiments, the antisense oligonucleotide is a modified antisense oligonucleotide. In certain embodiments, the antisense oligonucleotide comprises one or more phosphorothioate linkages. In certain embodiments, the antisense oligonucleotide comprises one or more 2'-O-methyl ribonucleotides. In certain embodiments, the antisense oligonucleotide comprises a nucleic acid sequence selected from the group consisting of SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, and SEQ ID NO: 107.

In certain embodiments, the modified antisense oligonucleotide comprises the nucleic acid sequence mC*mC*mA*mC*mU*mU*C*C*T*T*G*A*C*C*C*T*C*C*mU*mC*mU*mC*mC*mU (ASO5, SEQ ID NO: 16), wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

In a particular embodiment, the modified antisense oligonucleotide has the sequence mU*mC*mC*mU*mC*mC*T*C*T*T*T*C*T*C*A*C*C*T*mU*mU*mC*mU*mC*mU (ASO6, SEQ ID NO: 17) or mU*mC*mC*mU*mC*mU*T*C*T*T*T*C*T*C*A*C*C*T*mU*mU*mC*mU*mC*mU (ASO6 variant 1, SEQ ID NO: 41), wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

In a further particular embodiment, the modified antisense oligonucleotide comprises a nucleic acid sequence selected from the group consisting of:

```
(ASO10, SEQ ID NO: 21)
5'-mU*mC*mU*mC*mC*A*C*C*T*C*C*T*C*C*T*mC*mU*
mC*mC*mA-3';

(ASO11, SEQ ID NO: 22)
5'-mG*mU*mC*mU*mC*C*A*C*C*T*C*C*T*C*C*mU*mC*
mU*mC*mC-3';
```

-continued (AS012, SEQ ID NO: 23)
5'-mC*mU*mC*mC*mA*C*C*T*C*C*T*C*C*T*C*mU*mC*
mC*mA*mU-3';

(AS013, SEQ ID NO: 24)
5'-mC*mU*mC*mU*mU*mC*C*T*C*T*G*C*C*T*C*A*T*
C*mA*mU*mC*mA*mC*mU-3';

(AS014, SEQ ID NO: 25)
5'-mU*mC*mU*mC*mU*mU*C*C*T*C*T*G*C*C*T*C*A*
T*mC*mA*mU*mC*mA*mC-3';

(AS015, SEQ ID NO: 26)
5'-mU*mU*mC*mU*mC*mU*T*C*C*T*C*T*G*C*C*T*C*
A*mU*mC*mA*mU*mC*mA-3';

(AS016, SEQ ID NO: 27)
5'-mU*mU*mU*mC*mU*mC*T*T*C*C*T*C*T*G*C*C*T*
C*mA*mU*mC*mA*mU*mC-3';

(AS017, SEQ ID NO: 28)
5'-mC*mU*mU*mU*mC*mU*C*T*T*C*C*T*C*T*G*C*C*
T*mC*mA*mU*mC*mA*mU-3;

(AS018, SEQ ID NO: 29)
5'-mA*mU*mG*mC*mC*mC*T*G*A*A*T*T*C*C*A*A*C*
T*mG*mA*mC*mC*mU*mU-3';

(AS019, SEQ ID NO: 30)
5'-mA*mA*mU*mG*mC*mC*C*T*G*A*A*T*T*C*C*A*A*
C*mU*mG*mA*mC*mC*mU-3';

(AS020, SEQ ID NO: 31)
5'-mC*mA*mA*mU*mG*mC*C*C*T*G*A*A*T*T*C*C*A*
A*mC*mU*mG*mA*mC*mC-3';

(AS021, SEQ ID NO: 32)
5'-mU*mG*mC*mC*mC*mU*G*A*A*T*T*C*C*A*A*C*T*
G*mA*mC*mC*mU*mU*mC-3';

(AS022, SEQ ID NO: 33)
5'-mG*mC*mA*mA*mU*mG*C*C*C*T*G*A*A*T*T*C*C*
A*mA*mC*mU*mG*mA*mC-3';
and (AS023, SEQ ID NO: 34)
5'-mA*mC*mU*mG*mA*mG*A*C*C*A*G*G*C*T*C*T*T*
C*mC*mC*mA*mU*mC*mA-3', wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

In certain embodiments of the aforementioned methods, the metabolic syndrome comprises type 2 diabetes. In certain embodiments, the metabolic syndrome comprises type 1 diabetes. In certain embodiments, the metabolic syndrome comprises insulin resistance. In certain embodiments, the metabolic syndrome comprises insulin insufficiency. In certain embodiments, the metabolic syndrome comprises obesity. In certain embodiments, the metabolic syndrome comprises hyperinsulinemia. In certain embodiments, the metabolic syndrome comprises impaired glucose tolerance (IGT).

In certain embodiments of the aforementioned methods, the subject with metabolic syndrome exhibits three or more of the following signs:
a) Blood pressure equal to or higher than 130/85 mmHg;
b) Fasting blood glucose equal to or higher than 100 mg/dL;
c) Large waist circumference wherein a large waist circumference is 40 inches or more for men and 35 inches or more for women;
d) Low HDL cholesterol wherein low LDH cholesterol is under 40 mg/dL for men and under 50 mg/dL; and
e) Triglycerides equal to or higher than 150 mg/dL.

In certain embodiments, treating the metabolic syndrome comprises normalizing a blood glucose level in the subject. In certain embodiments, treating the metabolic syndrome comprises normalizing an Hb1Ac level in the subject. In certain embodiments, treating the metabolic syndrome comprises prevention of at least one complication of diabetes associated with poor circulation. In certain embodiments, treating the metabolic syndrome comprises amelioration of at least one sign or symptom of type 2 diabetes. In certain embodiments, treating the metabolic syndrome comprises amelioration of at least one sign or symptom of type 1 diabetes. In certain embodiments, treating the metabolic syndrome comprises amelioration of at least one sign or symptom of insulin resistance. In certain embodiments, treating the metabolic syndrome comprises amelioration of at least one sign or symptom of insulin insufficiency. In certain embodiments, treating the metabolic syndrome comprises amelioration of at least one sign or symptom of hyperinsulinemia. In certain embodiments, treating the metabolic syndrome comprises amelioration of at least one sign or symptom of impaired glucose tolerance (IGT). In certain embodiments, treating the metabolic syndrome comprises amelioration of at least one sign or symptom of obesity. In certain embodiments, treating the metabolic syndrome comprises amelioration of at least one of
a) Blood pressure equal to or higher than 130/85 mmHg;
b) Fasting blood glucose equal to or higher than 100 mg/dL;
c) Large waist circumference wherein a large waist circumference is 40 inches or more for men and 35 inches or more for women;
d) Low HDL cholesterol wherein low LDH cholesterol is under 40 mg/dL for men and under 50 mg/dL; and
e) Triglycerides equal to or higher than 150 mg/dL.

In one embodiment, treating the metabolic syndrome comprises amelioration of elevated blood pressure equal to or higher than 130/85 mmHg. In one embodiment, treating the metabolic syndrome comprises amelioration of elevated fasting blood glucose equal to or higher than 100 mg/dL. In one embodiment, treating the metabolic syndrome comprises amelioration of large waist circumference wherein a large waist circumference is 40 inches or more for men and 35 inches or more for women. In one embodiment, treating the metabolic syndrome comprises amelioration of low HDL cholesterol by increasing HDL cholesterol wherein low LDH cholesterol is under 40 mg/dL for men and under 50 mg/dL. In one embodiment, treating the metabolic syndrome comprises amelioration of elevated triglycerides equal to or higher than 150 mg/dL.

In certain embodiments of the aforementioned methods, treating metabolic syndrome comprises amelioration of fatty liver. In certain embodiments, treating metabolic syndrome comprises modulation of fat deposition.

In certain embodiments, treating metabolic syndrome comprises one or more of decreased expression of pyruvate dehydrogenase kinase isoenzyme 4 (PDK4), decreased phosphorylation of PDH-E1α, modulated expression of adipose triglyceride lipase (ATGL), modulated expression of PFKM (phosphofructokinase, muscle), modulated expression of ALDOA (aldolase A), modulated expression of GYS1 (glycogen synthase 1) ACCA (Acetyl-CoA carboxylase), modulated expression of HSL (Hormone sensitive lipase), SCD1 (Stearoyl-CoA desaturase), modulated expression of ACADL (Acyl-CoA Dehydrogenase), and modulated expression of CPT1b (Carnitine palmitoyltransferase I) in the subject relative to a control.

In certain embodiments, treating metabolic syndrome comprises an altered lipidomic profile in muscle of the subject relative to a control subject. In certain embodiments, the altered lipidomic profile comprises one or more of increased 18:2 enriched species of cardiolipin in muscle, decreased steric free fatty acids (FFA), decreased oleic free fatty acids (FFA), decreased linoleic free fatty acids (FFA), and decreased 18:0 and/or 18:0-OH acylcarnitines in the subject relative to a control.

In certain embodiments, the antisense oligonucleotide is targeted to a muscle cell.

In certain embodiments, the HSP90β specific inhibitor further comprises a muscle targeting moiety, and wherein the muscle targeting moiety and the antisense oligonucleotide are in a complex. In certain embodiments, the muscle targeting moiety comprises a muscle targeting peptide (MTP). In certain embodiments, the MTP comprises an amino acid sequence selected from the group consisting of: ASSLNIA (SEQ ID NO: 57); WDANGKT (SEQ ID NO: 58); GETRAPL (SEQ ID NO: 58); CGHHPVYAC (SEQ ID NO: 59); and HAIYPRH (SEQ ID NO: 60). In certain embodiments, the muscle targeting moiety comprises creatine.

In certain embodiments, the complex further comprises a linker. In certain embodiments, the linker is selected from the group consisting of a covalent linker, a non-covalent linkage, and a reversible linker. In certain embodiments, the complex further comprises a pharmaceutically acceptable dendrimer. In certain embodiments, the pharmaceutically acceptable dendrimer is a PAMAM dendrimer. In certain embodiments, the pharmaceutically acceptable dendrimer is a G5 dendrimer. In certain embodiments, the pharmaceutically acceptable dendrimer is an uncharged dendrimer. In certain embodiments, the pharmaceutically acceptable dendrimer is an acylated dendrimer.

In certain embodiments of the aforementioned methods, the inhibitor further comprises a liposome. In certain embodiments, the inhibitor further comprises a microparticle. In certain embodiments, the inhibitor further comprises an in situ forming composition. In certain embodiments, the antisense oligonucleotide is released from the complex upon delivery to a muscle cell.

In another aspect, the invention relates to a pharmaceutical composition comprising an HSP90β specific inhibitor and a pharmaceutically acceptable carrier, wherein the inhibitor comprises an antisense oligonucleotide. In certain embodiments, the antisense oligonucleotide is a modified antisense oligonucleotide. In certain embodiments, the antisense oligonucleotide comprises one or more phosphorothioate linkages. In certain embodiments, the antisense oligonucleotide comprises one or more 2'-O-methyl ribonucleotides.

In certain embodiments, the antisense oligonucleotide comprises a nucleic acid sequence selected from the group consisting of SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, and SEQ ID NO: 107.

In certain embodiments, the modified antisense oligonucleotide comprises the nucleic acid sequence mC*mC*mA*mC*mU*mU*C*C*T*T*G*A*C*C*C* T*C*C*mU*mC*mU*mC*mC*mU (ASO5, SEQ ID NO: 16), wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

In certain embodiments, the modified antisense oligonucleotide comprises the nucleic acid sequence mU*mC*mC*mU*mC*mC*mC*T*C*T*T*T*C*T*C*A* C*C*T*mU*mU*mC*mU*mC*mU (ASO6, SEQ ID NO: 17) or mU*mC*mC*mU*mC*mU*T*C*T*T*T*C*T* C*A*C*C*T*mU*mU*mC*mU*mC*mU (ASO6 variant 1, SEQ ID NO: 41), wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

In certain embodiments of the aforementioned compositions, the modified antisense oligonucleotide comprises a nucleic acid sequence selected from the group consisting of:

```
(ASO10, SEQ ID NO: 21)
5'-mU*mC*mU*mC*mC*A*C*C*T*C*C*T*C*C*T*mC*mU*
mC*mC*mA-3';

(ASO11, SEQ ID NO: 22)
5'-mG*mU*mC*mU*mC*C*A*C*C*T*C*C*T*C*C*mU*mC*
mU*mC*mC-3';

(ASO12, SEQ ID NO: 23)
5'-mC*mU*mC*mC*mA*C*C*T*C*C*T*C*C*T*C*mU*mC*
mC*mA*mU-3';

(ASO13, SEQ ID NO: 24)
5'-mC*mU*mC*mU*mU*mC*C*T*C*T*G*C*C*T*C*A*T*
C*mA*mU*mC*mA*mC*mU-3';

(ASO14, SEQ ID NO: 25)
5'-mU*mC*mU*mC*mU*mU*C*C*T*C*T*G*C*C*T*C*A*
T*mC*mA*mU*mC*mA*mC-3';

(ASO15, SEQ ID NO: 26)
5'-mU*mU*mC*mU*mC*mU*T*C*C*T*C*T*G*C*C*T*C*
A*mU*mC*mA*mU*mC*mA-3';

(ASO16, SEQ ID NO: 27)
5'-mU*mU*mU*mC*mU*mC*T*T*C*C*T*C*T*G*C*C*T*
C*mA*mU*mC*mA*mU*mC-3';

(ASO17, SEQ ID NO: 28)
5'-mC*mU*mU*mU*mC*mU*C*T*T*C*C*T*C*T*G*C*C*
T*mC*mA*mU*mC*mA*mU-3;

(ASO18, SEQ ID NO: 29)
5'-mA*mU*mG*mC*mC*mC*T*G*A*A*T*T*C*C*A*A*C*
T*mG*mA*mC*mC*mU*mU-3';

(ASO19, SEQ ID NO: 30)
5'-mA*mA*mU*mG*mC*mC*C*T*G*A*A*T*T*C*C*A*A*
C*mU*mG*mA*mC*mC*mU-3';

(ASO20, SEQ ID NO: 31)
5'-mC*mA*mA*mU*mG*mC*C*C*T*G*A*A*T*T*C*C*A*
A*mC*mU*mG*mA*mC*mC-3';

(ASO21, SEQ ID NO: 32)
5'-mU*mG*mC*mC*mC*mU*G*A*A*T*T*C*C*A*A*C*T*
G*mA*mC*mC*mU*mU*mC-3';

(ASO22, SEQ ID NO: 33)
5'-mG*mC*mA*mA*mU*mG*C*C*C*T*G*A*A*T*T*C*C*
A*mA*mC*mU*mG*mA*mC-3';
and
```

```
            (ASO23, SEQ ID NO: 34)
     5'-mA*mC*mU*mG*mA*mG*A*C*C*A*G*G*C*T*C*T*T*
     C*mC*mC*mA*mU*mC*mA-3',
``` wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

In certain embodiments, the antisense oligonucleotide is targeted to a muscle cell. In certain embodiments, the HSP90β specific inhibitor further comprises a muscle targeting moiety, and wherein the muscle targeting moiety and the antisense oligonucleotide are in a complex. In certain embodiments, the muscle targeting moiety comprises a muscle targeting peptide (MTP). In certain embodiments, the MTP comprises an amino acid sequence selected from the group consisting of: ASSLNIA (SEQ ID NO: 57); WDANGKT (SEQ ID NO: 58); GETRAPL (SEQ ID NO: 58); CGHHPVYAC (SEQ ID NO: 59); and HAIYPRH (SEQ ID NO: 60). In certain embodiments, the muscle targeting moiety comprises creatine.

In certain embodiments, the complex further comprises a linker. In certain embodiments, the linker is selected from the group consisting of a covalent linker, a non-covalent linkage, and a reversible linker. In certain embodiments, the complex further comprises a pharmaceutically acceptable dendrimer. In certain embodiments, the pharmaceutically acceptable dendrimer is a PAMAM dendrimer. In certain embodiments, the pharmaceutically acceptable dendrimer is a G5 dendrimer. In certain embodiments, the pharmaceutically acceptable dendrimer is an uncharged dendrimer. In certain embodiments, the pharmaceutically acceptable dendrimer is an acylated dendrimer.

In certain embodiments, the inhibitor further comprises a liposome. In certain embodiments, the inhibitor further comprises a microparticle. In certain embodiments, the inhibitor further comprises an in situ forming composition. In certain embodiments, the antisense oligonucleotide is released from the complex upon delivery to a muscle cell.

In yet another aspect, the invention relates to an HSP90AB1 specific inhibitor comprising an antisense oligonucleotide specific for HSP90AB1. In certain embodiments, the antisense oligonucleotide is a modified antisense oligonucleotide. In certain embodiments, the antisense oligonucleotide comprises one or more phosphorothioate linkages. In certain embodiments, the antisense oligonucleotide comprises one or more 2'-O-methyl ribonucleotides.

In certain embodiments, the antisense oligonucleotide comprises a nucleic acid sequence selected from the group consisting of SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, and SEQ ID NO: 107.

In certain embodiments, the modified antisense oligonucleotide comprises the nucleic acid sequence mC*mC*mA*mC*mU*mU*C*C*T*T*G*A*C*C*C*T*C*C*mU*mC*mU*mC*mC*mU (ASO5, SEQ ID NO: 16), wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

In certain embodiments, the modified antisense oligonucleotide has the sequence mU*mC*mC*mU*mC*mC*T*C*T*T*T*C*T*C*A*C*C*T*mU*mU*mC*mU*mC*mU (ASO6, SEQ ID NO: 17) or mU*mC*mC*mU*mC*mU*T*C*T*T*T*C*T*C*A*C*C*T*mU*mU*mC*mU*mC*mU (ASO6 variant 1, SEQ ID NO: 41), wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

In certain embodiments, the modified antisense oligonucleotide comprises a nucleic acid sequence selected from the group consisting of:

```
     (ASO10, SEQ ID NO: 21)
     5'-mU*mC*mU*mC*mC*A*C*C*T*C*C*T*C*C*T*mC*mU*
     mC*mC*mA-3';

(ASO11, SEQ ID NO: 22)
     5'-mG*mU*mC*mU*mC*C*A*C*C*T*C*C*T*C*C*mU*mC*
     mU*mC*mC-3';

(ASO12, SEQ ID NO: 23)
     5'-mC*mU*mC*mC*mA*C*C*T*C*C*T*C*C*T*C*mU*mC*
     mC*mA*mU-3';

(ASO13, SEQ ID NO: 24)
     5'-mC*mU*mC*mU*mU*mC*C*T*C*T*G*C*C*T*C*A*T*
     C*mA*mU*mC*mA*mC*mU-3';

(ASO14, SEQ ID NO: 25)
     5'-mU*mC*mU*mC*mU*mU*C*C*T*C*T*G*C*C*T*C*A*
     T*mC*mA*mU*mC*mA*mC-3';

(ASO15, SEQ ID NO: 26)
     5'-mU*mU*mC*mU*mC*mU*T*C*C*T*C*T*G*C*C*T*C*
     A*mU*mC*mA*mU*mC*mA-3';

(ASO16, SEQ ID NO: 27)
     5'-mU*mU*mU*mC*mU*mC*T*T*C*C*T*C*T*G*C*C*T*
     C*mA*mU*mC*mA*mU*mC-3';

(ASO17, SEQ ID NO: 28)
     5'-mC*mU*mU*mU*mC*mU*C*T*T*C*C*T*C*T*G*C*C*
     T*mC*mA*mU*mC*mA*mU-3;

(ASO18, SEQ ID NO: 29)
     5'-mA*mU*mG*mC*mC*mC*T*G*A*A*T*T*C*C*A*A*C*
     T*mG*mA*mC*mC*mU*mU-3';

(ASO19, SEQ ID NO: 30)
     5'-mA*mA*mU*mG*mC*mC*C*T*G*A*A*T*T*C*C*A*A*
     C*mU*mG*mA*mC*mC*mU-3';

(ASO20, SEQ ID NO: 31)
     5'-mC*mA*mA*mU*mG*mC*C*C*T*G*A*A*T*T*C*C*A*
     A*mC*mU*mG*mA*mC*mC-3';

(ASO21, SEQ ID NO: 32)
     5'-mU*mG*mC*mC*mC*mU*G*A*A*T*T*C*C*A*A*C*T*
     G*mA*mC*mC*mU*mU*mC-3';

(ASO22, SEQ ID NO: 33)
     5'-mG*mC*mA*mA*mU*mG*C*C*C*T*G*A*A*T*T*C*C*
     A*mA*mC*mU*mG*mA*mC-3';
     and (ASO23, SEQ ID NO: 34)
     5'-mA*mC*mU*mG*mA*mG*A*C*C*A*G*G*C*T*C*T*T*
     C*mC*mC*mA*mU*mC*mA-3',
``` wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

In certain embodiments of the aforementioned HSP90AB1 specific inhibitors, the antisense oligonucleotide is targeted to a muscle cell. In certain embodiments, the HSP90β specific inhibitor further comprises a muscle targeting moiety, and wherein the muscle targeting moiety and the antisense oligonucleotide are in a complex. In certain embodiments, the muscle targeting moiety comprises a muscle targeting peptide (MTP). In certain embodiments, the MTP comprises an amino acid sequence selected from the group consisting of: ASSLNIA (SEQ ID NO: 57); WDANGKT (SEQ ID NO: 58); GETRAPL (SEQ ID NO: 58); CGHHPVYAC (SEQ ID NO: 59); and HAIYPRH (SEQ ID NO: 60). In certain embodiments, the muscle targeting moiety comprises creatine.

In certain embodiments, the complex further comprises a linker. In certain embodiments, the linker is selected from the group consisting of a covalent linker, a non-covalent linkage, and a reversible linker. In certain embodiments, the complex further comprises a dendrimer. In certain embodiments, the dendrimer is a PAMAM dendrimer. In certain embodiments, the dendrimer is a G5 dendrimer. In certain embodiments, the dendrimer is an uncharged dendrimer. In certain embodiments, the dendrimer is an acylated dendrimer.

In certain embodiments, the inhibitor further comprises a liposome. In certain embodiments, the inhibitor further comprises a microparticle. In certain embodiments, the inhibitor further comprises an in situ forming composition. In certain embodiments, the antisense oligonucleotide is released from the complex upon delivery to a muscle cell.

In another aspect, the invention provides a method of treating a metabolic syndrome in a subject, comprising administering to the subject an HSP90β specific inhibitor, wherein the inhibitor is an antisense oligonucleotide, thereby treating the metabolic syndrome in the subject.

In one embodiment, the antisense oligonucleotide has a sequence selected from the sequences AS01, ASO2, ASO3, ASO4, ASO5, ASO6, ASO7, ASO8 and ASO9 shown in FIG. 18.

In one embodiment, the antisense oligonucleotide has the sequence of ASO2 shown in FIG. 18.

In one embodiment, the antisense oligonucleotide has the sequence of ASO6 shown in FIG. 18.

In one embodiment, the antisense oligonucleotide has the sequence mU*mC*mC*mU*mC*mC*T*C*T*T*T*C*T*C*A*C*C*T*mU*mU*mC*mU*mC*mU (ASO6, SEQ ID NO: 17) or mU*mC*mC*mU*mC*mU*T*C*T*T*T*C*T*C*A*C*C*T*mU*mU*mC*mU*mC*mU (ASO6 variant 1, SEQ ID NO: 41).

Throughout the specification, an asterisk (*) in an antisense oligonucleotide sequence indicates a phosphorothioate linkage, and an "m" immediately before a nucleotide in an antisense oligonucleotide sequence indicates that the nucleotide is a 2'-O-methyl ribonucleotide. Nucleotides in an antisense oligonucleotide sequence that are not immediately preceded by an "m" are deoxyribonucleotides.

In one embodiment, the antisense oligonucleotide has the sequence selected from the group consisting of:

```
(ASO10; SEQ ID NO: 21)
5'-mU*mC*mU*mC*mC*A*C*C*T*C*C*T*C*C*T*mC*mU*
mC*mC*mA-3';
```

```
(ASO11; SEQ ID NO: 22)
5'-mG*mU*mC*mU*mC*C*A*C*C*T*C*C*T*C*C*mU*mC*
mU*mC*mC-3';

(ASO12; SEQ ID NO: 23)
5'-mC*mU*mC*mC*mA*C*C*T*C*C*T*C*C*T*C*mU*mC*
mC*mA*mU-3';

(ASO13; SEQ ID NO: 24)
5'-mC*mU*mC*mU*mU*mC*C*T*C*T*G*C*C*T*C*A*T*
C*mA*mU*mC*mA*mC*mU-3';

(ASO14; SEQ ID NO: 25)
5'-mU*mC*mU*mC*mU*mU*C*C*T*C*T*G*C*C*T*C*A*
T*mC*mA*mU*mC*mA*mC-3';

(ASO15; SEQ ID NO: 26)
5'-mU*mU*mC*mU*mC*mU*T*C*C*T*C*T*G*C*C*T*C*
A*mU*mC*mA*mU*mC*mA-3';

(ASO16; SEQ ID NO: 27)
5'-mU*mU*mU*mC*mU*mC*T*T*C*C*T*C*T*G*C*C*T*
C*mA*mU*mC*mA*mU*mC-3';

(ASO17; SEQ ID NO: 28)
5'-mC*mU*mU*mU*mC*mU*C*T*T*C*C*T*C*T*G*C*C*
T*mC*mA*mU*mC*mA*mU-3;

(ASO18; SEQ ID NO: 29)
5'-mA*mU*mG*mC*mC*mC*T*G*A*A*T*T*C*C*A*A*C*
T*mG*mA*mC*mC*mU*mU-3';

(ASO19; SEQ ID NO: 30)
5'-mA*mA*mU*mG*mC*mC*C*T*G*A*A*T*T*C*C*A*A*
C*mU*mG*mA*mC*mC*mU-3';

(ASO20; SEQ ID NO: 31)
5'-mC*mA*mA*mU*mG*mC*C*C*T*G*A*A*T*T*C*C*A*
A*mC*mU*mG*mA*mC*mC 3';
and (ASO21; SEQ ID NO: 32)
5'-mU*mG*mC*mC*mC*mU*G*A*A*T*T*C*C*A*A*C*T*
G*mA*mC*mC*mU*mU*mC-3'.
```

In one embodiment, the metabolic syndrome comprises type 2 diabetes.

In one embodiment, the metabolic syndrome comprises type 1 diabetes.

In one embodiment, the metabolic syndrome comprises insulin resistance.

In one embodiment, the metabolic syndrome comprises insulin insufficiency.

In one embodiment, the metabolic syndrome comprises obesity.

In one embodiment, the metabolic syndrome comprises hyperinsulinemia.

In one embodiment, the metabolic syndrome comprises impaired glucose tolerance (IGT).

In one embodiment, a subject with metabolic syndrome exhibits three or more of the following signs:
a) Blood pressure equal to or higher than 130/85 mmHg;
b) Fasting blood glucose equal to or higher than 100 mg/dL;
c) Large waist circumference wherein a large waist circumference is 40 inches or more for men and 35 inches or more for women;
d) Low HDL cholesterol wherein low LDH cholesterol is under 40 mg/dL for men and under 50 mg/dL; and
e) Triglycerides equal to or higher than 150 mg/dL.

In one embodiment, treating the metabolic syndrome comprises normalizing a blood glucose level in a subject.

In one embodiment, treating the metabolic syndrome comprises normalizing an Hb1Ac level in a subject.

In one embodiment, treating the metabolic syndrome comprises prevention of at least one complication of diabetes associated with poor circulation.

In one embodiment, treating the metabolic syndrome comprises amelioration of at least one sign or symptom of type 2 diabetes.

In one embodiment, treating the metabolic syndrome comprises amelioration of at least one sign or symptom of type 1 diabetes.

In one embodiment, treating the metabolic syndrome comprises amelioration of at least one sign or symptom of insulin resistance.

In one embodiment, treating the metabolic syndrome comprises amelioration of at least one sign or symptom of insulin insufficiency.

In one embodiment, treating the metabolic syndrome comprises amelioration of at least one sign or symptom of hyperinsulinemia.

In one embodiment, treating the metabolic syndrome comprises amelioration of at least one sign or symptom of impaired glucose tolerance (IGT).

In one embodiment, treating the metabolic syndrome comprises amelioration of at least one sign or symptom of obesity.

In one embodiment, treating the metabolic syndrome comprises amelioration of at least one of
  a) Blood pressure equal to or higher than 130/85 mmHg;
  b) Fasting blood glucose equal to or higher than 100 mg/dL;
  c) Large waist circumference wherein a large waist circumference is 40 inches or more for men and 35 inches or more for women;
  d) Low HDL cholesterol wherein low LDH cholesterol is under 40 mg/dL for men and under 50 mg/dL; and
  e) Triglycerides equal to or higher than 150 mg/dL.

In one embodiment, treating the metabolic syndrome comprises amelioration of elevated blood pressure equal to or higher than 130/85 mmHg.

In one embodiment, treating the metabolic syndrome comprises amelioration of elevated fasting blood glucose equal to or higher than 100 mg/dL.

In one embodiment, treating the metabolic syndrome comprises amelioration of large waist circumference wherein a large waist circumference is 40 inches or more for men and 35 inches or more for women.

In one embodiment, treating the metabolic syndrome comprises amelioration of low HDL cholesterol by increasing HDL cholesterol wherein low LDH cholesterol is under 40 mg/dL for men and under 50 mg/dL.

In one embodiment, treating the metabolic syndrome comprises amelioration of elevated triglycerides equal to or higher than 150 mg/dL.

In one embodiment, treating metabolic syndrome comprises amelioration of fatty liver.

In one embodiment, treating metabolic syndrome comprises modulation of fat deposition.

In one embodiment, the antisense oligonucleotide is for delivery to a muscle cell.

In one embodiment, the antisense oligonucleotide is formulated as a microparticle.

In one embodiment, the antisense oligonucleotide is formulated as an in situ forming composition.

In one embodiment, the antisense oligonucleotide is formulated as a liposome.

In one embodiment, the antisense oligonucleotide is conjugated to a dendrimer.

In one embodiment, the antisense oligonucleotide is complexed with a muscle targeting moiety.

In one embodiment, the muscle targeting moiety comprises a smooth muscle targeting peptide (SMTP).

In one embodiment, the SMTP comprises an amino acid sequence selected from the group consisting of: ASSLNIA (SEQ ID NO: 57); WDANGKT (SEQ ID NO: 58); GETRAPL (SEQ ID NO: 59); CGHHPVYAC (SEQ ID NO: 60); and HAIYPRH (SEQ ID NO: 61).

In one embodiment, the complex further comprises a linker.

In one embodiment, the linker is selected from the group consisting of a covalent linker, a non-covalent linkage, and a reversible linker.

In one embodiment, the complex further comprises a pharmaceutically acceptable dendrimer.

In one embodiment, the pharmaceutically acceptable dendrimer is a PAMAM dendrimer.

In one embodiment, the pharmaceutically acceptable dendrimer is a G5 dendrimer.

In one embodiment, the pharmaceutically acceptable dendrimer is an uncharged dendrimer.

In one embodiment, the pharmaceutically acceptable dendrimer is an acylated dendrimer.

In one embodiment, the complex further comprises a liposome.

In one embodiment, the complex further comprises a microparticle.

In one embodiment, the complex further comprises an in situ forming composition.

In one embodiment, the antisense oligonucleotide is released from the complex upon delivery to a muscle cell.

In another aspect, the invention provides a pharmaceutical composition comprising an HSP90AB1 specific inhibitor for delivery to a muscle cell.

In one embodiment, the HSP90AB1 specific inhibitor comprises a nucleic acid inhibitor.

In one embodiment, the nucleic acid inhibitor comprises an antisense nucleic acid molecule.

In one embodiment, the nucleic acid inhibitor comprises a double stranded nucleic acid molecule.

In one embodiment, the nucleic acid inhibitor comprises a double stranded RNA selected from the group consisting of an siRNA, a shRNA, and a dicer substrate siRNA (DsiRNA).

In one embodiment, the HSP90AB1 specific inhibitor comprises an antibody.

In one embodiment, the HSP90AB1 specific inhibitor comprises a small molecule.

In one embodiment, the small molecule is selected from the group consisting of lonidamine or an analog thereof, celastrol or analog thereof, gedunin or an analog thereof, and coumermycin or an analog thereof.

In one embodiment, the composition further comprises a microparticle.

In one embodiment, the composition further comprises an in situ forming composition.

In one embodiment, the composition further comprises a liposome.

In one embodiment, the composition further comprises a dendrimer.

In one embodiment, the composition comprises a complex comprising the HSP90AB1 inhibitor and a muscle targeting moiety.

In one embodiment, the muscle targeting moiety comprises a smooth muscle targeting peptide (SMTP).

In one embodiment, the SMTP comprises an amino acid sequence selected from the group consisting of: ASSLNIA (SEQ ID NO: 57); WDANGKT (SEQ ID NO: 58); GETRAPL (SEQ ID NO: 59); CGHHPVYAC (SEQ ID NO: 60); and HAIYPRH (SEQ ID NO: 61).

In one embodiment, the complex further comprises a linker.

In one embodiment, the linker is selected from the group consisting of a covalent linker, a non-covalent linkage, and a reversible linker.

In one embodiment, the complex further comprises a pharmaceutically acceptable dendrimer.

In one embodiment, the pharmaceutically acceptable dendrimer is a PAMAM dendrimer.

In one embodiment, the pharmaceutically acceptable dendrimer is a G5 dendrimer.

In one embodiment, the pharmaceutically acceptable dendrimer is an uncharged dendrimer.

In one embodiment, the pharmaceutically acceptable dendrimer is an acylated dendrimer.

In one embodiment, the complex further comprises a liposome.

In one embodiment, the complex further comprises a microparticle.

In one embodiment, the complex further comprises an in situ forming composition.

In one embodiment, the HSP90AB1 inhibitor is an antisense oligonucleotide having a sequence selected from the sequences AS01, ASO2, ASO3, ASO4, ASO5, ASO6, ASO7, ASO8 and ASO9 shown in FIG. 18.

In one embodiment, the HSP90AB1 inhibitor is an antisense oligonucleotide having the sequence of ASO2 shown in FIG. 18.

In one embodiment, the HSP90AB1 inhibitor is an antisense oligonucleotide having the sequence of ASO6 shown in FIG. 18.

In one embodiment, the HSP90AB1 inhibitor is an antisense oligonucleotide having the sequence

```
                                       (SEQ ID NO: 17)
mU*mC*mC*mU*mC*mC*T*C*T*T*T*C*T*C*A*C*C*T*mU*
mU*mC*mU*mC*mU
or
                                       (SEQ ID NO: 41)
mU*mC*mC*mU*mC*mU*T*C*T*T*T*C*T*C*A*C*C*T*mU*
mU*mC*mU*mC*mU.
```

In one embodiment, the HSP90AB1 inhibitor of the pharmaceutical composition is an antisense oligonucleotide having the sequence selected from the group consisting of:

```
(ASO10; SEQ ID NO: 21)
5'-mU*mC*mU*mC*mC*A*C*C*T*C*C*T*C*C*T*mC*mU*
mC*mC*mA-3';

(ASO11; SEQ ID NO: 22)
5'-mG*mU*mC*mU*mC*C*A*C*C*T*C*C*T*C*C*mU*mC*
mU*mC*mC-3';

(ASO12; SEQ ID NO: 23)
5'-mC*mU*mC*mC*mA*C*C*T*C*C*T*C*C*T*C*mU*mC*
mC*mA*mU-3';

(ASO13; SEQ ID NO: 24)
5'-mC*mU*mC*mU*mU*mC*C*T*C*T*G*C*C*C*T*C*A*T*
C*mA*mU*mC*mA*mC*mU-3';
```

```
-continued
(ASO14; SEQ ID NO: 25)
5'-mU*mC*mU*mC*mU*mU*C*C*T*C*T*G*C*C*T*C*A*
T*mC*mA*mU*mC*mA*mC-3';

(ASO15; SEQ ID NO: 26)
5'-mU*mU*mC*mU*mC*mU*T*C*C*T*C*T*G*C*C*T*C*
A*mU*mC*mA*mU*mC*mA-3';

(ASO16; SEQ ID NO: 27)
5'-mU*mU*mU*mC*mU*mC*T*T*C*C*T*C*T*G*C*C*T*
C*mA*mU*mC*mA*mU*mC-3';

(ASO17; SEQ ID NO: 28)
5'-mC*mU*mU*mU*mC*mU*C*T*T*C*C*T*C*T*G*C*C*
T*mC*mA*mU*mC*mA*mU-3;

(ASO18; SEQ ID NO: 29)
5'-mA*mU*mG*mC*mC*mC*T*G*A*A*T*T*C*C*A*A*C*
T*mG*mA*mC*mC*mU*mU-3';

(ASO19; SEQ ID NO: 30)
5'-mA*mA*mU*mG*mC*mC*C*T*G*A*A*T*T*C*C*A*A*
C*mU*mG*mA*mC*mC*mU-3';

(ASO20; SEQ ID NO: 31)
5'-mC*mA*mA*mU*mG*mC*C*C*T*G*A*A*T*T*C*C*A*
A*mC*mU*mG*mA*mC*mC 3';
and (ASO21; SEQ ID NO: 32)
5'-mU*mG*mC*mC*mC*mU*G*A*A*T*T*C*C*A*A*C*T*
G*mA*mC*mC*mU*mU*mC-3'.
```

In another aspect, the invention provides a method of treating a metabolic syndrome in a subject, comprising administering to the subject any one of the pharmaceutical compositions provided herein.

Other embodiments are provided infra.

BRIEF DESCRIPTION OF THE DRAWINGS

FIGS. 12A-12D show the effect of siRNA-mediated knockdown of HSP90β on glycolytic flux in skeletal muscle myotubes in (A) glucose induced ECAR; (B) oligomycin induced ECAR; (C) basal OCR; and (D) uncoupled OCR.

FIGS. 13A and 13B show the effect of siRNA-mediated knockdown of HSP90β on the ratio of phosphorylated-Erk levels to total Erk levels in an inflammatory insulin resistance model in muscle myotubes as shown in (A) western blot and (B) quantitatively.

FIG. 15 shows the sequence of human HSP90AA1 gene (SEQ ID NO: 7) and HSP90α protein (SEQ ID NO: 8).

FIG. 16 shows the sequence of human HSP90AB gene (SEQ ID NO: 9) and HSP90β protein (SEQ ID NO: 10).

FIG. 17 shows alignments of the sequences of the HSP90AA1 gene (SEQ ID NO: 7) with the human HSP90AB gene (SEQ ID NO: 9); and of the human HSP90α protein (SEQ ID NO: 8) with the human HSP90β protein (SEQ ID NO: 10).

FIG. 18A shows the sequences of a panel of antisense oligonucleotides derived from the mouse HSP90AB1 gene that were tested for their ability to knockdown human Hsp90AB1 mRNA level in cultured human cells. An asterisk (*) in the sequence indicates a phosphorothioate linkage, and an "m" before a nucleotide in the sequence indicates that the nucleotide is a 2'-O-methyl ribonucleotide. Nucleotides in the sequences that are not preceded by an "m" are deoxyribonucleotides. Sequences shown are: NC1 ASO (SEQ ID NO: 11); ASO1 (SEQ ID NO: 12); ASO2 (SEQ ID NO: 13); ASO3 (SEQ ID NO: 14); ASO4 (SEQ ID NO: 15); ASO5 (SEQ ID NO: 16); ASO6 (SEQ ID NO: 17); ASO7 (SEQ ID NO: 18); ASO8 (SEQ ID NO: 19); and ASO9 (SEQ ID NO: 20).

FIG. 18B shows sequence alignments between the DNA sequences corresponding to ASO1, ASO2, ASO6 and ASO8 (Query) and the human Hsp90ab1 sequence (Sbjct). Variant sequences of ASO1, ASO2, ASO6 and ASO8 with greater sequence homology with the human Hsp90ab1 were derived by substituting one or more nucleotides in the ASO sequence with the corresponding nucleotide in the human HSp90ab1 sequence. The substituted nucleotides are shown in bold and underlined. The sequences of ASO1, ASO2, ASO6 and ASO8 are shown 5' to 3'. ASO3, ASO4, ASO5, ASO7, and ASO9 do not share significant homology with the human Hsp90ab1 sequence. Sequences shown are: ASO1 (SEQ ID NO: 12); ASO1 Query (SEQ ID NO: 45); ASO1 Sbjct (SEQ ID NO: 46); ASO1 Variant 1 (SEQ ID NO: 35); ASO1 Variant 2 (SEQ ID NO: 36); ASO1 Variant 3 (SEQ ID NO: 37); ASO2 (SEQ ID NO: 13); ASO2 Query (SEQ ID NO: 47); ASO2 Sbjct (SEQ ID NO: 48); ASO2 variant 1 (SEQ ID NO: 38); ASO2 variant 2 (SEQ ID NO: 39); ASO2 variant 3 (SEQ ID NO: 40); ASO6 (SEQ ID NO: 17); ASO6 Query (SEQ ID NO: 49); ASO6 Sbjct (SEQ ID NO: 50); ASO6 Variant 1 (SEQ ID NO: 41); ASO8 (SEQ ID NO: 19); ASO8 Query (SEQ ID NO: 51); ASO8 Sbjct (SEQ ID NO: 52); ASO8 Variant 1 (SEQ ID NO: 42); ASO8 Variant 2 (SEQ ID NO: 43); and ASO8 Variant 3 (SEQ ID NO: 44).

FIG. 24 is a set of two bar graphs showing that treatment of mice with ASO1 and ASO2 for eight weeks improves heat production. The upper and lower panels show heat production in light and dark conditions, respectively.

ASO11 monkey (SEQ ID NO: 63); ASO11 mouse (SEQ ID NO: 64); ASO12 (SEQ ID NO: 22); ASO12 human (SEQ ID NO: 62); ASO12 monkey (SEQ ID NO: 63); ASO12 mouse (SEQ ID NO: 64); ASO13 (SEQ ID NO: 24); ASO13 human (SEQ ID NO: 65); ASO13 monkey (SEQ ID NO: 66); ASO13 mouse (SEQ ID NO: 67); ASO14 (SEQ ID NO: 25); ASO14 human (SEQ ID NO: 65); ASO14 monkey (SEQ ID NO: 66); ASO14 mouse (SEQ ID NO: 67); ASO15 (SEQ ID NO: 26); ASO15 human (SEQ ID NO: 65); ASO15 monkey (SEQ ID NO: 66); ASO15 mouse (SEQ ID NO: 67); ASO16 (SEQ ID NO: 27); ASO16 human (SEQ ID NO: 65); ASO16 monkey (SEQ ID NO: 66); ASO16 mouse (SEQ ID NO: 67); ASO17 (SEQ ID NO: 28); ASO17 human (SEQ ID NO: 65); ASO17 monkey (SEQ ID NO: 66); ASO17 mouse (SEQ ID NO: 67); ASO18 (SEQ ID NO: 29); ASO18 human (SEQ ID NO: 68); ASO18 monkey (SEQ ID NO: 69); ASO18 mouse (SEQ ID NO: 70); ASO19 (SEQ ID NO: 30); ASO19 human (SEQ ID NO: 68); ASO19 monkey (SEQ ID NO: 69); ASO19 mouse (SEQ ID NO: 70); ASO20 (SEQ ID NO: 31); ASO20 human (SEQ ID NO: 68); ASO20 monkey (SEQ ID NO: 69); ASO20 mouse (SEQ ID NO: 70); ASO21 (SEQ ID NO: 32); ASO21 human (SEQ ID NO: 68); ASO21 monkey (SEQ ID NO: 69); ASO21 mouse (SEQ ID NO: 70); ASO22 (SEQ ID NO: 33); ASO22 human (SEQ ID NO: 68); ASO22 monkey (SEQ ID NO: 69); ASO22 mouse (SEQ ID NO: 70); ASO23 (SEQ ID NO: 34); ASO23 human (SEQ ID NO: 71); ASO23 monkey (SEQ ID NO: 72); and ASO23 mouse (SEQ ID NO: 73).

Figure 32:
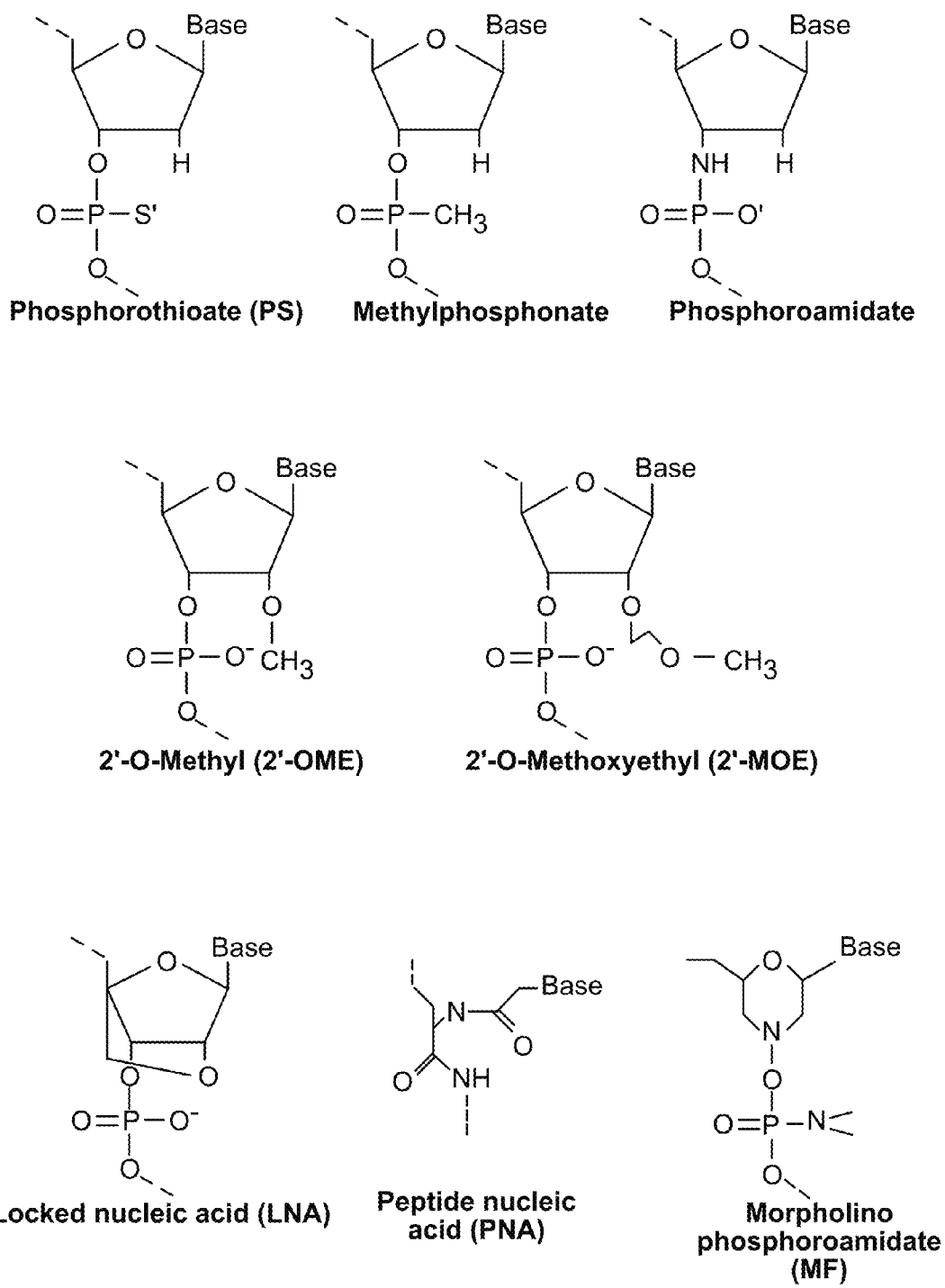

FIG. 32 shows three chemical modifications that are commonly made to antisense oligonucleotides to improve their performance. The modifications shown at the top consist of replacement of the non-bridging oxygen atom of the phosphate group, the modifications in the middle contain changes to the 2' position of ribose, and the modifications at the bottom consist of changes to the ribose moiety.

Figure 33A:
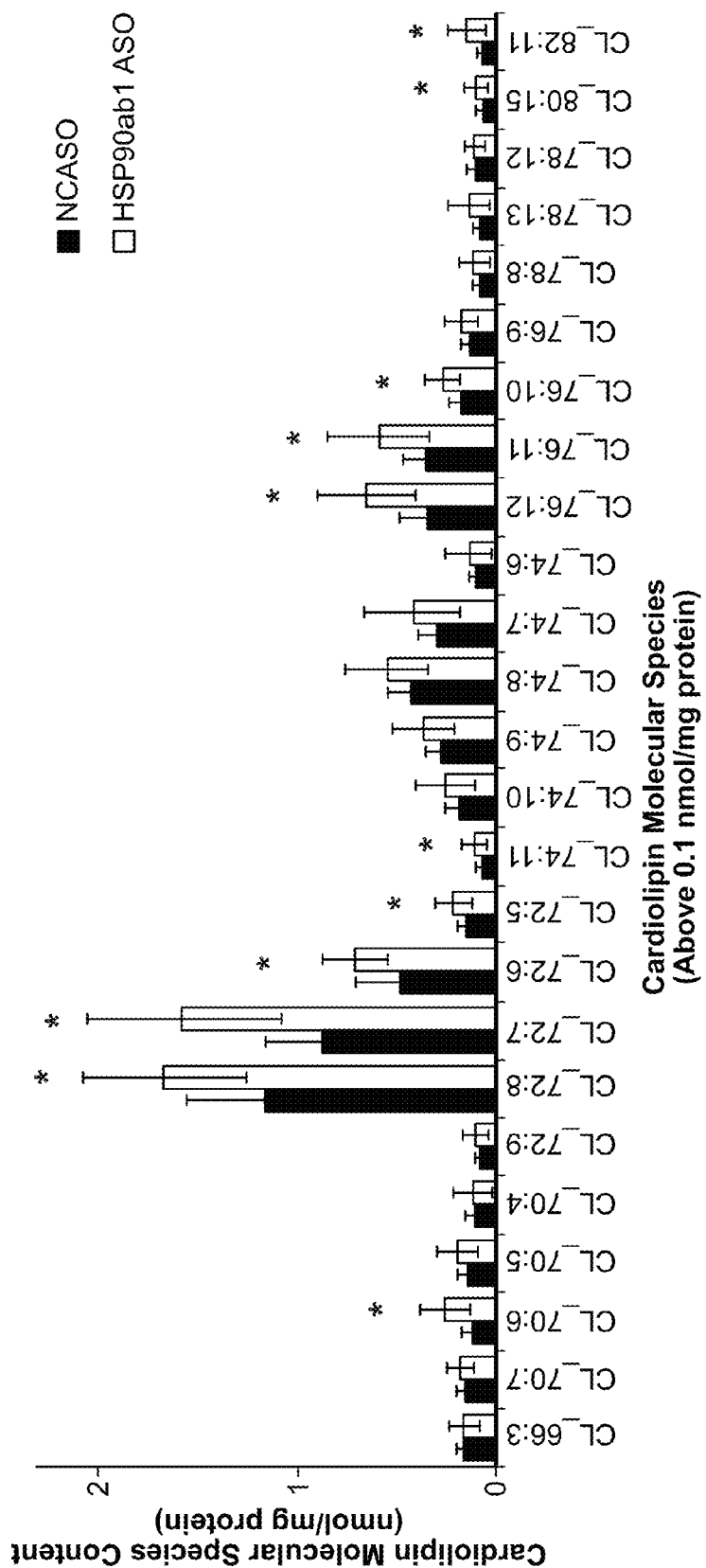

FIG. 33A shows that lipidomic analysis revealed selective alterations in structural lipids and metabolic intermediates in muscle of ASO mediated knockdown of Hsp90ab1. ASO knockdown increased 18:2 enriched species of cardiolipin in muscle.

FIG. 33B shows that lipidomic analysis revealed selective alterations in structural lipids and metabolic intermediates in muscle of ASO mediated knockdown of Hsp90ab1. ASO knockdown decreased steric, oleic, as well as linoleic FFA as well as selectively decreased 18:0 and 18:0-OH acylcarnitines in the muscle of Hsp90ab1 KD mice.

Figure 34:
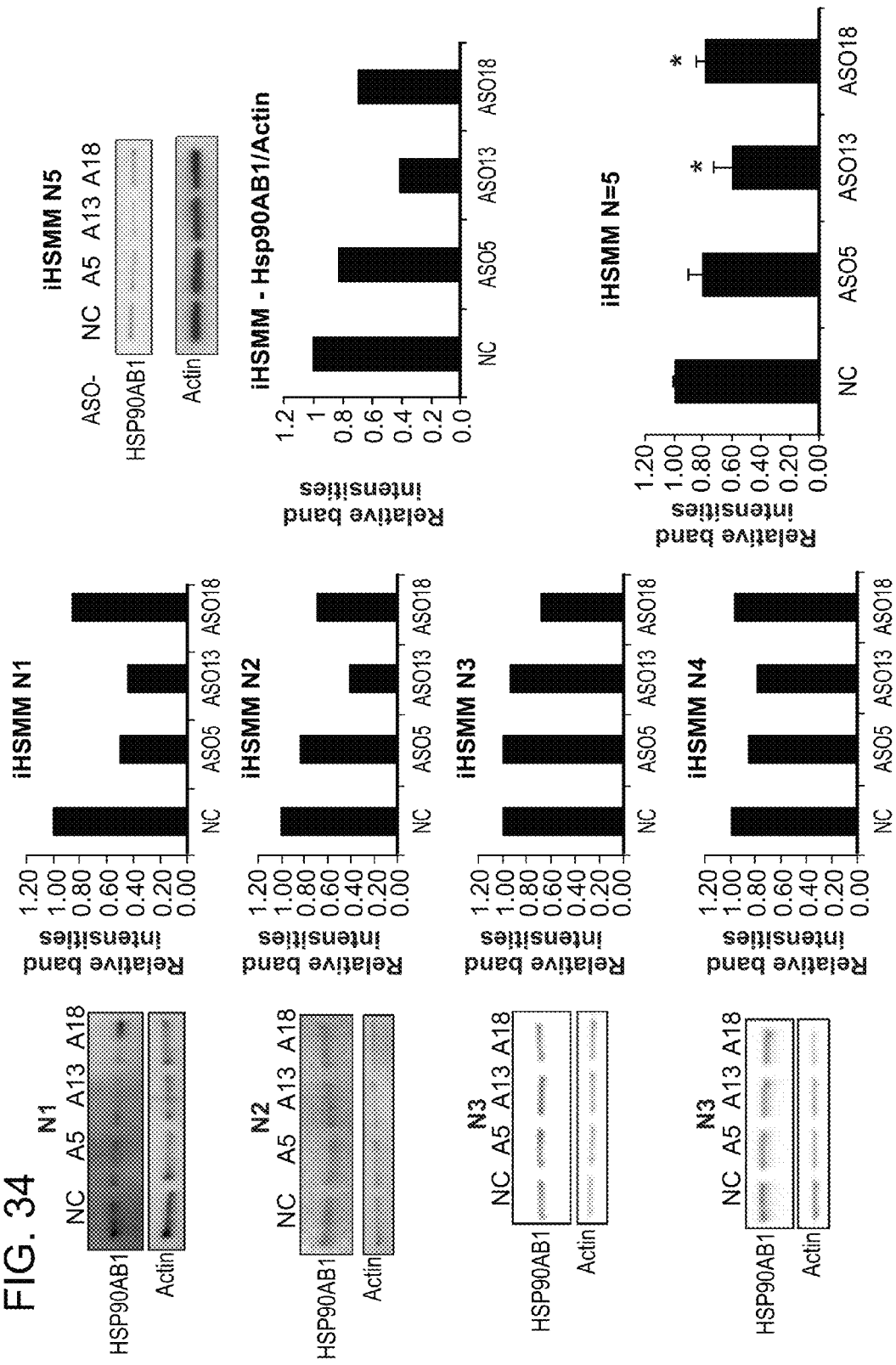

FIG. 34 shows protein expression levels of Hsp90AB1 in human skeletal muscle myoblasts (HSMM) treated with ASO5, ASO13 or ASO18. Protein expression levels were determined by Western blot in five separate experiments (N1-N5) and then averaged to determine overall changes in protein expression. Treatment of HSMM with ASO13 or ASO18 significantly decreased Hsp90AB1 protein levels.

Figure 35:
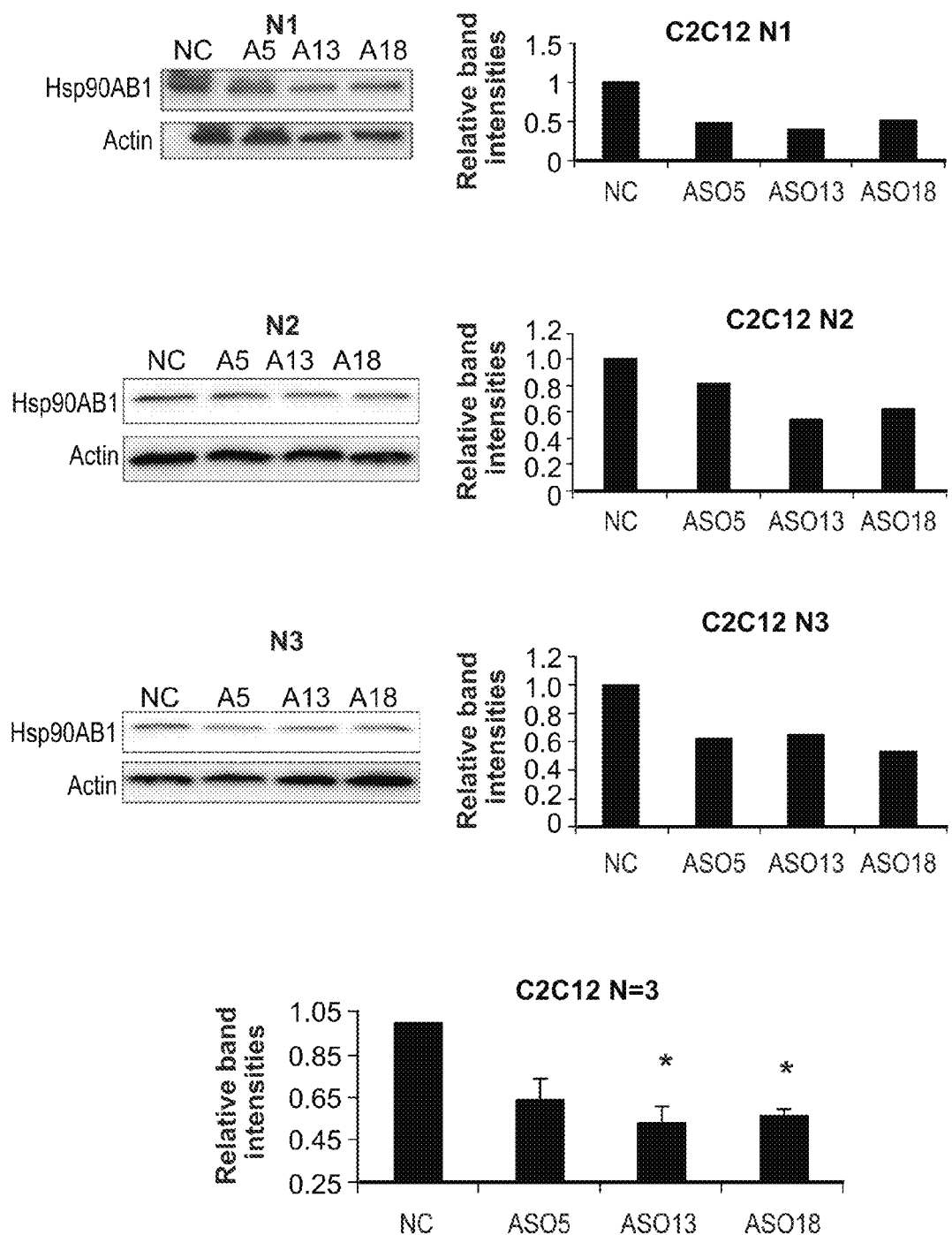

FIG. 35 shows protein expression levels of Hsp90AB1 in C2C12 mouse myoblasts treated with ASO5, ASO13 or ASO18. Protein expression levels were determined by Western blot in three separate experiments (N1-N3) and then averaged to determine overall changes in protein expression. Treatment of C2C12 myoblasts with ASO13 or ASO18 significantly decreased Hsp90AB1 protein levels.

DETAILED DESCRIPTION AND PREFERRED EMBODIMENTS

A discovery platform technology was used to delineate distinct molecular signatures that drive the pathophysiology of diabetes and metabolic syndrome. Hsp90β was identified through this discovery platform technology as a critical node that is significantly modulated in human primary in vitro models of diabetes, and is associated with multiple mechanisms that are involved with lipid metabolism, proteasome function, endosomal trafficking, and RNA splicing.

Heat shock proteins (HSPs) are molecular chaperones that stabilize a large set of client proteins. Vertebrates have two isoforms of cytosolic HSP90, HSP90α (gene HSP90AA1) and HSP90β (gene HSP90AB1). In vertebrates, the HSP90 isoforms are generally about 85% identical at the amino acid sequence level. In humans, the HSP90α amino acid sequence is 86% identical and 93% similar to the HSP90β amino acid sequence. Both proteins include an ATP binding domain. HSP90β is expressed constitutively at a high level in most cells and is generally more abundant than HSP90α. HSP90α expression is stress-inducible and the protein is overexpressed in many cancer cells. The client proteins of the HSP90 isoforms are largely overlapping, however HSP90α is responsible for chaperoning many signaling proteins, e.g., c-Src, A-raf, after heat shock.

Although in vitro analysis suggests similar and largely redundant functions, phenotypes for HSP90 knockout mice are strikingly different. The Hsp90β knockout mouse displays early embryonic lethality. In contrast, the only defect identified in Hsp90α-deficient mice occurs in adult males, which exhibit a failure of spermatogenesis. In the case of Hsp90β, lethality occurs at embryonic day 9, due to an inability of the embryo to develop a placenta, leading to a failure of implantation and death within 24 hours. These mutants express Hsp90α, yet failure still occurred, suggesting that Hsp90α cannot compensate for HSP90β in this crucial developmental step. In contrast to Hsp90β, both male and female Hsp90α knockout mice are viable and phenotypically normal into adulthood, with the exception of sterility in male mice. These results demonstrate that the two HSP90 isoforms play different roles in vivo in mice.

Using various functional assays with primary human skeletal muscle cells (HSMM) and hepatoma (HepG2) cells, Applicants have demonstrated that RNAi mediated knockdown of HSP90β resulted in a decrease of the basal OCR/ECAR ratio by ~50%. The decreased ratio was due to decreased OCR and elevated ECAR in both HSMM and HepG2 cells, indicating that HSP90β regulates oxidative respiration and glycolysis. Moreover, HSP90β knockdown in HSMM cells increased glucose induced ECAR, demonstrating enhanced glycolysis induced by reduced HSP90β.

Further, Applicants have demonstrated that in primary human skeletal muscle cells, knocking down of HSP90β induced an increase in insulin stimulated glucose uptake, indicating that HSP90β is involved with skeletal muscle glucose metabolism and insulin action. Further, the observation by Applicants that knockdown of Hsp90β in myotubes results in significant downstream induction of pERK and a moderate influence on pAKT and pGSK3β suggests a functional bifurcation of insulin signaling and that Hsp90β is involved in a selective mechanism. In further experiments, Applicants have shown that a pan HSP90 small molecule inhibitor (CCT018159) that inhibits both HSP90α and HSP90β had a less profound effect than HSP90β knockdown alone on insulin signaling and bioenergetics. Accordingly, specific HSP90β inhibition was found to be more efficacious than a pan HSP90 inhibition approach.

Applicants have also demonstrated significant improvements in glucose tolerance and fed glucose levels and a significant reduction of fed insulin levels in diet induced obesity (DIO) mice administered an antisense oligonucleotides (ASO) specific to HSP90AB1. These results show that reduction in the level of HSP90AB1 improves insulin sensitivity and directly or indirectly regulate insulin secretion by the pancreas. It was further observed that ASO treatment significantly improved heat production in DIO mice. Increase in heat production is suggestive of improved metabolic effects produced by systemic metabolic change induced by HSP90AB1 knockdown. Knockdown of Hsp90ab1 protein levels in DIO mice using an Hsp90ab1 targeting ASO also significantly decreased the expression of pyruvate dehydrogenase kinase isoenzyme 4 (PDK4). PDK4 is known to phosphorylate pyruvate dehydrogenase (PDH)-E1α subunit, thereby inhibiting PDH and downregulating mitochondrial glucose oxidation. In the studies described herein, the decrease in PDK4 expression was found to be associated with a decrease in phosphorylation of PDH-E1α. This decrease in phosphorylation is indicative of an increase in active PDH-E1α and a resultant increase in mitochondrial glucose oxidation. Thus, Applicants have demonstrated that ASO mediated Hsp90ab1 knock-down is effective for enhancing substrate metabolism through suppression of PDK4 expression.

In further observations by the Applicants, knockdown of Hsp90ab1 by an Hsp90ab1 targeting ASO in DIO mice was found to be associated with changes in the expression of several key genes involved in the regulation of glycolysis, fatty acid oxidation, and mitochondrial glucose oxidation, such as adipose triglyceride lipase (ATGL), PFKM (phosphofructokinase, muscle), ALDOA (aldolase A), GYS1 (glycogen synthase 1) ACCA (Acetyl-CoA carboxylase), HSL (Hormone sensitive lipase), SCD1 (Stearoyl-CoA desaturase), ACADL (Acyl-CoA Dehydrogenase), and CPT1b (Carnitine palmitoyltransferase I). Gene expression was examined in the skeletal muscles of the mice.

Applicants also observed significant alteration in the lipidomic profile in the muscles of DIO mice treated with an Hsp90ab1 targeting ASO, such as increased 18:2 enriched species of cardiolipin in muscle, decreased steric, oleic, and linoleic free fatty acids (FFA), and selectively decreased 18:0 and 18:0-OH acylcarnitines. Thus, cardiolipin molecular species were significantly increased while selective free fatty acids and acyl carnitines were decreased in muscle, suggesting an increase in mitochondria activity reengaging bioenergetics capacity.

In summary, the knockdown of HSP90β was found by Applicants to have a significant effect on bioenergetics and mitochondrial substrate metabolism. In particular, HSP90β emerged from the studies described herein as a critical regulator of cellular metabolism and a molecular switch between oxidative respiration and glycolysis in skeletal muscle cells. HSP90β is therefore a therapeutic target in diabetes.

Definitions

As used herein, an "HSP90 inhibitor" is a therapeutic agent that reduces the expression or activity of HSP90. An HSP90 inhibitor may reduce HSP90 activity either by directly interacting with HSP90 or by reducing or preventing the formation of the HSP90/CDC37 complex such that the expression and proper folding of at least one client protein of HSP90 is inhibited. As used herein, an "HSP90" inhibitor can act by any mechanism, e.g., by inhibiting the expression of HSP90 at the RNA or protein level; by inhibiting the activity of HSP90, e.g., by inhibiting ATP binding or hydrolysis; or by inhibiting the interaction of HSP90 with one or more of its interacting proteins; or by decreasing the stability of HSP90. HSP90 inhibitors can inhibit the activity of one or more HSP90 isoforms. For example, an inhibitor of HSP90α may also inhibit HSP90β. Similarly, an inhibitor of HSP90β may also inhibit HSP90α. In one embodiment, HSP90 inhibitors can be specific for the inhibition of a specific HSP90 isoform, for example, specific for the inhibition of HSP90β, i.e., predominantly inhibiting HSP90β while inhibiting HSP90α far less.

HSP90 inhibitors include (i) small molecule inhibitors, many of which inhibit the activity of multiple isoforms of HSP90, e.g., radicicol and geldanamycin and its derivatives; (ii) nucleic acid inhibitors, e.g., antisense, siRNA, shRNA, dsiRNA, etc. that can target one or more specific isoforms of HSP90 (see, e.g., examples provided herein; Kuo et al., 2007, J. Immunol. 178:600; Didelot et al., 2008, Cell. Death Diff., 15:859, the entire contents of each of which are incorporated herein by reference); and (iii) antibodies that can target one or more specific isoforms of HSP90 (Cortes-González et al., 2010, Cell Physiol. Biochem. 26:657, the entire contents of which is incorporated herein by reference). Specific classes and examples of HSP90 inhibitors are discussed in detail herein.

As used herein, an HSP90 inhibitor that is "specific" for a particular HSP90 isoform, e.g., specific for HSP90β, may have a significantly lower activity against another HSP isoform. However, as used herein, a "specific" inhibitor of a particular HSP90 isoform is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 50-fold, at least 75-fold, or at least 100-fold more effective at inhibiting the activity or expression of the specific HSP90 isoform. For example, if the inhibitor is an siRNA specific for HSP90β that is at least 10-fold more effective at inhibiting a specific HSP90 isoform, then 1 nM of the siRNA will decrease expression of HSP90β to the same extend as 10 nM of the siRNA will decrease the expression of HSP90α. Similar analyses can be performed to compare the effect of inhibitors on the activity of the HSP90 isoforms, e.g., level of inhibition of phosphorylation of downstream effectors, inhibition of folding of client proteins, inhibition of inorganic phosphate production, etc. In certain embodiments, a specific inhibitor of an HSP90β isoform inhibits the expression or activity of HSP90β by at least 50%, but does not inhibit the expression or activity of HSP90α by 50%, 40%, 30%, 20%, or 10% at the same concentration. In certain embodiments, a specific inhibitor of an HSP90β isoform inhibits the expression or activity of HSP90β by at least 60%, but does not inhibit the expression or activity of HSP90α by 50%, 40%, 30%, 20%, or 10% at the same concentration. In certain embodiments, a specific inhibitor of an HSP90β isoform inhibits the expression or activity of HSP90β by at least 70%, but does not inhibit the expression or activity of HSP90α by 50%, 40%, 30%, 20%, or 10% at the same concentration. In certain embodiments, a specific inhibitor of an HSP90β isoform inhibits the expression or activity of HSP90β by at least 80%, but does not inhibit the expression or activity of HSP90α by 50%, 40%, 30%, 20%, or 10% at the same concentration. In certain embodiments, a specific inhibitor of an HSP90β isoform inhibits the expression or activity of HSP90β by at least 90%, but does not inhibit the expression or activity of HSP90α by 50%, 40%, 30%, 20%, or 10% at the same concentration.

Assay methods to determine the specificity and activity of HSP90 inhibitors are within the ability of those of skill in the art. The specific assay method can depend on the inhibitor used, e.g, an inhibitor of activity or an inhibitor of expression. Kits to assay HSP90α and HSP90β activity are commercially available (e.g., BPS Bioscience, San Diego, Calif.). Methods to assay activity of HSP90α and HSP90β are also known in the art (see, e.g., Kim et al., *J. Biomol. Screening* 2004; 9: 375-381; and Howes et al., *Anal. Biochem.* 2006; 350:202-213, the entire contents of both of which is incorporated herein by reference).

For instance, inhibition of the Hsp90 activity can be determined in an assay for ATPase activity, e.g., Malachite Green Assay as described in Methods Mol Med, 2003, 85:149. Briefly, an Hsp90 protein (e.g., Hsp90α and Hsp90β proteins) in assay buffer (100 mM Tris-HCl, pH 7.4, 20 mM KCl, 6 mM MgCl$_2$) is mixed with ATP alone (a negative control), ATP with geldanamycin (a positive control), ATP with a test compound at varying concentrations, or a test compound alone (another negative control) in a 96-well plate. For detecting inorganic phosphate produced by hydrolysis of ATP, Malachite green reagent is then added to the reaction. The mixtures are incubated at 37° C. for 4 hours and, at the end of the incubation, sodium citrate buffer (34% w/v sodium citrate) is added to the reaction. The plate is read by an ELISA reader with an absorbance at 620 nm. Activity against HSP90α and Hsp90β can be compared to determine the specificity, if any, of the inhibitor. Such assays allow for direct comparison of activity of inhibitors against each of the HSP90 isoforms.

Alternatively, inhibition of Hsp90 activity can be determined in a competitive binding assay. Geldanamycin is known to interact with the ATP-binding site of Hsp90α or Hsp90β and can be readily displaced by other Hsp90 inhibitors. The determination of the displacement is facilitated by labeling geldanamycin either fluorescently or non-fluorescently. An exemplary competitive binding assay using fluorescently-labeled geldanamycin is described in Yin, et al., Int J Cancer. 2010 Mar. 1; 126(5):1216-25 (incorporated herein by reference). Briefly, a FITC-geldanamycin probe is first reduced with TCEP at room temperature for 3 h, after which the solution is aliquoted and stored at −80° C. until used. Recombinant human Hsp90α or Hsp90β and reduced FITC-geldanamycin are incubated in a 96-well microplate at room temperature for 3 h in the presence of assay buffer containing 20 mM HEPES (pH 7.4), 50 mM KCl, 5 mM MgCl$_2$, 20 mM Na$_2$MoO$_4$, 2 mM DTT, 0.1 mg/mL BGG, and 0.1% (v/v) CHAPS. As a negative control, Hsp90 protein is not included in the preincubation. Following this preincubation, a test compound (as a competitor) in a solvent is then added to final concentrations of 0.2 nM to 10 μM (final volume 100 μL). As a positive control, a non-labeled geldanamycin is used as a competitor. As a negative control, neither a test compound nor non-labeled geldanamycin is added. The reaction is incubated for 16 h at room temperature and fluorescence is then measured in an Analyst plate reader, excitation=485 nm, emission=535 nm. High and low controls contained no compound or no Hsp90, respectively. The data are fit to a four-parameter curve using GraphPad Prism and IC$_{50}$ values are generated. The IC$_{50}$ values are converted into inhibition constants (Ki) using the modified Cheng-Prusoff equation as described in, e.g., Machida, et al., Cancer Sci 2005; 96:911-17 (31). Activity against HSP90α and Hsp90β can be compared to determine the specificity, if any, of the inhibitor.

Alternatively, HSP90 activity can be assayed in cells that express only a single HSP90 isoform is present (e.g., yeast, *C. elegans*, or mammalian cells expressing only HSP90α or HSP90β). Inhibition of folding and/or stability of a client protein of both isoforms of HSP90 is assayed to determine the relative activities of the inhibitors. As used herein, a "nucleic acid" inhibitor of HSP90 is any nucleic acid based inhibitor that causes a decrease in the expression of an HSP90 by hybridizing with at least a portion of the RNA transcript from the HSP90AA1 and/or HSP90AB1 gene to result in a decrease in the expression of the HSP90α or HSP90β. Nucleic acid inhibitors include, for example, single stranded nucleic acid molecules, e.g., antisense nucleic acids, and double stranded nucleic acids such as siRNA, shRNA, dsiRNA (see, e.g., US Patent publication 20070104688). As used herein, double stranded nucleic acid molecules are designed to be double stranded over at least 12, preferably at least 15 nucleotides. Double stranded nucleic acid molecules can be a single nucleic acid strand designed to hybridize to itself, e.g., an shRNA. It is understood that a nucleic acid inhibitor of HSP90 can be administered as an isolated nucleic acid. Alternatively, the nucleic acid inhibitor can be administered as an expression construct to produce the inhibitor in the cell. In certain embodiments, the nucleic acid inhibitor includes one or more chemical modifications to improve the activity and/or stability of the nucleic acid inhibitor. Such modifications are well known in the art. The specific modifications to be used will depend, for example, on the type of nucleic acid inhibitor.

As used herein, an "antibody" is a protein that includes at least one complementary determining region that binds to a specific target antigen. An antibody frequently includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')2, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda. In one embodiment, the antibody is glycosylated. For example, an antibody can be a polyclonal antibody, a monoclonal antibody, a modified antibody, a chimeric antibody, a reshaped antibody, a humanized antibody, a Fab fragment, a F(ab')2 fragment, a Fd fragment, a Fv fragment, a dAb fragment, single chain Fv, a dimerized variable region (V region) fragment (diabody), a disulfide-stabilized V region fragment (dsFv), affibodies, antibody mimetics, and one or more isolated complementarity determining regions (CDR) that retain specific binding to the payload. As used herein, an "isolated" CDR is a CDR not in the context of a naturally occurring antibody. The antibody can be any immunoglobulin type, e.g, IgG, IgM, IgA1, IgA2, IgD, or IgE. In an embodiment, the antibody can be a human antibody.

As used herein, a "small molecule" inhibitor is an inhibitor molecule that has a molecular weight of less than 1000 Da, preferably less than 750 Da, or preferably less than 500 Da. In certain embodiments, a small molecule does not include a nucleic acid molecule. In certain embodiments, a small molecule does not include a peptide more than three amino acids in length.

As used herein, for the sake of simplicity, a change or modulation in the expression or activity, i.e., increase or decrease, of an HSP90, e.g., HSP90α and/or HSP90β, expression or activity is understood to include a change in expression or activity of the gene and/or the protein. In an embodiment, expression or activity is reduced by at least about 10%, 20%, 30%, 40%, 50%, 60%, 70%, 75%, 80%, 85%, 90%, 95%, or 99%.

As used herein, a change in HSP90 "activity" can be detected, for example, by detecting a change in the ATP hydrolysis activity of HSP90, e.g., HSP90α and/or HSP90β, by detecting a change in the folding of client proteins of the specific HSP90. Methods for detection of ATP hydrolysis are well known in the art. Folding of client proteins can be assessed, for example, by determining the amount of a client protein present in the sample or by determining the activity of the client protein in the sample when the client protein is a signaling protein that has enzymatic activity, e.g., kinase activity. Kits to assay HSP90α and HSP90β activity are also commercially available (e.g., from BPS Bioscience).

As used herein, a subject suffering from "metabolic syndrome" is intended to refer to a subject having one or more of the following conditions: type 2 diabetes, insulin resistance, insulin insufficiency, obesity, hyperinsulinemia, or impaired glucose tolerance (IGT); or as having three or more of the following signs of metabolic syndrome.
 a) Blood pressure equal to or higher than 130/85 mmHg;
 b) Fasting blood glucose equal to or higher than 100 mg/dL;
 c) Large waist circumference wherein a large waist circumference is 40 inches or more for men and 35 inches or more for women;
 d) Low HDL cholesterol wherein low LDH cholesterol is under 40 mg/dL for men and under 50 mg/dL; and
 e) Triglycerides equal to or higher than 150 mg/dL.

Methods to diagnose the indicated conditions and to detect the indicated signs of metabolic syndrome are routine in the art. In certain embodiments, metabolic syndrome further includes type 1 diabetes. In certain embodiments, metabolic syndrome does not include type 1 diabetes. Associated diseases and signs include hyperuricemia, fatty liver (especially in concurrent obesity) progressing to non-alcoholic fatty liver disease (NAFLD), polycystic ovarian syndrome (in women), and acanthosis nigricans. In certain embodiments, the invention includes treatment of one or more of these associated diseases or signs. In certain embodiments, the invention does not include treatment of one or more of these associated diseases or signs.

As used herein, "diabetes" is intended to refer to either type 1 diabetes or type 2 diabetes, or both type 1 and type 2 diabetes, optionally in combination with gestational diabetes. In certain embodiments, diabetes includes type 2 diabetes. In certain embodiments, diabetes does not include type 1 diabetes. In certain embodiments, diabetes includes gestational diabetes. In certain embodiments, diabetes does not include gestational diabetes. In certain embodiments, diabetes includes pre-diabetes. In certain embodiments, diabetes does not include pre-diabetes. In certain embodiments, diabetes includes pre-diabetes, type 1 diabetes, and type 2 diabetes. In certain embodiments, diabetes includes pre-diabetes and type 2 diabetes.

As used herein, "insulin resistance" and "insulin insensitivity" can be used interchangeably and refers to conditions wherein the amount of insulin is less effective at lowering blood sugar than in a normal subject resulting in an increase in blood sugar above the normal range that is not due to the absence of insulin. Without being bound by mechanism, the conditions are typically associated with a decrease in signaling through the insulin receptor. Typically, insulin resistance in muscle and fat cells reduces glucose uptake and storage as glycogen and triglycerides, respectively. Insulin resistance in liver cells results in reduced glycogen synthesis and a failure to suppress glucose production and release into the blood.

Insulin resistance is often present in the same subject together with "insulin insufficiency", which also results in an increase in blood sugar above the normal range that is not due to the absence of insulin. Insulin insufficiency is a condition related to a lack of insulin action in which insulin is present and produced by the body. It is distinct from type 1 diabetes in which insulin is not produced due to the lack of islet cells.

For the purposes of determining if a subject has metabolic syndrome, it is not important to distinguish if a subject suffers from insulin resistance, insulin insufficiency, or both.

As used herein, "obesity" can be defined using any clinically relevant definitions. For example, in adults, body mass index (BMI, $kg/m^2$) is frequently used as a measure of overweight and obesity, with overweight being defined as a BMI 25-29.9 $kg/m^2$, obesity as a BMI equal to or greater than 30 $kg/m^2$, and morbid obesity being defined as BMIs over 40 $kg/m^2$. Obesity can also be defined in adults by central adiposity as measured by waist circumference, with raised waist circumference defined as equal to or greater than 102 cm in men and equal to or greater than 88 cm in women. Treatment of obesity does not require a decrease of BMI or waist circumference to normal levels. Instead, treatment preferably includes a decrease of at least 2%, at least 3%, at least 4%, at least 5%, at least 7%, at least 10%, at least 15%, at least 20%, 30%, 40%, 50%, 60%, 70%, or more of the excess BMI value or excess waist circumference over an upper normal limit for the subject. For example a woman with a waist circumference of 100 cm would have an excess waist circumference of 12 cm (100 cm–88 cm). Reduction of the excess by 20% would be a 2.4 cm reduction.

"Hyperinsulinemia" is defined as the condition in which a subject with insulin resistance, with or without euglycemia, in which the fasting or postprandial serum or plasma insulin concentration is elevated above that of normal, lean individuals without insulin resistance (i.e., >100 mg/dl in a fasting plasma glucose test or >140 mg/dl in an oral glucose tolerance test), further having a waist-to-hip ratio <1.0 (for men) or <0.8 (for women).

The term "impaired glucose tolerance" (IGT) or "pre-diabetes" is used to describe a person who, when given a glucose tolerance test, has a blood glucose level that falls between normal and hyperglycemic. Such a person is at a higher risk of developing diabetes although they are not considered to have diabetes. For example, impaired glucose tolerance refers to a condition in which a patient has a fasting blood glucose concentration or fasting serum glucose concentration greater than 110 mg/dl and less than 126 mg/dl (7.00 mmol/L), or a 2 hour postprandial blood glucose or serum glucose concentration greater than 140 mg/dl (7.78 mmol/L) and less than 200 mg/dl (11.11 mmol/L). Mounting evidence suggests that the pre-diabetes condition may be a risk factor for developing cardiovascular disease (Diabetes Care 26:2910-2914, 2003). Prediabetes, also referred to as impaired glucose tolerance or impaired fasting glucose is a major risk factor for the development of type 2 diabetes mellitus, cardiovascular disease and mortality. Much focus has been given to developing therapeutic interventions that prevent the development of type 2 diabetes by effectively treating prediabetes (Pharmacotherapy, 24:362-71, 2004).

The condition of "hyperglycemia" (high blood sugar) is a condition in which the blood glucose level is too high. Typically, hyperglycemia occurs when the blood glucose level rises above 180 mg/dl. Symptoms of hyperglycemia include frequent urination, excessive thirst and, over a longer time span, weight loss.

The condition of "hypoglycemia" (low blood sugar) is a condition in which the blood glucose level is too low. Typically, hypoglycemia occurs when the blood glucose level falls below 70 mg/dl. Symptoms of hypoglycemia include moodiness, numbness of the extremities (especially in the hands and arms), confusion, shakiness or dizziness. Since this condition arises when there is an excess of insulin over the amount of available glucose it is sometimes referred to as an insulin reaction.

As used herein, an "HbA1c level" is understood as a hemoglobin A1c (HbA1c) level determined from an HbA1c test, which assesses the average blood glucose levels during the previous two and three months, may be employed. A person without diabetes typically has an HbA1c value that ranges between 4% and 6%. Prediabetes is characterized by an HbA1c level of 5.7% to 6.5%, with an Hb1Ac level greater than 6.5% being indicative of diabetes. For every 1% increase in HbA1c, blood glucose levels increases by approximately 30 mg/dL and the risk of complications due to persistent elevated blood glucose increases. Preferably, the HbA1c value of a patient being treated according to the present invention is reduced to less than 9%, less than 7%, less than 6%, and most preferably to around 5%. Thus, the excess HbA1c level of the patient being treated (i.e., the Hb1Ac level in excess of 5.7%) is preferably lowered by at least 10%, 20%, 30%, 40%, 50%, 60%, 70%, 80%, 90%, or more relative to such levels prior to treatment.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refer, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state. As used herein, treatment can include one or more of reduction of insulin resistance, increasing insulin sensitivity, decreasing insulin deficiency, improving or normalizing HbAc1 levels, improving or normalizing blood glucose levels, reducing body weight, reducing waist measurement, normalizing or reducing HDL levels, normalizing or reducing triglyceride levels, and ameliorating at least one sign or symptom of diabetes. Treatment does not need to be curative. Treatment outcomes need not be determined quantitatively. However, in certain embodiments, treatment outcomes can be quantitated by considering percent improvement towards a normal value at the end of a range. For example, metabolic syndrome is characterized by an excess of some measures (e.g., weight/BMI, waist circumference, triglyceride levels) and a deficiency in other measures (e.g., a deficiency in HDL cholesterol or insulin response). A woman with a waist circumference of 100 cm would have an excess waist circumference of 12 cm (100 cm−88 cm, the maximum normal waist circumference). Reduction of the excess waist circumference by 20% would be a 2.4 cm reduction in excess waist circumference. Similar calculations can be made for other values. A man with an HDL of 30 mg/dl would have a deficiency of 20 mg/dl (normal value for men is at least 50 mg/dl). An increase of 5 mg/dl to 25 mg/dl would be considered to reduce the deficiency of HLD by 25%.

As used herein, "reducing glucose levels" means reducing the elevated level of glucose by at least 10%, 20%, 30%, 40%, 50%, 60%, 70%, 80%, 90%, 95%, or more to achieve a normalized glucose level, i.e., a glucose level no greater than 150 mg/dl. Desirably, glucose levels are reduced to normoglycemic levels, i.e., between 150 to 60 mg/dL, between 140 to 70 mg/dL, between 130 to 70 mg/dL, between 125 to 80 mg/dL, and preferably between 120 to 80 mg/dL. Such reduction in glucose levels may be obtained by increasing any one of the biological activities associated with the clearance of glucose from the blood. Accordingly, an agent having the ability to reduce glucose levels may increase insulin production, secretion, or action. Insulin action may be increased, for example, by increasing glucose uptake by peripheral tissues and/or by reducing hepatic glucose production. Alternatively, the agent of the invention may reduce the absorption of carbohydrates from the intestines, alter glucose transporter activity (e.g., by increasing GLUT4 expression, intrinsic activity, or translocation), increase the amount of insulin-sensitive tissue (e.g., by increasing muscle cell or adipocyte cell differentiation), or alter gene transcription in adipocytes or muscle cells (e.g., altered secretion of factors from adipocytes expression of metabolic pathway genes). Desirably, the agent of the invention increases more than one of the activities associated with the clearance of glucose.

By "reducing lipid levels" is meant reducing the level of excess lipids by at least 1%, 5%, 10%, 20%, 30%, 40%, 50%, 60%, 70%, 80%, 90%, 95%, or more to achieve a normal lipid level, i.e., no greater than 150 mg/dl.

By "alter insulin signaling pathway such that glucose levels are reduced" is meant to alter (by increasing or reducing) any one of the activities involved in insulin signaling such that the overall result is an increase in the clearance of glucose from plasma. For example, altering the insulin signaling pathway thereby causing an increase in insulin production, secretion, or action, an increasing glucose uptake by peripheral tissues, a reducing hepatic glucose production, or a reducing the absorption of carbohydrates from the intestines.

A "therapeutically effective amount" is that amount sufficient to treat a disease in a subject. A therapeutically effective amount can be administered in one or more administrations.

By "diagnosing" and the like, as used herein, refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. Diagnostic methods provide an indicator that a disease is or is not present. A single diagnostic test typically does not provide a definitive conclusion regarding the disease state of the subject being tested.

As used herein, "monitoring" is understood as assessing at least one sign or symptom of a disease in a subject at a first time point and at a later second time point, comparing the severity of the sign(s) or symptom(s) of the condition, and determining of the condition became more or less severe over time.

The terms "administer", "administering" or "administration" include any method of delivery of a pharmaceutical composition or agent into a subject's system or to a particular region in or on a subject. In certain embodiments, the agent is administered enterally or parenterally. In certain embodiments of the invention, an agent is administered intravenously, intramuscularly, subcutaneously, intradermally, intranasally, orally, transcutaneously, or mucosally. In certain preferred embodiments, an agent is administered intravenously. In certain embodiments, the agent is administered locally or systemically. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, etc.

The term "sample" as used herein refers to a collection of similar fluids, cells, or tissues isolated from a subject. The term "sample" includes any body fluid (e.g., urine, serum, blood fluids, lymph, gynecological fluids, cystic fluid, ascetic fluid, ocular fluids, and fluids collected by bronchial lavage and/or peritoneal rinsing), ascites, tissue samples (e.g., tumor samples) or a cell from a subject. Other subject samples include tear drops, serum, cerebrospinal fluid, feces, sputum, and cell extracts. In a particular embodiment, the sample is urine or serum. In another embodiment, the sample does not include ascites or is not an ascites sample. In one embodiment, the sample comprises cells. In another embodiment, the sample does not comprise cells.

The term "control sample," as used herein, refers to any clinically relevant comparative sample, including, for example, a sample from a healthy subject not afflicted with metabolic syndrome or a sample from a subject from an earlier time point, e.g., prior to treatment, at an earlier stage of treatment. A control sample can be a purified sample, protein, and/or nucleic acid provided with a kit. Such control samples can be diluted, for example, in a dilution series to allow for quantitative measurement of analytes in test samples. A control sample may include a sample derived from one or more subjects. A control sample may also be a sample made at an earlier time point from the subject to be assessed. For example, the control sample could be a sample taken from the subject to be assessed before the onset of metabolic syndrome, at an earlier stage of disease, or before the administration of treatment or of a portion of treatment. The control sample may also be a sample from an animal model, or from a tissue or cell lines derived from the animal model of metabolic syndrome. The level of HSP90, e.g., HSP90α and/or HSP90β, activity or expression in a control sample that consists of a group of measurements may be determined, e.g., based on any appropriate statistical measure, such as, for example, measures of central tendency including average, median, or modal values.

The term "control level" refers to an accepted or predetermined level of a sign of a metabolic disorder in a subject or a subject sample. The following levels are considered to be normal levels:

Blood pressure less than or equal to 120/80 mmHG
Fasting blood glucose less than or equal to 100 mg/dl.
Waist cirucumference, less than 40 inches (102 cm) for men and less than 35 inches (88 cm) for women.
HDL at least 50 mg/dl for women, at least 40 mg/dl for men.
Triglycerides less than or equal to 150 mg/dl.
HbA1c less than or equal to 5.7%.
Oral glucose tolerance test less than or equal to 140 mg/dl.

As used herein, the term "obtaining" is understood to refer to manufacturing, purchasing, or otherwise coming into possession of.

As used herein, "detecting", "detection" and the like are understood to refer to an assay performed for identification of a specific analyte in a sample, e.g., an HSP90, e.g., HSP90α and/or HSP90β, expression or activity level in a sample. The amount of analyte or activity detected in the sample can be none or below the level of detection of the assay or method.

The terms "modulate" or "modulation" refer to upregulation (i.e., activation or stimulation), downregulation (i.e., inhibition or suppression) of a level, or the two in combination or apart. A "modulator" is a compound or molecule that modulates, and may be, e.g., an agonist, antagonist, activator, stimulator, suppressor, or inhibitor.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

As used herein, "level of activity" is understood as the amount of protein activity, typically enzymatic activity, as determined by a quantitative, semi-quantitative, or qualitative assay. Activity is typically determined by monitoring the amount of product produced in an assay using a substrate that produces a readily detectable product, e.g., colored product, fluorescent product, or radioactive product. The specific assay performed depends, for example, on the activity to be measured.

As used herein, a "muscle targeting moiety" refers to a moiety or molecule capable of increasing delivery of a payload (e.g., ASO) to a muscle cell. A muscle targeting moiety includes, at least, a muscle targeting peptide (MTP), for example a smooth muscle targeting peptide or a skeletal muscle targeting peptide. As used herein, a "smooth muscle targeting peptide" or "SMTP" is understood as a peptide sequence that increases the delivery of its payload (e.g., Hsp90ab1 inhibitor targeting ASO or siRNA) to a muscle cell. MTPs are known in the art and are provided, for example, in U.S. Pat. No. 6,329,501 and US Patent Publication No. 20110130346, both of which are incorporated herein in their entirety. Muscle targeting peptides include, but are not limited to peptides comprising the following sequences: ASSLNIA (SEQ ID NO: 57); WDANGKT (SEQ ID NO: 58); GETRAPL (SEQ ID NO: 59); CGHHPVYAC (SEQ ID NO: 60); and HAIYPRH (SEQ ID NO: 61). In a preferred embodiment, the MTP comprises the amino acid sequence ASSLNIA (SEQ ID NO: 57). In one embodiment, a muscle targeting moiety includes creatine.

As used herein, "payload" is understood as a moiety for delivery to a target cell by a targeting moiety. In certain embodiments, the payload is a Hsp90ab1 inhibitor (e.g., Hsp90ab1 inhibitor targeting ASO or siRNA). In certain embodiments, the payload further comprises additional components (e.g., dendrimers, liposomes, microparticles) or agents (e.g., therapeutic agents) for delivery with the Eno1 payload to the target cell.

As used herein, a "linker" is understood as a moiety that juxtaposes a targeting moiety and a payload in sufficiently close proximity such that the payload is delivered to the desired site by the targeting moiety. In certain embodiments, the linker is a covalent linker, e.g., a cross-linking agent including a reversible cross-linking agent; a peptide bond. In certain embodiments, the linker is covalently joined to one of the payload or the targeting moiety and non-covalently linked to the other. In certain embodiments, the linker comprises a dendrimer. In certain embodiments, the dendrimer is covalently linked to the targeting moiety and non-covalently linked to the payload, e.g., an antisense oligonucleotide. In certain embodiments, the linker is a liposome or a microparticle, and the targeting moiety is exposed on the surface of the liposome and the payload, e.g., an antisense oligonucleotide is encapsulated in the liposome or microparticle. In certain embodiments, the linker and the ASO are present on the surface of the microparticle.

As used herein, "linked", "operably linked", "joined" and the like refer to a juxtaposition such that the components described are present in a complex permitting them to function in their intended manner. The components can be linked covalently (e.g., peptide bond, disulfide bond, non-natural chemical linkage), through hydrogen bonding (e.g., knob-into-holes pairing of proteins, see, e.g., U.S. Pat. No. 5,582,996; Watson-Crick nucleotide pairing), or ionic binding (e.g., chelator and metal) either directly or through linkers (e.g., peptide sequences, typically short peptide sequences; nucleic acid sequences; or chemical linkers, including the use of linkers for attachment to higher order or larger structures including microparticles, beads, or dendrimers). As used herein, components of a complex can be linked to each other by packaging in and/or on a liposome and/or dendrimer wherein some of the components of the complex can be attached covalently and some non-covalently. Linkers can be used to provide separation between active molecules so that the activity of the molecules is not substantially inhibited (less than 10%, less than 20%, less than 30%, less than 40%, less than 50%) by linking the first molecule to the second molecule. Linkers can be used, for example, in joining an antisense oligonucleotide to a targeting moiety. As used herein, molecules that are linked, but not covalently joined, have a binding affinity (Kd) of less than $10^{-3}$, $10^{-4}$, $10^{-5}$, $10^{-6}$, $10^{-7}$, $10^{-8}$, $10^{-9}$, $10^{-10}$, $10^{-11}$, or $10^{-12}$, or any range bracketed by those values, for each other under conditions in which the reagents of the invention are used, i.e., typically physiological conditions.

A number of chemical linkers are known in the art and available from commercial sources (e.g., Pierce Thermo Fisher Scientific Inc., see, e.g., www.piercenet.com/cat/crosslinking-reagents). Such agents can be used to chemically link, reversibly or irreversibly, one or more targeting moieties to ASO1. Linkers can also be used to attach targeting moieties and ASO to a structure, e.g., microparticle, dendrimer, rather than attaching the targeting moiety directly to ASO. In certain embodiments, the linker attaching ASO to the targeted complex is reversible so that the ASO is released from the complex after administration, preferably substantially at the muscle.

In certain embodiments, the payload, e.g., an antisense oligonucleotide and the targeting moiety are present in a complex at about a 1:1 molar ratio. In certain embodiments, the targeting moiety is present in a complex with a molar excess of the payload (e.g., 2:1, 3:1, 4:1, 5:1, 6:1, 7:1; 8:1, 9:1, 10:1, 11:1, 12:1, 13:1, 14:1, 15:1, 16:1, 17:1; 18:1, 19:1, 20:1, 21:1, 22:1, 23:1, 24:1, 25:1, 26:1, 27:1; 28:1, 29:1, 30:1, or more; or any range bracketed by any two values). In certain embodiments, the ratio of payload to targeting moiety is about 0.1:1, about 0.2:1, about 0.3:1, about 0.4:1, about 0.5:1, about 0.6:1, about 0.7:1, about 0.8:1, about 0.9:1, about 1:1, about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1.

It is understood that the compositions and methods of the invention include the administration of more than one, i.e., a population of, targeting moiety-payload complexes. Therefore, it is understood that the number of targeting moieties per payload can represent an average number of targeting moieties per payload in a population of complexes. In certain embodiments, at least 70% of the complexes have the selected molar ratio of targeting moieties to payload. In certain embodiments, at least 75% of the complexes have the selected molar ratio of targeting moieties to payload. In certain embodiments, at least 80% of the complexes have the selected molar ratio of targeting moieties to payload. In certain embodiments, at least 85% of the complexes have the selected molar ratio of targeting moieties to payload. In certain embodiments, at least 90% of the complexes have the selected molar ratio of targeting moieties to payload.

The term "pharmaceutically acceptable carrier" refers to a carrier for administration of a therapeutic agent. Such carriers include, but are not limited to, saline, buffered saline, dextrose, water (e.g. water suitable for injection or sterile water), glycerol, ethanol, and combinations thereof.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical group(s) in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

I. Metabolic Syndrome

Metabolic syndrome (Syndrome X) is a name for a group of risk factors that occur together and increase the risk for coronary artery disease, stroke, and type 2 diabetes (www.ncbi.nlm.nih.gov/pubmedhealth/PMH0004546/). Metabolic syndrome is becoming more and more common in the United States. Researchers are not sure whether the syndrome is due to one single cause, but all of the risks for the syndrome are related to obesity. As used herein, metabolic syndrome is understood to include insulin resistance, insulin insufficiency, pre-diabetes, type 2 diabetes, and obesity. A subject who meets the diagnostic criteria below is also understood as having metabolic syndrome. In some embodiments of the invention, metabolic syndrome can also include type 1 diabetes. In other embodiments, metabolic syndrome does not include type 1 diabetes.

The two most important risk factors for metabolic syndrome are extra weight around the middle and upper parts of the body (central obesity) and insulin resistance, in which the body cannot use insulin effectively. Insulin controls the amount of sugar in the body. In subjects in which the body does not produce enough insulin and/or the body does not respond to the level of insulin that is produce, blood sugar and fat levels rise. Other risk factors for metabolic syndrome include aging, genetic factors, hormone changes, and a sedentary lifestyle. People with metabolic syndrome frequently suffer from one or both of excessive blood clotting and low levels of systemic inflammation, both of which can exacerbate the condition.

The American Heart Association and the National Heart, Lung, and Blood Institute, consider metabolic syndrome to be present in subjects having three or more of the following signs:

Blood pressure equal to or higher than 130/85 mmHg
Fasting blood sugar (glucose) equal to or higher than 100 mg/dL
Large waist circumference (length around the waist):
  Men—40 inches or more
  Women—35 inches or more
Low HDL cholesterol:
  Men—under 40 mg/dL
  Women—under 50 mg/dL
Triglycerides equal to or higher than 150 mg/dL Treatment includes recommended lifestyle changes or medicines to help reduce blood pressure, LDL cholesterol, and blood sugar, e.g., lose weight, increase exercise. Blood pressure and cholesterol may also be regulated using appropriate drugs.

In addition to having an increased long-term risk for developing cardiovascular disease and type 2 diabetes, complications of metabolic syndrome further include atherosclerosis, heart attack, kidney disease, non-alcoholic fatty liver disease, peripheral artery disease, and stroke, as well as complications typically associated with diabetes.

A. Diabetes, Insulin Resistance, and Insulin Insufficiency

Diabetes mellitus (DM), often simply referred to as diabetes, is a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger).

Type 2 diabetes results from insulin resistance, a condition in which cells fail to use insulin properly, sometimes combined with an absolute insulin deficiency. The defective responsiveness of body tissues to insulin is believed, at least in part, to involve the insulin receptor. However, the specific defects are not known.

In the early stage of type 2 diabetes, the predominant abnormality is reduced insulin sensitivity. At this stage, hyperglycemia can be reversed by a variety of measures and medications that improve insulin sensitivity or reduce glucose production by the liver. Prediabetes indicates a condition that occurs when a person's blood glucose levels are higher than normal but not high enough for a diagnosis of type 2 diabetes.

Type 2 diabetes is due to insufficient insulin production from beta cells in the setting of insulin resistance. Insulin resistance, which is the inability of cells to respond adequately to normal levels of insulin, occurs primarily within the muscles, liver and fat tissue. In the liver, insulin normally suppresses glucose release. However in the setting of insulin resistance, the liver inappropriately releases glucose into the blood. The proportion of insulin resistance verses beta cell dysfunction differs among individuals with some having primarily insulin resistance and only a minor defect in insulin secretion and others with slight insulin resistance and primarily a lack of insulin secretion.

Other potentially important mechanisms associated with type 2 diabetes and insulin resistance include: increased breakdown of lipids within fat cells, resistance to and lack of incretin, high glucagon levels in the blood, increased retention of salt and water by the kidneys, and inappropriate regulation of metabolism by the central nervous system. However not all people with insulin resistance develop diabetes, since an impairment of insulin secretion by pancreatic beta cells is also required.

Type 1 diabetes results from the body's failure to produce insulin, and presently requires treatment with injectable insulin. Type 1 diabetes is characterized by loss of the insulin-producing beta cells of the islets of Langerhans in the pancreas, leading to insulin deficiency. Most affected people are otherwise healthy and of a healthy weight when onset occurs. Sensitivity and responsiveness to insulin are usually normal, especially in the early stages. However, particularly in late stages, insulin resistance can occur.

B. Secondary Pathologies of Diabetes, Insulin Resistance, and Insulin Insufficiency Abnormal glucose regulation resulting from diabetes, both type 1 and type 2, insulin resistance, and insulin insufficiency are associated with secondary pathologies, many of which result from poor circulation. Such secondary pathologies include macular degeneration, peripheral neuropathies, ulcers and decrease wound healing, and decreased kidney function. It has been suggested that maintaining glucose levels and/or HbAc1 levels within normal ranges decreases the occurrence of these secondary pathologies. It is understood that normalization of blood glucose, insulin, and Hb1Ac levels will reduce the development of secondary pathologies by limiting the primary pathology, e.g., metabolic syndrome. In certain embodiments, HSP90 inhibitors, especially HSP90β inhibitors and HSP90β specific inhibitors, are not used for the treatment of secondary pathologies associated with diabetes and metabolic syndromes. In certain embodiments, HSP90 inhibitors, especially HSP90β inhibitors and HSP90β specific inhibitors, are used for the treatment of secondary pathologies associated with diabetes and metabolic syndromes.

II. Dosages and Modes of Administration

Techniques and dosages for administration vary depending on the type of compound (e.g., chemical compound, antibody, or nucleic acid) and are well known to those skilled in the art or are readily determined.

Therapeutic compounds of the present invention may be administered with a pharmaceutically acceptable diluent, carrier, or excipient, in unit dosage form. Administration may be parenteral, intravenous, subcutaneous, oral, topical, or local. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc; or for delivery by a trained professional, e.g., intravenous delivery, intramuscular delivery, intratumoral delivery, etc.

The composition can be in the form of a pill, tablet, capsule, liquid, or sustained release tablet for oral administration; or a liquid for intravenous, subcutaneous, or parenteral administration; or a polymer or other sustained release vehicle for local administration.

Methods well known in the art for making formulations are found, for example, in "Remington: The Science and Practice of Pharmacy" (20th ed., ed. A. R. Gennaro, 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The compound may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids and the like; polymeric acids such as tannic acid, carboxymethyl cellulose, and the like; and inorganic acid such as hydrochloric acid, hydrobromic acid, sulfuric acid phosphoric acid, and the like. Metal complexes include zinc, iron, and the like.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The dosage and the timing of administering the compound depend on various clinical factors including the overall health of the subject and the severity of the symptoms of disease, e.g., diabetes, metabolic syndrome.

III. Nucleic Acid Therapeutics

Nucleic acid therapeutics are well known in the art. Nucleic acid therapeutics include both single stranded and double stranded (i.e., nucleic acid therapeutics having a complementary region of at least 15 nucleotides in length) nucleic acids that are complementary to a target sequence in a cell. Nucleic acid therapeutics can be delivered to a cell in culture, e.g., by adding the nucleic acid to culture media either alone or with an agent to promote uptake of the nucleic acid into the cell. Nucleic acid therapeutics can be delivered to a cell in a subject, i.e., in vivo, by any route of administration. The specific formulation will depend on the route of administration.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs as is common in double stranded nucleic acid therapeutics, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between an antisense nucleic acid or the antisense strand of dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding HSP90, especially HSP90β) including a 5' UTR, an open reading frame (ORF), or a 3' UTR. For example, a polynucleotide is complementary to at least a part of a HSP90, especially HSP90β mRNA if the sequence is substantially complementary to a non-interrupted portion of an mRNA encoding HSP90, especially HSP90β.

A. Single Stranded Nucleic Acid Therapeutics

Antisense nucleic acid therapeutic agents are single stranded nucleic acid therapeutics, typically about 16 to 30 nucleotides in length, and are complementary to a target nucleic acid sequence in the target cell, either in culture or in an organism.

In some embodiments, the agent is a single-stranded antisense RNA molecule, a single-stranded antisense DNA molecule, or a single-stranded antisense polynucleotide comprising both DNA and RNA. In a particular embodiment, the antisense molecule is an antisense oligonucleotide (ASO) comprising both DNA and RNA. An antisense molecule is complementary to a sequence within the target mRNA. Antisense molecules can inhibit translation in a stoichiometric manner by base pairing to the mRNA and physically obstructing the translation machinery, see Dias, N. et al., (2002) *Mol Cancer Ther* 1:347-355. The antisense molecule may have about 15-30 nucleotides that are complementary to the target mRNA. For example, the antisense molecule may have a sequence of at least 15, 16, 17, 18, 19, 20, 21, 22, 23, 24 or 25 or more contiguous nucleotides that are complementary to the target mRNA.

In some embodiments, the ASO comprises at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. Any of these values may be used to define a range for the number of nucleotides in the ASO. For example, the ASO may comprise at least 8-50, 15-30, or 20-25 nucleotides. In some embodiments, the ASO consists of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides. Any of these values may be used to define a range for the number of nucleotides in the ASO. For example, the ASO may consist of 8-50, 15-30, or 20-25 nucleotides.

Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. The entire contents of each of the patents listed in this paragraph are incorporated herein by reference. In one aspect of the invention, the agent is a single-stranded antisense nucleic acid molecule (ASO). Antisense oligonucleotides (ASOs) are synthetic molecules approximately 18-21 nucleotides in length and complementary to the mRNA sequence of the target gene. ASOs bind cognate mRNA sequences through sequence-specific hybridization resulting in cleavage or disablement of the mRNA and inhibition of the expression of the target gene (reviewed in Mansoor M and Melemdez M. *Gene Regulation and Systems Biology* 2008:2 275-295).

A1. Modification of ASOs

In certain embodiments, the ASOs of the invention may be modified. A "modified ASO" refers to a molecule in which one or more of the components of the nucleic acid, namely sugars, bases, and phosphate moieties, are different from that which occur in nature, for example, different from that which occurs in the human body. Several modifications to ASOs are described in the art (see for example, FIG. 32). These modifications are aimed at improving ASO properties such as resistance to nucleases, permeability across biological membranes, solubility, stability, or modulation of pharmacokinetic and pharmacodynamics properties while maintaining specificity to the target mRNA. For example, the modifications on the nucleotides can include, but are not limited to, LNA, HNA, CeNA, 2'-methoxyethyl, 2'-O-alkyl, 2'-O-allyl, 2'-C-allyl, 2'-fluoro, 2'-deoxy, 2'-hydroxyl, and combinations thereof.

Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. Each of the patents listed in this paragraph are incorporated herein by reference in their entirety.

1. Modified Bases

Therapeutic nucleic acid may include natural (i.e. A, G, U, C, or T) or modified (e.g. 7-deazaguanosine, inosine, etc.) bases. Modification of bases includes the incorporation of modified bases (or modified nucleoside or modified nucleotides) that are variations of standard bases, sugars and/or phosphate backbone chemical structures occurring in ribonucleic (i.e., A, C, G and U) and deoxyribonucleic (i.e., A, C, G and T) acids. Included within this scope are, for example: Gm (2'-methoxyguanylic acid), Am (2'-methoxyadenylic acid), Cf (2'-fluorocytidylic acid), Uf (2'-fluorouridylic acid), Ar (riboadenylic acid). The aptamers may also include cytosine or any cytosine-related base including 5-methylcytosine, 4-acetylcytosine, 3-methylcytosine, 5-hydroxymethyl cytosine, 2-thiocytosine, 5-halocytosine (e.g., 5-fluorocytosine, 5-bromocytosine, 5-chlorocytosine, and 5-iodocytosine), 5-propynyl cytosine, 6-azocytosine, 5-trifluoromethylcytosine, N4,N4-ethanocytosine, phenoxazine cytidine, phenothiazine cytidine, carbazole cytidine or pyridoindole cytidine. The aptamer may further include guanine or any guanine-related base including 6-methylguanine, 1-methylguanine, 2,2-dimethylguanine, 2-methylguanine, 7-methylguanine, 2-propylguanine, 6-propylguanine, 8-haloguanine (e.g., 8-fluoroguanine, 8-bromoguanine, 8-chloroguanine, and 8-iodoguanine), 8-aminoguanine, 8-sulfhydrylguanine, 8-thioalkylguanine, 8-hydroxylguanine, 7-methylguanine, 8-azaguanine, 7-deazaguanine or 3-deazaguanine. The aptamer may still further include adenine or any adenine-related base including 6-methyladenine, N6-isopentenyladenine, N6-methyladenine, 1-methyladenine, 2-methyladenine, 2-methylthio-N6-isopentenyladenine, 8-haloadenine (e.g., 8-fluoroadenine, 8-bromoadenine, 8-chloroadenine, and 8-iodoadenine), 8-aminoadenine, 8-sulfhydryladenine, 8-thioalkyladenine, 8-hydroxyladenine, 7-methyladenine, 2-haloadenine (e.g., 2-fluoroadenine, 2-bromoadenine, 2-chloroadenine, and 2-iodoadenine), 2-aminoadenine, 8-azaadenine, 7-deazaadenine or 3-deazaadenine. Also included are uracil or any uracil-related base including 5-halouracil (e.g., 5-fluorouracil, 5-bromouracil, 5-chlorouracil, 5-iodouracil), 5-(carboxyhydroxylmethyl)uracil, 5-carboxymethylaminomethyl-2-thiouracil, 5-carboxymethylaminomethyluracil, dihydrouracil, 1-methylpseudouracil, 5-methoxyaminomethyl-2-thiouracil, 5'-methoxycarbonylmethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid, pseudouracil, 5-methyl-2-thiouracil, 2-thiouracil, 3-(3-amino-3-N-2-carboxypropyl)uracil, 5-methylaminomethyluracil, 5-propynyl uracil, 6-azouracil, or 4-thiouracil.

Examples of other modified base variants known in the art include, without limitation, e.g., 4-acetylcytidine, 5-(carboxyhydroxylmethyl)uridine, 2'-methoxycytidine, 5-carboxymethylaminomethyl-2-thioridine, 5-carboxymethylaminomethyluridine, dihydrouridine, 2'-O-methylpseudouridine, b-D-galactosylqueosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, b-D-mannosylqueosine, 5-methoxycarbonylmethyluridine, 5-methoxyuridine, 2-methylthio-N6-isopentenyladenosine, N-((9-b-D-ribofuranosyl-2-methylthiopurine-6-yl)carbamoyl)threonine, N-((9-b-D-ribofuranosylpurine-6-yl)N-methyl-carbamoyl) threonine, urdine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-b-D-ribofuranosylpurine-6-yl)carbamoyl)threonine, 2'-O-methyl-5-methyluridine, 2'-O-methyluridine, and wybutosine, 3-(3-amino-3-carboxypropyl)uridine.

Also included are the modified nucleobases described in U.S. Pat. Nos. 3,687,808, 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, and 5,681,941, each of which is incorporated herein by reference in its entirety.

2. Modified Sugars

Modified sugar moieties for use in ASOs are well known in the art and are described for example in U.S. Pat. No. 9,045,754 which is incorporated by reference herein in its entirety. Modified sugars can be used to alter, typically increase, the affinity of the ASO for its target and/or increase nuclease resistance. For example, in some embodiments, the binding affinity of the ASOs to their target can be increased by incorporating substituent groups in the nucleoside subunits of the ASOs. In some embodiments, the substituent groups are T substituent groups, substituent groups located at the 2' position of the pentofuranosyl sugar moieties of the nucleoside subunits of the ASOs. Substituent groups include, but are not limited to, fluoro, alkoxy, amino-alkoxy, allyloxy, imidazolylalkoxy and polyethylene glycol. Alkoxy and aminoalkoxy groups generally include lower alkyl groups, particularly $C_1$-$C_9$ alkyl. In a particular embodiment, the 2' substituent group is 2'-O-methyl. Polyethylene glycols are of the structure (O—$CH_2$—$CH_2$)$_n$—O-alkyl. In a particular embodiment, the substituent is a polyethylene glycol substituent of the formula (—O—$CH_2$—$CH_2$)$_n$—O-alkyl, wherein n=1 and alkyl=$CH_3$. This modification has been shown to increase both affinity of an oligonucleotide for its target and nuclease resistance of an oligonucleotide. See U.S. Pat. No. 7,629,321 cited above. A further particularly useful 2'-substituent group for increasing the binding affinity is the 2'-fluoro group.

Examples of modified nucleoside and nucleotide sugar backbone variants known in the art include, without limitation, those having, e.g., 2' ribosyl substituents such as F, SH, $SCH_3$, OCN, Cl, Br, CN, $CF_3$, $OCF_3$, $SOCH_3$, $SO_2$, $CH_3$, $ONO_2$, $NO_2$, $N_3$, $NH_2$, $OCH_2CH_2OCH_3$, $O(CH_2)_2ON$ $(CH_3)_2$, $OCH_2OCH_2N(CH_3)_2$, $O(C_{1-10}$ alkyl), $O(C_{2-10}$ alkenyl), $O(C_{2-10}$ alkynyl), $S(C_{1-10}$ alkyl), $S(C_{2-10}$ alkenyl), S(C2-10 alkynyl), NH(C1-10 alkyl), NH($C_{2-10}$ alkenyl), NH(C2-10 alkynyl), and O-alkyl-O-alkyl. Desirable 2' ribosyl substituents include 2'-methoxy (2'-$OCH_3$), 2'-aminopropoxy (2' $OCH_2CH_2CH_2NH_2$), 2'-O-allyl (2'-$CH_2$—CH=$CH_2$), 2'-O-allyl (2'-O—$CH_2$—CH=$CH_2$), 2'-amino (2'-$NH_2$), and 2'-fluoro (2'-F). The 2'-substituent may be in the arabino (up) position or ribo (down) position.

Another class of modified ASOs known in the art and that may be utilized in the ASOs of the invention contain alkyl modifications at the 2' position of the ribose moiety. These ASOs were developed to improve the binding affinity and hybridization stability with target mRNA, and to increase the nuclease resistance of the ASOs. In this category, the most commonly used ASOs are 2'-O-Methyl (2'-OME) and 2'-O-Methoxyethyl (2'-MOE) ASOs (FIG. 32 middle). ASOs with this type of modification are incapable of activating RNAse H. Therefore, to induce RNAse H activation, chimeric ASOs have been developed in which a central gap region consisting of a phosphorothioate deoxyribose core is flanked with nuclease resistant arms such as 2'-OME or 2'-MOE that possess greater nuclease resistance. A "gapmer" is produced as a result, in which RNAse H can sit in the central gap and activate target specific mRNA degradation, while the arms prevent the ASO degradation. ASOs in this category possess higher affinity for mRNA, show better tissue uptake, and have increased resistance to nucleases, longer in vivo half life, and lesser toxicity, as compared to the modified ASOs of the first class.

A further class of ASOs known in the art and that may be utilized in the ASOs of the invention contain modifications of the furanose ring along with modifications of the phosphate linkage, the ribose moiety, or the nucleotides. These modifications were designed to improve the nuclease stability, target affinity and pharmacokinetic profiles of the ASOs. Common examples of third category of ASOs are Locked nucleic acid (LNA), Peptide nucleic acid (PNA) and Morpholino phosphoroamidates (MF) (FIG. 32 bottom). ASOs in this category are more stable in biological fluids because of their high resistance to degradation by nucleases and peptidases. They also exhibit a strong hybridization affinity with the mRNA. Further, PNAs recognize double stranded DNA, and are able to modulate gene expression or induce mutation by strand invasion of chromosomal duplex DNA. ASOs in this category also do not activate RNAse H and rely on sterically hindering the ribosomal machinery to cause translational arrest. They do not bind to serum proteins as they are uncharged. Lack of charge reduces the odds of non-specific interactions but increases the rate of clearance from the body. Their electrostatically neutral backbones may reduce solubility and make uptake more difficult.

A representative list of preferred modified sugars includes but is not limited to bicyclic modified sugars (BNA's), including methyleneoxy (4'-CH$_2$—O-2') BNA and ethyleneoxy (4'-(CH$_2$)$_2$—O-2' bridge) BNA; substituted sugars, especially 2'-substituted sugars having a 2'-F, 2'-OCH$_3$ or a 2'-O(CH$_2$)$_2$—OCH$_3$ substituent group; and 4'-thio modified sugars. Sugars can also be replaced with sugar mimetic groups among others. Methods for the preparations of modified sugars are well known to those skilled in the art. Some representative patents and publications that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; and 6,600,032; and WO 2005/121371.

3. Modified Internucleotide Linkages

Nucleic acid therapeutics may further comprise at least one phosphorothioate or methylphosphonate internucleotide linkage. The phosphorothioate or methylphosphonate internucleotide linkage modification may occur on any nucleotide of the sense strand or antisense strand or both (in nucleic acid therapeutics including a sense strand) in any position of the strand. For instance, the internucleotide linkage modification may occur on every nucleotide on the sense strand or antisense strand; each internucleotide linkage modification may occur in an alternating pattern on the sense strand or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In certain embodiments, the ASOs of the invention comprise one or more nucleoside subunits connected by phosphorus linkages including phosphodiester, phosphorothioate, 3'(or -5')deoxy-3'-(or -5')thio-phosphorothioate, phosphorodithioate, phosphoroselenates, 3'-(or -5')deoxy phosphinates, borano phosphates, 3'-(or 5'-)amino phosphoramidates, hydrogen phosphonates, borano phosphate esters, phosphoramidates, alkyl or aryl phosphonates and phosphotriester phosphorus linkages. In some embodiments, the ASOs of the invention comprise nucleoside subunits connected by carbonate, carbamate, silyl, sulfur, sulfonate, sulfonamide, formacetal, thioformacetal, oxime, methyleneimino, methylenemethylimino, methylenehydrazo, methylenedimethylhydrazo and methyleneoxymethylimino linkages.

For example, one class of modified ASO described in the art and that may be utilized in the ASOs of the invention are those that have one of the non-bridging oxygen atoms in the phosphate group of the ASO replaced with either a sulfur group (phosphorothioates), a methyl group (methyl phosphonates) or an amine group (phosphoramidates). (FIG. 32 top). These ASOs have greater resistance to nucleases and longer plasma half life as compared with phosphodiester oligonucleotides. They are capable of activating RNAse H, carry negative charges which facilitate their delivery to cells, and have suitable pharmacokinetics. Among these modifications, phosphorothioate modifications are used most widely. For example, Vitravene, an FDA approved ASO drug, and most of the other ASO drugs in clinical trials are phosphorothioate ASOs.

In addition, the bases in nucleotide may be joined by a linkage other than a phosphodiester bond, so long as it does not interfere with hybridization. Thus, inhibitory nucleic acids may be peptide nucleic acids in which the constituent bases are joined by peptide bonds rather than phosphodiester linkages. The inhibitory nucleic acids may be prepared by converting the RNA to cDNA using known methods (see, e.g., Ausubel et. al., Current Protocols in Molecular Biology Wiley 1999). The inhibitory nucleic acids can also be cRNA (see, e.g., Park et. al., (2004) Biochem. Biophys. Res. Commun. 325(4):1346-52).

4. ASO Ligands

A wide variety of ligands can be conjugated to an ASO to improve various properties of the oligonucleotide such as transport, targeting, hybridization, specificity or nuclease resistance. Suitable ligands for ASOs are well known in the art and are described for example, in U.S. Pat. No. 8,796,436, which is incorporated by reference herein in its entirety. Ligands can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics.

Ligands for ASOs can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands for ASOs can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B 12, biotin, or an RGD peptide or RGD peptide mimetic. In a particular embodiment, the cell targeting ligand is selected from the group consisting of N-acetylgalactosamine, RVG-9R peptide, Aptamer, LFA-1 integrin, IGF1 binding peptide, Peptide mimetic of IGF1, Vitamin A coupled liposomes, RGD peptide, asialo-glycoprotein receptor in liver, nicotinic acetycholine in neuronal cells, PSMA, leukocytes, IGF1 receptor, Insulin receptor signaling protein, and GP 46 αVβ3 integrins.

In a particular embodiment, the ligand is a muscle targeting peptide (MTP) selected from the group consisting of ASSLNIA (SEQ ID NO: 57); WDANGKT (SEQ ID NO: 58); GETRAPL (SEQ ID NO: 59); CGHHPVYAC (SEQ ID NO: 60); and HAIYPRH (SEQ ID NO: 61).

In certain embodiments the ligand for the ASO is a protein, e.g., a glycoprotein, or a peptide, e.g., a molecule having a specific affinity for a co-ligand, or an antibody e.g., an antibody, that binds to a specified cell type. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-.kappa.B.

In some embodiments, the ligand is a peptide or peptidomimetic. A peptidomimetic is a molecule capable of folding into a defined three-dimensional structure similar to a natural peptide. The attachment of peptide and peptidomimetics to ASOs can affect pharmacokinetic distribution of the ASO, such as by enhancing cellular recognition and absorption. In some embodiments, the peptide or peptidomimetic moiety is about 5-50 amino acids long, e.g., about 5, 10, 15, 20, 25, 30, 35, 40, 45, or 50 amino acids long.

Peptide and petidomimetic ligands include those having naturally occurring or modified peptides, e.g., D or L peptides; alpha, beta, or gamma peptides; N-methyl peptides; azapeptides; peptides having one or more amide, i.e., peptide, linkages replaced with one or more urea, thiourea, carbamate, or sulfonyl urea linkages; or cyclic peptides.

In a particular embodiment, the peptide ligand is creatine. In a further particular embodiment, creatine is conjugated to the ASO via a disulfide linkage.

In some embodiments the peptide ligand is a "cell penetrating peptide." A "cell penetrating peptide" is capable of permeating a cell, e.g., a human cell. A microbial cell-permeating peptide can be, for example, an alpha-helical linear peptide (e.g., LL-37 or Ceropin P1), a disulfide bond-containing peptide (e.g., alpha-defensin, beta-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003). Suitable cell penetrating peptides include, but are not limited to, Penetratin (R6) (RQIKIW-FQNRRMKWKK-NH2; SEQ ID NO: 53; Derossi et al., 1994, J. Biol. Chem. 269:10444), HIV TAT, Transportan (AGYLLGK*INLKALAALAKKIL-NH2; SEQ ID NO: 54), Oligoarginine (R9) peptide, MPG peptide, KALA peptide, M918 (MVTVLFRRLRIRRACGPPRVRV-NH2; SEQ ID NO: 55), YDEEGGGE-NH2 (SEQ ID NO: 56). Additional cell penetrating peptides are described, for example, in U.S. Pat. No. 8,796,436.

In some embodiments, a targeting peptide conjugated to an ASO can be an amphipathic alpha-helical peptide. Exemplary amphipathic alpha-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, $H_2A$ peptides, *Xenopus* peptides, esculentinis-1, and caerins. A number of factors will be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by +3, or +4 positions can provide stability. For example, cationic residues such as lysine, arginine, homo-arginine, ornithine or histidine can form salt bridges with the anionic residues glutamate or aspartate.

The ligand can be a substance, e.g, a drug, which can increase the uptake of the ASO agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the ASO into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule may bind a serum protein, e.g., human serum albumin (HSA). An HSA binding conjugate allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. In another aspect, the ligand is a cell-permeation agent, such as a helical cell-permeation agent.

In some embodiments, the ligand is a substituted amine, e.g. dimethylamino. In certain embodiments the substituted amine can be rendered cationic, e.g., by quaternization, e.g., protonation or alkylation. In certain embodiments, the substituted amine can be at the terminal position of a relatively hydrophobic chain, e.g., an alkylene chain.

In some embodiments the ligand for the ASO is a nano-carier selected from the group consisting of a cationic polymer complex, a pegylated polycation, a polyethyleneamine (PEI), a dendrimer (e.g. a PEI dendrimer or a PAMAM dendrimer), and a polymer micelle.

In some embodiments the ligand for the ASO is a carbohydrate. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiments, a carbohydrate ligand comprises a monosaccharide. In one embodiment, the monosaccharide is an N-acetylgalactosamine (GalNAc). GalNAc ligands are described, for example, in U.S. Pat. No. 8,106,022, the entire content of which is hereby incorporated herein by reference. In some embodiments, the GalNAc ligand targets the ASO to particular cells.

In some embodiments, the carbohydrate ligand comprises one or more GalNAc derivatives. The GalNAc derivatives may be attached via a linker, e.g., a bivalent or trivalent branched linker. In some embodiments the GalNAc ligand is conjugated to the 3' end of the ASO. In some embodiments, the GalNAc ligand is conjugated to the ASO (e.g., to the 3' end of the ASO) via a linker, e.g., a linker as described herein. Additional carbohydrate ligands are described, for example, in U.S. Patent Application Publication No. 2015/0111841, which is incorporated by reference herein in its entirety.

Other examples of ligands for ASOS include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, glycerol (e.g., esters and ethers thereof, e.g., 1,3-bis-O(hexadecyl) glycerol, 1,3-bis-O(octaadecyl)glycerol), geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

5. ASO Linkers

In some embodiments, a ligand is attached to the ASO through a covalent linker. In some embodiments, the ligand is associated with the ASO by a non-covalent linkage. The ligands may be conjugated to the ASO directly or indirectly via an intervening linker. In some embodiments, the ligand described herein can be attached to the ASO with various linkers that can be cleavable or non-cleavable. Linkers typically comprise a direct bond or an atom such as oxygen or sulfur, a unit such as NRB, C(O), C(O)NH, SO, SO$_2$, SO$_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO$_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms. Linkers for conjugating a ligand to an ASO are described, for example, in U.S. Patent Application Publication No. 2015/0111841.

In a particular embodiment, the linker is a disulphide linker or a maleimide linker.

A2. ASO Sequences

Exemplary ASOs are provided in Table 1 below.

TABLE 1

ASO sequences and exemplary modified* sequences.

| ASO sequence | Exemplary Modified Sequence |
|---|---|
| SEQ ID NO: 75<br>5' UCUCCUTCTC CCGTTCCTUCUCC A 3' | mHsp90ab1_ASO1:(SEQ ID NO: 12)<br>5' mU*mC*mU*mC*mC*mU*T*C*T*C*C*C*G*T*T*C*C*T*mU*mC*mU*mC*mC*mA 3' |
| SEQ ID NO: 76<br>5' AUCUCCTTCT CCCGTTCCUUCUC C 3' | mHsp90ab1_ASO2:(SEQ ID NO: 13)<br>5' mA*mU*mC*mU*mC*mC*T*T*C*T*C*C*C*G*T*T*C*C*mU*mU*mC*mU*mC*mC 3' |
| SEQ ID NO: 77<br>5' ACUUCCTTGA CCCTCCTCUCCUC C 3' | mHsp90ab1_ASO3:(SEQ ID NO: 14)<br>5' mA*mC*mU*mU*mC*mC*T*T*G*A*C*C*C*T*C*C*T*C*mU*mC*mC*mU*mC*mC 3' |
| SEQ ID NO: 78<br>5' CUUCCUTGAC CCTCCTCTCCUCC A 3' | mHsp90ab1_ASO4:(SEQ ID NO: 15)<br>5' mC*mU*mU*mC*mC*mU*T*G*A*C*C*C*T*C*C*T*C*T*mC*mC*mU*mC*mC*mA 3' |
| SEQ ID NO: 79<br>5' CCACUUCCTT GACCCTCCUCUCC U 3' | mHsp90ab1_ASO5:(SEQ ID NO: 16)<br>5' mC*mC*mA*mC*mU*mU*C*C*T*T*G*A*C*C*C*T*C*C*mU*mC*mU*mC*mC*mU 3' |
| SEQ ID NO: 80<br>5' UCCUCCTCTT TCTCACCTUUCUC U 3' | mHsp90ab1_ASO6:(SEQ ID NO: 17)<br>5' mU*mC*mC*mU*mC*mC*T*C*T*T*T*C*T*C*A*C*C*T*mU*mU*mC*mU*mC*mU 3' |
| SEQ ID NO: 81<br>5' ACCACUTCCT TGACCCTCCUCUC C 3' | mHsp90ab1_ASO7:(SEQ ID NO: 18)<br>5' mA*mC*mC*mA*mC*mU*T*C*C*T*T*G*A*C*C*C*T*C*mC*mU*mC*mU*mC*mC 3' |
| SEQ ID NO: 82<br>5' CUCCUUCTCC CGTTCCTTCUCCA A 3' | mHsp90ab1_ASO8:(SEQ ID NO: 19)<br>5' mC*mU*mC*mC*mU*mU*C*T*C*C*C*G*T*T*C*C*T*T*mC*mU*mC*mC*mA*mA 3' |

TABLE 1-continued

ASO sequences and exemplary modified* sequences.

| ASO sequence | Exemplary Modified Sequence |
|---|---|
| SEQ ID NO: 83<br>5' CACUUCCTTG<br>ACCCTCCTCUCCU<br>C 3' | mHsp90ab1_ASO9:(SEQ ID NO: 20)<br>5' mC*mA*mC*mU*mU*mC*C*T*T*G*A*<br>C*C*C*T*C*C*T*mC*mU*mC*mC*mU*<br>mC 3' |
| SEQ ID NO: 84<br>5' UCUCCACCTC<br>CTCCTCUCCA 3' | ASO10:(SEQ ID NO: 21)<br>5' mU*mC*mU*mC*mC*A*C*C*T*C*<br>T*C*C*T*mC*mU*mC*mC*mA 3' |
| SEQ ID NO: 85<br>5' GUCUCCACCT<br>CCTCCUCUCC 3' | ASO11:(SEQ ID NO: 22)<br>5' mG*mU*mC*mU*mC*C*A*C*C*T*C*<br>C*T*C*C*mU*mC*mU*mC*mC 3' |
| SEQ ID NO: 86<br>5' CUCCACCTCC<br>TCCTCUCCAU 3' | ASO12:(SEQ ID NO: 23)<br>5' mC*mU*mC*mC*mA*C*C*T*C*C*T*<br>C*C*T*C*mU*mC*mC*mA*mU 3' |
| SEQ ID NO: 87<br>5' CUCUUCCTCT<br>GCCTCATCAUCAC<br>U 3' | ASO13:(SEQ ID NO: 24)<br>5' mC*mU*mC*mU*mU*mC*C*T*C*T*G*<br>C*C*T*C*A*T*C*mA*mU*mC*mA*mC*<br>mU 3' |
| SEQ ID NO: 88<br>5' UCUCUUCCTC<br>TGCCTCATCAUCA<br>C 3' | ASO14:(SEQ ID NO: 25)<br>5' mU*mC*mU*mC*mU*mU*C*C*T*C*T*<br>G*C*C*T*C*A*T*mC*mA*mU*mC*mA*<br>mC 3' |
| SEQ ID NO: 89<br>5' UUCUCUTCCT<br>CTGCCTCAUCAUC<br>A 3' | ASO15:(SEQ ID NO: 26)<br>5' mU*mU*mC*mU*mC*mU*mU*T*C*C*T*C*<br>T*G*C*C*T*C*A*mU*mC*mA*mU*mC*<br>mA 3' |
| SEQ ID NO: 90<br>5' UUUCUCTTCC<br>TCTGCCTCAUCAU<br>C 3' | ASO16:(SEQ ID NO: 27)<br>5' mU*mU*mU*mC*mU*mC*mU*T*T*C*C*T*<br>C*T*G*C*C*T*C*mA*mU*mC*mA*mU*<br>mC 3' |
| SEQ ID NO: 91<br>5' CUUUCUCTTC<br>CTCTGCCTCAUCA<br>U 3' | ASO17:(SEQ ID NO: 28)<br>5' mC*mU*mU*mU*mC*mU*mC*T*T*C*C*<br>T*C*T*G*C*C*T*mC*mA*mU*mC*mA*<br>mU 3' |
| SEQ ID NO: 92<br>5' AUGCCCTGAA<br>TTCCAACTGACCU<br>U 3' | ASO18:(SEQ ID NO: 29)<br>5' mA*mU*mG*mC*mC*mC*T*G*A*A*T*<br>T*C*C*A*A*C*T*mG*mA*mC*mC*mU*<br>mU 3' |
| SEQ ID NO: 93<br>5' AAUGCCCTGA<br>ATTCCAACUGACC<br>U 3' | ASO19:(SEQ ID NO: 30)<br>5' mA*mA*mU*mG*mC*mC*C*T*G*A*A*<br>T*T*C*C*A*A*C*mU*mG*mA*mC*mC*<br>mU 3' |
| SEQ ID NO: 94<br>5' CAAUGCCCTG<br>AATTCCAACUGAC<br>C 3' | ASO20:(SEQ ID NO: 31)<br>5' mC*mA*mA*mU*mG*mC*C*C*T*G*A*<br>A*T*T*C*C*A*A*mC*mU*mG*mA*mC*<br>mC 3' |
| SEQ ID NO: 95<br>5' UGCCCUGAAT<br>TCCAACTGACCUU<br>C 3' | ASO21:(SEQ ID NO: 32)<br>5' mU*mG*mC*mC*mC*mU*G*A*A*T*T*<br>C*C*A*A*C*T*G*mA*mC*mC*mU*mU*<br>mC 3' |
| SEQ ID NO: 96<br>5' GCAAUGCCCT<br>GAATTCCAACUGA<br>C 3' | ASO22:(SEQ ID NO: 33)<br>5' mG*mC*mA*mA*mU*mG*C*C*C*T*G*<br>A*A*T*T*C*C*A*mA*mC*mU*mG*mA*<br>mC 3' |
| SEQ ID NO: 97<br>5' ACUGAGACCA<br>GGCTCTTCCCAUC<br>A 3' | ASO23:(SEQ ID NO: 34)<br>5' mA*mC*mU*mG*mA*mG*A*C*C*A*G*<br>G*C*T*C*T*T*C*mC*mC*mA*mU*mC*<br>mA 3' |
| SEQ ID NO: 98<br>5' UUUCCUTCTC<br>TCGTTCCTTCUCC<br>A 3' | ASO1 Variant 1: (SEQ ID NO: 35)<br>5' mU*mU*mU*mC*mC*mU*T*C*T*C*<br>C*G*T*T*C*C*T*mU*mC*mU*mC*mC*<br>mA 3' |
| SEQ ID NO: 99<br>5' UCUCCUTCTC<br>TCGTTCCTUCUCC<br>A 3' | ASO1 Variant 2 (SEQ ID NO: 36)<br>5' mU*mC*mU*mC*mC*mU*mU*T*C*T*<br>C*G*T*T*C*C*T*mU*mC*mU*mC*mC*<br>mA 3' |
| SEQ ID NO: 100<br>5' UUUCCUTCTC<br>CCGTTCCTUCUCC<br>A 3' | ASO1 Variant 3 (SEQ ID NO: 37)<br>5' mU*mU*mU*mC*mC*mU*T*C*T*C*<br>C*G*T*T*C*C*T*mU*mC*mU*mC*mC*<br>mA 3' |
| SEQ ID NO: 101<br>5' AUUUCCTTCT<br>CTCGTTCCUUCUC<br>C 3' | ASO2 Variant 1 (SEQ ID NO: 38)<br>5' mA*mU*mU*mU*mC*mC*T*T*C*T*<br>T*C*G*T*T*C*C*mU*mU*mC*mU*mC*<br>mC 3' |
| SEQ ID NO: 102<br>5' AUCUCCTTCT<br>CTCGTTCCUUCUC<br>C 3' | ASO2 Variant 2 (SEQ ID NO: 39)<br>5' mA*mU*mC*mU*mC*mC*T*T*C*T*<br>T*C*G*T*T*C*C*mU*mU*mC*mU*mC*<br>mC 3' |
| SEQ ID NO: 103<br>5' AUUUCCTTCT<br>CCCGTTCCUUCUC<br>C 3' | ASO2 Variant 3 (SEQ ID NO: 40)<br>5' mA*mU*mU*mU*mC*mC*T*T*C*T*<br>C*C*G*T*T*C*C*mU*mU*mC*mU*mC*<br>mC 3' |
| SEQ ID NO: 104<br>5' UCCCUTCTT<br>TCTCACCTUUCUC<br>U 3' | ASO6 Variant 1 (SEQ ID NO: 41)<br>5' mU*mC*mC*mU*mC*mU*T*C*T*T*<br>C*T*C*A*C*C*T*mU*mU*mC*mU*mC*<br>mU 3' |
| SEQ ID NO: 105<br>5' UUCCUUCTCT<br>CGTTCCTTCUCCA<br>A 3' | ASO8 Variant 1 (SEQ ID NO: 42)<br>5' mU*mU*mC*mC*mU*mU*C*T*C*T*<br>G*T*T*C*C*T*T*mC*mU*mC*mC*mA*<br>mA 3' |
| SEQ ID NO: 106<br>5' CUCCUUCTCT<br>CGTTCCTTCUCCA<br>A 3' | ASO8 Variant 2 (SEQ ID NO: 43)<br>5' mC*mU*mC*mC*mU*mU*C*T*C*T*<br>G*T*T*C*C*T*T*mC*mU*mC*mC*mA*<br>mA 3' |
| SEQ ID NO: 107<br>5' UUCCUUCTCC<br>CGTTCCTTCUCCA<br>A 3' | ASO8 Variant 3 (SEQ ID NO: 44)<br>5' mU*mU*mC*mC*mU*mU*C*T*C*C*<br>G*T*T*C*C*T*T*mC*mU*mC*mC*mA*<br>mA 3' |

*In the modified sequences (SEQ ID NO: 12-44), an asterisk (*) indicates a phosphorothioate linkage, an "m" immediately preceding a nucleotide indicates that the nucleotide is a 2'-O-methyl ribonucleotide, and nucleotides that are not immediately preceded by an "m" are deoxyribonucleotides.

In some embodiments, the ASOs of the invention comprise only deoxyribonueleotides. For example, in some embodiments, all of the nucleotides in SEQ ID NO: 75 to SEQ ID NO: 107 are deoxyribonucleotides, such that a thymidine (T) is substituted for each uridine (U) shown in the sequence. In other embodiments, the ASOs comprise only ribonucleotides. For example, in some embodiments, all of the nucleotides in SEQ ID NO: 75 to SEQ ID NO: 107 are ribonucleotides, such that a uridine (U) is substitued for each thymidine (T) shown in the sequence. In some embodiments, the ASOs comprise at least one deoxyribonucleotide and at least one ribonucleotide. For example, in some embodiments, at least one nucleotide in SEQ ID NO: 75 to SEQ ID NO: 107 is a deoxyribonucleotide and at least one nucleotide in SEQ ID NO: 75 to SEQ ID NO: 107 is a ribonucleotide.

In certain embodiments, the ASOs of the invention comprise at least one DNA region and at least one RNA region. The DNA region may comprise at least 2, 3, 4, 5, 6, 7, 8, 9, 10, 11, 12 or more contiguous deoxyribonucleotides. The RNA region may comprise at least 2, 3, 4, 5, 6, 7, 8, 9, 10, 11, 12 or more contiguous ribonucleotides. In certain embodiments, the DNA region is flanked by RNA regions on both sides. In certain embodiments, the RNA flanking regions comprise one or more ribonucleotides comprising a 2' substituent group, e.g. a 2'-O-methyl (2'OMe) ribonucleotide. In certain embodiments, the RNA flanking regions consist of ribonucleotides comprising a 2' substituent group, e.g. a 2'-O-methyl (2'OMe) ribonucleotide. In certain embodiments, the ASO (for example SEQ ID NO: 75 to SEQ ID NO: 107) comprises one or more phosphorothioate linkages. In certain embodiments, all of the linkages in the ASO for example SEQ ID NO: 75 to SEQ ID NO: 107) are phoshphorothioate linkages. In a particular embodiment, the RNA flanking regions consist of 2'-O-methyl (2'OMe) ribonucleotides, and the ASO comprises one or more phosphorothioate linkages, e.g. at least 2, 3, 4, 5, 6, 7, 8, 9, 10, 11, 12, 13, 14, 15, 16, 17, 18, 19, 20, 21, 22, 23, 24, or 25 phosphorothioate linkages. In a further particular embodiment, the RNA flanking regions consist of 2'-O-methyl (2'OMe) ribonucleotides, and all of the linkages in the ASO (for example SEQ ID NO: 75 to SEQ ID NO: 107) are phosphorothioate linkages. In some embodiments, the ASO comprises a DNA region at the 5' end and an RNA region at the 3' end. In some embmodiments, the ASO comprises an RNA region at the 5' end and a DNA region at the 3' end. In certain embodiments, the ASO comprises an RNA region flanked by DNA regions on both sides.

ASOs specific to HSP90β mRNA and having any one or more of the modifications described in the preceeding paragraphs are within the contemplation of the current invention.

Therapeutic nucleic acids such as ASOs can be produced from synthetic methods such as phosphoramidite methods, H-phosphonate methodology, and phosphite trimester methods. Inhibitory nucleic acids can also be produced by PCR methods. Such methods produce cDNA and cRNA sequences complementary to the mRNA. The method of synthesis of a therapeutic nucleic acid is not a limitation of the invention.

In some embodiments, the ASO comprises a nucleic acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the nucleic acid sequence of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107.

In some embodiments, the ASO consists of a nucleic acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the nucleic acid sequence of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107.

In some embodiments, the ASO consists of a nucleic acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the nucleic acid sequence of SEQ ID NO: 17. In some embodiments, the ASO consists of a nucleic acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the nucleic acid sequence of SEQ ID NO: 41. In some embodiments, the ASO consists of a nucleic acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the nucleic acid sequence of SEQ ID NO: 80. In some embodiments, the ASO consists of a nucleic acid sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to the nucleic acid sequence of SEQ ID NO: 104.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percentage sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol. 147(1); 195-7).

The term "hybridization" as defined herein is a process wherein substantially homologous complementary nucleotide sequences anneal to each other. The term "stringency" refers to the conditions under which a hybridization takes place. The stringency of hybridization is influenced by conditions such as temperature, salt concentration, ionic strength and hybridization buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridization conditions are typically used for isolating hybridizing sequences that have high sequence similarity to the target nucleic acid sequence. However, nucleic acids may deviate in sequence and still encode a substantially identical polypeptide, due to the degeneracy of the genetic code. Therefore medium stringency hybridization conditions may sometimes be needed to identify such nucleic acid molecules.

For example, typical high stringency hybridization conditions for DNA hybrids longer than 50 nucleotides encompass hybridization at 65° C. in 1×SSC or at 42° C. in 1×SSC and 50% formamide, followed by washing at 65° C. in 0.3×SSC. Examples of medium stringency hybridization conditions for DNA hybrids longer than 50 nucleotides encompass hybridization at 50° C. in 4×SSC or at 40° C. in 6×SSC and 50% formamide, followed by washing at 50° C. in 2×SSC. 1×SSC is 0.15M NaCl and 15 mM sodium citrate; the hybridization solution and wash solutions may additionally include 5×Denhardt's reagent, 0.5-1.0% SDS, 100 µg/ml denatured, fragmented salmon sperm DNA, 0.5% sodium pyrophosphate. In a preferred embodiment high stringency conditions mean hybridization at 65° C. in 0.1× SSC comprising 0.1% SDS and optionally 5×Denhardt's reagent, 100 µg/ml denatured, fragmented salmon sperm DNA, 0.5% sodium pyrophosphate, followed by the washing at 65° C. in 0.3×SSC. For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

In some embodiments, the ASO hybridizes to the complement of the nucleic acid sequence of SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107 under high stringency hybridization conditions or medium stringency hybridization conditions as defined above.

A3. Delivery of Antisense Oligonucleotides

A variety of methods for the delivery of ASOs to cells in vitro as well as in vivo are known in the art. To be effective an ASO has to penetrate the target cells. The large size and high ionic charge of a typical ASO makes cell penetration difficult. ASOs enter cells mainly by endocytosis, caveolar potocytosis, or by pinocytosis. After entry they accumulate in the endosomal/lysosomal compartment. Only a small portion escapes to the cytoplasm and the nucleus and is responsible for its pharmacological effects. The rest is degraded in the endosomal/lysosomal compartment. Further, the integrity of ASOs has to be maintained in the blood for a sufficient length of time to allow ASOs to reach their target sites. Therefore, a variety of delivery systems have been developed and are described in the art for enhancing the cellular uptake of ASOs, protection from degradation, and for improving their intracellular, and particularly, intranuclear delivery. The ASOs of the invention may be delivered using any of such delivery systems known in the art. Exemplary but not limiting examples of such delivery systems are described below. It will be understood that other delivery systems known in the art are within the contemplation of the current invention Liposomes are one form of delivery system suitable for the delivery of ASOs. Liposomal delivery systems known in the art include formulations to limit systemic exposure, thereby reducing systemic exposure and off target effects. For example, Doxil® is a composition in which doxorubicin is encapsulated in long-circulating pegylated liposomes that further comprise cholesterol for treatment of certain types of cancer. Various liposomal formulations of amphotericin B including Ambisome®, Abelcet®, and Amphotec® are formulated for intravenous administration in liposomes or a lipid complex containing various phospholipids,cholesterol, and cholesteryl sulfate. Visudine® is verteporfin formulated as a liposome in egg phosphotidyl glycerol and DMPC for intravenous administration. Liposomal formulations are also known for intramuscular injection. Epaxal® is an inactivated hepatitis A virus and Inflexal V® is an inactivated hemaglutinine of influenza virus strains A and B. Both viral preparations are formulated in combinations of DOPC and DOPE. Such liposomes, or other physiologically acceptable liposomes, can be used for the packaging of an ASO and subsequent surface decoration with targeting moieties to deliver ASO to a specific tissue, e.g. the muscle. Additional moieties to modulate intracellular trafficking of the liposome can also be included. Upon uptake of the liposome into the cell, the liposome releases the ASO thereby allowing it to have its therapeutic effect.

Cationic liposomes (e.g. Lipofectin and Transfectam) encapsulate ASOs and protect them from nuclease degradation while neutralizing their negative charge to facilitate entry into the cell. Addition of fusogenic lipids, such as dioleyl phosphatidylethanolamine (DOPE) to liposome formulations helps destabilize the endosomal membrane, thus facilitating the delivery of ASOs to the target site.

Carrier molecules based on receptor mediated endocytosis (RME) are also known. These molecules use import mechanisms used by the cell for the transport of essential nutrients. ASOs are linked to the carrier proteins, either by covalent bond, or may be linked non-covalently via poly-L lysine-carrier conjugates.

ASOs covalently conjugated to macromolecules such as dendrimers are also known in the art (Bielinska, A. et al. 1996 Regulation of in vitro gene expression using antisense oligonucleotides or antisense expression plasmids transfected using starburst PAMAM dendrimers *Nucleic Acids Res.,* 24(11):2176-82; Delong, R. et al. 1997 Characterization of complexes of oligonucleotides with polyamidoamine starburst dendrimers and effects on intracellular delivery. *J. Pharm. Sci.,* 86(6):762-40). ASO-dendrimer complexes enhance the uptake and retention of ASOs in the cells and are stable in the presence of serum (Bielinska, A. et al. 1996; Delong, R. et al. 1997).

ASOs specific to HSP90β mRNA in complex with a dendrimer, or covalently conjugated to dendrimers are within the contemplation of the current invention. Dendrimers can also be used in the context of the current invention as the backbone for producing targeted complexes for the delivery of non-intramuscularly administred ASO to a specific tissue, e.g. muscle. Alternatively, dendrimers can be used to modulate the pharmacokinetic and pharmacodynamic properties of intramuscularly administered ASO. In the compositions and methods of the invention, dendrimers are understood to be pharmaceutically acceptable dendrimers.

A "dendrimer" is a polymeric molecule composed of multiple, theoretically perfectly branched monomers that eminate radially from a central core. Due to the structure and synthetic methods used to generate dendrimers, the products from dendrimer synthesis are theoretically monodisperse. When the core of a dendrimer is removed, a number of identical fragments called dendrons remain with the numer of dendrons dependent on the multiplicity of the central core. The core-shell structure which allows approximate doubling of the size and the number of surface functional groups with the addition of each shell (or generation) to the core. Shells are synthesized by alternating monomer reactions by means well known in the art. Successive reactions create sequentially higher generations (Gs). The nubmer of branch points encountered upon moving outward from the core to the periphery also indicates the generation, e.g., G-1, G-2, G-3, etc., with dendrimers of higher generations being larger, more branched, and having more end groups than dendrimers of lower generations. Dendrimers with different number of generations tend to have different properties. Lower generations are relatively flexible molecules with no appreciable inner regions. Medium sized (G-3 or G-4) have internal space that is essentially separated from the outer shell of the dendrimer. Dendrimers that are G-7 or greater are large dendrimers and have properties more like those of solid particles.

Dendrimer-based platforms have attracted attention for use in pharmaceutical applications. Similar to other polymeric carriers, dendrimers can be synthesized to avoid structural toxicity and immunogenicity. The dendrimer's ability to mimic the size, solubility, and shape of human proteins makes the technology an ideal choice for many therapeutic and diagnostic applications. Being 1-10 nanometers in size enables dendrimers to efficiently diffuse across the vascular endothelium, internalize into cells, and be rapid cleared by the kidneys. This helps to avoid long-term toxicities and reduces the need for a rapidly degradable platform. The availability of multiple reactive surface groups enables the dendrimer to carry a higher payload of functional molecules, enhancing targeted delivery to the site of action, thereby increasing efficacy.

Specialized dendrimer backbones can be synthesized by varying the monomer units. The biological properties of the dendrimer are largely influenced by the chemical backbone and surface termination. For a dendrimer to be an appropriate vehicle for drug delivery in vivo, they must be non-toxic, non-immunogenic, and be capable of targeting and reaching specific locations by crossing the appropriate barriers while being stable enough to remain in circulation. The vast majority of dendrimers synthesized and published in the literature are insoluble in physiological conditions or are incapable of remaining soluble after the addition of functional molecules and are inappropriate for biological applications. However, several classes of dendrimers have been shown to be useful scaffolds for biomedical applications; examples include polyesters, polylysine, and polypropyleneimine (PPI or DAB) dendrimers.

The most widely used dendrimers in biomedical applications are poly(amidoamine) (PAMAM) dendrimers. The polyamide backbone synthesized from repeating reactions of methyl acrylate and ethylene-diamine helps the macromolecule maintain water solubility and minimizes immunogenicity. PAMAM dendrimers of different generation also are able to mimic the size and properties of globular proteins found in the body. The amine-terminated surface of full generation PAMAM dendrimers allows for easy surface modification, enabling the platform to carry and solubilize hydrophobic therapeutic molecules, such as methotrexate, in physiological conditions. PAMAM dendrimers exhibit little non-specific toxicity if the surface amines have been neutralized or appropriately modified (e.g., acylated).

Dendrimers have been produced or are under commercial development for several biomedical applications. A topical, polylysine dendrimer-based microbicide, VivaGel™, has been developed by Starpharma. SuperFect® is a dendrimer-based material used for gene transfection. Dendrimer based diagnostic tools include Gadomer-17, a magnetic resonance imaging (MRI) contrast agent containing a polylysine dendrimer functionalized with gadolinium chelates, and Stratus® CS, a biosensor for cardiac markers to rapidly diagnosis heart attacks.

Active targeting uses a molecule, such as targeting moiety, to mediate delivery of its payload (drug, e.g., ASO of the invention, or otherwise) to cells by binding to cell-specific molecules. Targeting moieties, such as those provided herein, frequently bind through receptors highly expressed on target cells. The interactions between the targeting ligand and cell-surface receptor allow the therapeutic agent or payload to selectively reach the target cells, e.g., muscle cells and even be ushered inside the cell via receptor-mediated processes.

The multivalent effect associated with the display of multiple binding ligands on the dendrimer surface enhances the uptake of the dendritic scaffold compared to single ligands. Multivalent interactions, caused by the simultaneous binding of multiple ligands, allow for the dendrimers to increase the binding avidities of the platform, even when individual ligands have low affinities for the targeted receptor receptor. The PAMAM platform has been successfully used as a scaffold for the attachment of multivalent targeting molecules including antibodies, peptides, T-antigens, and folic acid. The targeting ligands anchor the dendrimers to locations where specific receptors are expressed on cell surfaces. Targeted dendrimer-drug conjugates deliver a higher dose of the drug specifically to targeted cells while avoiding normal cells, thus avoiding the potential systemic toxicity. For example, in certain embodiments the dendrimer (e.g. a PAMAM dendrimer) is conjugated to one or more ligands described herein, for example a protein ligand. In a particular embodiment, a PAMAM dendrimer is conjugated to one or more creatine molecules, e.g. 1, 2, 3, 4, 5, 6, 7, 8, 9, 10, 11, 12, 13, 14, 15, 16, 17, 18, 19 or 20 creatine molecules per PAMAM dendrimer molecule.

Neutralizing the surface amines of PAMAM dendrimers with acetyl groups minimizes toxicity and non-specific dendrimer uptake. The acetyl capping of the dendrimer also allows for increased clearance from the body, minimizing effects from long-term treatment. PEGylation of amino-terminated PAMAM dendrimers reduces immunogenicity and increases solubility. PEG terminated dendrimers have an increased half-life in the blood stream as compared to the cationic parent material. Hydroxyl and methyoxyl terminated polyester dendrimers have been shown to be nontoxic in vivo up at concentrations up to 40 mg/kg. The differences in toxicities between cationic and anionic dendrimers have also been confirmed in vivo. Using a zebrafish embryo model, carboxyl terminated dendrimer was found to be significantly less toxic than G4 amine-terminated dendrimer. In the same study, surface modification with RGD also reduced toxicity.

Several kinds of peptides have also been described in the art for aiding in the delivery of ASOs. These peptides are: fusogenic peptides that aid in the fusion of ASO peptide conjugates with the cellular membranes; signal import peptides that improve the cellular uptake of ASOs; or nuclear localization signal (NLS) peptides that help in targeting the ODNs to the nucleus. These peptides when coupled to the ASOs enhance penetration into the cells by receptor and transporter independent mechanisms. Such peptides are contemplated as being included in the compositions and methods of the current invention.

Further, biodegradable nanoparticles for the delivery of ASOs are known to the ordinary person of skill in the art. In this mode of delivery ASOs are adsorbed to the surface of nanoparticles by hydrophobic interactions. Hydrophobic cations, such as quarternary ammonium salts, are typically used to promote the binding between As-ODNs and nanoparticles. These nanoparticles have been shown to be effective carriers of ASOs.

Another approach to enhance ASO internalization into the cells described in the art is to generate transient permeabilization of the plasma membrane, thus allowing ASOs to enter the cells by diffusion. In this mode of delivery transitory pores are formed in the cell membrane, either chemically by streptolysin O, or mechanically by electroporation, shockwave or ultrasound waves.

Targeted ASO complexes can be administered by a route other than intramuscular injection (e.g., subcutaneous injection, intravenous injection) while providing delivery of the ASO to muscle. Targeted complexes can include one or more targeting moieties attached either directly or indirectly to the ASO. Formation of the targeted complex does not substantially or irreversibly inhibit the activity of ASO and its effect on normalizing blood glucose levels and insulin response. In certain embodiments, use of a targeted complex can reduce the total amount of ASO required to provide an effective dose. Targeted ASO complexes can also be administered by intramuscular injection.

B. Double Stranded Nucleic Acid Therapeutics

Nucleic acid therapeutic agents of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs. The term "siRNA" is also used herein to refer to an RNAi agent as described above.

In many embodiments, the duplex region is 15-30 nucleotide pairs in length. In some embodiments, the duplex region is 17-23 nucleotide pairs in length, 17-25 nucleotide pairs in length, 23-27 nucleotide pairs in length, 19-21 nucleotide pairs in length, or 21-23 nucleotide pairs in length.

In certain embodiments, each strand has 15-30 nucleotides.

The RNAi agents that are used in the methods of the invention include agents with chemical modifications as disclosed, for example, in U.S. Provisional Application No. 61/561,710, filed on Nov. 18, 2011, International Application No. PCT/US2011/051597, filed on Sep. 15, 2010, and PCT Publication WO 2009/073809, the entire contents of each of which are incorporated herein by reference. The term "antisense strand" refers to the strand of a double stranded RNAi agent which includes a region that is substantially complementary to a target sequence (e.g., a human TTR mRNA). As used herein, the term "region complementary to part of an mRNA encoding transthyretin" refers to a region on the antisense strand that is substantially complementary to part of a TTR mRNA sequence. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

IV. Diagnostic and Therapeutic Antibodies

Both diagnostic and therapeutic methods of the invention can include the use of antibodies, including polyclonal and monoclonal antibodies. The term "monoclonal antibody" or "monoclonal antibody composition", as used herein, refers to a population of antibody molecules that contain only one species of an antigen binding site capable of immunoreacting with a particular epitope. Antibodies for use in the invention include antibodies that bind to HSP90, preferably antibodies that are HSP90β-specific. Antibodies can be obtained from commercial sources or produced using known methods.

Polyclonal antibodies can be prepared by immunizing a suitable subject with a protein of the invention as an immunogen. The antibody titer in the immunized subject can be monitored over time by standard techniques, such as with an enzyme linked immunosorbent assay (ELISA) using immobilized polypeptide. At an appropriate time after immunization, e.g., when the specific antibody titers are highest, antibody-producing cells can be obtained from the subject and used to prepare monoclonal antibodies (mAb) by standard techniques, such as the hybridoma technique originally described by Kohler and Milstein (1975) Nature 256:495-497, the human B cell hybridoma technique (see Kozbor et al., 1983, Immunol. Today 4:72), the EBV-hybridoma technique (see Cole et al., pp. 77-96 In Monoclonal Antibodies and Cancer Therapy, Alan R. Liss, Inc., 1985) or trioma techniques. The technology for producing hybridomas is well known (see generally Current Protocols in Immunology, Coligan et al. ed., John Wiley & Sons, New York, 1994). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a protein of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) Bio/Technology 9:1370-1372; Hay et al. (1992) Hum. Antibod. Hybridomas 3:81-85; Huse et al. (1989) Science 246:1275-1281; Griffiths et al. (1993) EMBO J. 12:725-734.

Recombinant antibodies that specifically bind a protein of interest can also be used in the methods of the invention. In preferred embodiments, the recombinant antibodies specifically binds a protein of interest or fragment thereof. Recombinant antibodies include, but are not limited to, chimeric and humanized monoclonal antibodies, comprising both human and non-human portions, single-chain antibodies and multi-specific antibodies. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.) Single-chain antibodies have an antigen binding site and consist of a single polypeptide. They can be produced by techniques known in the art, for example using methods described in Ladner et. al U.S. Pat. No. 4,946,778 (which is incorporated herein by reference in its entirety); Bird et al., (1988) Science 242: 423-426; Whitlow et al., (1991) Methods in Enzymology 2:1-9; Whitlow et al., (1991) Methods in Enzymology 2:97-105; and Huston et al., (1991) Methods in Enzymology Molecular Design and Modeling: Concepts and Applications 203:46-88. Multi-specific antibodies are antibody molecules having at least two antigen-binding sites that specifically bind different antigens. Such molecules can be produced by techniques known in the art, for example using methods described in Segal, U.S. Pat. No. 4,676,980 (the disclosure of which is incorporated herein by reference in its entirety); Holliger et al., (1993) Proc. Natl. Acad. Sci. USA 90:6444-6448; Whitlow et al., (1994) Protein Eng. 7:1017-1026 and U.S. Pat. No. 6,121,424.

Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; and Shaw et al. (1988) J. Natl. Cancer Inst. 80:1553-1559); Morrison (1985) Science 229:1202-1207; Oi et al. (1986) Bio/Techniques 4:214; U.S. Pat. No. 5,225,539; Jones et al. (1986) Nature 321:552-525; Verhoeyan et al. (1988) Science 239: 1534; and Beidler et al. (1988) J. Immunol. 141:4053-4060.

More particularly, humanized antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide corresponding to a marker of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al., 1994, *Bio/technology* 12:899-903).

The antibodies of the invention can be isolated after production (e.g., from the blood or serum of the subject) or synthesis and further purified by well-known techniques. For example, IgG antibodies can be purified using protein A chromatography. Antibodies specific for a protein of the invention can be selected or (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those of the desired protein of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein of the invention.

An antibody directed against a protein can be used to isolate the protein by standard techniques, such as affinity chromatography or immunoprecipitation. Moreover, such an antibody can be used to detect the marker protein, e.g., HSP90β, or fragment thereof (e.g., in a cellular lysate or cell supernatant) in order to evaluate the level and pattern of expression of the marker. The antibodies can also be used diagnostically to monitor protein levels in tissues or body fluids (e.g. in disease sate or toxicity state associated body fluid) as part of a clinical testing procedure, e.g., to, for example, determine the efficacy of a given treatment regimen. Detection can be facilitated by the use of an antibody derivative, which comprises an antibody of the invention coupled to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S, or $^{3}$H.

Antibodies may also be used as therapeutic agents in treating metabolic syndrome and/or diabetes.

V. Small Molecule Inhibitors of HSP90

Small molecule inhibitors of HSP90 include, but are not limited to,

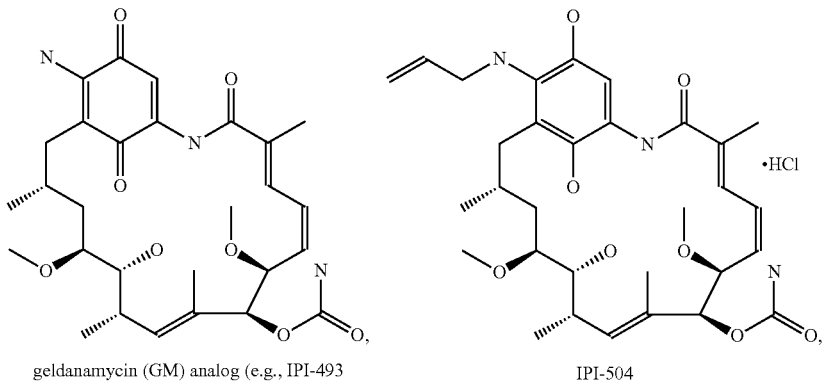

geldanamycin (GM) analog (e.g., IPI-493)　　　　IPI-504

-continued
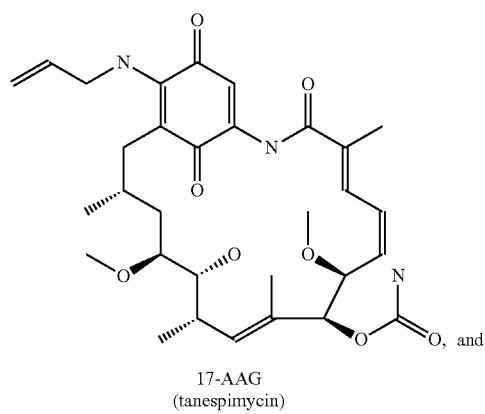
17-AAG
(tanespimycin)
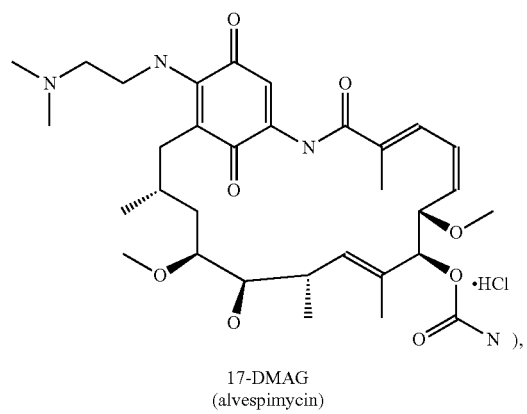
17-DMAG
(alvespimycin)
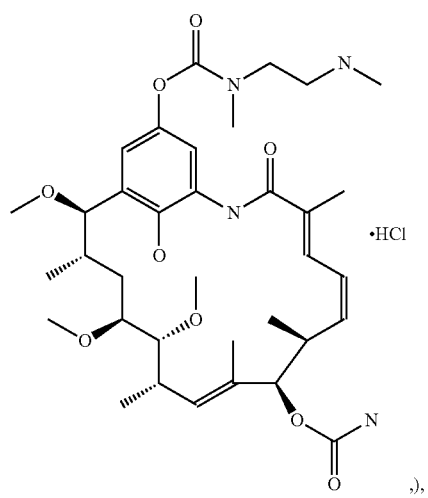
macbecin analog (e.g., BC-274
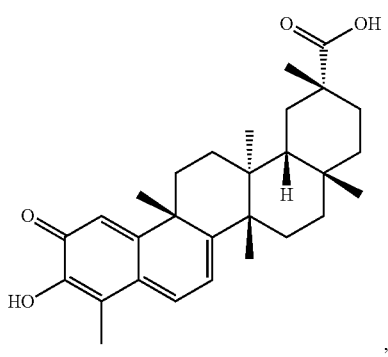
tripterin (celastrol)
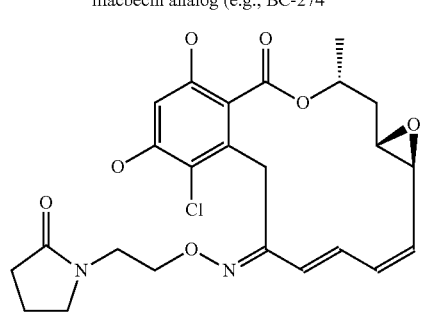
radicicol analog (e.g., KF-55823
and
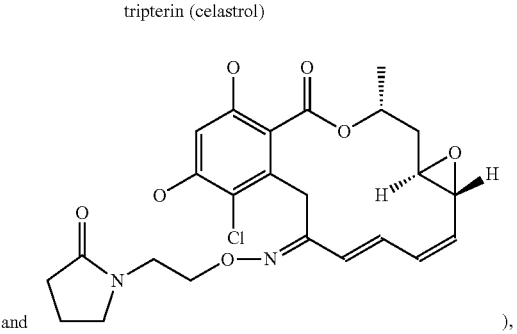
KF-58333
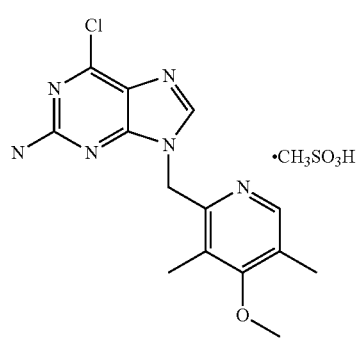
BIIB-021
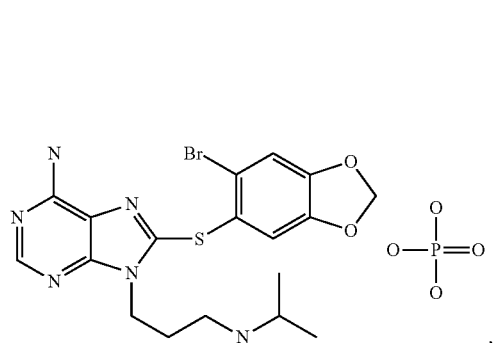
BIIB-028
PU-H64

-continued
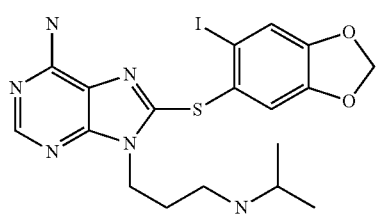
PU-H71
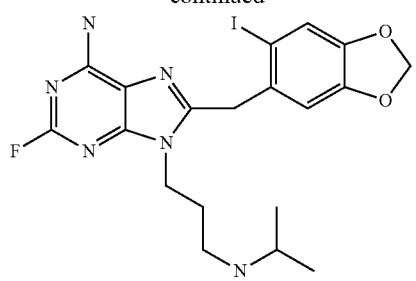
PU-DZ8
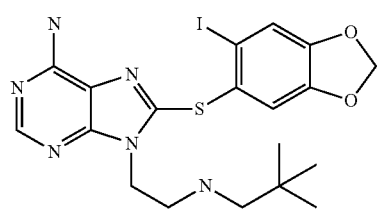
PU-HZ151
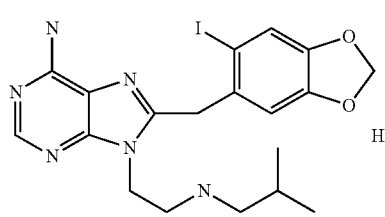
PU-DZ13 HCl
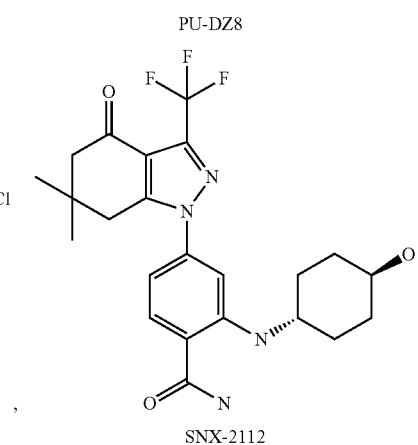
SNX-2112
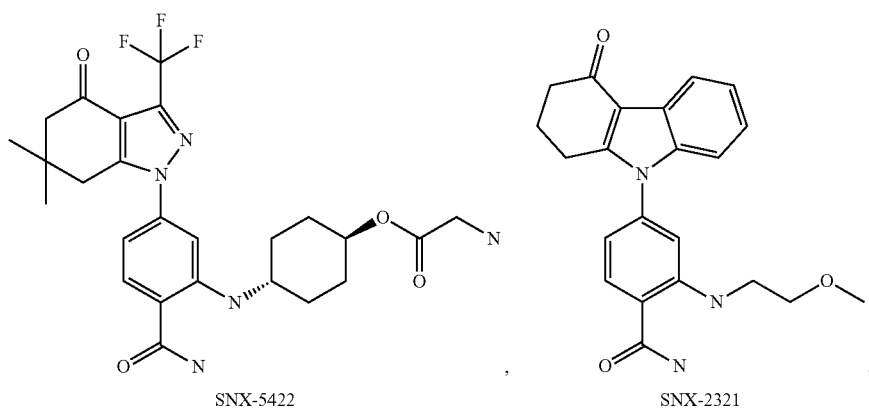
SNX-5422
SNX-2321
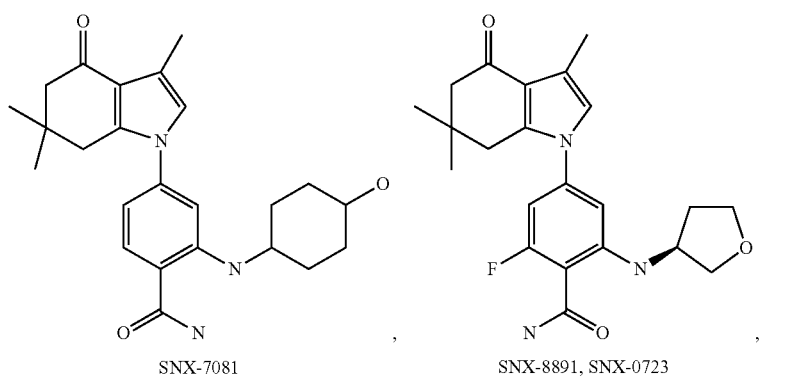
SNX-7081
SNX-8891, SNX-0723

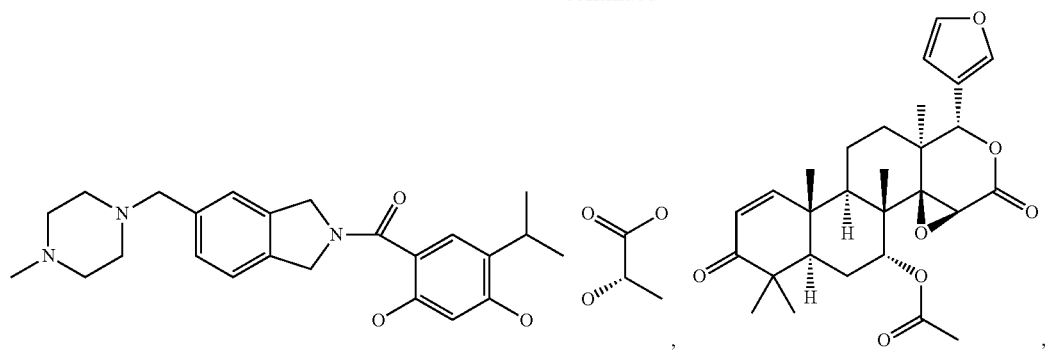
SAR-567530, ABI-287, ABI-328, AT-13387         NSC-113497
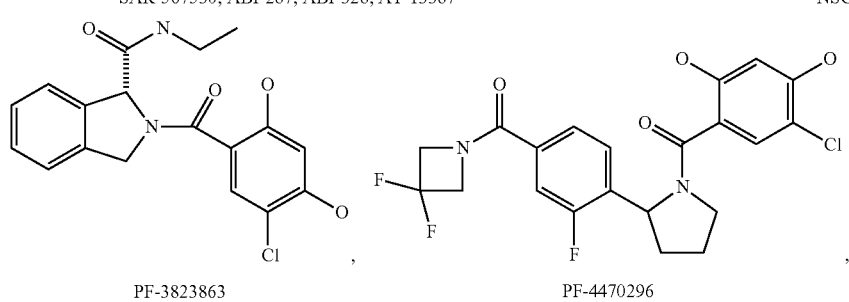
PF-3823863         PF-4470296
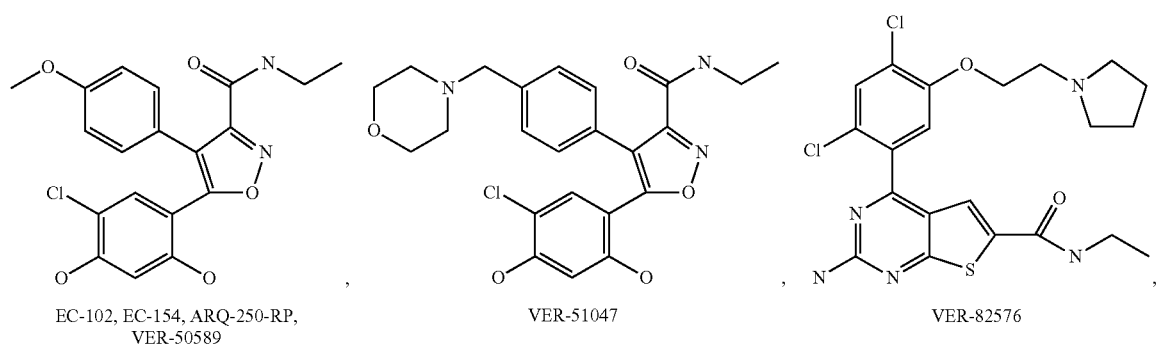
EC-102, EC-154, ARQ-250-RP,    VER-51047         VER-82576
VER-50589
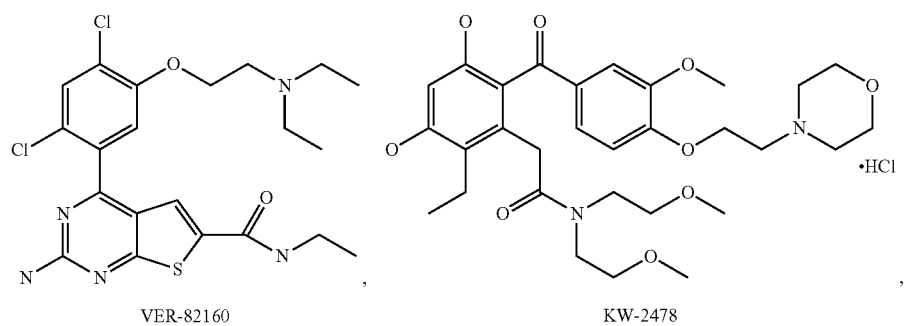
VER-82160         KW-2478
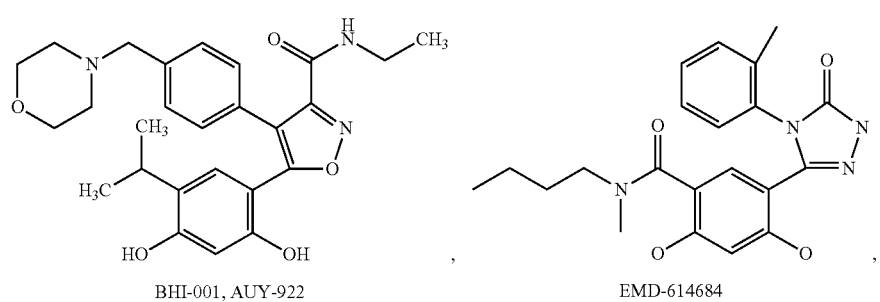
BHI-001, AUY-922         EMD-614684

-continued
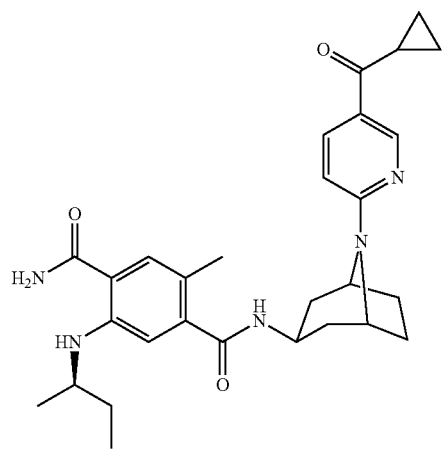
EMD-683671, XL-888
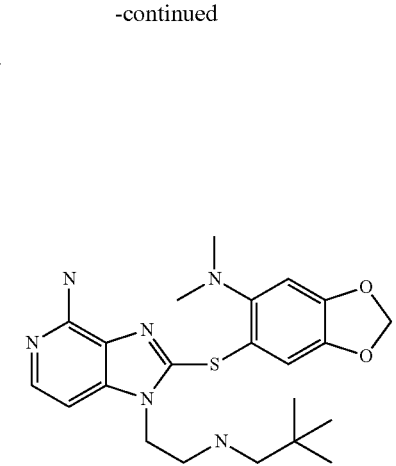
KOS-2484, KOS-2539, CUDC-305
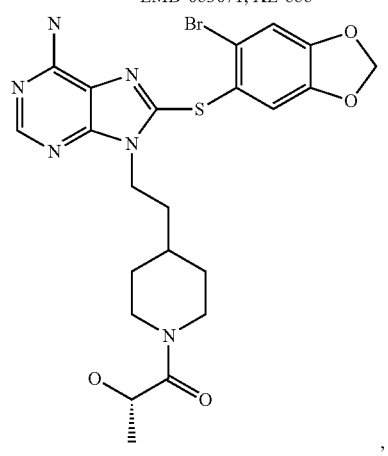
MPC-3100
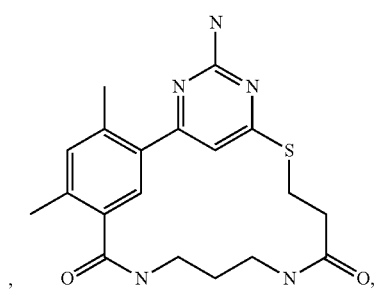
CH-5164840
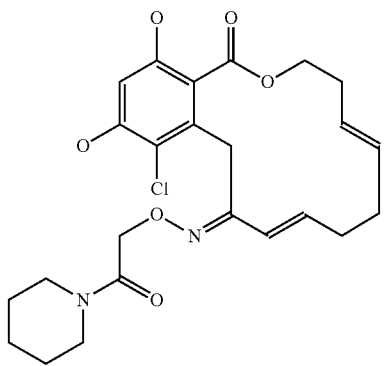
NXD-30001
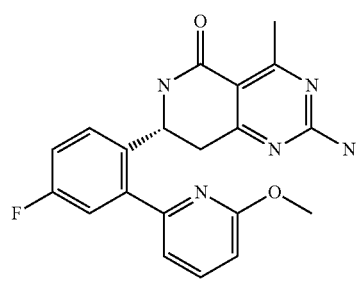
NVP-HSP990
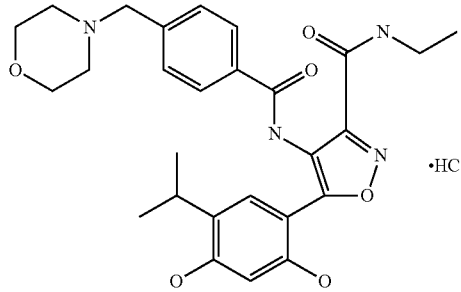
SST-0201CL1
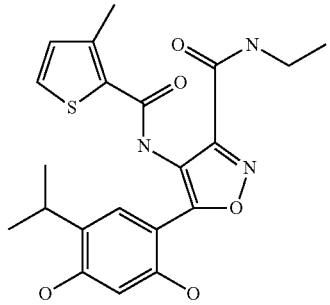
SST-0115AA1
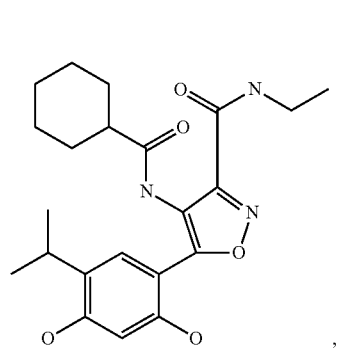
SST-0221AA1
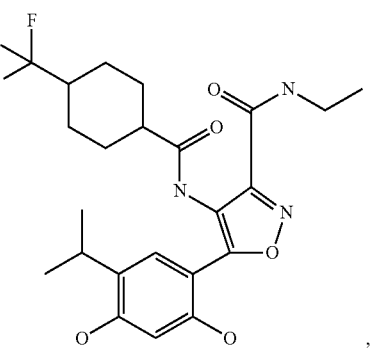
SST-0223AA1
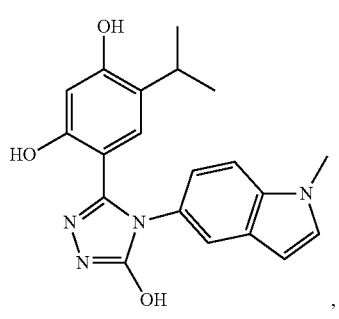
novobiocin (a C-terminal Hsp90i), herbinmycin A, ganetespib -continued
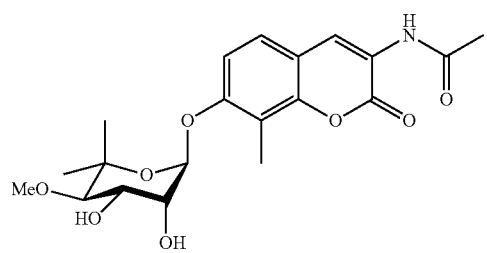
CCT018059, KU32
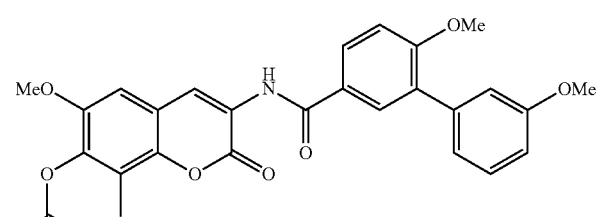
KU135,
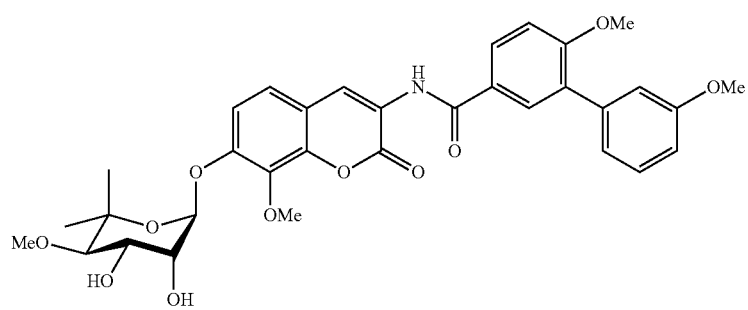
KU174
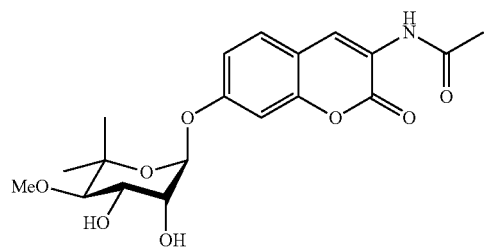
A4
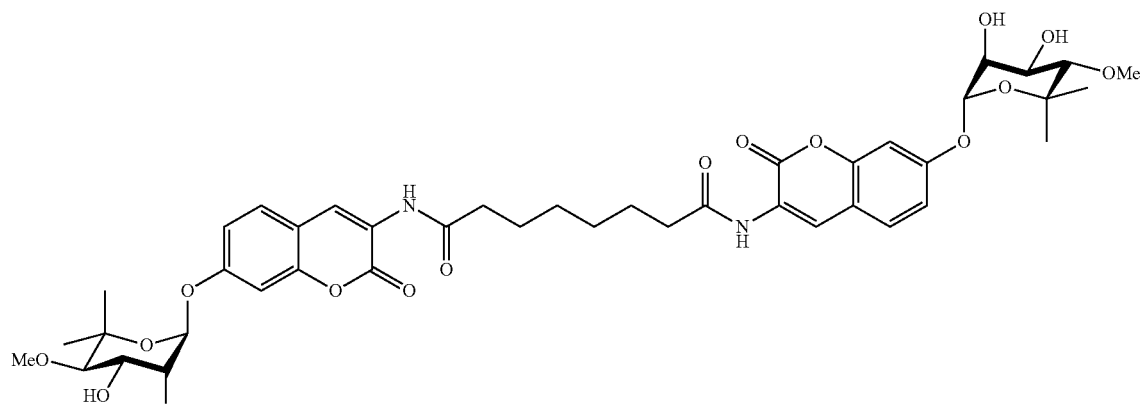
A4 Dimer

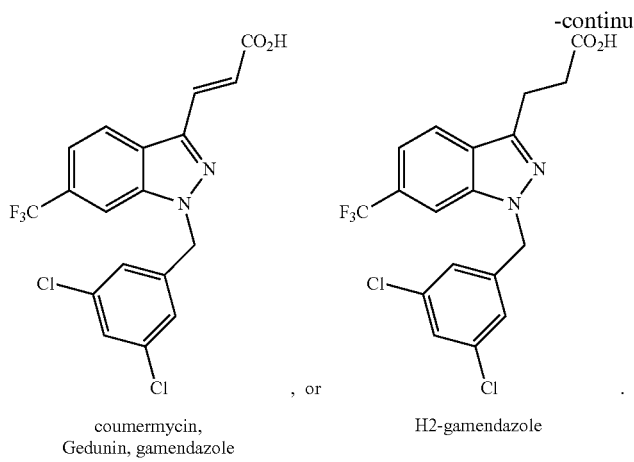

coumermycin,
Gedunin, gamendazole , or  H2-gamendazole

Depending on their mechanism of action, some small molecule inhibitors preferably inhibit HSP90 by interfering with the binding and/or hydrolysis of ATP at the N-terminal ATP-bindind domain, e.g., geldanamycin (see Sausville, et al., Annu Rev Pharmacol Toxicol 2003; 43: 199-231, incorporated herein by reference). Other HSP90 inhibitors inhibit HSP90 by interfering with the binding and/or hydrolysis of ATP at the C-terminal ATP-binding domain, e.g., novobiocin (see Marcu, et al., J Biol Chem 2000; 275: 37181-37186, incorporated herein by reference). Not all HSP90 inhibitors act on HSP90 by interacting with the ATP-binding site at either terminus of Hsp90 protein. Examples of those HSP90 inhibitors include KU174, coumermycin A1, celastrol, gedunin, H2-gamendazole, and gamendazole (see Matts, et al., Bioorganic & Medicinal Chemistry 19 (2011) 684-692 and Tash, et al., Biology of Reproduction 2008; 78, 1139-1152, incorporated herein by reference). Among these inhibitors, for example, celastrol disrupts interaction between Hsp90 and the kinase co-chaperone Cdc37 to effectively disable Hsp90 (see Matts, et al., Bioorganic & Medicinal Chemistry 19 (2011) 684-692, incorporated herein by reference).

Many known HSP 90 inhibitors inhibit both the HSP90α and HSP90β isoforms, e.g., geldanamycin and NVP-HS990. Others inhibitors show a preference for one of the two isotypes, such as gamendazole and H2-gamendazole, which are specific for HSP90β (see Tash, et al., Biology of Reproduction 2008; 78, 1139-1152). In addition, HSP90β is more sensitive to radicicol than HSP90α (see Millson et al., FEBS J 2007; 274, 4453-4463, incorporated herein by reference). Additionally, novel inhibitors that are specific for HSP90β can be selected from known HSP90β inhibitors or developed by the skilled artisan by modifying the known specific inhibitors, such as gamendazole, or by designing inhibitors based on the binding domain determined by co-crystalography of HSP90β and an HSP90β-specifc inhibitor, e.g., gamendazol.

The above-mentioned gamendazole, an HSP90β-specific inhibitor, is an analogue of lonidamine. Lonidamine analogs are known in the art. Some non-limiting examples of lonidamine analogues are described in WO2006/023704 and WO2011/005759 (the entire contents of both of which are incorporated herein by reference) and represented by the following formula:

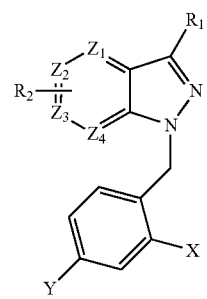

Wherein $R_1$ is carboxyl,

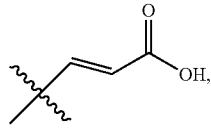 [SMILES: */C=C/C(=O)O]

or carboxylic acid hydrazide;
wherein $R_2$ is hydrogen, halogen, alcohol, alkyl, alkoxy, aralkyl, cycloalkyl, haloalkyl, haloalkoxy, amino, or carboxyl;
wherein X and Y are the same or different from each other and are halogen or lower alkyl;
wherein $Z_1$, $Z_2$, $Z_3$, and $Z_4$ are independently nitrogen or carbon; and pharmaceutically acceptable salts and esters thereof.

Examples of such lonidamine analogues include,
6-chloro-1-(2,4-dichlorobenzyl)-1H-indazole-3-carboxylic acid hydrazide;
1-(2,4-dichlorobenzyl)-6-fluoro-1H-indazole-3-carboxylic acid methyl ester;
6-fluoro-1-(2,4-dichlorobenzyl)-1H-indazole-3-carboxylic acid hydrazide;
3-[1-(2,4-dichlorobenzyl)-6-fluoro-1H-indazol-3-yl]-acrylic acid;
3-[1-(2,4-dichlorobenzyl)-6-chloro-1H-indazol-3-yl]-acrylic acid;
3-[1-(2,4-dichlorobenzyl)-6-trifluoromethoxy-1H-indazol-3-yl]acrylic acid;
3-[1-(2,4-dichlorobenzyl)-6-chloro-1H-indazol-3-yl]-propionic acid;

3-[1-(2,4-dichlorobenzyl)-6-methyl-1H-indazol-3-yl] acrylic acid (TH 2-192);

1-(2,4-dichlorobenzyl)-6-methyl-1H-indazole-3-carboxylic acid (TH 2-178);

1-(2,4-dichlorobenzyl)-6-methyl-1H-indazole-3-carboxylic acid hydrazide (TH 2-179);

3-[1-(2,4-dichlorobenzyl)-6-chloro-1H-indazol-3-yl]-acrylic acid (JWS 1-190);

1-(2-chloro-4-fluorobenzyl)-6-chloro-1H-indazole-3-carboxylic acid hydrazide (JWS 2-22); and 1-(2,4-difluorobenzyl)-6-chloro-1H-indazole-3-carboxylic acid hydrazide (JWS 1-282).

Additional lonidamine analogues are further described in WO2006/015263 and WO2006/015191 and also in Mok et al., Reproduction, 2011, 141, 571-580 (each of which is incorporated herein by reference). Examples of such lonidamine analogues include lonidamin, Adjudin (AF-2364), AF2785, and CDB-4022.

Some analogues of coumermycin and coumermycin A1 are described in WO2001/87309 and WO2012/162054 (both of which is incorporated herein by reference). in which a cumermycin analog is represented by the following formula:

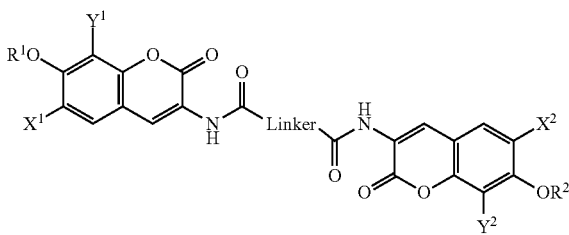

wherein:

$R^1$, $R^2$, $X^1$, $Y^1$, and $Y^2$ includes a moiety independently selected from hydrogen, halogens, hydroxyls, alkoxys, straight aliphatics, branched aliphatics, cyclic aliphatics, heterocyclic aliphatics, substituted aliphatics, unsubstituted aliphatics, saturated aliphatics, unsaturated aliphatics, aromatics, polyaromatics, substituted aromatics, hetero-aromatics, amines, primary amines, secondary amines, tertiary amines, aliphatic amines, carbonyls, carboxyls, amides, esters, amino acids, peptides, polypeptides, sugars, sugar mimics, derivatives thereof, or combinations thereof, the aliphatic groups having carbon chains of about 0-20 carbons or hetero atoms or O, N, S, or P; and linker including a straight aliphatic, branched aliphatic, cyclic aliphatic, heterocyclic aliphatic, substituted aliphatic, unsubstituted aliphatic, saturated aliphatic, unsaturated aliphatic, aromatic, polyaromatic, substituted aromatic, hetero-aromatic, amine, primary amine, secondary amine, tertiary amine, aliphatic amine, carbonyl, carboxyl, amide, ester, amino acid, peptide, polypeptide, sugars, sugar mimic, derivatives thereof, or combinations thereof.

Examples of the coumermycin analogs are represented by the following formula:

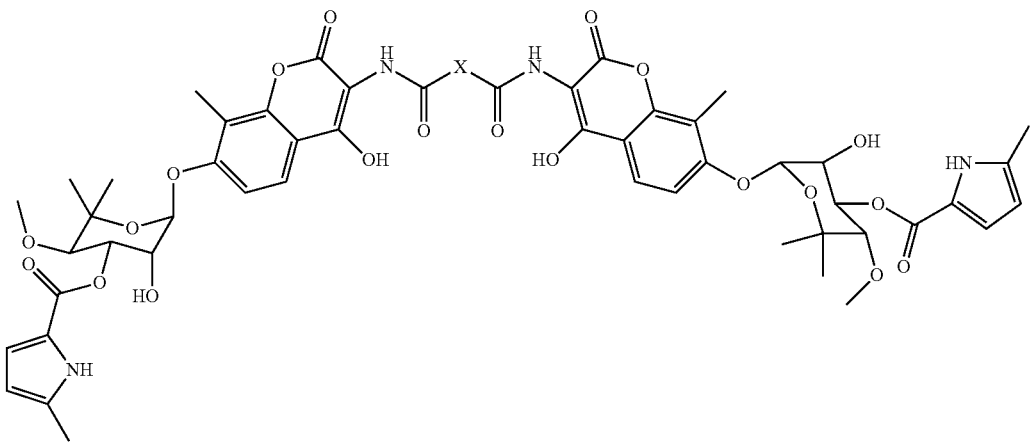

wherein X is a linker containing from about 1 to about 54 atoms that connects the two halves of the molecule.

Some analogues of celastrol and gendunin are described in WO2007/117466 (which is incorporated herein by reference). In certain embodiments, the small molecule inhibitors of HSP90 inhibit HSP90β. In certain embodiments, the small molecule inhibitors of HSP90 specifically inhibit HSP90β.

VI. Diagnostic Methods for Metabolic Syndrome

The invention further provides methods of identifying a subject as having or being at risk of having metabolic syndrome and/or diabetes comprising detecting the level of expression of a marker protein and/or a nucleic acid in a sample from the subject.

An exemplary method for detecting the presence or absence of a marker protein or nucleic acid in a biological sample, e.g., HSP90, particularly HSP90β, involves obtaining a biological sample (e.g. tissue sample) from a test subject and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo for the diagnosis of metabolic syndrome. For example, in vitro techniques for detection of mRNA include northern hybridizations and in situ hybridizations. In vitro techniques for detection of a marker protein include enzyme linked immunosorbent assays (ELISAs), western blots, immunoprecipitations and immunofluorescence. In vitro techniques for detection of genomic DNA include Southern hybridizations. In vivo techniques for detection of mRNA include polymerase chain reaction (PCR), northern hybridizations and in situ hybridizations. Furthermore, in vivo techniques for detection of a marker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In a preferred embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. A FRET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, *J. Mol. Recognit. Winter* 11(1-6):141-8; Hage, D. S., and Tweed, S. A. *J Chromatogr B Biomed Sci Appl* 1997 Oct. 10; 699(1-2):499-525). Gel electrophoresis may also be employed to separate complexed assay components from unbound components (see, e.g., Ausubel et al., ed., *Current Protocols in Molecular Biology*, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of marker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

An alternative method for determining the level of mRNA marker in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a patient sample, to another sample, e.g., a non-disease samples from different sources.

Alternatively, the expression level can be provided as a relative expression level. To determine a relative expression level of a marker, the level of expression of the marker is determined for 10 or more samples of normal versus disease cell isolates, preferably 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

Preferably, the samples used in the baseline determination will be from non-disease cells. The choice of the cell source is dependent on the use of the relative expression level. Using expression found in normal tissues as a mean expression score aids in validating whether the marker assayed is disease specific (versus normal cells). In addition, as more data is accumulated, the mean expression value can be revised, providing improved relative expression values based on accumulated data. Expression data from disease cells provides a means for grading the severity of the disease state.

In another embodiment of the present invention, a marker protein, HSP90, preferably HSP90β, is detected. A preferred agent for detecting marker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from cells can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), western blot analysis and enzyme linked immunoabsorbant assay (ELISA). A skilled artisan can readily adapt known protein/antibody detection methods for use in determining whether cells express a marker of the present invention.

In one format, antibodies, or antibody fragments or derivatives, can be used in methods such as western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from disease cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound detectably labeled antibody. The amount of bound labeled antibody on the solid support can then be detected by conventional means.

The invention also encompasses kits for detecting the presence of a marker protein or nucleic acid in a biological sample. Such kits can be used to determine if a subject is suffering from or is at increased risk of developing certain diseases, e.g., diabetes and/or metabolic syndrome. For example, the kit can comprise a labeled compound or agent capable of detecting a marker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a marker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a marker protein or (2) a pair of primers useful for amplifying a marker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

In the methods provided herein, a modulated level of HSP90, specifically HSP90β, may be used as a diagnostic indicator in conjunction with one or more indicators of metabolic syndrome such as those provided herein.

Repeated diagnostic assays can be used to monitor the disease state of the subject.

VII. Treatment of Metabolic Syndrome

As demonstrated herein, inhibition of HSP90 expression or activity, specifically HSP90β expression or activity, improves glucose uptake, insulin signaling, and lipid metabolism. The invention provides methods of treatment of subjects suffering from metabolic syndrome comprising administering an inhibitor of HSP90, preferably an HSP90β inhibitor, more preferably an HSP90β-specific inhibitor, such as those provided herein, to ameliorate at least one sign or symptom of metabolic syndrome. In certain embodiments, the inhibitor of HSP90, preferably the HSP90β-specific inhibitor, can be administered to a subject wherein at least one additional agent for the treatment of metabolic syndrome is administered to the subject. As used herein, the agents can be administered sequentially, in either order, or at the same time. Administration of multiple agents to a subject does not require co-formulation of the agents or the same administration regimen.

The method of treatment of metabolic syndrome using HSP90β inhibitors can be combined with known methods and agents for the treatment of metabolic syndrome. Many agents and regimens are currently available for treatment of metabolic syndrome and diabetes. The specific agent selected for treatment depends upon the subject, the specific symptoms and the severity of the disease state. For example, in certain embodiments, the HSP90β inhibitors can be administered in conjunction with dietary and/or behavior modification, e.g., caloric restriction, alone or in combination with bariatric surgery, and/or with increased physical activity. In certain embodiments, the HSP90β inhibitors can be administered with agents for the treatment of type 2 diabetes, e.g., metformin (Glucophage, Glumetza, others), glitazones, e.g., pioglitazone (Actos), glipizide (Glucotrol), glyburide (Diabeta, Glynase), glimepiride (Amaryl), acarbose (Precose), metformin (Glucophage), Sitagliptin (Januvia), Saxagliptin (Onglyza), Repaglinide (Prandin), Nateglinide (Starlix), Exenatide (Byetta), Liraglutide (Victoza), or insulin.

VIII. Animal Models of Metabolic Syndrome

A number of genetic and induced animal models of metabolic syndromes such as type 1 and type 2 diabetes, insulin resistance, hyperlipidemia, are well characterized in the art. Such animals can be used to demonstrate the effect of HSP90 inhibitors, e.g., HSP90β inhibitors in the treatment of diabetes. Models of type 1 diabetes include, but are not limited to, NOD mice and streptozotocin-induced diabetic rats and mice (models of type 1 diabetes). Genetic and induced models of type 2 diabetes include, but are not limited to, the leptin deficient ob/ob mouse, the leptin receptor deficient db/db mouse, and high fat fed mouse or rat models. In each of the models, the timeline for development of specific disease characteristics are well known. HSP90 inhibitors can be administered before or after the appearance of symptoms of diabetes to demonstrate the efficacy of HSP90 inhibitors, particularly HSP90β inhibitors, in the prevention or treatment of diabetes in these animal models.

Depending on the specific animal model selected and the time of intervention, e.g., before or after the appearance of metabolic syndrome, the animal models can be used to demonstrate the efficacy of the methods provide herein for the prevention, treatment, diagnosis, and monitoring of metabolic syndrome.

IX. Kits

The invention also provides compositions and kits for diagnosing a disease state, e.g. metabolic syndrome. These kits include one or more of the following: a detectable antibody that specifically binds to HSP90β and one or more of a detectable antibody that specifically binds to the HSP90β antibody, reagents for obtaining and/or preparing subject tissue samples for staining, and instructions for use.

The kits of the invention may optionally comprise additional components useful for performing the methods of the invention. By way of example, the kits may comprise fluids (e.g., SSC buffer, TBST) suitable for annealing complementary nucleic acids or for binding an antibody with a protein with which it specifically binds, one or more sample compartments, an instructional material which describes performance of a method of the invention and tissue specific controls/standards.

The invention also provides kits for treatment of metabolic disorder. The kits include at least one HPS90 inhibitor, preferably an HSP90β-specific inhibitor, and one or more of instructions for use and a device for administration, as appropriate.

Description of Sequences

| SEQ ID NO: | Description |
|---|---|
| 1 | H1 duplex sequence for Hsp90β siRNA |
| 2 | H1 duplex sequence for Hsp90β siRNA |
| 3 | H2 duplex sequence for Hsp90β siRNA |
| 4 | H2 duplex sequence for Hsp90β siRNA |
| 5 | H3 duplex sequence for Hsp90β siRNA |
| 6 | H3 duplex sequence for Hsp90β siRNA |
| 7 | human HSP90AA1 DNA sequence |
| 8 | human HSP90α protein encoded by HSP90AA1 gene |
| 9 | human HSP90ab DNA sequence |
| 10 | human HSP90β protein encoded by HSP90ab gene |
| 11 | NC1, negative control ASO sequence |
| 12 | ASO1 |
| 13 | ASO2 |
| 14 | ASO3 |
| 15 | ASO4 |
| 16 | ASO5 |
| 17 | ASO6 |
| 18 | ASO7 |
| 19 | ASO8 |
| 20 | ASO9 |
| 21 | ASO10 |
| 22 | ASO11 |
| 23 | ASO12 |
| 24 | ASO13 |
| 25 | ASO14 |
| 26 | ASO15 |
| 27 | ASO16 |
| 28 | ASO17 |
| 29 | ASO18 |
| 30 | ASO19 |
| 31 | ASO20 |
| 32 | ASO21 |
| 33 | ASO22 |
| 34 | ASO23 |
| 35 | ASO1 variant 1 (FIG. 18B) |
| 36 | ASO1 variant 2 (FIG. 18B) |
| 37 | ASO1 variant 3 (FIG. 18B) |
| 38 | ASO2 variant 1 (FIG. 18B) |
| 39 | ASO2 variant 2 (FIG. 18B) |
| 40 | ASO2 variant 3 (FIG. 18B) |
| 41 | ASO6 variant 1 (FIG. 18B) |
| 42 | ASO8 variant 1 (FIG. 18B) |

-continued

Description of Sequences

| SEQ ID NO: | Description |
|---|---|
| 43 | ASO8 variant 2 (FIG. 18B) |
| 44 | ASO8 variant 3 (FIG. 18B) |
| 45 | ASO1 Query sequence (FIG. 18B) |
| 46 | ASO1 Subject sequence (FIG. 18B) |
| 47 | ASO2 Query sequence (FIG. 18B) |
| 48 | ASO2 Subject sequence (FIG. 18B) |
| 49 | ASO6 Query sequence (FIG. 18B) |
| 50 | ASO6 Subject sequence (FIG. 18B) |
| 51 | ASO8 Query sequence (FIG. 18B) |
| 52 | ASO8 Subject sequence (FIG. 18B) |
| 53 | Penetratin amino acid sequence |
| 54 | Transportan amino acid sequence |
| 55 | M918 amino acid sequence |
| 56 | Cell penetrating peptide amino acid sequence (YDEEGGGE) |
| 57 | muscle targeting peptide |
| 58 | muscle targeting peptide |
| 59 | muscle targeting peptide |
| 60 | muscle targeting peptide |
| 61 | muscle targeting peptide |
| 62 | ASO10-ASO12 human Hsp90ab1 sequence (FIG. 31) |
| 63 | ASO10-ASO12 monkey Hsp90ab1 sequence (FIG. 31) |
| 64 | ASO10-ASO12 mouse Hsp90ab1 sequence (FIG. 31) |
| 65 | ASO13-ASO17 human Hsp90ab1 sequence (FIG. 31) |
| 66 | ASO13-ASO17 monkey Hsp90ab1 sequence (FIG. 31) |
| 67 | ASO13-ASO17 mouse Hsp90ab1 sequence (FIG. 31) |
| 68 | ASO18-ASO22 human Hsp90ab1 sequence (FIG. 31) |
| 69 | ASO18-ASO22 monkey Hsp90ab1 sequence (FIG. 31) |
| 70 | ASO18-ASO22 mouse Hsp90ab1 sequence (FIG. 31) |
| 71 | ASO23 human Hsp90ab1 sequence (FIG. 31) |
| 72 | ASO23 monkey Hsp90ab1 sequence (FIG. 31) |
| 73 | ASO23 mouse Hsp90ab1 sequence (FIG. 31) |
| 74 | ASO sequence related to NC1, negative control ASO sequence |
| 75 | ASO sequence related to ASO1 |
| 76 | ASO sequence related to ASO2 |
| 77 | ASO sequence related to ASO3 |
| 78 | ASO sequence related to ASO4 |
| 79 | ASO sequence related to ASO5 |
| 80 | ASO sequence related to ASO6 |
| 81 | ASO sequence related to ASO7 |
| 82 | ASO sequence related to ASO8 |
| 83 | ASO sequence related to ASO9 |
| 84 | ASO sequence related to ASO10 |
| 85 | ASO sequence related to ASO11 |
| 86 | ASO sequence related to ASO12 |
| 87 | ASO sequence related to ASO13 |
| 88 | ASO sequence related to ASO14 |
| 89 | ASO sequence related to ASO15 |
| 90 | ASO sequence related to ASO16 |
| 91 | ASO sequence related to ASO17 |
| 92 | ASO sequence related to ASO18 |
| 93 | ASO sequence related to ASO19 |
| 94 | ASO sequence related to ASO20 |
| 95 | ASO sequence related to ASO21 |
| 96 | ASO sequence related to ASO22 |
| 97 | ASO sequence related to ASO23 |
| 98 | ASO sequence related to ASO1 variant 1 |
| 99 | ASO sequence related to ASO1 variant 2 |
| 100 | ASO sequence related to ASO1 variant 3 |
| 101 | ASO sequence related to ASO2 variant 1 |
| 102 | ASO sequence related to ASO2 variant 2 |
| 103 | ASO sequence related to ASO2 variant 3 |
| 104 | ASO sequence related to ASO6 variant 1 |
| 105 | ASO sequence related to ASO8 variant 1 |
| 106 | ASO sequence related to ASO8 variant 2 |
| 107 | ASO sequence related to ASO8 variant 3 |

EXAMPLES

Example 1—Employing Platform Technology to Identify HSPAB1 (HSP90β) as an Important Node of Activity in the Etiology of Diabetes In this example, the platform technology described in detail in international Patent Application No. PCT/US2012/027615 was employed to integrate data obtained from a custom built diabetes model, and to identity novel proteins/pathways driving the pathogenesis of diabetes. Relational maps resulting from this analysis have identified HSPAB1 (HSP90β) as an important node of activity in the etiology of diabetes. Therefore, HSPAB1 (HSP90β) is an important diabetes treatment target, as well as a diagnostic/prognostic marker associated with diabetes.

Five primary human cell lines, namely adipocytes, myotubes, hepatocytes, aortic smooth muscle cells (HASMC), and proximal tubular cells (HK2) were subject to one of five conditions simulating an environment experienced by these disease-relevant cells in vivo. Specifically, each of the five cell lines were exposed separately to each of the following conditions: hyperglycemic conditions, hyperlipidemic conditions, hyperinsulinemic conditions, hypoxic conditions and exposure to lactic acid. The hyperglycemic condition was induced by culturing cells in media containing 22 mM glucose. The hyperlipidemic condition was induced by culturing the cells in media containing 0.15 mM sodium palmitate. The hyperinsulinemic condition was induced by culturing the cells in media containing 1000 nM insulin. The hypoxic condition was induced by placing the cells in a Modular Incubator Chamber (MIC-101, Billups-Rothenberg Inc. Del Mar, Calif.), which was flooded with an industrial gas mix containing 5% $CO_2$, 2% $O_2$ and 93% nitrogen. Each cell line was also treated with 0 or 12.5 mM lactic acid.

In addition, cross talk experiments between two different pairs of cells, human aortic smooth muscle cells (HASMC) (cell system 1) and human kidney 2 (HK2) cells (cell system 2); or liver cells (cell system 1) and adipocytes (cell system 2) were carried out in which the paired cells were co-cultured. This co-culturing approach is referred to as an extracellular secretome (ECS) experiment. The first cell system (e.g., HASMC) was first seeded in the inserts of the wells of a transwell type growth chamber. Six well plates were used to enable better statistical analysis. At the time of seeding with the first cell system in the inserts, the inserts were placed in a separate 6-well plate. The second cell system (e.g., HK2) was seeded on the primary tray. The insert tray containing the first cell system and the primary tray containing the second cell system were incubated at 37° C. overnight. Each of the cell systems was grown in the specific cell specific media (wherein alternatively, each of the cell systems could be grown in a medium adapted to support the growth of both cell types). On the second day, the pre-determined treatment was given by media exchange. Specifically, the inserts containing the first cell system were placed into the primary tray containing the second cell system. The tray was then incubated for a pre-determined time period, e.g., 24 hour or 48 hours. Duplicate wells were set up with the same conditions, and cells were pooled to yield sufficient material for 2D analysis. The media (1 ml aliquot), the cells from the inserts and the cells from the wells of the primary tray were harvested as separate samples. The experiments were conducted in triplicate in order to provide better statistical analysis power.

Cross-talk experiments were also conducted by "media swap" experiments. Specifically, a cultured media or "secretome" from the first cell system, HASMC was collected after 24 hrs or 48 hrs following perturbation or conditioning and then added to the second cell system, Adipoctes, for 24-48 hrs. The final cultured media or "secretome" from the second cell system was then collected. All final secretomes were subjected to proteomic analysis.

The cell model comprising the above-mentioned cells, wherein the cells were exposed to each condition described above, was additionally "interrogated" by exposing the cells to an "environmental perturbation" by treating with Coenzyme Q10. Specifically, the cells were treated with Coenzyme Q10 at 0, 50 μM, or 100 μM.

Cell samples for each cell line, condition and Coenzyme Q10 treatment were collected at various times following treatment, including after 24 hours and 48 hours of treatment. For certain cells and under certain conditions, media samples were also collected and analyzed.

iProfiling of changes in total cellular protein expression by quantitative proteomics was performed for cell and media samples collected for each cell line at each condition and with each "environmental perturbation", i.e, Coenzyme Q10 treatment, using the techniques described above in the detailed description.

Proteomics data collected for each cell line listed above at each condition and with each perturbation, and bioenergetics profiling data collected for each cell line at each condition and with each perturbation, were then processed by the REFS™ system. A composite perturbed network was generated from combined data obtained from all the cell lines for one specific condition (e.g., hyperglycemia) exposed to perturbation (CoQ10). A composite unperturbed network was generated from combined data obtained from all of the cell lines for the same one specific condition (e.g., hyperglycemia), without perturbation (without CoQ10). Similarly, a composite perturbed network was generated from combined data obtained from all of the cell lines for a second, control condition (e.g., normal glycemia) exposed to perturbation (CoQ10). A composite unperturbed network was generated from combined data obtained from all of the cell lines for the same second, control condition (e.g., normal glycemia), without perturbation (without CoQ10).

Each node in the consensus composite networks described above was simulated (by increasing or decreasing by 10-fold) to generate simulation networks using REFS™, as described in detail above in the detailed description.

The area under the curve and fold changes for each edge connecting a parent node to a child node in the simulation networks were extracted by a custom-built program using the R programming language, where the R programming language is an open source software environment for statistical computing and graphics.

Delta networks were generated from the simulated composite networks. To generate a Diabetes disease condition vs. normal condition differential network in response to Coenzyme Q10 (delta-delta network), steps of comparison were performed as illustrated in FIG. 1, by a custom built program using the PERL programming language.

Figure 1:
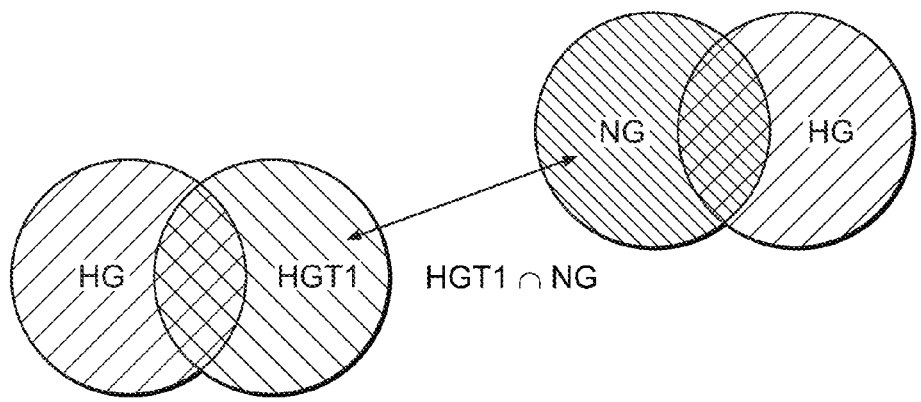
FIG. 1 is a schematic representation of the Delta-Delta networks used in the interrogatory platform method employing the diabetes model. HG is hyperglycemia; HGT1 is hyperglycemia with coenzyme Q10 treatment; and NG is normal glycemia.

Specifically, as shown in FIG. 1, Treatment T1 refers to Coenzyme Q10 treatment and NG and HG refer to normal and hyperglycemia as conditions. Unique edges from NG in the NG∩HG delta network was compared with unique edges of HGT1 in the HG∩GT1 delta network. Edges in the intersection of NG and HGT1 are HG edges that are restored to NG with T1. HG edges restored to NG with T1 were superimposed on the NG∩HG delta network (shown in darker colored circles in FIG. 2).

Specifically, a simulated composite map of normal glycemia (NG) condition and a simulated composite map of hyperglycemia (HG) condition were compared using a custom-made PERL program to generate unique edges of the normal glycemia condition. A simulated composite map of hyperglycemia condition without Coenzyme Q10 treatment (HG) and a simulated map of hyperglycemia condition with Coenzyme Q10 treatment (HGT1) were compared using a custom-made PERL program to generate unique edges of the hyperglycemia condition with Coenzyme Q10 treatment (HGT1). Edges in the intersection of the unique edges from normal glycemia condition (NG) and the unique edges from hyperglycemia condition with Coenzyme Q10 treatment (HGT1) were identified using the PERL program. These edges represent factors/networks that are restored to normal glycemia condition from hyperglycemia condition by the treatment of Coenzyme Q10. The delta-delta network of hyperglycemic edges restored to normal with Coenzyme Q10 treatment was superimposed on the normal glycemia ∩ hyperglycemia delta network.

Figure 2:
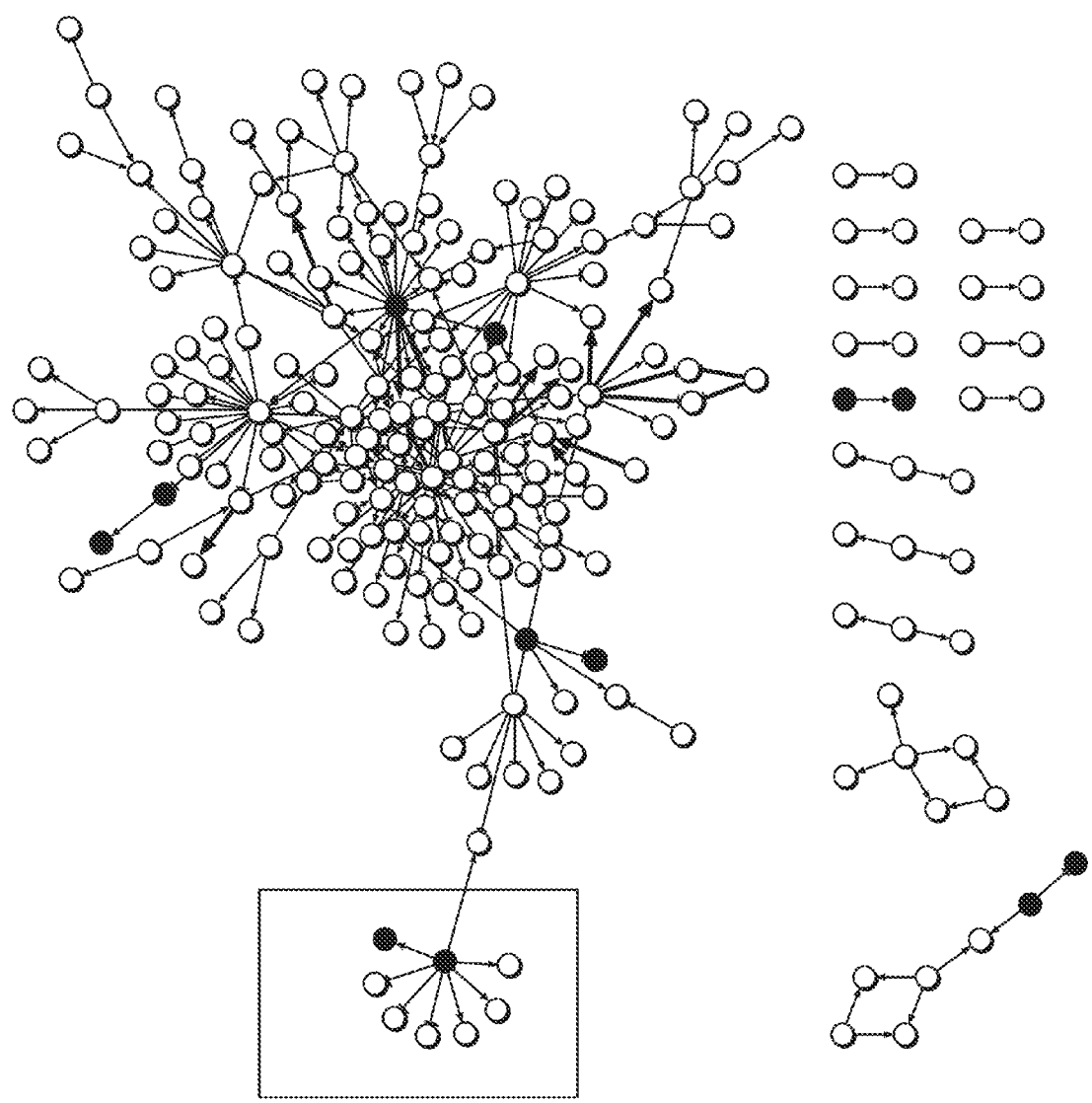
FIG. 2 is a schematic representation of a network in diabetic versus normal cellular models that were generated by the interrogatory platform method discussed herein. The darker nodes represent the five predominant hubs of activity identified using the method.

Output from the PERL and R programs were inputted into Cytoscape, an open source program, to generate a visual representation of the superimposed network between the hyperglycemic edges restored to normal condition with Coenzyme Q10 treatment delta-delta network and the normal glycemia vs. hyperglycemia delta network. An output from the Cytpscape program representing the superimposed network is shown in FIG. 2. Darker colored circles in FIG. 2 are identified edges which were restored to a normal glycemia condition from a hyperglycemia condition by the treatment of Coenzyme Q10. Lighter colored circles in FIG. 2 are identified unique normal hypercemia edges. The subnetwork in the box shown in FIG. 2 is enlarged and represented in FIG. 3. HSP90AB1 (HSP90β) is one of the identified markers which are edges restored to a normal glycemia condition from a hyperglycemia condition by the treatment of Coenzyme Q10 (see FIG. 3).

Figure 4:
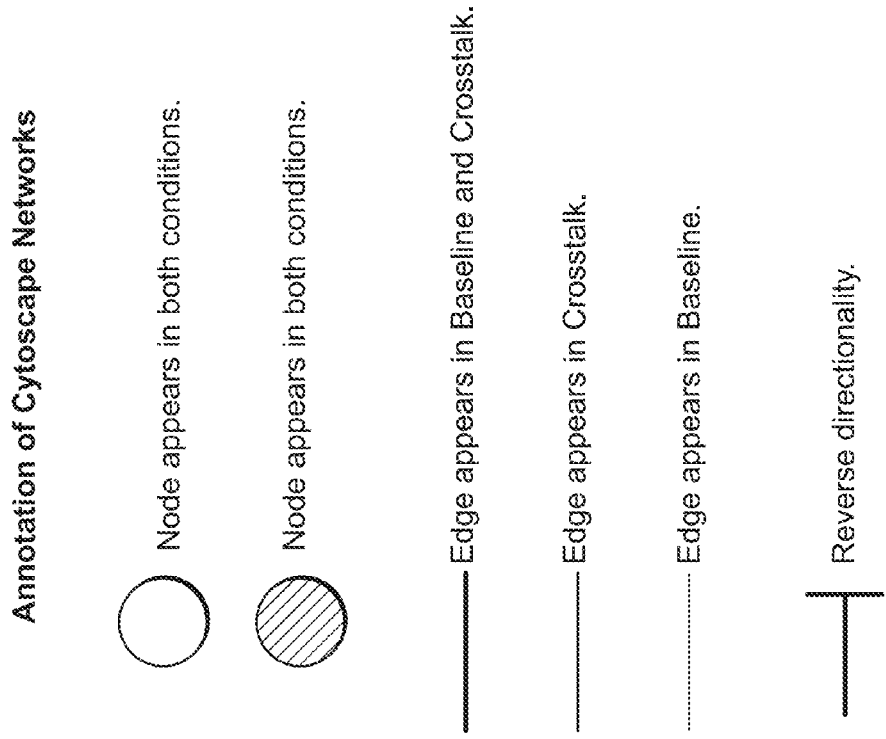
FIG. 4 provides a key to the symbols and color codes used to delineate causal protein associations in delta-delta networks.
Figure 3:
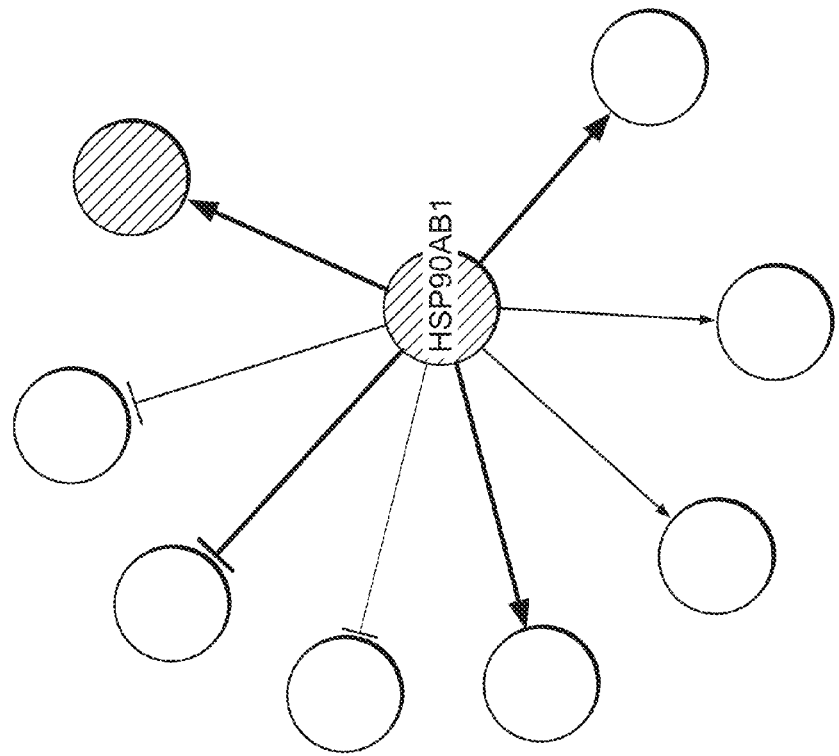
FIG. 3 is a magnified version of the section of the network indicated by the box in FIG. 2, showing an association map of HSP90AB1 (HSP90β) and causal nodes of interest from the platform method diabetes output discussed herein.

FIG. 3 represents an association map of HSP90AB1 (HSP90β) and causal nodes of interest from the Interrogative Biology® diabetes outputs. FIG. 4 represents list of symbols and color codes used in the differential network maps to delineate causal associations of proteins in disease and normal cell models. HSP90AB1 (HSP90β) was identified in this superimposed delta-delta network as a potential therapeutic factor, drug target and biomarker for diabetes.

Example 2—HSP90β Regulation of Cellular Substrate Metabolism and Insulin Signaling A. Materials and Methods:
1. Differentiation of Human Myoblasts into Myotubes:

Human skeletal muscle myoblasts (HSMM) were procured from PromoCell and were cultured in growth media recommended by the vendor. Confluent cultures were replaced with differentiation media (DMEM, 2% horse serum, pyruvate and HEPES) and cells allowed to differentiate for 7 to 10 days.

2. siRNA of Hsp90β/Inhibition of HSP90:

Commercially available trifecta siRNA from IDT® was used for specific knockdown of Hsp90β. As a control a scrambled siRNA was included in all experiments. All three siRNA provided by IDT® was separately transfected using a Minis® TKO® transfection reagent. Hsp90β knockdown was confirmed by western blotting and qPCR using commercially available antibody and primer probes that are specific to human Hsp90β protein and mRNA. HSP90 inhibitor CCT018159 was obtained from Tocris Bioscience.

3. siHsp90β Sequence Information:

H1:
Duplex Sequences
                                          (SEQ ID NO: 1)
5'-rArGrG rCrCrG rArCrA rArGrA rArUrG rArUrA
rArGrG rCrAG T-3'

(SEQ ID NO: 2)
5'-rArCrU rGrCrC rUrUrA rUrCrA rUrUrC rUrUrG
rUrCrG rGrCrC rUrCrA-3'

H2:
Duplex Sequences
                                          (SEQ ID NO: 3)
5'-rCrArA rCrGrA rUrGrA rUrGrA rArCrA rGrUrA
rUrGrC rUrUG G-3'

(SEQ ID NO: 4)
5'-rCrCrA rArGrC rArUrA rCrUrG rUrUrC rArUrC
rArUrC rGrUrU rGrUrG-3'

H3:
Duplex Sequences
                                          (SEQ ID NO: 5)
5'-rCrGrU rUrGrC rUrCrA rCrUrA rUrUrA rCrGrU
rArUrA rArUC C-3'

(SEQ ID NO: 6)
5'-rGrGrA rUrUrA rUrArC rGrUrA rArUrA rGrUrG
rArGrC rArArC rGrUrA-3'

4. Insulin Signaling Experiments:

Human HSMM myotubes cells that were plated in 12 well plates the previous week were used. The media was aspirated and fresh media with appropriate dilutions of the NC and H3 siRNA for Hsp90 knockdown were added such that the final concentration in the wells of the plate was 100 nM. Minis TKO transfection reagent was used for transfecting the cells. The plate was then incubated at 37° C. overnight.

The media was aspirated and the cells were washed off twice—first with warm PBS and second with 0.1% BSA containing growth media. The cells were then serum starved for 2-3 hours in 0.1% differentiation media containing the appropriate inhibitors at 37° C. followed by insulin stimulation for 5 minutes (0, 10, and 100 nM insulin).

The wells were then washed once with PBS and harvested into 100 μl of RIPA buffer containing protease and phosphatase inhibitors. The plate was placed on ice and, using a cell scraper, the cells were scraped from the plate. The lysates were collected in 1.5 ml Eppendorf tubes and homogenized by using a syringe and needle. The lysates were then centrifuged at 4° C. for 10 mins at 14,000 RPM. The lysates can be stored at −20° C. for future use.

Protein content was estimated by BCA assay and samples were prepared for gel electrophoresis and western blotting as described in subsequent sections. The total volume required to load 10 μg of total protein was calculated.

The samples were loaded onto a bis-tris or a tris-glycine-SDS gel. Proteins were transferred to a PVDF or a nitrocellulose membrane using routine wet or dry transfer methods. The membranes were then blocked for at least an hour using the blocking buffer. The membranes were then cut prior to exposure to the appropriate primary antibodies diluted in blocking buffer for incubation. Primary antibodies to pAKT (p-Akt, S473), pERK(p-Erk, Phospho-p44/42 MAPK (Erk1/2) (Thr202/Tyr204), and pGSK3β (Phospho-GSK-3β (Ser9) were obtained from Cell Signaling Inc.® Other antibodies were also obtained from commercial sources. The membrane was placed in the shaker and incubated in the refrigerator (4° C.) overnight.

Visualization of proteins and quantification of western blots was performed as follows. The membranes were washed thrice using 1×PBS-T (10 minutes each). The appropriate HRP conjugated secondary antibodies were diluted (1:10,000) in blocking buffer and added to each of the membranes. Membranes were incubated for at least an hour in the shaker at room temperature. The membranes were washed three times (10 minutes each) with PBS-T. After the final wash the membranes were kept in the PBS-T until detection of the proteins.

Each strip of membrane was taken out arranged in a clean flat surface. The chemiluminescent substrate (Pierce® PICO or DURA) was added to each of the membranes and incubated for 5 minutes. The membranes were then placed in a clean sheet of plastic for visualization using the BIO-RAD® chemiluminescence imager. The bands were quantified using the BIORAD® software.

5. Insulin Stimulated Glucose Uptake:

HSMM myoblasts (20,000 cells/well) were differentiated with 2% horse serum in 96 well plates for 7 days before experiment. Cells were washed twice with 200 ul MBSS buffer containing 0.1% BSA, and then serum starved with 100 ul MBSS 0.1% BSA for 4 hours. Some wells were also pretreated with 25 uM LY compound for 20 minutes. Upon initiation of insulin stimulation, 100 ul 2× reagents in MBSS 0.1% BSA buffer was added to 100 ul starvation media to make 1× concentration for the experiment. The 2× reagents are: insulin (0, 20 nM, and 200 nM); 2NBDG (500 uM). Cells were treated with insulin and 2NBDG for 30 min, then washed twice with MBSS buffer, then 50 ul MBSS buffer were added to wells. Glucose uptake was detected with fluorometer along with background detection with wells with no cells in them. After fluorometer readout, a fixative (formalin, 50 ul) was added to 50 ul MBSS in the wells, then 100 ul 1 uM DAPI was added to 100 ul formalin and MBSS mixture.

6. Bioenergetic Profiling of Myotubes:

HSMM myotubes cultured in wells in a Seahorse® assay cartridge were differentiated with 2% horse serum myocyte differentiation media for 7 days. Cells were transfected with either negative control scrambled siRNA or siHsp siRNA with TKO transfection reagents at concentration of 50 nM following vendor instructions as described above (Minis Bio®). After 48 hours transfection, cells were subjected to Seahorse® bioenergetics analysis using drugs to modulate cell energetics, i.e., oligomycin, carbonyl cyanide-M-chlorophenyl hydrazine (CCCP), and rotenone. Oligomycin inhibits mitochondrial ATP synthase (complex V of ET chain) and allows analysis of glycolytic capacity. CCCP is an uncoupler that pumps proton out of the mitochondrial membrane, thereby inducing maximum compensatory oxygen consumption, and allows analysis of uncoupled OCR. Rotenone inhibits NADH dehydrogenase (complex I of ET chain) and allows analysis of non-mitochondrial OCR.

To perform the assay, each well of the Seahorse® assay cartridge was washed with 1 ml running media. 500 ul of running media was added to each well and the plate was placed in an 37° C. ($CO_2$ free) incubator. Drugs to modulate mitochondrial activity were prepared at a 10× (10 uM) concentration, so that after addition to the cartridge, the final concentration would be 1× (1 μM). Oligomycin (50 ul), CCCP (55 ul) and rotenone (55 ul) were added to ports A, B, and C of the cartridge and the cartridge was placed back in the incubator. The Seahorse® assay wizard was opened and the cycle parameters and times were setup. The Seahorse® assay was then performed using the instrument. After the Seahorse® assay, cells were lysed with 50 ul 450 mM NaOH and then neutralized with 5 ul Tris 6.8. DNA lysates were subjected to spectrophotometric analysis at $OD_{260}$ using BioTek® Take3 DNA plate reader. The data were normalized with DNA contents of the cells.

B. Results

Figure 5:
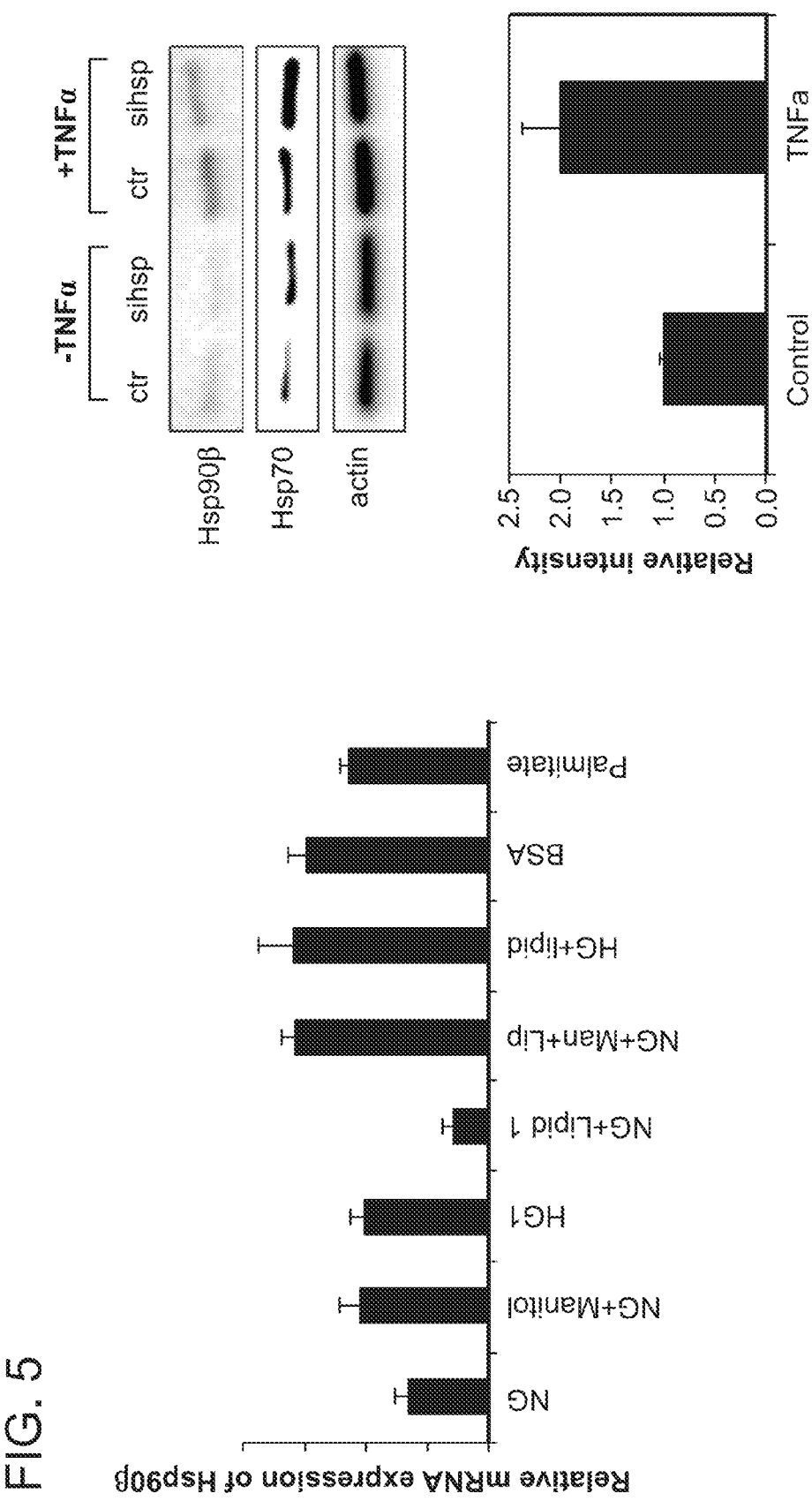
FIG. 5 shows the induction of Hsp90β expression mRNA and protein in response to metabolic factors and inflammation. NG=normal glucose; HG=high glucose; lipid=a mixture of oleic acid and linoleic acid; Man=(mannitol).

1. Metabolic and Stress Factors Induce Expression of Hsp90β:

Acute treatment of myotubes with metabolic and stress factors was shown to modulate expression of Hsp90β. HSMM myoblasts were differentiated in media containing 2% horse serum for 7 days, then subjected to different nutrient conditions for 24 hours including: normal glucose (NG 5 mM glucose), high glucose (HG 25 mM), NG+mannitol (mannitol is used to equilibrate the osmotic pressure), mixture of oleic acid and linoleic acid (150 uM), palmitate (150 uM), and a combination of these different conditions. Results showed that after 24 hours, high glucose did not have significant effects on Hsp90β mRNA expression, despite the effects induced by osmotic stress. With normal glucose conditions, the lipid mixture suppressed HSP90β mRNA expression, while it elevated HSP90β mRNA expression at high glucose condition. Palmitate with NG suppressed HSP90β mRNA expression as compared with BSA control. These data indicated that HSP90β expression is regulated by different metabolic factors such as lipidemia, demonstrating a relationship with oxidative metabolism and stress responses. Hsp90β expression was induced upon treatment of myotubes with TNFα (FIG. 5).

Figure 6:
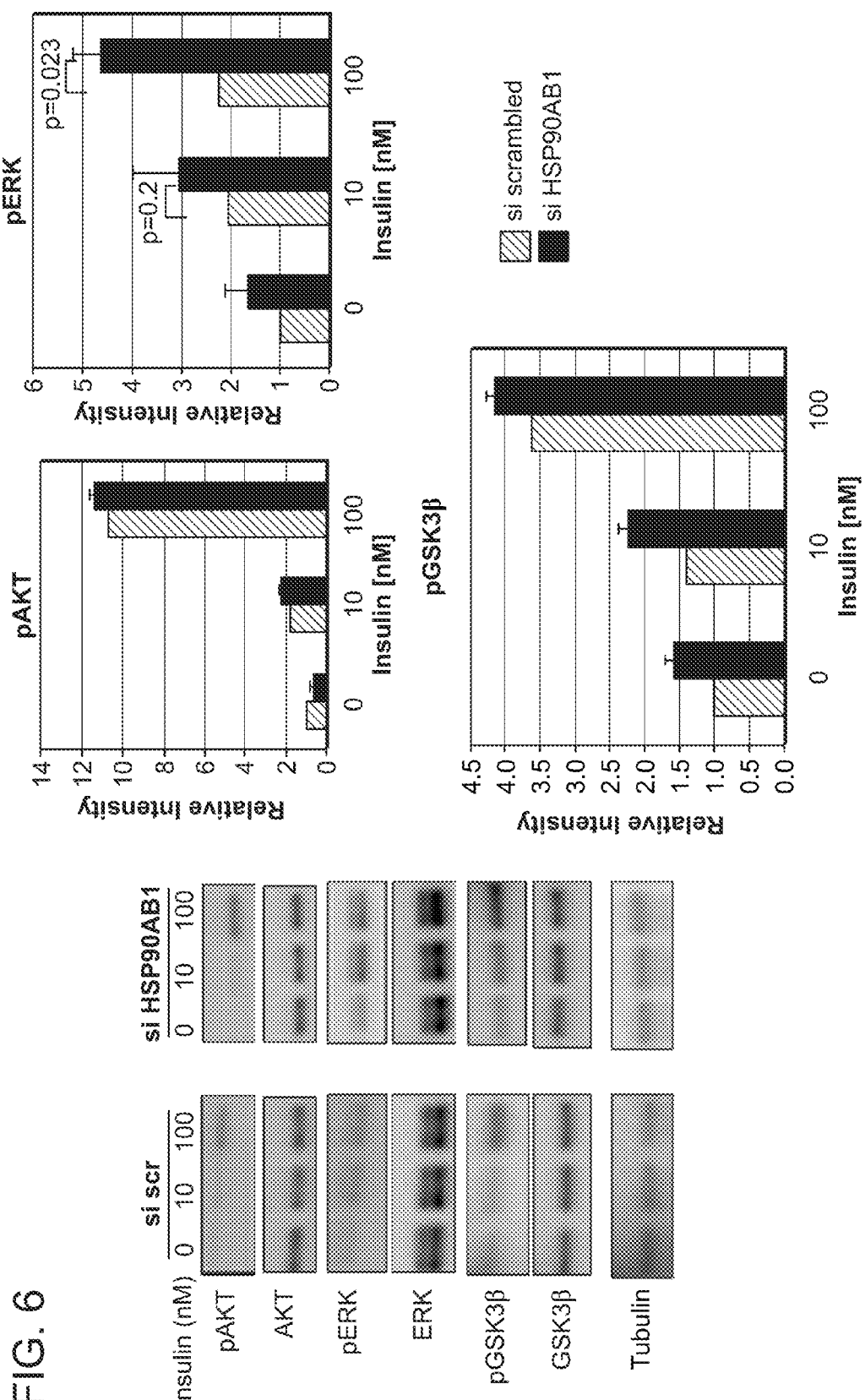
FIG. 6 shows the results of knockdown of Hsp90β in myotubes leading to a significant increase in insulin stimulated phosphorylation of AKT, ERK, and GSK3β. The effect of knockdown on pERK was significant when compared to scrambled siRNA.

2. Knockdown of Hsp90β in Myotubes Resulted in Increased Insulin Signaling:

HSMM myotubes were sequentially (1) transfected with 3 different siRNAs targeting HSP90AB1 for 48 hours, (2) serum starved for 3 hours, and (3) subjected to stimulation of different concentrations of insulin (0, 10, 100 nM). Signaling events downstream of insulin stimulation were assessed by western blotting for levels of total and phosphorylated Akt, Erk, and GSK3β. Quantification of western blots showed that HSP90AB1 knockdown induced significantly elevated insulin stimulated phosphorylation of Akt, ERK, and GSK3β. Akt is activated by phospholipid binding and activation loop phosphorylation at Thr308 by PDK1 and by phosphorylation within the carboxy terminus at Ser473. MEK1 and MEK2 activate p44 and p42 through phosphorylation of activation loop residues Thr202/Tyr204 and Thr185/Tyr187, respectively. GSK-3 is a critical downstream element of the PI3K/Akt cell survival pathway whose activity can be inhibited by Akt-mediated phosphorylation at Ser21 of GSK-3α and Ser9 of GSK-3β (FIG. 6).

Figure 7:
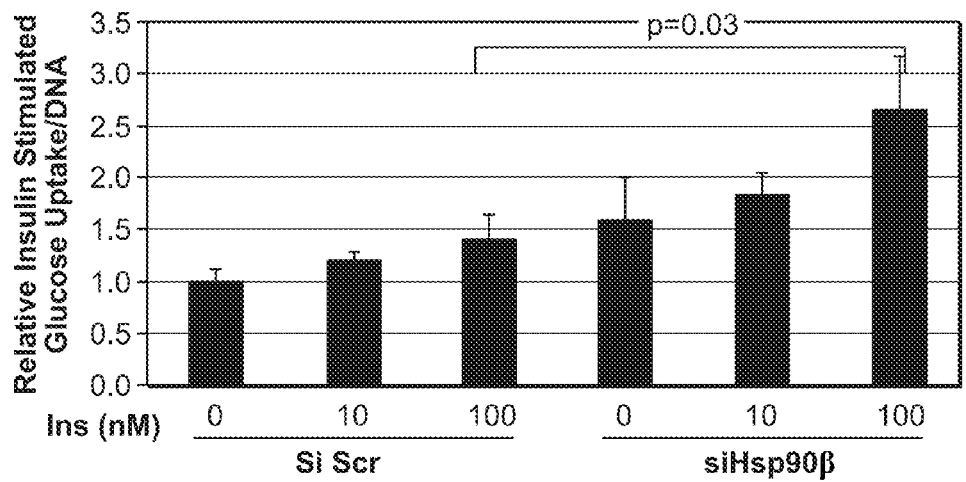
FIG. 7 shows the results of knockdown of Hsp90β in myotubes, leading to a significant increase in insulin stimulated glucose uptake when compared to a scrambled siRNA (si scrambled).

3. Knockdown of Hsp90β in Myotubes Resulted in Increased Insulin Stimulated Glucose Uptake:

Consistent with elevated signaling events induced by Hsp90β knockdown, insulin stimulated glucose uptake was measured in HSMM myotubes using the fluorescent glucose analog 2-NBDG. Using the methods provided above, cells were sequentially transfected with either control or Hsp90β siRNA for 48 hours, serum starved for 4 hours, and stimulated with different concentrations of insulin with presence of 250 uM 2-NBDG for 30 min. The cells were then washed with PBS and fluorescence was detected using a plate reader. The fluorescence of the cell reflects the amount of the glucose taken up by the cells. The results demonstrated that the siHsp90β treated cells, with reduced HSP90β expression, showed significantly enhanced insulin stimulated glucose uptake when compared to cells treated with the non-specific si-srambled under the same conditions. These data demonstrate that inhibition or knockdown of Hsp90β in myotubes enhances insulin stimulated glucose uptake (FIG. 7).

4. Knockdown of Hsp90β in Myotubes Resulted in Increased Mitochondrial Efficiency:

HSMM myotubes were transfected with siRNA of either control or siHsp90β for 48 hours as described above, then subjected to Seahorse® bioenergetic profiling (XF24 Analyzer) using different mitochondrial drugs including oligomycin, CCCP, and rotenone; and monitored changes on oxygen consumption rate (OCR) that reflects either basal or maximum mitochondrial oxidative capacity. The results were normalized by DNA content.

Figure 8:
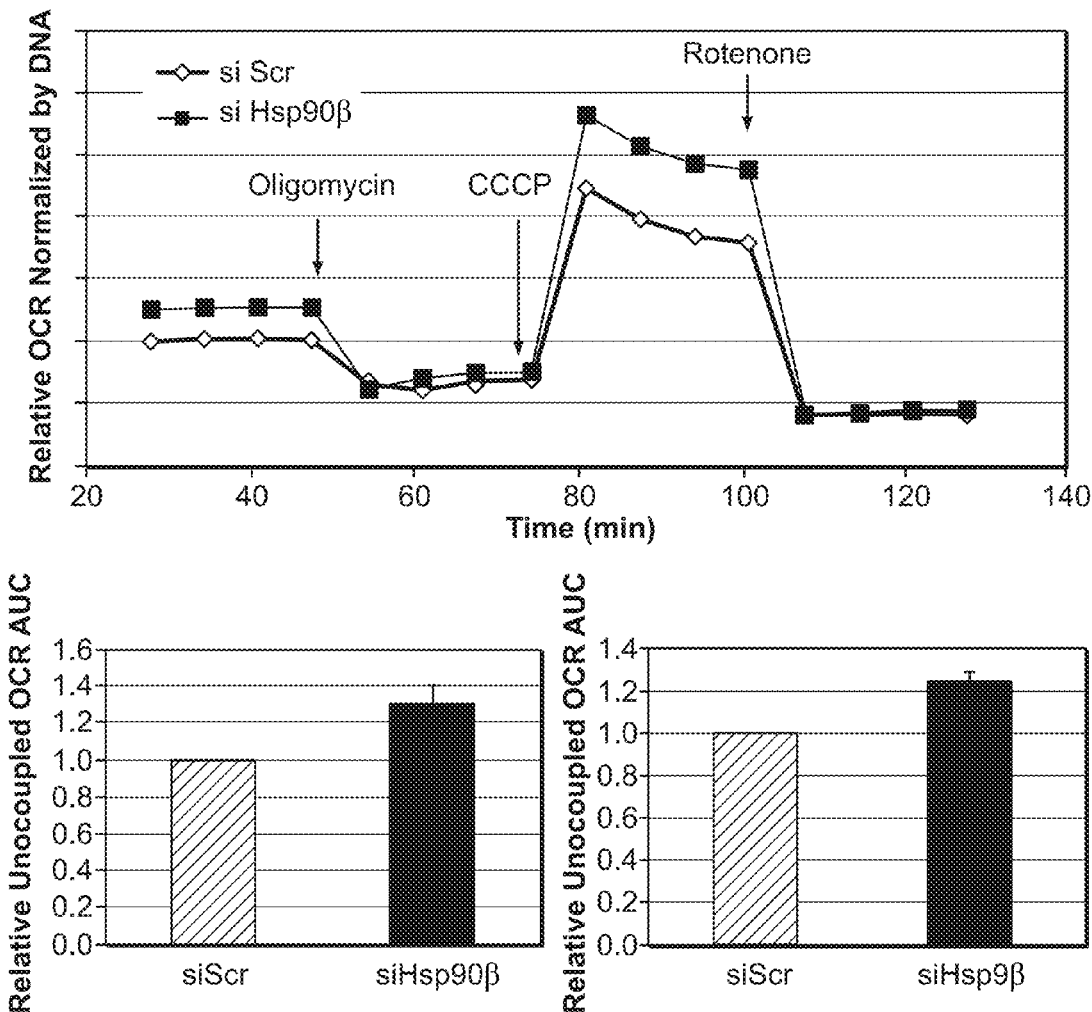
FIG. 8 shows the results of knockdown of Hsp90β in myotubes, leading to a significant increase in CCCP induced uncoupling in comparison with scrambled siRNA. Basal respiration in myotubes in which Hsp90β was knocked down was observed to be moderately higher than in myotubes treated with a scrambled siRNA (si scrambled).

The results demonstrated that in both basal and uncoupled conditions, HSP90β knockdown myotubes displayed enhanced oxidative respiration. This demonstrates that Hsp90β knockdown induces profound metabolic changes on mitochondrial in myotubes, indicating a role for Hsp90β in regulation of mitochondrial functions via its chaperone activity, likely by targeting the incorporation of different mitochondrial proteins. Quantification of area under the curve (AUC) for both basal and uncoupled OCR in myotubes, with either control or siHSP90AB1 siRNAs from the bioenergetics profiling study, revealed significantly increased basal and uncoupled OCR in Hsp90β knockdown cells, thereby demonstrating improved mitochondrial efficiency (FIG. 8) upon knockdown of Hsp90β expression.

Figure 9A:
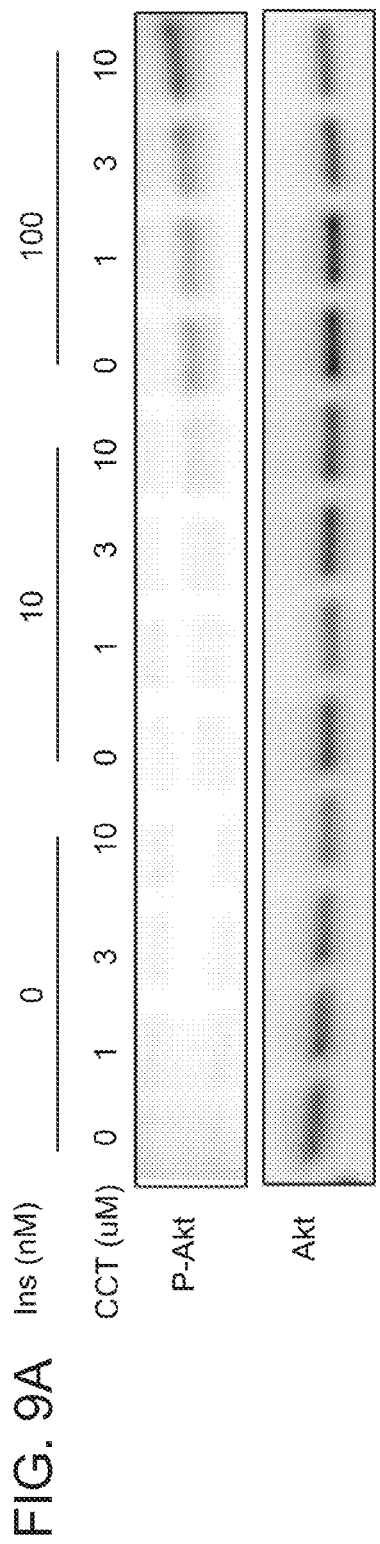
FIGS. 9A and 9B show (A) a western blot and (B) quantitative analysis demonstrating the effects of the treatment of myotubes with the Hsp90 inhibitor CCT018159 (CCT) and insulin (Ins), which were observed to increase levels of phospho-AKT in comparison with untreated cultures. No significant changes in pERK or pGSK3β was observed.
Figure 9B:
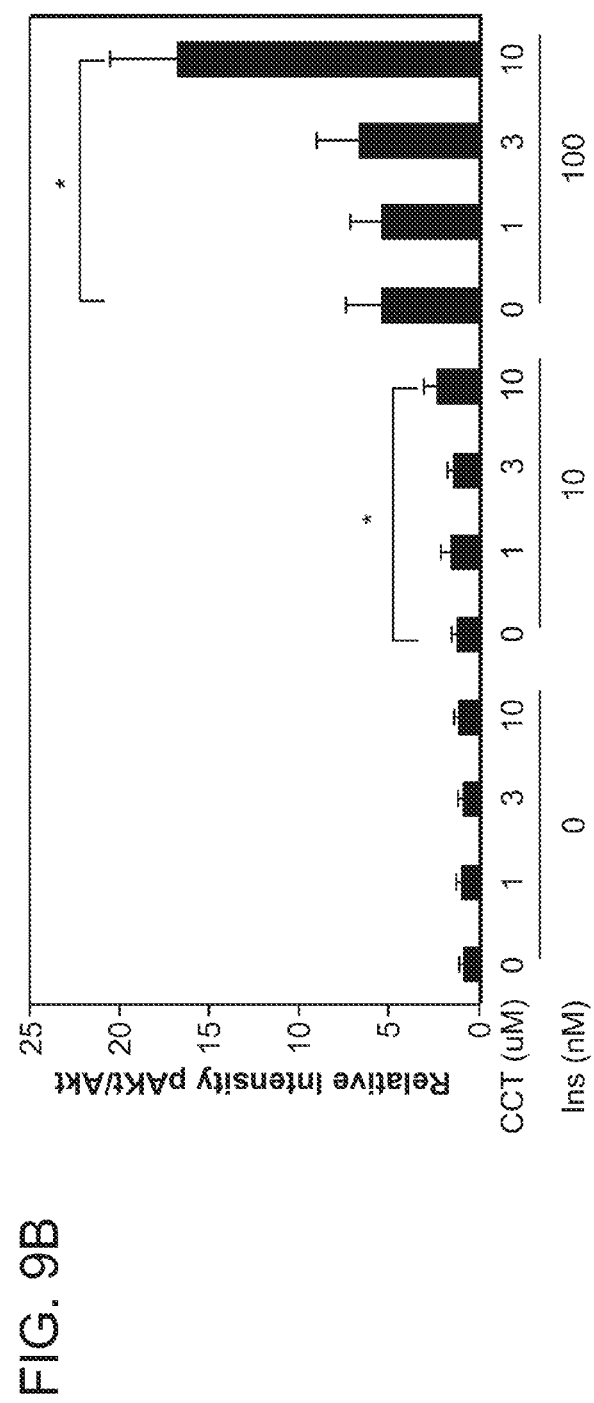

5. HSP90 Inhibition by Small Molecule Inhibitor (CCT018159) Increased Phosphorylation of AKT, but Not ERK and GSK3β:

Myotubes were treated with a small molecule inhibitor of HSP90 (CCT018159) then subjected to insulin stimulation. The small molecule inhibitor of HSP90 (CCT018159) inhibits both HSP90α and HSP90β. The effect of the small molecule inhibitor on insulin signaling was assessed by measuring insulin stimulated phosphorylation of the downstream targekts Akt, ERK, and GSK3β by western blot. The results demonstrated that the higher concentration of CCT018159, specifically 10 uM, significantly enhanced insulin stimulated phosphorylation of Akt, indicating that the HSP90 inhibition enhanced insulin sensitivity in myotubes. However, no change in the level of pERK or pGSK3β was observed (FIG. 9).

Figure 10:
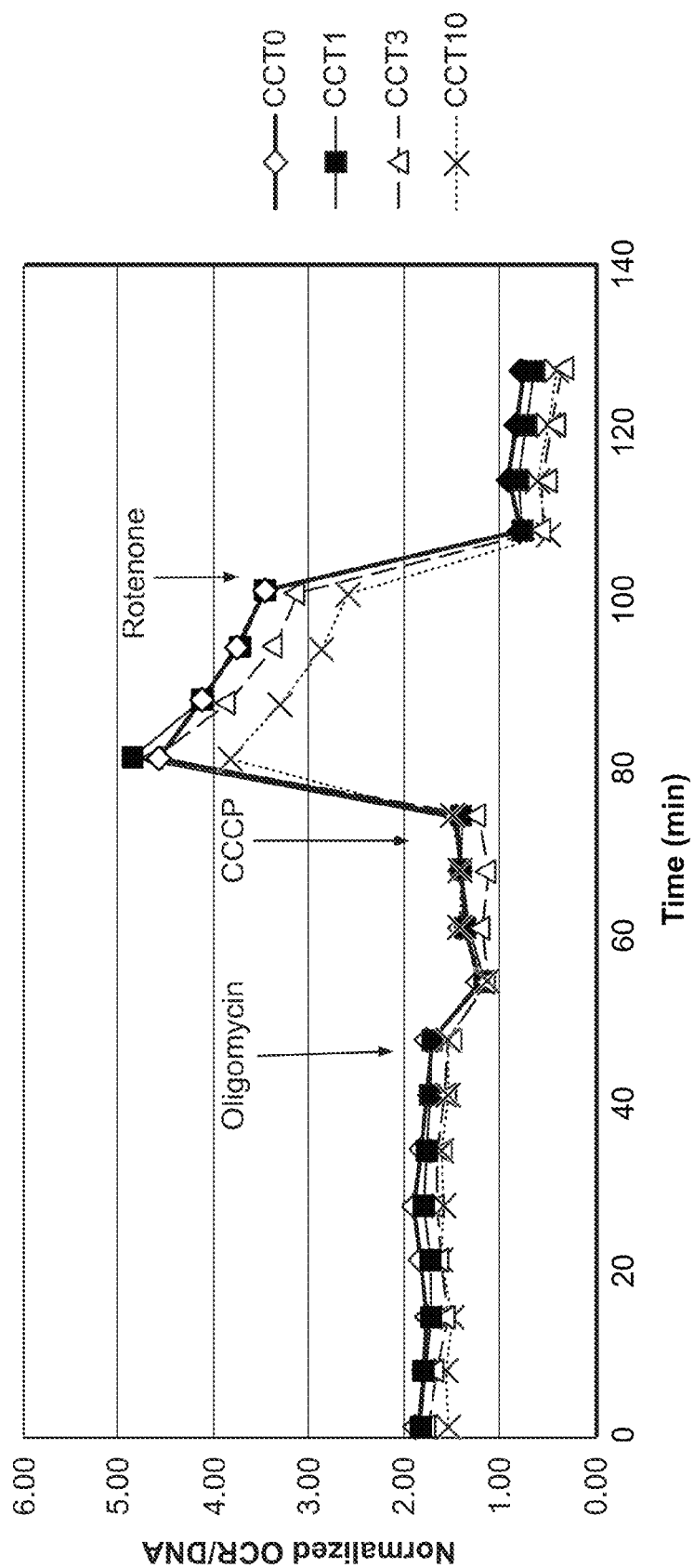
FIG. 10 shows the results from the treatment of skeletal muscle myotubes with the Hsp90 inhibitor CCT018159 (CCT) at 1 μM, 3 μM, and 10 μM, which did not have a significant effect on CCCP induced uncoupling response on mitochondrial metabolism.

A differential effect of Hsp90 small molecule inhibitors on cellular bioenergetics was observed in comparison with that of Hsp90β-specific knockdown. The bioenergetic profile of myotubes following treatment with CCT018159 at different concentrations showed a different profile from what was observed with Hsp90β knockdown cells. There was no observed change on basal OCR, and yet the uncoupled OCR was actually decreased in a concentration dependent manner, where 10 uM CCT018159 induced greater suppression of CCCP induced OCR. This different profile indicates that increased OCR in both basal and uncoupled states is Hsp90β specific, while CCT018159 inhibits both Hsp90α and Hsp90β by blocking their ATP binding pockets. At a lower concentration of CCT018159 (1 μM), increased uncoupled OCR was observed in treated myotubes (FIG. 10).

C. Conclusions:

In summary, Hsp90β regulates insulin signaling, glucose uptake, and substrate metabolism in skeletal muscle myotubes. Induction of Hsp90β mRNA and protein in response to hyperlipidemia, hyperglycemia and pro-inflammatory cues demonstrates a role of the protein in the pathophysiology of diabetes. Knockdown of Hsp90β in myotubes resulted in a significant increase in glucose uptake demonstrating its role in glucose regulation. Knockdown of Hsp90β in myotubes also resulted in a large increase in phosphorylation of ERK and as well as an increase in the phosphorylation of AKT and GSK3β, demonstrating a functional bifurcation of insulin signaling and indicating that Hsp90β is involved in a selective mechanism. Hsp90β knockdown has a significant effect on bioenergetics and mitochondrial substrate metabolism. The HSP90 inhibitor CCT018159, which inhibits both Hsp90α and Hsp90β, had a less profound effect on insulin signaling and bioenergetics, indicating that Hsp90β-specific inhibition is more efficacious than a pan Hsp90 inhibition approach.

Figure 11A:
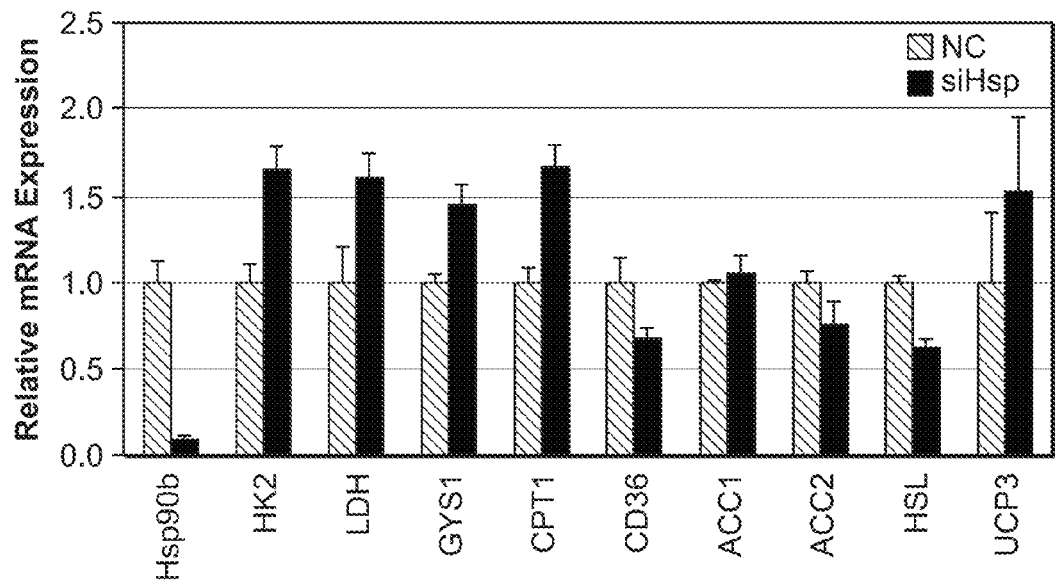
FIGS. 11A and 11B show the effects of siRNA-mediated knockdown of Hsp90β in myotubes on (A) metabolic enzyme gene expression (hexokinase 2 (HK2); lactate dehydrogenase (LDH); glycogen synthase 1 (GYS1); carnitine palmitoyl transferase 1 (CPT-1); Acetyl CoA carboxylase 1 and 2 (ACC1 and ACC2); hormone sensitive lipase (HSL); and mitochondrial uncoupling protein 3 (UCP 3)); and on (B) UCP3 expression in skeletal muscle myotubes.
Figure 11B:
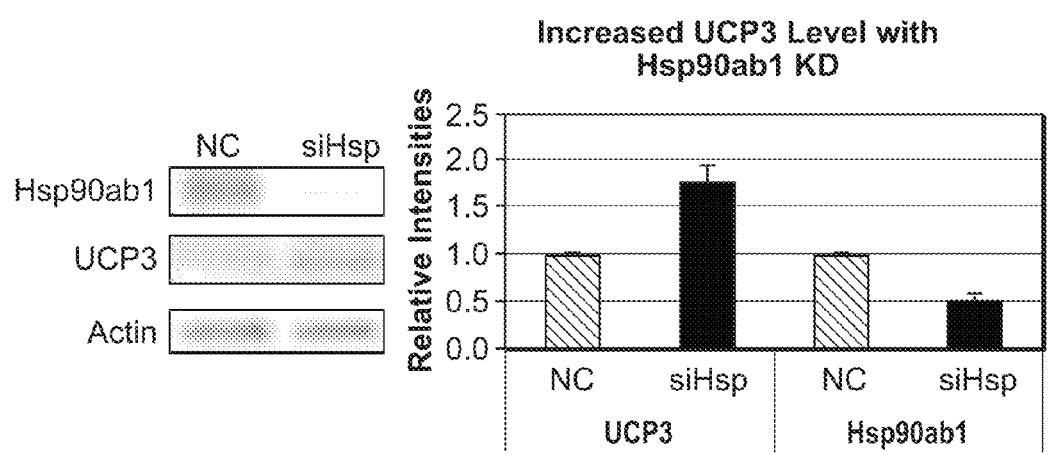

Example 3—HSP90β Regulation of Metabolic Enzyme Expression in Skeletal Muscle Myotubes Myoblasts were cultured and differentiated into myotubes and treated with siRNAs essentially as described above. mRNA expression of a series of metabolic enzymes involved in various metabolic pathways was assayed by rtPCR using routine methods. The enzymes include those involved in glycolysis (HK2, LDH, GYS1), lipid oxidation (CPT1, UCP3), fatty acid transport (CD36), and fatty acid synthesis (ACC1 and ACC2), lipolysis (HSL). mRNA expression in the cells treated with the HSP90β siRNA was normalized to the expression of the gene in the cells treated with the scrambled siRNA. The results are shown in FIG. 11A. mRNA expression levels of HK2, LDH, GYS1, CPT1 and UCP3 were found to be increased upon knockdown of HSP90β expression, whereas the expression levels of CD36 and HSL were found to be decreased upon knockdown of HSP90β expression. A decreasing trend of expression of ACC2, involved in fatty acid synthesis, was also observed. UCP3 protein levels were found to be substantially increased upon knockdown of HSP90 (FIG. 11B). The UPC3 protein expression level in skeletal muscle is typically low in diabetics, but its expression is induced by exercise, Without being bound by mechanism, it is suggested that knockdown of HSP90β expression could be exerting a beneficial effect in the treatment of metabolic syndrome by modulation of proteins such as UCP3.

Example 4—HSP90β Regulation of Glycolytic Flux in Skeletal Muscle Myotubes

Myoblasts were cultured and differentiated into myotubes essentially as described above, subject to growth under normoglycemic and hyperglycemic conditions. The cells subject to hyperglycemic conditions were grown and differentitated in 5 mM glucose, and cultured in 11 mM glucose prior to transfection with siRNA. Cells grown under both normoglycemic and hyperglycemic conditions were transfected with HSP90β siRNA or a scrambled control siRNA. The cells were then subject to Searhorse® analysis as described above to analyze glycolytic flux, with the hyperglycemic cells being assayed in 11 mM glucose.

Figure 12C:
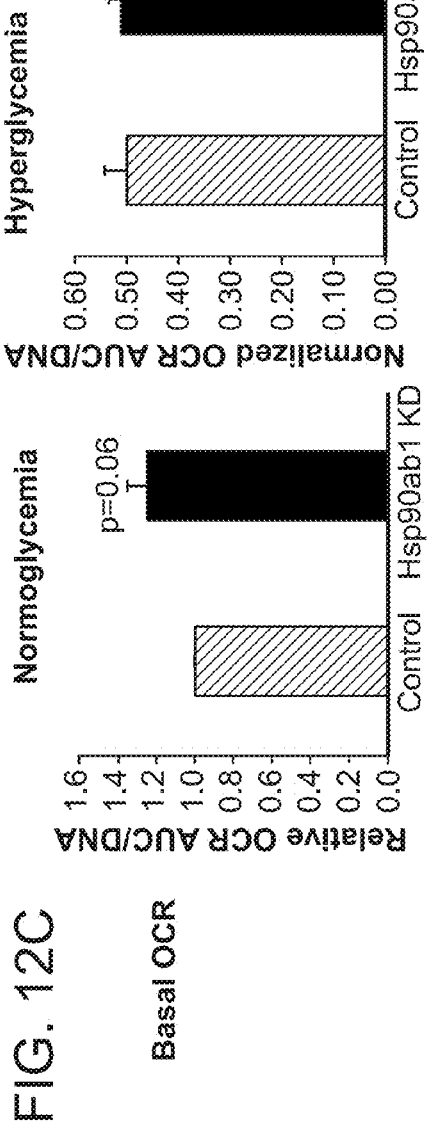
Figure 12D:

As shown in FIGS. 12A and 12B, knockdown of HSP90β increased glucose induced ECAR and oligomycin induced ECAR under both normoglycemic and hyperglycemic conditions. However, although knockdown of HSP90β increased basal OCR and uncoupled OCR under normoglycemic conditions, no change in basal OCR or uncoupled OCR were observed under hyperglycemic conditions (FIGS. 12C and 12D). These results demonstrate the Hsp90AB1 regulates both mitochondrial respiration and glycolysis under different conditions. Without wishing to be bound by mechanism, these results suggest that reduced Hsp90AB1 protein levels may elevate the overall substrate metabolism, thereby improving systemic metabolism in vivo.

Figure 13A:
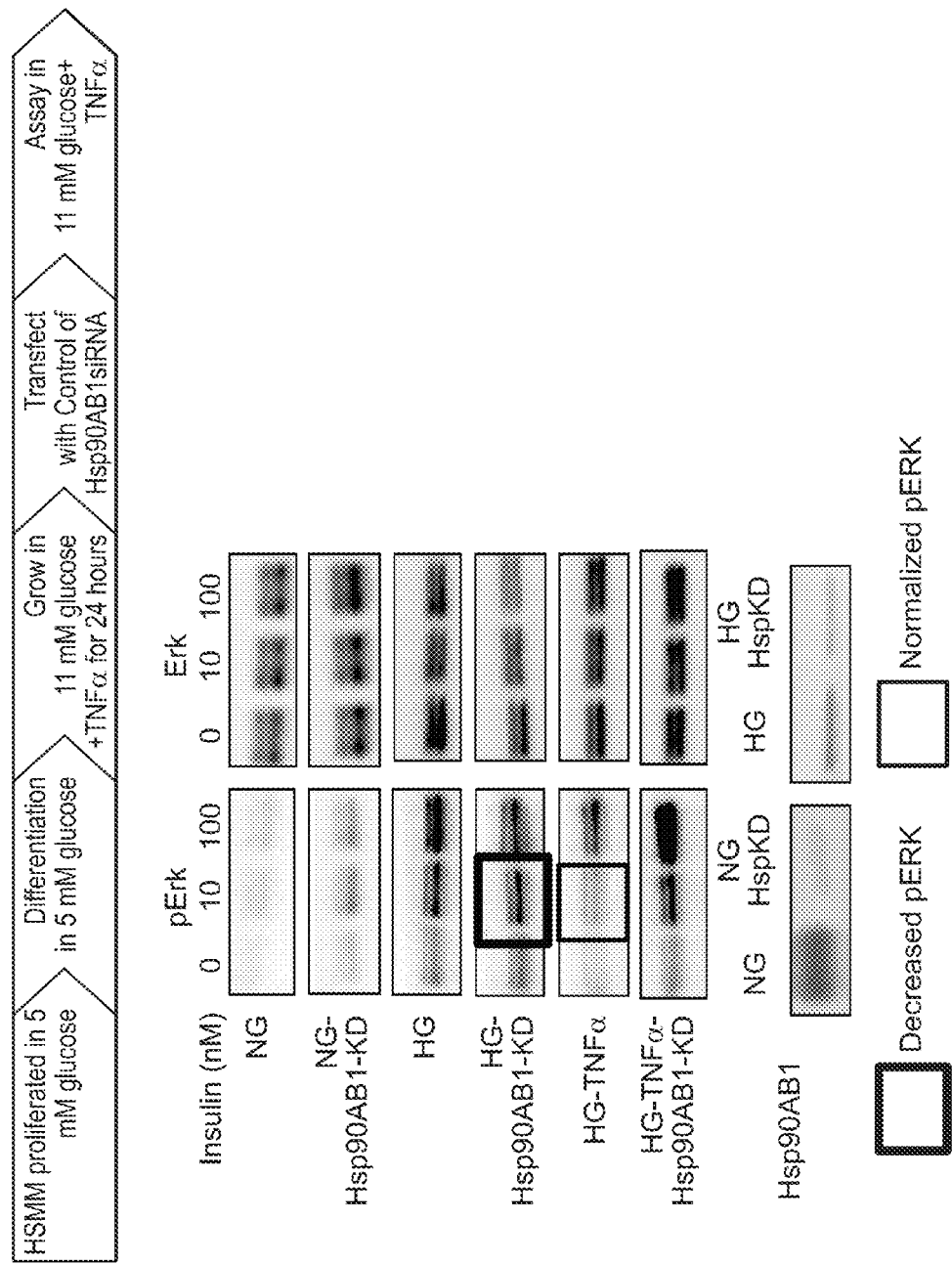

Example 5—HSP90β Regulation of pERK Levels in an Inflammatory Insulin Resistance Model in Skeletal Muscle Myotubes Myoblasts were cultured and differentiated into myotubes essentially as described above, subject to growth under normoglycemic and hyperglycemic conditions. The cells subject to hyperglycemic conditions were grown and differentitated in 5 mM glucose, and cultured in 11 mM glucose for 24 hours prior to transfection with siRNA and/or treatment with TNF-α. Cells grown under normoglycemic conditions, hyperglycemic conditions, or hyperglycemic conditions in the presence of TNF-α were transfected with HSP90β siRNA or a scrambled control siRNA. Cells grown under hyperglycemic conditions were then cultured in the presence of 11 mM glucose and/or TNF-α accordingly. Cells were exposed to increasing concentrations of insulin (0, 10, 100 nM) for 5 min prior to harvest and analysis by western blot. Briefly, cells were harvested into RIPA buffer containing protease and phosphatase inhibitors. Cells were lysed using a syringe and needle. Total protein concentrations were determined for each of the samples. Equivalent amounts of proteins were resolved by SDS-PAGE. Proteins were transferred to nitrocellulose and probed with commercially available antibodies for the detection of both total and phosphorylated ERK (FIG. 13A). The amount of total ERK and phosphorylated ERK were determined quantitatively using a phosphorimager and ratios of phosphorylated ERK to total ERK were calculated (FIG. 13B).

As shown in FIGS. 13A and 13B, under normoglycemic conditions, both basal levels of ERK phosphorylation and insulin signaling, as determined by ERK phosphorylation, is increased by the knockdown of HSP90β expression. Increased insulin stimulated ERK phosphorylation in NG skeletal muscle myotubes was observed with Hsp90AB1 knockdown. Although HG alone did not suppress insulin signaling and ERK phosphorylation, HG conditions in the presence of TNFα strongly suppressed insulin stimulated ERK phosphorylation in the presence of HSP90β. However, under the same HG and TNFα condition, Hsp90AB1 knockdown rescued ERK phosphorylation suppressed by TNFα, indicating the Hsp90AB1 knockdown rescued TNFα induced insulin resistance in HG condition.

Example 6—HSP90β Regulation of Lipid Metabolism in Skeletal Muscle Myotubes

Figure 14:
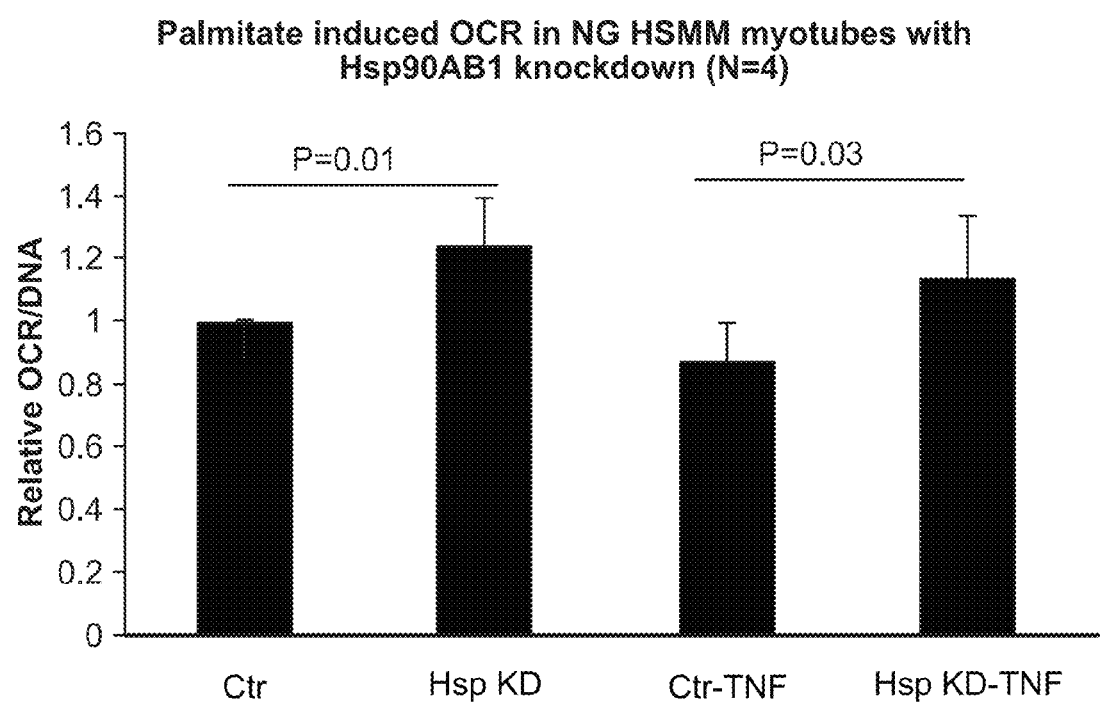
FIG. 14 shows the effect of siRNA-mediated HSP90β knockdown on the relative OCR/DNA ratio in a palmitate induced OCR under normal-glucose conditions in skeletal muscle myotubes.

Having demonstrated the effects of both HSP90β knockdown in the presence and absence of TNF-α on insulin signaling in skeletal muscle, the effects of HSP90β and TNF-α on lipid metabolism were analyzed. Briefly, myocytes were cultured and differentiated under normal and glycemic conditions essentially as described above and treated with HSP90β or scrambled siRNA. Lipid metabolism was analysed using an OCR Seahorse® assay essentially as described above. As shown in FIG. 14, in the presence of HSP90β, TNF-α decreases lipid metabolism. However, knockdown of HSP90β increases OCR under normoglycemic conditions in muscle myotubes both in the absence and the presence of TNF-α. These results demonstrate that HSP90β regulates lipid metabolism, as measured by the Seahorse® assay. Although TNF-α decreases lipid metabolism in the presence of HSP90β, knockdown of HSP90β re-estabilshes lipid metabolism in the presence of TNF-α induced decrease in lipid metabolism.

Example 7—Treatment of Metabolic Syndrome Using an HSP90 Inhibitor

A number of genetic and induced animal models of metabolic syndromes such as type 1 and type 2 diabetes, insulin resistance, and hyperlipidemia, are well characterized in the art. Such animals are used to demonstrate the effect of HSP90 inhibitors, e.g., HSP90β inhibitors, in the treatment of metabolic syndrome, including diabetes. Models of type 1 diabetes include, but are not limited to, NOD mice and streptozotocin-induced diabetic rats and mice (models of type 1 diabetes). Genetic and induced models of type 2 diabetes include, but are not limited to, the leptin deficient ob/ob mouse, the leptin receptor deficient db/db mouse, and high fat fed mouse or rat models. In each of the models, the timeline for development of specific disease characteristics are well known. HSP90 inhibitors can be administered before or after the appearance of symptoms of diabetes to demonstrate the efficacy of HSP90 inhibitors, particularly HSP90β inhibitors in the treatment of diabetes, metabolic disorder, and/or one or more signs of metabolic disorder.

Animals with or without genetic predispositions to metabolic syndrome are raised under appropriate conditions to induce the desired disease state. The animals are divided into at least two groups, treated and control. Treated animals are treated with one or more doses of HSP90 inhibitors, e.g., siRNAs targeted to HSP90, antibodies targeted to HSP90, or small molecule inhibitors of HSP90. Preferably, the small molecules, siRNAs, and antibodies are targeted specifically to HSP90α or HSP90β. The animals are monitored for the development of metabolic syndrome by any of a number of known methods. For example, basal insulin secretion, glucose levels, Hb1Ac levels, inflammatory marker levels, cholesterol and triglyceride levels, weight, fat deposition including fat deposition in the liver, blood pressure, urine output and urine glucose levels, and other relevant markers can be monitored or measured. Markers are analyzed after a period of fast, e.g., overnight fast, or in response to glucose challenge or other metabolic challenge. At predetermined intervals, or at the end of the experiment, animals are euthanized to assess fat deposition, kidney status, and other appropriate indicators of metabolic syndrome.

The outcome of the treatment group(s) is compared to the outcome of the control (untreated or vehicle treated) group. Inhibitors of HSP90β are demonstrated to ameliorate metabolic syndrome in various assessment methods.

Example 8—Validation of HSP90β as a Liver Target for Treatment of Metabolic Syndrome The liver plays an essential role in the regulation of blood glucose. In a healthy subject, insulin promotes glucose uptake by the liver for conversion into glycogen, reducing blood glucose levels. In metabolic syndrome, the liver does not respond to insulin, either due to insensitivity to insulin or insufficient insulin production, or both, resulting in elevated levels of glucose in the blood, which is toxic.

Hepatic cells (e.g., THLE-2 cells) are analyzed using methods similar to those set forth above for the analysis of insulin signaling and glucose uptake. Briefly, cells are treated with HSP90 inhibitors, preferably HSP90β inhibitors, and assayed for insulin signaling, e.g., by analysis of phosphorylation of AKT, ERK, and GSK3β; glucose uptake, glycogen synthesis; bioenergetics; gene expression of genes involved in gluconeogenesis or lipid/cholesterol metabolism, e.g., by qPCR. Markers of inflammation and endoplasmic reticulum (ER) stress can also be assessed.

Hepatic cells treated with HSP90 inhibitors, particularly HSP90β inhibitors, are found to have better insulin signaling, glucose uptake, and/or lipid metabolism as compared to cells not treated with the inhibitors. The hepatic cells treated with the inhibitors are also found to have less ER stress and/or lower expression of inflammatory markers.

Example 9—Validation of HSP90β as Adipose Target for Treatment of Metabolic Syndrome Similar to hepatic cells, adipose tissue takes up glucose from the blood in response to insulin, converting the sugar into fat. Fat cells are assessed for insulin responsiveness and glucose uptake using the methods set forth above for analysis of muscle cells and liver cells. Similarly, inflammation and ER stress can also be assessed in the cells.

Adipose cells treated with HSP90 inhibitors, particularly HSP90β inhibitors, are found to have better insulin signaling, glucose uptake, and/or lipid metabolism as compared to cells not treated with the inhibitors. The adipose cells treated with the inhibitors are also found to have less ER stress and/or lower expression of inflammatory markers.

Example 10—Classification of the Specificity of an HSP90 Inhibitor

A number of HSP90 inhibitors are available, such as those provided herein, many of which have undergone or will undergo clinical trials for use in the treatment of various diseases or conditions, most commonly cancer. Depending on the specific mechanism of action or binding site of the inhibitor on the HSP90 transcript, protein, or HSP90 binding protein, the inhibitor may inhibit the activity of one or more HSP90 isoforms, e.g., HSP90α or HSP90β. For example, inhibitors that act at the ATP binding site of HSP90 are likely to have inhibitor activity against both HSP90α and HSP90β. Further, agents can be selected that inhibit interaction of an HSP90 with a specific binding partner (see, e.g., Tsaytler et al., 2009, Cell Stress Chap. 14:629). Similarly, based on the specific nucleic acid or amino acid sequence of the HSP90, nucleic acid based or antibody based inhibitors can be designed to specifically inhibit the expression or activity of HSP90α or HSP90β. Alternatively, nucleic acid based or antibody based inhibitors can be designed to specifically the expression or activity of both HSP90α or HSP90β. Alignments of the HSP90α and HSP90β nucleic acid and amino acid sequences are provided in FIG. 17. One of skill in the art can readily review the alignments to design nucleic acid inhibitors or identify epitopes on HSP90α and HSP90β that could be cross-reactive or specific for a single isoform of HSP90.

Methods to determine if an agent is an inhibitor of the expression or activity of HSP90α, HSP90β, or both are well within the ability of those of skill in the art. For example, nucleic acid and antibody inhibitors that inhibit the expression of at least one HSP90 can be tested for specificity in a cell culture system. For example, cells that express both HSP90α and HSP90β are contacted with a series of concentrations of the nucleic acid or antibody, and appropriate controls (e.g., scrambled nucleic acid, non-immune IgG) for an appropriate amount of time. Cells and/or media are harvested, as appropriate. Routine nucleic acid (e.g., RT-PCR, northern blot) and protein (e.g., ELISA, western blot) detection methods are used to determine the expression level of HSP90α and HSP90β as compared to an appropriate control. The specificity of the HSP90 inhibitor can be readily determined.

Competition assays and methods to perform ATP binding and hydrolysis assays are well known in the art and can be used to determine if an agent is an inhibitor of HSP90α, HSP90β, or both, i.e., if the agent can inhibit ATP binding or hydrolysis in one or both isoforms.

Yeast contain only a single copy of HSP90. Yeast strains not expressing HSP90 can be transformed with either HSP90α or HSP90β and the ability to fold client proteins can be monitored. Similarly, mammalian cell lines that express only a single HSP90 isoform, e.g., derived from HSP90α knockout mice, or cells treated with siRNA to inhibit expression of one HSP90 isoform, can be used to distinguish activity of an agent against one or both HSP90 isoforms.

Commercially available kits can also be used to distinguish between inhibitors for inhibitors of HSP90α and HSP90β (BPS Bioscience).

Example 11—Evaluation of Antisense Oligonucleotides (ASO) for Proof of Concept Knockdown of HSP90β in a Diet Induced Obese Model of Insulin Resistance An exemplary animal study model is provided below to further validate HSP90β as a therapeutic target in the prevention and/or treatment of metabolic syndrome, obesity, insulin resistance, and/or type 2 diabetes.

1. Purpose and Rationale

The goals of the study are
1. To identify and characterize antisense oligonucleotides (ASO) for efficient knock down the expression of HSP90β in appropriate in vivo models.
2. To demonstrate that knockdown of HSP90β in vivo results in a functional physiological response with therapeutic benefits.

The desired outcome is the prevent the obese phenotype and diabetic phenotype with knockdown of HSP90β.

The Proof of Concept (PoC) studies are carried out in diet induced obesity (DIO) and insulin resistance (IR) mouse models.

The study is carried out in two parts:
1. Identification of one or more ASOs that significantly knockdown HSP90β expression in the in vivo model by analysis of expression of HSP90β in various tissues.
2. Adminstration of the ASO(s) to mice subject to diet induced obesity and insulin resistance to demonstrate that inhibition of HSP90β expression prevents, diminishes, or delays the onset of weight gain and the development of a metabolic syndrome.

It is understood that the experimental methods provided below can be readily modified to assay other nucleic acid therapeutics (siRNA, dsiRNA, shRNA), antibody based therapeutics, and small molecule based therapeutics. Further, the study may be modified to include the use of other models of diabetes and metabolic disorders (such as those provided above). As discussed below, depending on the specific results obtained, the time and dosage ranges can be modified based on preliminary analyses of efficacy and toxicity. Such modifictaions are well within the ability of those of skill in the art.

2. Significance

The knockdown of expression of HSP90β delays, diminishes, or prevents weight gain as a result of a high fat diet and diet induced insulin resistance demonstrating the utility of HSP90β as a target for the treatment or management of one or more of obesity, insulin resistance, type 2 diabetes, and metabolic syndrome including one or more of elevated blood pressure, elevated lipid levels, central adiposity, low HDL, and elevated glucose at fasting and/or during a glucose tolerance test.

3. Experimental Approach

Part I: ASO Mediated Knockdown of HSP90β and In Vivo (Dose Escalation Study)

Oligonucleotide Selection.

Antisense oligonucleotides are made and tested in vitro to identify ASOs effective in the specific inhibition of expression of HSP90β. One or more ASOs identified in the preliminary in vitro assays are used for the subsequent in vivo studies.

Analysis of Efficacy and Toxicity.

A total of 6 groups of mice, containing 5 mice per group, are maintained on standard chow diet. Mice in Cohort 1, including two groups of 5 mice each, receive an intraperitoneal injection of a normal dose of ASO (30-40 mg/kg) or a high dose of ASO (100-150 mg/kg) twice a week for 2 weeks. Treatment of Cohort 2 and Cohort 3 is initiated after evaluation of the efficacy and toxicity of the preceding cohort (Cohort 1 for Cohort 2 and Cohort 2 for Cohort 3). Sequentially for each cohort, the treatment time increases by two weeks (Cohort 1, 2 weeks; Cohort 2, 4 weeks; Cohort 3, 6 weeks). The following decisions are made based on the results obtained in the prior cohort:

No efficacy—No toxicity: The treatment methods for Cohort Part 1 are repeated with the treatment dosage increased 10-fold. In addition the treatment time is extended by 2 weeks.

Efficacy—No toxicity: The treatment in Part 2 as set forth below is immediately initiated for this ASO. In addition, treatment methods of Part 1 are repeated with a four week dosing schedule rather that a 2 week dosing schedule as with Cohort 1, with the treatment dosage increased 50-fold in order to determine the toxic threshold.

Efficacy—toxicity: The treatment of Part 1 is repeated with the treatment dosage decreased 10 times and the same treatment time is used.

No efficacy—toxicity: This ASO is not be considered for further study.

For each cohort and in all groups, body weight, glucose level and plasma insulin level are measured before every injection and before sacrificing. In addition, plasma level of ASO is measured using a commercially available kit, e.g., OliGreen® ssDNA Quantitation Assay and Kit from Invitrogen®. After 2 weeks, mice are sacrificed and a cardiac puncture with a needle (0.5-1 mL) is immediately performed to retrieve blood. Necropsies are then performed. Selected tissues are collected, weighed, and snap frozen prior to storage at −80° C. until use (with exception of adipose tissues and liver).

The following samples and tissues are collected in a sequential manner:

Blood for plasma preparation
Liver (snap frozen, fixative for paraffin embedding)
Skeletal muscles (snap frozen), including hindlimb and dorsal muscles stored in separate vials.
Adipose tissues (snap frozen and fixed for paraffin embedding), including white adipose tissues (perigonadal, and inguinal) and brown adipose tissue stored in separate vials.
Pancreas (snap frozen)
Kidney (snap frozen)

The knockdown efficiency of HSP90β is determined by measuring expression level of the target using qPCR, western blotting, and/or immunohistochemistry. In addition, plasma insulin, plasma level of leptin, adiponectin, TNFα, PAI-1, serum amyloid A, and IL6 are measured using ELISA. The ASO with the most efficient knockdown is selected and used for subsequent experiments provided below in Part II.

Plasma and liver collected from animals are used for preliminary assessment of toxicity. LDH release assays along with ELISA for inflammatory markers is performed. In addition alanine amino transferase (ALT), aspartate aminotransferase (AST), glutamate dehydrogenase (GLDH) activity assays are performed on plasma and liver homogenates. GSH levels in the liver is ascertained as an additional readout of liver function.

Part II—Proof of Concept Study on Metabolic Effects of HSP90β Knockdown on High Fat Diet Induced Obesity and Insulin Resistance Model A proof of concept study on metabolic effects includes analysis of the following parameters: body weight, fed and fasting blood glucose levels, food intake, water intake, body mass composition, $O_2$ consumption, $CO_2$ production, glucose tolerance test (GTT), insulin tolerance test (ITT), pyruvate tolerance test (PTT), and voluntary activity.

Eight weeks old male lean C57BL/6 mice subject to a 60% kcal % fat high fat diet (HFD) are treated with empirically pre-determined dosages of HSP90β ASO, control ASO, or saline twice a week via intraperitoneal injections (IP). Separate lean control groups receive either saline or control ASO, and are maintained with a standard low fat chow diet (low fat standard diet (LFD) 10% kcal % fat). The treatment groups are shown below:

LFD saline treatment (21 mice)
LFD control ASO treatment (21 mice)
HFD saline treatment (21 mice)
HFD control ASO treatment (21 mice)
HFD HSP90β ASO treatment (21 mice)

Each of the groups of 21 mice are divided into 3 cohorts of animals with 7 mice each. The mice are treated and assessed for a duration of 4 weeks, 6 weeks, and 8 weeks. There are 2 weeks delay for the latter cohorts, i.e. Cohort 2 starts the ASO and HFD treatments 2 weeks after the initiation of treatment of Cohort 1. In this way, Cohort 2 treatment can be modified to 4 weeks treatment instead of 6 weeks treatment upon observation of encouraging results in Cohort 1. If Cohort 1 does not show expected results, the Cohort 2 undergoes 6 weeks treatments. In addition, for each cohort (4 weeks, 6 weeks and 8 weeks), upon demonstration of efficacy in the GTT and ITT studies, the treatments are extended by 1 week to accommodate an PTT (4 weeks become 5 weeks, 6 weeks become 7 weeks, 8 weeks become 9 weeks).

Body weight and fed blood glucose are monitored twice a week before the weekly IP injections from the beginning of the treatment.

For Cohort 1 (4 weeks ASO treatment), GTT and ITT are performed on day 17 and day 24 after the start of ASO treatment. If positive results from GTT and ITT are observed, and PTT is performed on day 31. After 4 weeks (or 5 weeks) of ASO and control treatment, mice from Cohort 1 are euthanized, and tissue and blood samples are collected for further analysis.

For Cohort 2 (6 weeks ASO treatment), GTT and ITT are performed on day 31 and day 38 after the start of ASO treatment. If positive results from GTT and ITT are observed, and PTT is performed on day 45. The mice of Cohort 2 are euthanized, and tissue and blood samples are collected for further analysis after the 6th week or 7th week of treatment.

For Cohort 3 (8 weeks ASO treatment), GTT and ITT are performed on day 45 and day 52 after the start of ASO treatment. If positive results from GTT and ITT are observed, and PTT are performed on day 59. The mice of Cohort 3 are euthanized, and tissue and blood samples are collected for further analysis after the 8th or 9th week of treatment.

The collected tissues are analyzed by qPCR, western blotting, and/or IHC for gene expression and target silencing. Expression of other genes and proteins in insulin signaling pathways can also be analyzed. Blood collected at each time point is processed into plasma and subjected to different biochemical analysis including: TG, FFA, total cholesterol, insulin, serum amyloid A (SAA), adiponectin, TNFα, and PAI-1.

An additional cohort of 10 animals is treated with the following regimens:

HFD control ASO treatment (5 mice)
HFD HSP90β ASO treatment (5 mice)

The mice are subject to monitoring in metabolic cages utilizing the Comprehensive Laboratory Animal Monitoring System (CLAMS) to assess food intake, water intake, voluntary activity and respiration by measuring $VO_2$, $VCO_2$, RQ (respiratory quotient) and heat production, from Day 54 to Day 57. Body composition is determined the same week by dual-energy x-ray absorptiometry (DEXA) on Day 51. This cohort is injected twice a week with different ASOs for 8 weeks.

Materials and Methods.

Animals

Mice of the same gender (male), age and genetic background are used for all comparisons. Male C57BL/6J mice (7 week-old) are obtained from Jackson Laboratories (Bar Harbor, Me.) and initially housed 4-5 per cage at 22° C. on a 12:12 hr day-night cycle. Mice are acclimated at the local animal facility for one week before treatment with the compounds.

Beginning at 8 weeks of age, mice are fed with a high fat diet (Research Diets Cat #: D12492; 60 kcal % fat, 20 kcal % protein, and 20 kcal % carbohydrate) or a standard, low fat diet (10% kcal % fat), depending of the study stage (Part I or Part II). Mice are injected with ASO or saline twice a week. Body weight, glucose level and plasma insulin level are measured before every injection.

Intraperitoneal Glucose Tolerance Test (IPGTT)

Glucose tolerance tests (GTT) are performed after 6 h of fasting. Initial fasting blood glucose levels are determined, followed by intraperitoneal (ip) injection of 20% dextrose solution at a dose of 2.0 g/kg body weight (2 g/kg body weight). Blood glucose levels are measured from the tail vein at 15, 30, 60, 90, 120, 150, and 180 minutes after the glucose injection using a commercially available glucose monitor, e.g., an Accu-chek® Advantage glucometer (Roche Diagnostics®, Indianapolis, Ind.). The area under the curve (AUC) during the GTT is calculated using a commercially available software program, e.g., GraphPad Prism software. GTT experiments for different groups are run in parallel. At each time point of the tail vein glucose measurements, ~40 μL of tail vein blood is collected and plasma is prepared for subsequent insulin level assays using ELISA/RIA for time points at 0, 15, and 30 min after glucose injections.

Intraperitoneal Insulin Tolerance Test (IPITT)

Insulin tolerance test (ITT) is performed after 1 hour fasting. Initial blood glucose levels is determined, followed by injection (ip) of human insulin (1-2 U/kg; Humulin R; Eli Lilly, Indianapolis, Ind.). Blood glucose levels are measured from the tail vein as described above at 15, 30, 60, 90, and 120 min after the insulin injection. The insulin injection amount is determined empirically by insulin response due to the onset of the hepatic insulin resistance in the mice subjected to the high fat diet.

Intraperitoneal Pyruvate Tolerance Test (IPPTT)

Pyruvate challenge test is administered after 6 h of fasting. Initial blood glucose levels are determined, followed by injection (ip) of pyruvate dissolved in saline (2 g/kg; Sigma, St. Louis, Mo.). Blood glucose levels are measured from the tail vein as described above at 15, 30, 60, 90, and 120 min after the pyruvate injection. The area under the curve (AUC) during the test is calculated.

Dual-Energy X-Ray Absorptiometry (DEXA)

The body mass composition of different treatment groups is determined by dual-energy x-ray absorptiometry (DEXA) scanning using LUNAR PIXImus® mouse densitometer following the procedures recommended by the manufacturer. Lean body mass, fat body mass, total body tissue weight, bone density, and bone mineral content are recorded and analyzed.

Comprehensive Lab Animal Monitoring System (CLAMS)

The CLAMS (Columbus Instruments, Columbus, Ohio, USA) metabolic monitoring cages are used to simultaneously monitor horizontal and vertical activity, feeding and drinking, oxygen consumption, and $CO_2$ production. ASO injected and control mice are individually placed in CLAMS cages and monitored over a 4-day period after acclimation to the cages for 1-2 days. The various parameters are recorded in both fasted and fed conditions. Food and water consumption are measured directly as accumulated data. Hourly files display all measurements for each parameter: volume of oxygen consumed, ml/kg per h ($VO_2$), volume of carbon dioxide produced, ml/kg per h ($VCO_2$), respiratory exchange ratio, heat (kcal/h), accumulated food (g), accumulated drink (g), XY total activity (all horizontal beam breaks in counts), XY ambulatory activity (minimum three different, consecutive horizontal beam breaks in counts), and Z activity (all vertical beam breaks in counts). The data are recorded during the 30-s sampling period. The CLAMS data are analyzed by normalizing with lean body mass.

Tissue Collection

At the end of each protocol, mice are euthanized in the following week, and tissues are collected and weighed prior to preservation by snap freezing prior to storage at −80° C. or fixation in formalin for paraffin embedding using standard methods. Blood is collected by cardiac puncture and plasma is prepared.

The following samples and tissues are collected:
Liver (snap frozen, fixative for paraffin embedding)
Skeletal muscles (snap frozen), including hindlimb and dorsal muscles stored in separate vials.
Adipose tissues (snap frozen and fixed for paraffin embedding), including white adipose tissues (perigonadal, and inguinal) and brown adipose tissue stored in separate vials.
Pancreas (snap frozen)
Kidney (snap frozen)

Example 12—Antisense Oligonucleotides (ASOs) are Effective to Knockdown HSP90β Expression A panel of nine exemplary novel antisense oligonucleotides (FIG. 18) were derived from the mouse HSP90AB1 gene and designated ASO1-ASO9. ASO1-ASO9 contain phosphorothioate linkages, as indicated by an asterisk in the sequences shown in FIG. 18. In addition, ASO1-ASO9 contain 2'-O-methyl ribonucleotides, as indicated by an "m" before a nucleotide in the sequences shown in FIG. 18. Nucleotides in the ASO sequences that are not preceded by an "m" are deoxyribonucleotides. Thus ASO1-ASO9 contain both DNA and RNA.

Variant sequences of ASO1, ASO2, ASO6 and ASO8 with greater sequence homology with the human Hsp90ab1 were derived by substituting one or more nucleotides in the ASO sequence with the corresponding nucleotide in the human HSp90ab1 sequence. FIG. 18B shows sequence alignments between the DNA sequences corresponding to ASO1, ASO2, ASO6 and ASO8 (Query) and the human Hsp90ab1 sequence (Sbjct). The substituted nucleotides are shown in bold and underlined. ASO3, ASO4, ASO5, ASO7, and ASO9 do not share significant sequence homology with the human Hsp90ab1 sequence.

Figures 19A, 19B:
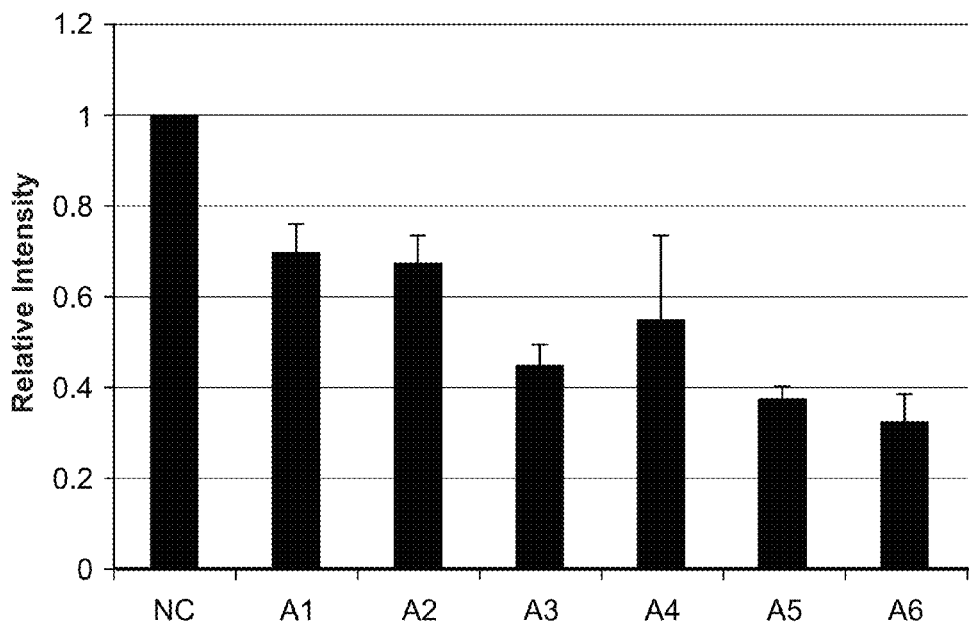
FIG. 19A is a bar graph showing changes in the levels of HSP90ab1 as normalized to Actin upon treatment of HSMM with antisense oligonucleotides ASO1 (A1), ASO2(A2), ASO3 (A3), ASO4(A4), ASO5 (A5), and ASO6 (A6), and a negative control ASO (NC). These results show that each of ASO1-ASO6 are effective in reducing the level of HSP90ab1.
FIG. 19B is a table showing quantification of the results shown in FIG. 19A.

ASO1-ASO6 were tested for their ability to knock down human Hsp90AB1 levels in HSMM myotubes. The effectiveness of oligonucleotides ASO1 (A1), ASO2 (A2) ASO3 (A3) ASO4 (A4) ASO5 (A5) and ASO6 (A6) in knocking down the expression of HSP90AB1 protein is shown by Western blotting in FIGS. 19A and 19B. The oligonucleotide NC1 was used as a negative control. HSP90Ab1 protein levels were normalized to the levels of actin. Each antisense oligonucleotide in the group ASO1-ASO6 was found to be effective in reducing the level of HSP90ab1 protein. ASO6 was the most effective in reducing the level of Hsp90ab1 protein and was selected for further confirmatory experiments.

Figure 20:
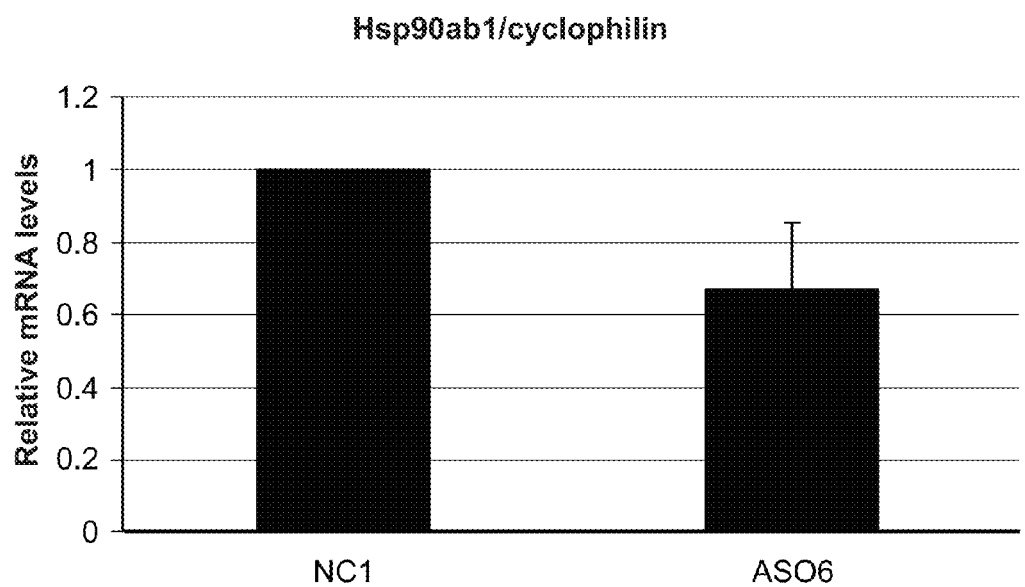
FIG. 20 is a bar graph showing knockdown of mRNA levels of human Hsp90AB1 (also referred to herein as HSP90AB gene) as normalized to cyclophilin in cultured human cells by an exemplary mouse antisense oligonucleotide ASO6 derived from the mouse HSP90AB1 gene (see FIG. 18 for the sequence) relative to that by a control antisense oligonucleotide NC1ASO.
Figure 21:
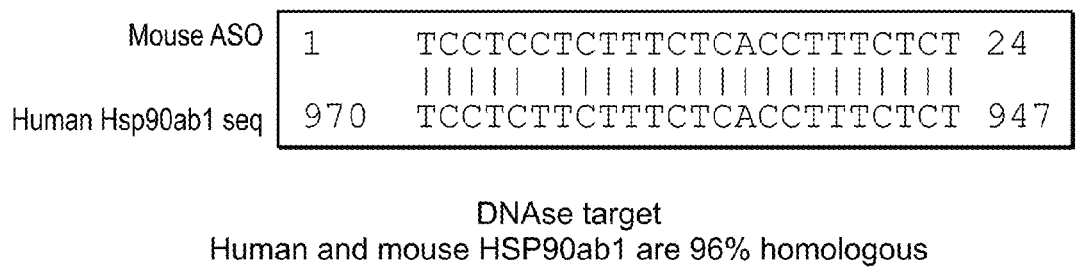
FIG. 21 shows the homology between the mouse antisense oligonucleotide ASO6 and a portion of the human Hsp90AB1 gene. ASO6 has 96% sequence identity with the corresponding region of the human Hsp90ab1 gene. Sequences shown are mouse ASO (ASO6, SEQ ID NO: 17) and Human Hsp90ab1 seq (ASO6 variant 1, SEQ ID NO: 41).

The level of human Hsp90AB1 at the mRNA level was similarly observed to be reduced in HSMM myotubes treated with the exemplary mouse antisense oligonucleotide ASO6 (FIG. 20). ASO6 (and ASOs 1-5 and 7-9) is derived from the mouse HSP90AB1 gene. The oligonucleotide NC1ASO was again used as a negative control. The level of HSP90 mRNA was normalized to a control (cyclophilin) mRNA. The homology between the mouse antisense oligonucleotide ASO6 and a portion of the human Hsp90AB1 gene is shown in FIG. 21. The human and the mouse Hsp90aB1 gene share 96% homology.

Figure 22:
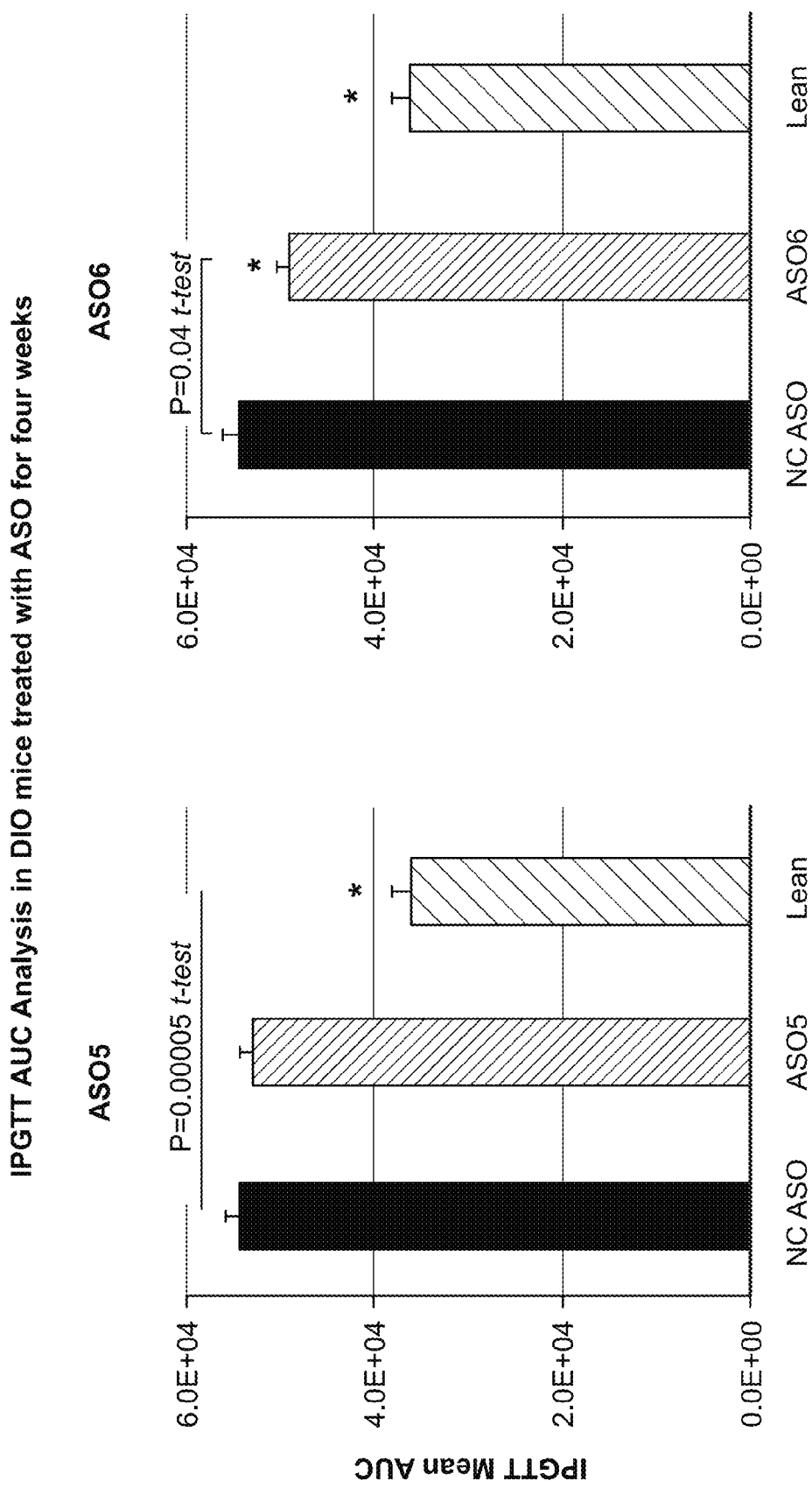
FIG. 22 is two sets of bar graphs showing the result of intraperitoneal glucose tolerance test (IPGTT) in diet induced obese (DIO) mice treated with ASO5 (left) or ASO6 (right). In each case the result is compared with the result of IPGTT in DIO mice treated with a negative control ASO (NC ASO). IPGTT results in lean mice is also shown.

Example 13—Effects of Administering HSP90AB1 (BPM 81916) Antisense Oligonucleotides to DIO Mice HSP90AB1 antisense oligonucleotides (ASO) specific to HSP90AB1 were administered to DIO mice. In one example, mice were treated for four weeks or eight weeks with ASO5, ASO6, or a negative control ASO (NC ASO). See FIG. 18 for the sequences of the ASOs. IPGTT was performed with blood drawn from mice administered with ASO and that drawn from lean mice. A significant improvement in the results of IPGTT was observed with ASO6 treatment for four weeks (FIG. 22 right panel).

Figure 23A:
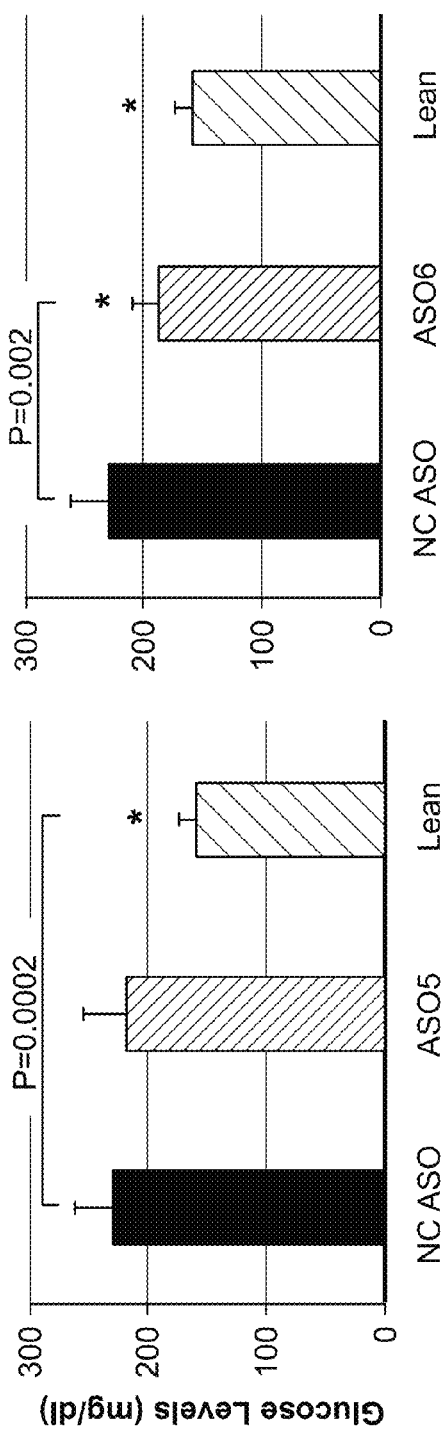
FIG. 23A is two sets of bar graphs showing measurements of glucose level under fed conditions (fed glucose level) in DIO mice treated for eight weeks with ASO1 (left panel), and ASO2 (right panel) compared to fed glucose level in mice treated with a control antisense oligonucleotide (NC ASO).

It was further observed that treatment with ASO6 for eight weeks led to a significant improvement in fed glucose level, indicating that HSP90AB1 is potentially regulated by feeding and fasting cycles (FIG. 23A).

Figure 23B:
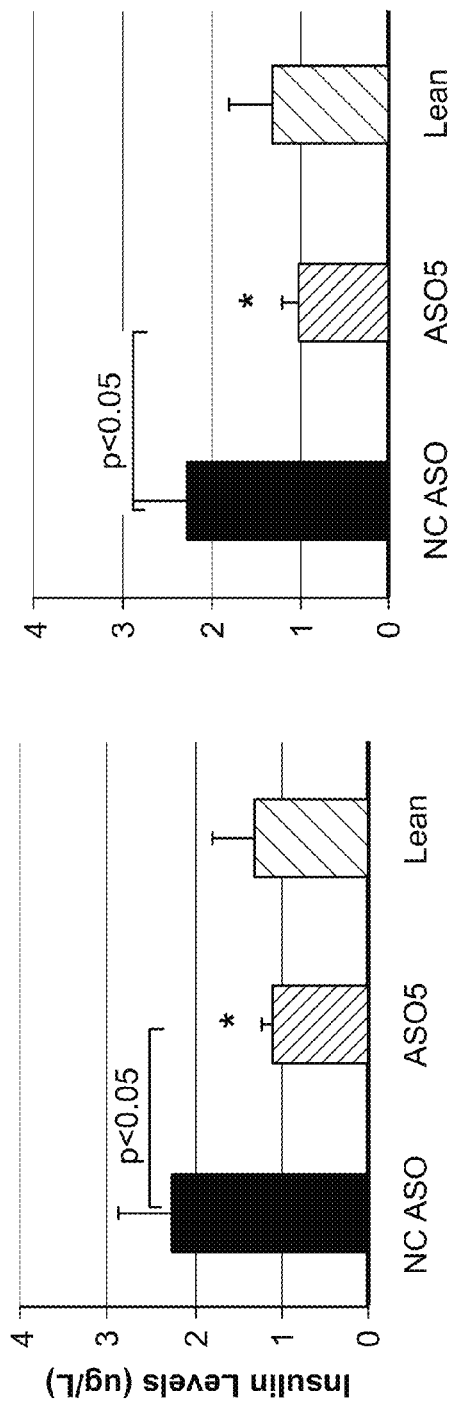
FIG. 23B shows measurements of insulin level in DIO mice treated for eight weeks with ASO1 (left panel), and ASO2 (right panel) compared to the insulin level in mice treated with a control antisense oligonucleotide (NC ASO).

In another experiment, it was observed that treatment with either ASO5 or ASO6 led to a significant reduction of fed insulin levels (FIG. 23B). The results show that reduction in the level of HSP90AB1 improves insulin sensitivity and directly or indirectly regulate insulin secretion by the pancreas.

It was further observed that eight weeks of ASO treatment significantly improved heat production (FIG. 24). In particular, ASO6 was found to have a very significant effect on heat production. Increase in heat production is suggestive of improved metabolic effects produced by systemic metabolic change induced by HSP90AB1 knockdown.

Example 14—Targeting of HSP90AB1 Antisense Oligonucleotides to Skeletal Muscle

Antisense oligonucleotides specific to HSP90Ab1 described herein are specifically targeted to skeletal muscle by conjugating the ASO with an MTP that has affinity for skeletal muscle cells. Exemplary MTPs for conjugation to an ASO of the invention have amino acid sequences that include one of the following: ASSLNIA (SEQ ID NO: 57); WDANGKT (SEQ ID NO: 58); GETRAPL (SEQ ID NO: 59); CGHHPVYAC (SEQ ID NO: 60); and HAIYPRH (SEQ ID NO: 61). In certain experiments, the conjugate includes a linker for linking the HSP90AB1 ASO and the MTP. The linker may be a covalent linker, a non-covalent linkage, and a reversible linker, where each type of linker can be tested independently and/or compared with others to determine the optimal linker.

These ASO-MTP conjugates are tested for their ability to deliver the ASO to skeletal muscle, and to effect knockdown of HSP90AB1, using routine methods in the art. Further, the effects of such targeted ASOs on parameters such as IPGTT, fed glucose, and blood glucose level are observed using the DIO mouse model by carrying out experiments as described in Examples 11 and 13 above.

In further experiments, the conjugate further includes a pharmaceutically acceptable dendrimer. In some experiments the dendrimer is a PAMAM dendrimer. In some experiments the dendrimer is a G5 dendrimer. In certain experiments, the dendrimer is an uncharged dendrimer or an acylated dendrimer. In additional experiments, the ASO-MTP conjugate is part of a liposome. It will be understood that in certain cases, the conjugate is formed in situ. All of these additional ASO-MTP conjugates are tested for their ability to deliver the ASO to skeletal muscle, to effect knockdown of HSP90AB1, and to effect parameters such as IPGTT, fed glucose and blood glucose levels using the DIO mouse model by carrying out experiments as described in Examples 11 and 13 above.

Figure 25A:
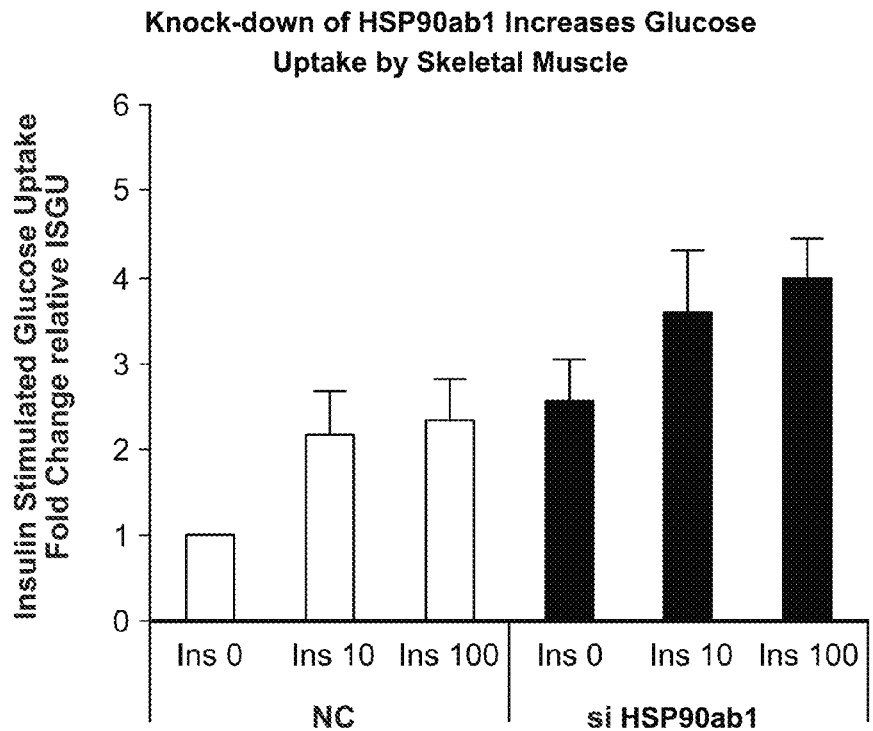
FIG. 25A is a bar graph showing that knockdown of HSP90ab1 protein level by an siRNA specific to the HSP90ab1 gene results in increase in insulin stimulated glucose uptake (ISGU) by skeletal muscle relative to that observed using a negative control siRNA (NC). Ins=insulin.
Figure 25B:
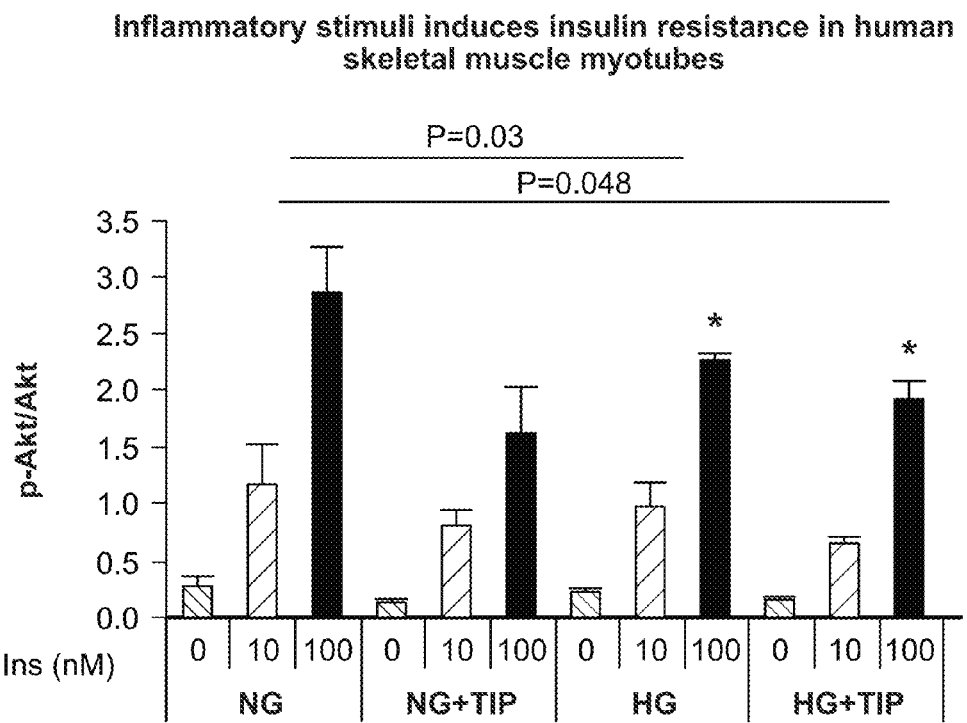
FIG. 25B is a bar graph showing that in both normoglycemic (NG) and hyperglycemic (HG) conditions, inflammatory stimulus TIP (a cocktail of TNFα, IL6, and Palmitate) induces insulin resistance in human skeletal muscle myotubes, as reflected by a reduction in the amount of phosphorylated Akt (p-Akt) relative to total Akt.

Example 15—Inflammation Induced Insulin Resistance is Associated with Increase in the Expression of HSP90ab1 in Human Skeletal Muscle Myotubes Experiments were carried out to test whether inflammatory stimulus induces insulin resistance in human cells. Toward this end an inflammation inducing cocktail TIP (TNFα, IL6, and palmitate) was used to induce inflammation in human skeletal muscle myotubes. Results of the experiments are shown in FIG. 25B. It was found that in both normoglycemic and hyperglycemic conditions TIP induced insulin resistance in the myotubes as reflected by a reduction in the amount of phosphorylated Akt relative to total Akt present in the myotubes.

In further experiments, levels of HSP90ab1 protein were measured in the myotubes that were either treated or not treated with TIP. The measurements were made under normoglycemic (NG), hyperglycemic (HG; 11 mM Glucose), as well very hyperglycemic (VHG; 25 mM Glucose) conditions. An increase in the level of HSP90ab1 protein was observed in the presence of an inflammatiory stimulus (FIG. 25C upper and lower panels), showing that in human skeletal muscle myotubes, inflammation induced insulin resistance is associated with an increase in the expression of HSP90ab1 protein.

Figure 26A:
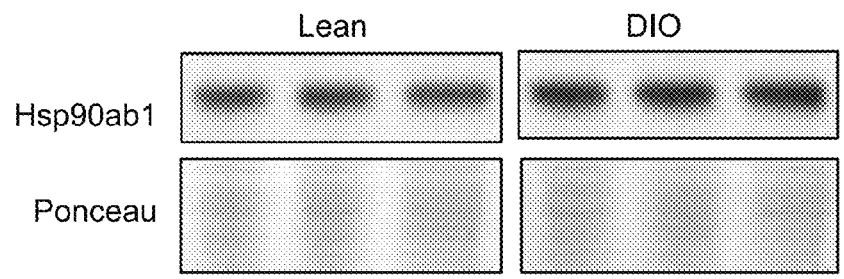
FIG. 26A is a Western Blot analysis showing that in the DIO mouse model of diabetes, feeding 60% High Fat Chow (HFD) to the mice is associated with a significant increase in Hsp90ab1 protein level in the gastrocnemius muscles of the mice.
Figure 26B:
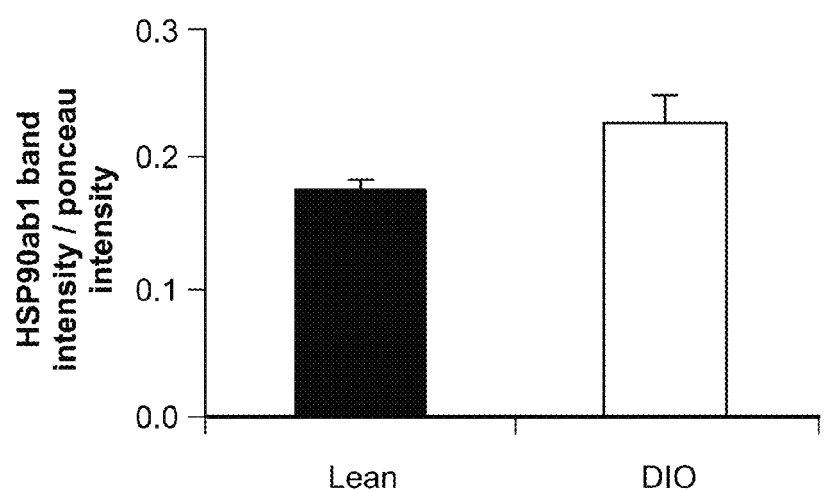
FIG. 26B is a bar graph for the quantification of the results of the Western Blot analysis shown in FIG. 29A (n=3).

Example 16—Increased Hsp90ab1 Levels are Associated with Obesity in DIO Mice Model of Diabetes The Diet Induced Obesity (DIO) mouse model of diabetes was used for in vivo validation of the involvement of Hsp90ab1 in diabetes. C57 BL/6 mice were fed 60% High Fat Chow diet (HFD) for 12 weeks. Western Blot analysis was then performed to examine the regulation of Hsp90ab1 in the skeletal muscle of the mice. Skeletal muscle was dissected after overnight fasting. Protein from the skeletal muscle was subjected to Western Blot analysis for measuring Hsp90ab1 protein levels. Results are shown in FIGS. 26A, 26B. DIO mice fed with HFD were found to have a significant increase in Hsp90ab1 protein levels in the gastrocnemius muscles of the mice (FIGS. 26A, 26B). These results indicate that increased Hsp90ab1 levels in the muscle cells are associated with obesity and that Hsp90ab1 should be decreased to treat an obese state Example 17—Effects of Administering Hsp90ab1 Antisense Oligonucleotide to DIO Mice Additional experiments were performed to examine the effect of the reduction of Hsp90ab1 protein level on different parameters of diabetes. DIO mice were fed an HFD and treated with an HSp90ab1 targeting ASO (ASO6) or a negative control ASO (NC). Dosing of mice with ASO was begun at the initiation of HFD.

Figure 27A:
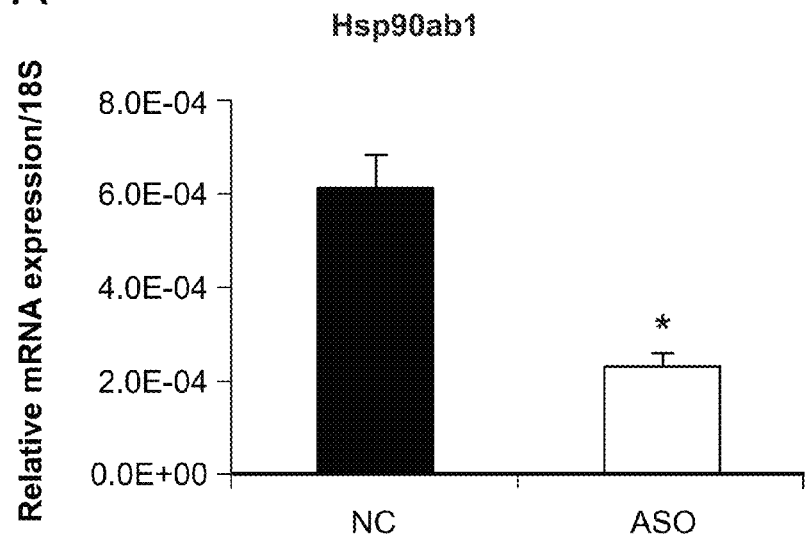
FIG. 27A is a bar graph showing that in the DIO mouse model of diabetes, the Hsp90ab1 targeting antisense oligonucleotide ASO6 is effective in reducing the level of Hsp90ab1 mRNA in the gastrocnemius muscles of mice.

The mice were divided into four groups: (1) lean (non-diabetic control); (2) diabetic receiving control ASO (NC-ASO); (3) diabetic receiving ASO5; and (4) diabetic receiving ASO6. In various experiments mice were dosed intraperitoneally with twice per week injection of ASO at 10 µg/kg body weight for 4 or 8 weeks. Skeletal muscles were subjected to quantitative PCR. Treatment with ASO6 was observed to reduce the Hsp90ab1 mRNA level in the gastrocnemius muscles of the mice (FIG. 27A).

Figure 27B:
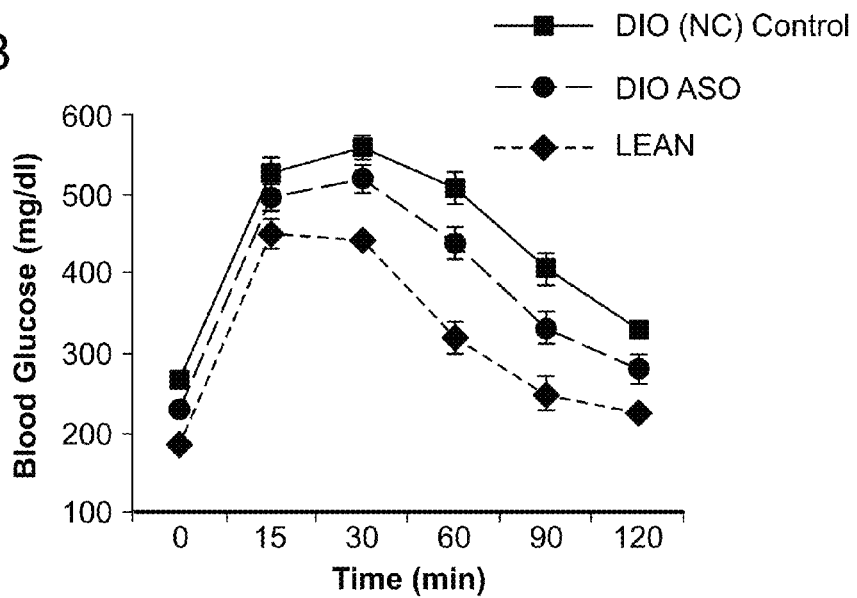
FIG. 27B is a graph showing that four week treatment of DIO mice with an ASO specific for Hsp90ab1 leads to a significant improvement (middle curve) in glucose tolerance compared to control DIO mice treated with the negative control antisense oligonucleotide (NC; upper curve), as determined by measurement of blood glucose levels.
Figure 27C:
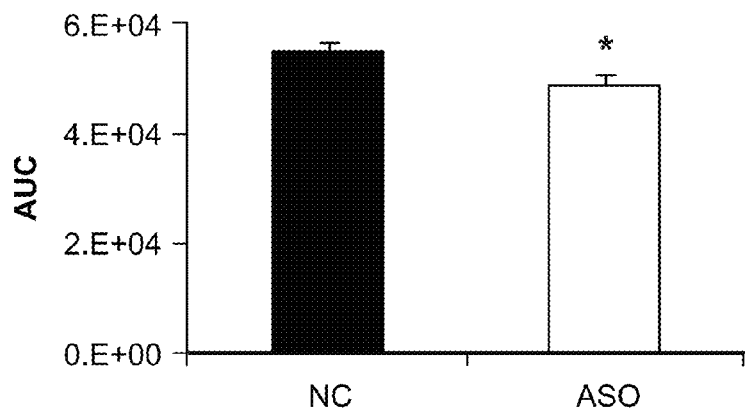
FIG. 27C is a graph showing the AUC of the curves in FIG. 20A corresponding to control DIO mice, and DIO mice treated with the Hsp90ab1 specific antisense oligonucleotide ASO6.
Figure 27D:
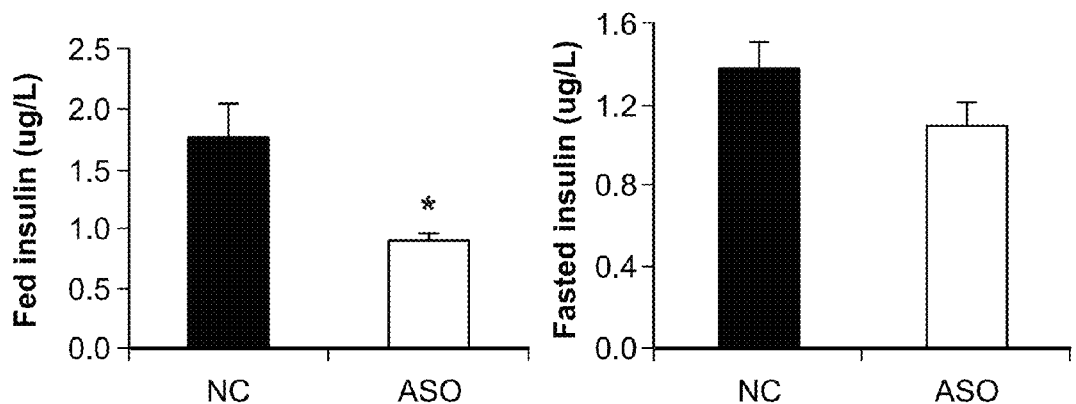
FIG. 27D is a set of two graphs showing that ASO mediated Hsp90ab1 knock-down is associated with decrease in plasma insulin levels in both Fed state (left), and in Fasting state (right). In the fasting state about 20% decrease in plasma insulin level was observed.
Figure 27E:
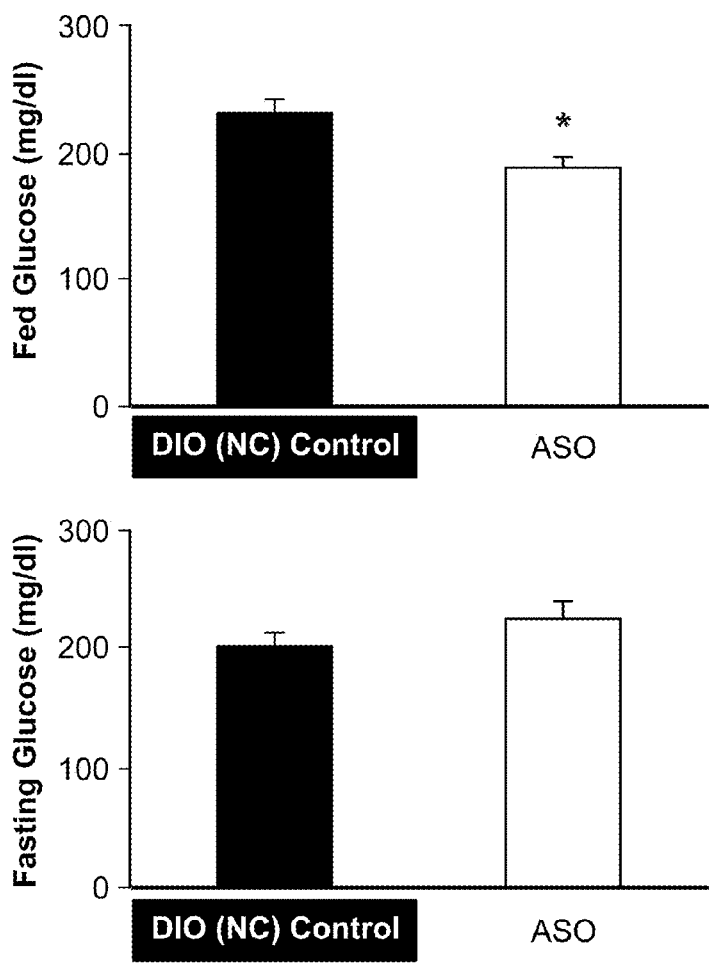
FIG. 27E is a set of two graphs showing the effect of ASO mediated Hsp90ab1 knock-down on plasma glucose levels. Hsp90ab1 knockdown is associated with a decrease in plasma glucose levels in Fed state (top).

At the end of the treatment period glucose tolerance was measured. Results of the experiment are provided in FIG. 27B, which shows that four week treatment of DIO mice (n=10) with Hsp90ab1 targeting ASO (ASO6) leads to a significant improvement in glucose tolerance (middle curve) as determined by measurement of blood glucose levels compared to control DIO mice treated with the negative control antisense oligonucleotide (NC; upper curve). Glucose tolerance test was also performed in lean mice (bottom curve). The IPGTT area under the curve, (AUC), for treatment with the specific and negative control ASO is shown in FIG. 27C. Fed glucose levels were observed to be decreased as a result of Hsp90ab1 ASO administration (FIGS. 23A and 27E).

Further, the effect of the reduction of Hsp90ab1 protein level on plasma insulin levels was examined. The results are provided in FIG. 27D which shows that ASO mediated Hsp90ab1 knock-down is associated with decrease in plasma insulin levels in both the Fed state (statistically significant; left), and in the Fasting state (trend; right). The results show that treatment with an Hsp90ab1 selective ASO improves insulin sensitivity in DIO mice.

Additional experiments were performed to determine the effect of the reduction of Hsp90ab1 protein level on the level of glucose in plasma. Results are provided in FIG. 27E, which shows that ASO mediated Hsp90ab1 knock-down is associated with a decrease in plasma glucose level in DIO mice (n=10) in fed state (FIG. 27E top panel). Thus, treatment with an Hsp90ab1 selective ASO is effective for improving glucose utilization in DIO mice.

Example 18—Mode of Action of Hsp90ab1 Inhibition by Using a Targeting siRNA

Figure 28A:
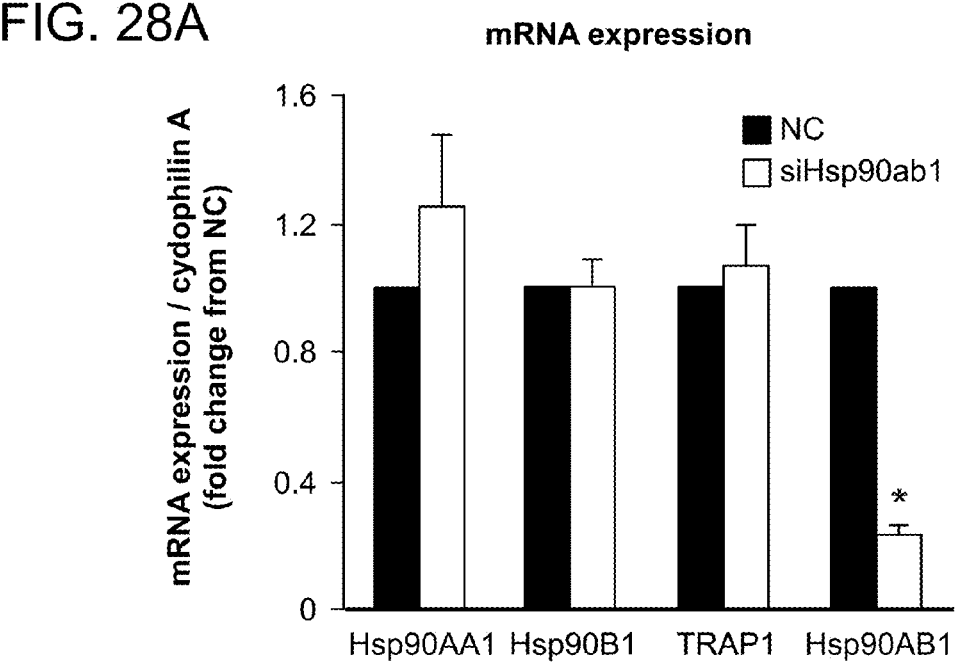
FIG. 28A is a bar graph showing the results of quantitative PCR for testing the specificity of an Hsp90ab1 targeting siRNA. Among the various HSP90 isoforms tested, the level only of Hsp90ab1 mRNA was reduced in HSMM cells treated with the siRNA.
Figure 28B:
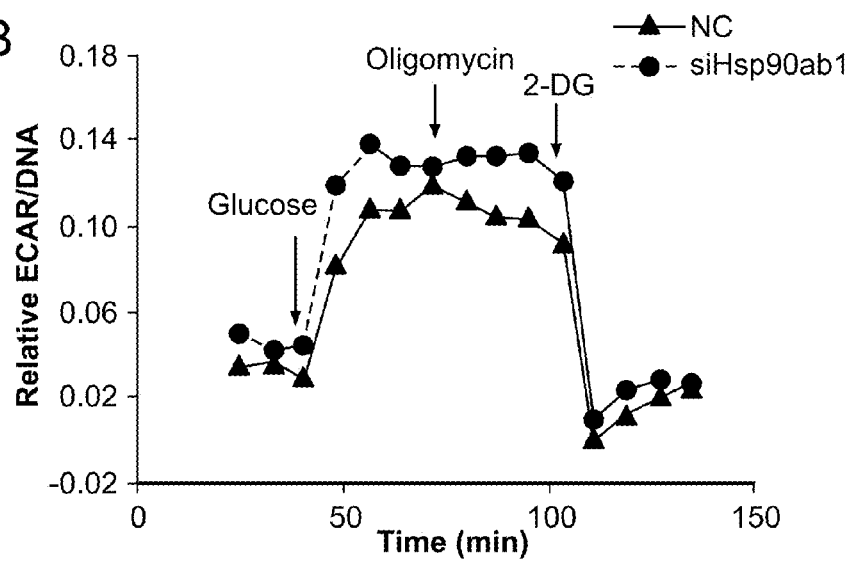
FIG. 28B is a graph showing ECAR measurements for utilization of glucose (glycolytic capacity) in skeletal muscle cells treated with an siRNA specific for Hsp90ab1 compared to ECAR values measured in control cells treated with a control siRNA (NC). Total cellular DNA was used for normalization of cells (and mitichondria) used in individual measurements. The graph shows an increase in glycolytic capacity as a result of Hsp90ab1 knockdown.
Figure 28C:
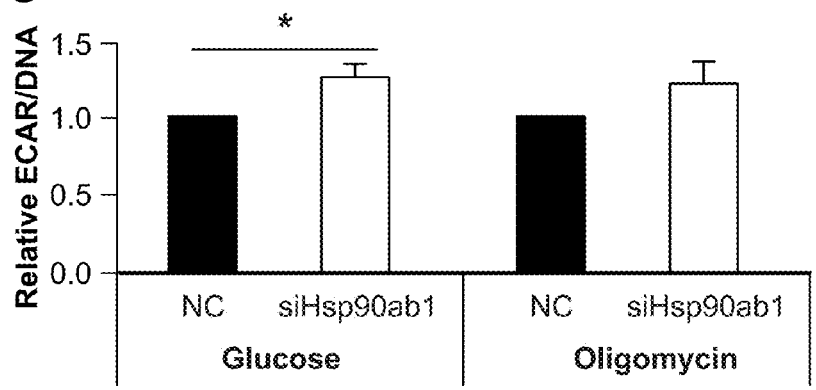
FIG. 28C is a bar graph showing peak changes in glycolytic capacity resulting from the addition of glucose, or oligomycin, for the measurements shown in FIG. 31A.

Knock-down of Hsp90ab1 in human skeletal muscle cultures using an Hsp90ab1 targeting siRNA (shown in FIG. 28A) was observed to be associated with increase in glucose uptake by skeletal muscle (FIG. 25A) and improved glucose tolerance, as shown by a significant increase in glycolysis (FIGS. 28B and 28C). The Figures show ECAR (extracellular acidification rate) measurements for utilization of glucose (glycolytic capacity) in skeletal muscle cells treated with the siRNA compared to ECAR measured in control cells treated with a control siRNA (NC). Total cellular DNA was used for normalization of cells used in individual measurements.

Figure 28D:
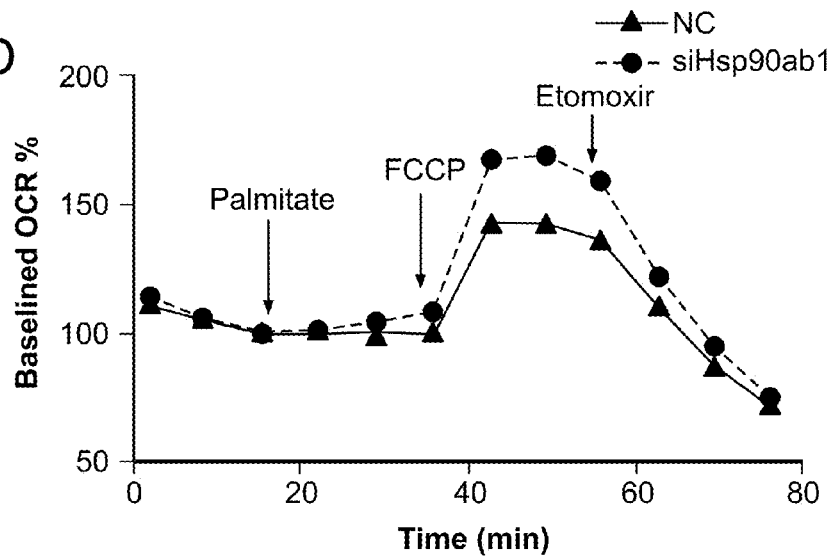
FIG. 28D is a graph showing OCR (oxygen consumption rate) measurements for the utilization of fatty acid (e.g., palmitate) in skeletal muscle cells treated with an siRNA specific for Hsp90ab1 compared to OCR values measured in control cells treated with a negative control siRNA (NC). An increase in fatty acid oxidation capacity was observed as a result of Hsp90ab1 knock-down.

Further, a significant increase in mitochondrial fatty acid acid oxidation (mitochondrial respiration) was also observed as is evident from FIG. 28D, which shows OCR (oxygen consumption rate) measurements for the utilization of fatty acid (e.g., palmitate) in skeletal muscle cells treated with an siRNA specific for Hsp90ab1. The results are compared to OCR values measured in control cells treated with a negative control siRNA (NC).

Figure 28E:
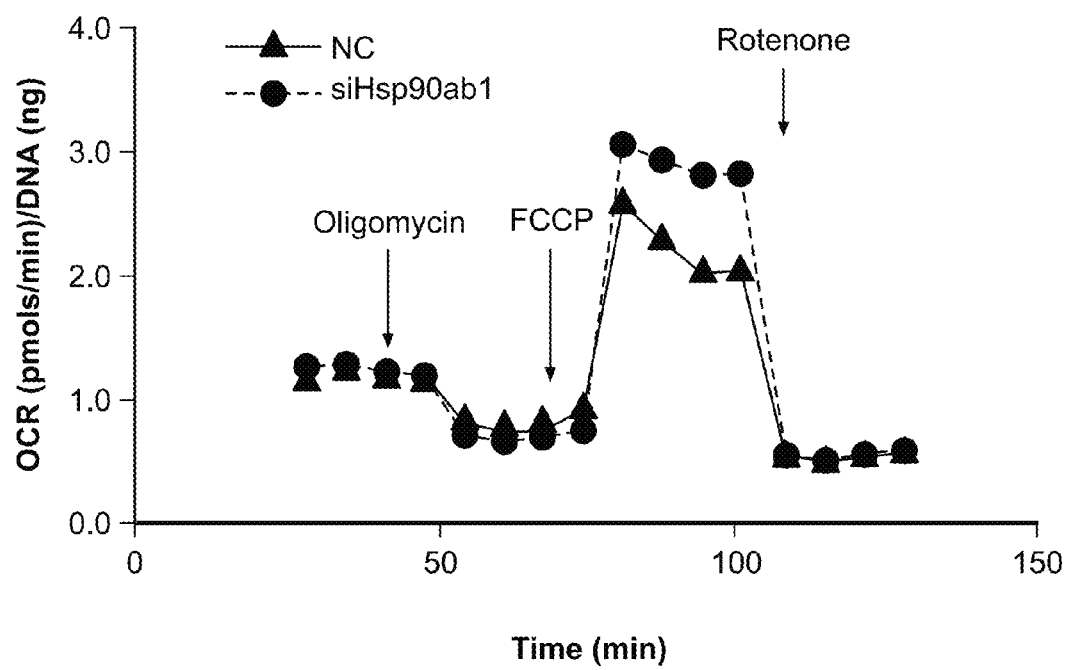
FIG. 28E is a graph showing OCR measurements for the oxidation of fatty acid in skeletal muscle cells treated with an Hsp90ab1 targeting siRNA. Agents that modulate specific points in the mitochondrial oxidation cycle were used to observe a change in mitochondrial electron transport chain activity. Compared to cells treated with a negative control siRNA (NC), an increase in the mitochondrial electron transport chain activity is observed as a result of Hsp90ab1 knock-down.
Figure 28F:
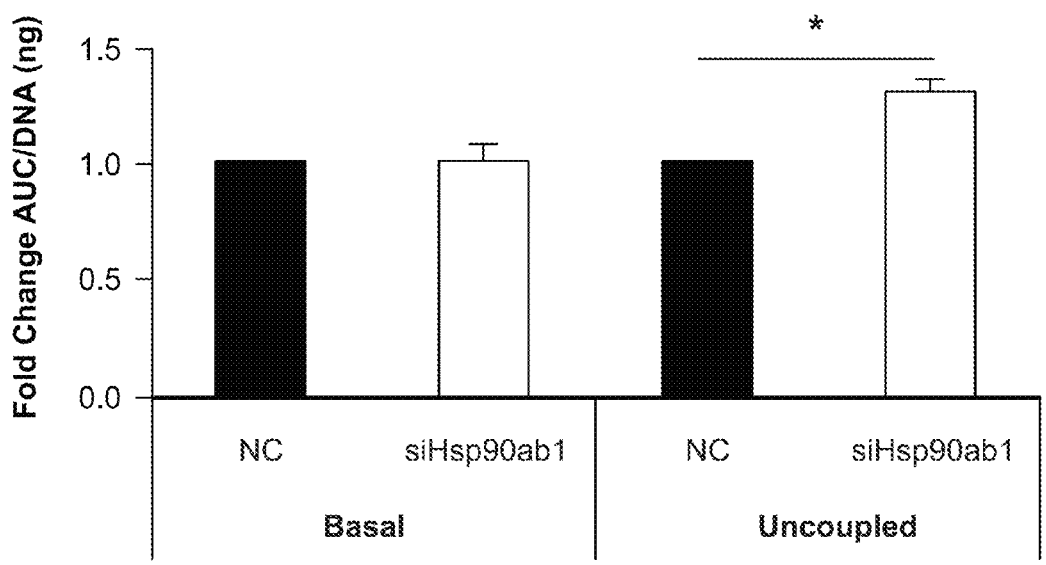
FIG. 28F is a graph showing changes in AUC corresponding to the curves in FIG. 28D under basal condition (uncoupling predominantly absent), and under condition of uncoupling produced by the addition of FCCP (Trifluorocarbonylcyanide Phenylhydrazone), a chemical uncoupler of electron transport and oxidative phosphorylation.

Results obtained also showed that siRNA mediated knock-down of Hsp90ab1 in human skeletal muscle cultures was associated with an increase in electron transport chain activity as seen in the graph (FIG. 28E) showing OCR measurements for the oxidation of fatty acid in skeletal muscle cells treated with an Hsp90ab1 targeting siRNA. For these observations agents that modulate specific points in the mitochondrial oxidation cycle were used. Compared to cells treated with a negative control siRNA (NC), bioenergetics profiling showed an increase in the mitochondrial electron transport chain activity (oxidative respiration) as a result of Hsp90ab1 knock-down. Changes in AUC corresponding to the curves as shown in FIG. 28F under basal condition (uncoupling predominantly absent), and under condition of uncoupling produced by the addition of FCCP (Trifluoro-carbonylcyanide Phenylhydrazone), a chemical uncoupler of electron transport and oxidative phosphorylation, shows that Hsp90ab1 downregulation kickstarts mitochondrial function.

Example 19—Mode of Action of Hsp90ab1 Inhibition by Using a Targeting ASO

Figure 29A:
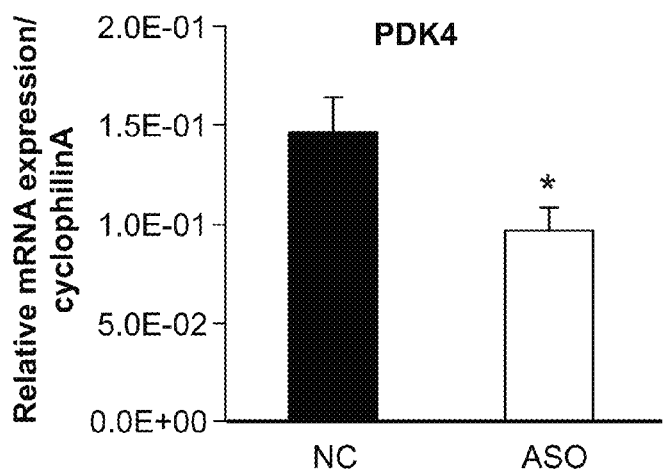
FIG. 29A is a bar graph showing that ASO6 mediated Hsp90ab1 knock-down is associated with a significant decrease in the PDK4 (pyruvate dehydrogenase kinase, isozyme 4) mRNA levels in the skeletal muscles of DIO mice compared to that observed in the skeletal muscles of DIO mice treated with a negative control ASO (NC).
Figure 29B:
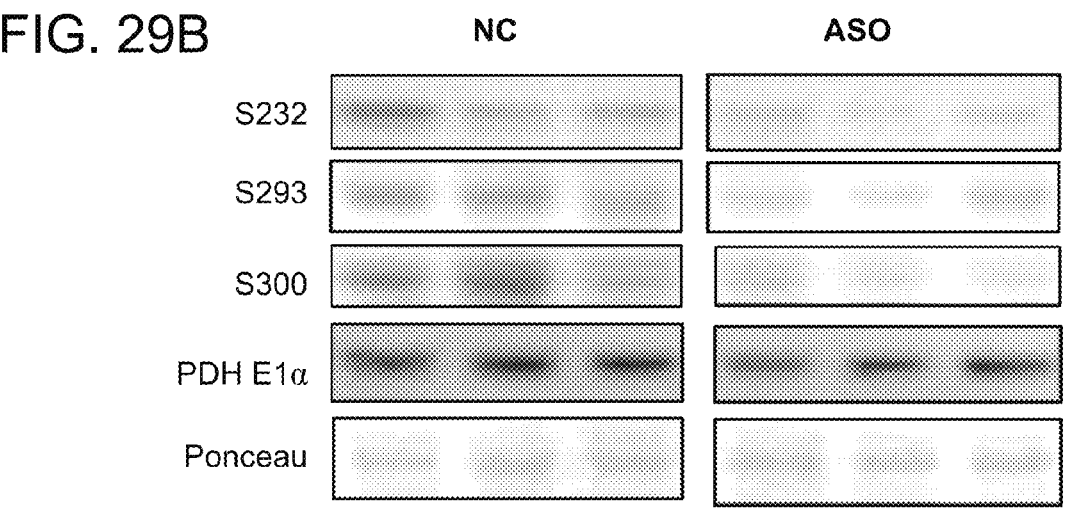
FIG. 29B is a Western Blot analysis showing that ASO6 mediated Hsp90ab1 knockdown in DIO mice is associated with a decrease in the phosphorylation of pyruvate dehydrogenase (PDH)-E1α subunit in the skeletal muscles of the mice, as determined by a decrease in phosphorylation at the amino acids S232, S293, and S300 of the protein. Protein derived from DIO mice treated with irrelevant ASO was used as control in the Western Blot Analysis.
Figure 29C:
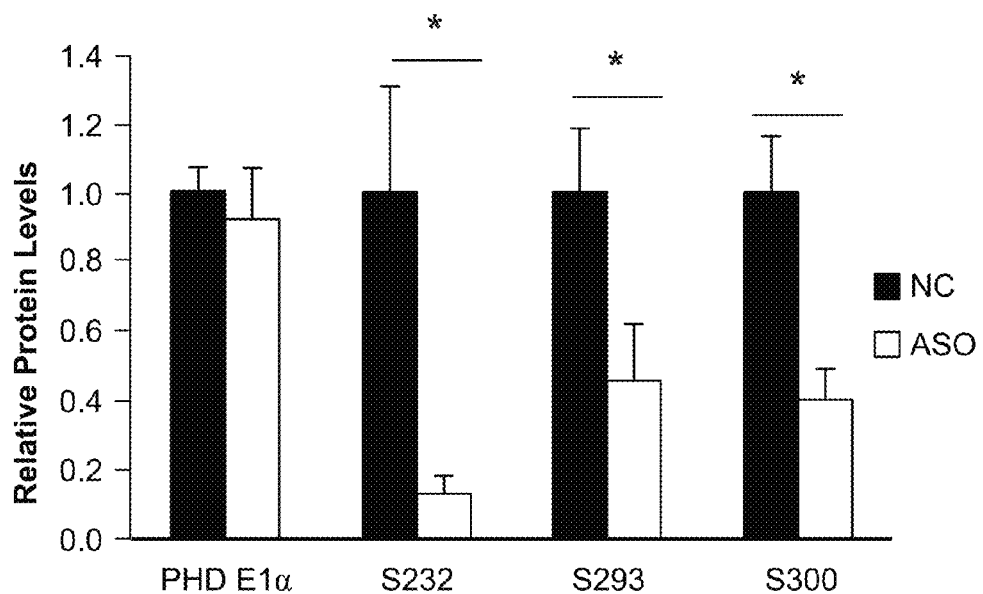
FIG. 29C shows quantitation of the results of the Western Blot analysis (FIG. 29B) in the form of a bar graph.

Further in vivo studies carried out with Hsp90ab1 targeting antisense oligonucleotide ASO6 revealed further information related to the mode of action. Knock-down of Hsp90ab1 protein levels (4 weeks) in DIO mice (fed HFD) using an Hsp90ab1 targeting ASO was observed to be associated with a significant decrease in the expression of pyruvate dehydrogenase kinase isoenzyme 4 (PDK4; FIG. 29A). PDK4 is known to phosphorylate pyruvate dehydrogenase (PDH)-E1α subunit, thereby inhibiting PDH and downregulating mitochondrial glucose oxidation. In the studies herein, the decrease in PDK4 expression was found to be associated with a decrease in phosphorylation of PDH-E1α at amino acids S232, S293, and S300 of the protein (FIGS. 29B and 29C). This decrease in phosphorylation is indicative of an increase in active PDH-E1α and a resultant increase in mitochondrial glucose oxidation. Thus, ASO mediated Hsp90ab1 knock-down is effective for enhancing substrate metabolism through suppression of PDK4 expression.

Figure 30A:
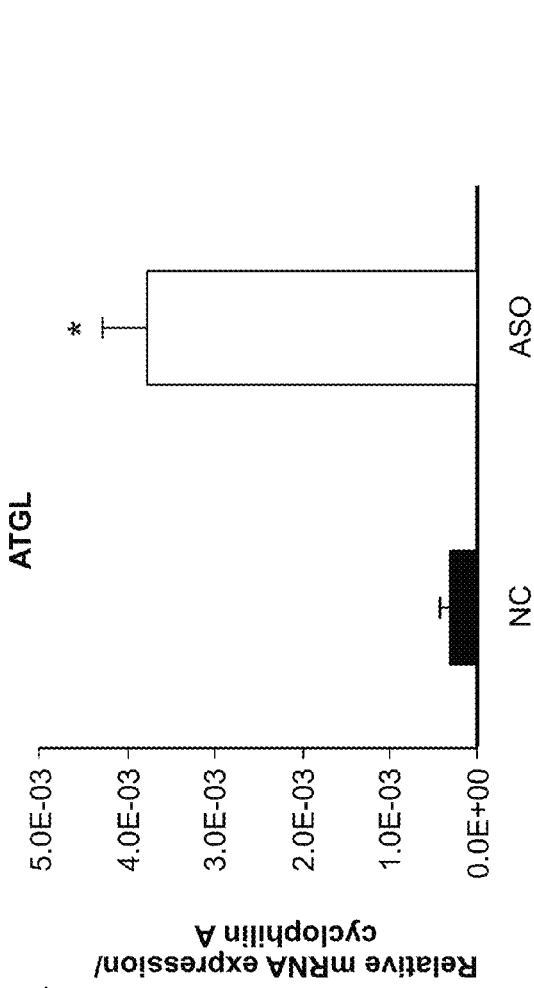
FIG. 30A is a bar graph showing that ASO6 mediated Hsp90ab1 knockdown for four weeks in DIO mice is associated with a sharp increase in the skeletal muscle mRNA level of Adipose triglyceride lipase (ATGL), an enzyme that functions to initiate the breakdown of intracellular triglycerides into fatty acid monomers. Skeletal muscle mRNA derived from DIO mice treated with irrelevant ASO (NC) was used as control.
Figure 30B:
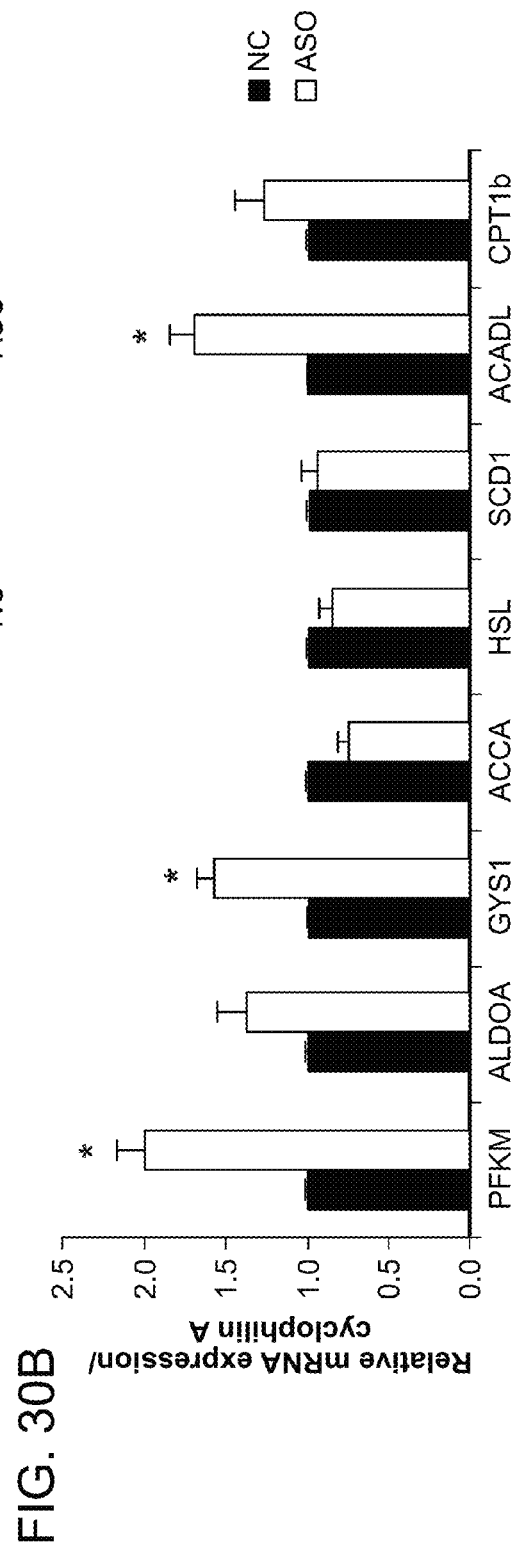
FIG. 30B is a bar graph showing the effect of four weeks of ASO6 mediated Hsp90ab1 knockdown in DIO mice on the expression of key genes that regulate glycolysis and lipid oxidation. Gene expression was examined in the skeletal muscles of the mice. These genes are PFKM (phosphofructokinase, muscle), ALDOA (aldolase A), GYS1 (glycogen synthase 1) ACCA (Acetyl-CoA carboxylase), HSL (Hormone sensitive lipase), SCD1 (Stearoyl-CoA desaturase), ACADL (Acyl-CoA Dehydrogenase), and CPT1b (Carnitine palmitoyltransferase I).

In further observations knockdown of Hsp90ab1 by ASO6 was found to be associated with changes in the expression of several key genes involved in the regulation of glycolysis, fatty acid oxidation, and mitochondrial glucose oxidation. As shown in FIG. 30A, in DIO mice, ASO6 mediated Hsp90ab1 knockdown for four weeks was found to be associated with a sharp increase in the skeletal muscle mRNA level of Adipose triglyceride lipase (ATGL), an enzyme that initiates the breakdown of intracellular triglycerides into fatty acid monomers. FIG. 30B shows that four weeks of ASO6 mediated Hsp90ab1 knockdown in DIO influences the expression of several key genes that regulate glycolysis and lipid oxidation. These genes are PFKM (phosphofructokinase, muscle), ALDOA (aldolase A), GYS1 (glycogen synthase 1) ACCA (Acetyl-CoA carboxylase), HSL (Hormone sensitive lipase), SCD1 (Stearoyl-CoA desaturase), ACADL (Acyl-CoA Dehydrogenase), and CPT1b (Carnitine palmitoyltransferase I). Gene expression was examined in the skeletal muscles of the mice.

Figure 31:
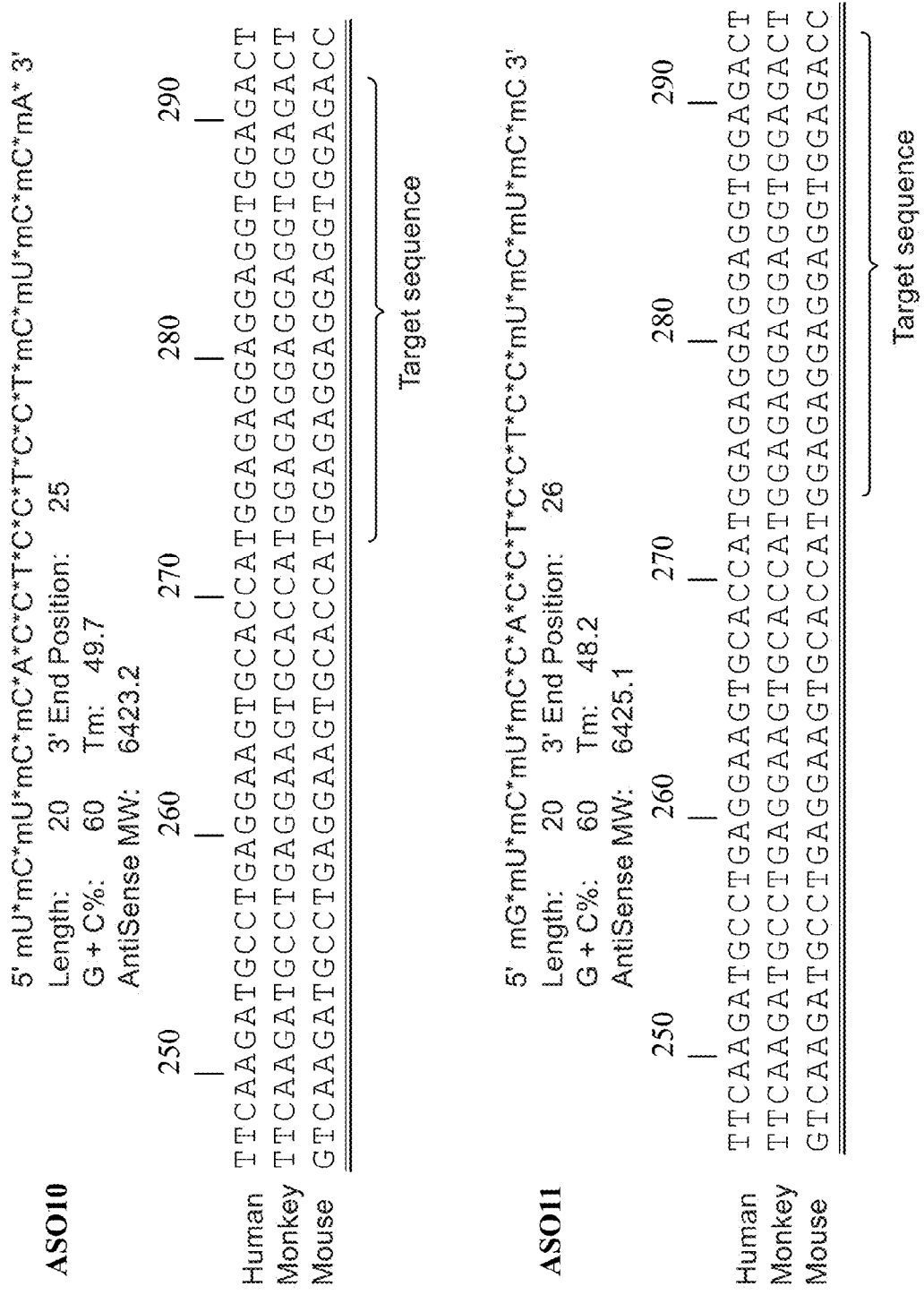
FIG. 31 shows a set of fourteen antisense oligonucleotides ASO10-ASO23 for knocking down the expression of the human HSP90ab1 gene. These oligonucleotides have been designed based on regions of shared homology among the mouse, monkey and human HSP90ab1 genes, i.e. ASO10-ASO23 have 100% sequence identity to the mouse, monkey and human HSP90ab1 gene sequences. The homology region for each ASO is shown below the sequence of the ASO. An asterisk (*) in the sequence of the ASO indicates a phosphorothioate linkage, and an "m" immediately preceding a nucleotide in the ASO sequence indicates that the nucleotide is a 2'-O-methyl ribonucleotide. Nucleotides in the ASO sequences that are not immediately preceded by an "m" are deoxyribonucleotides. Sequences shown are ASO10 (SEQ ID NO: 21); ASO10 human (SEQ ID NO: 62); ASO10 monkey (SEQ ID NO: 63); ASO10 mouse (SEQ ID NO: 64); ASO11 (SEQ ID NO: 22); ASO11 human (SEQ ID NO: 62)
Figure 31:
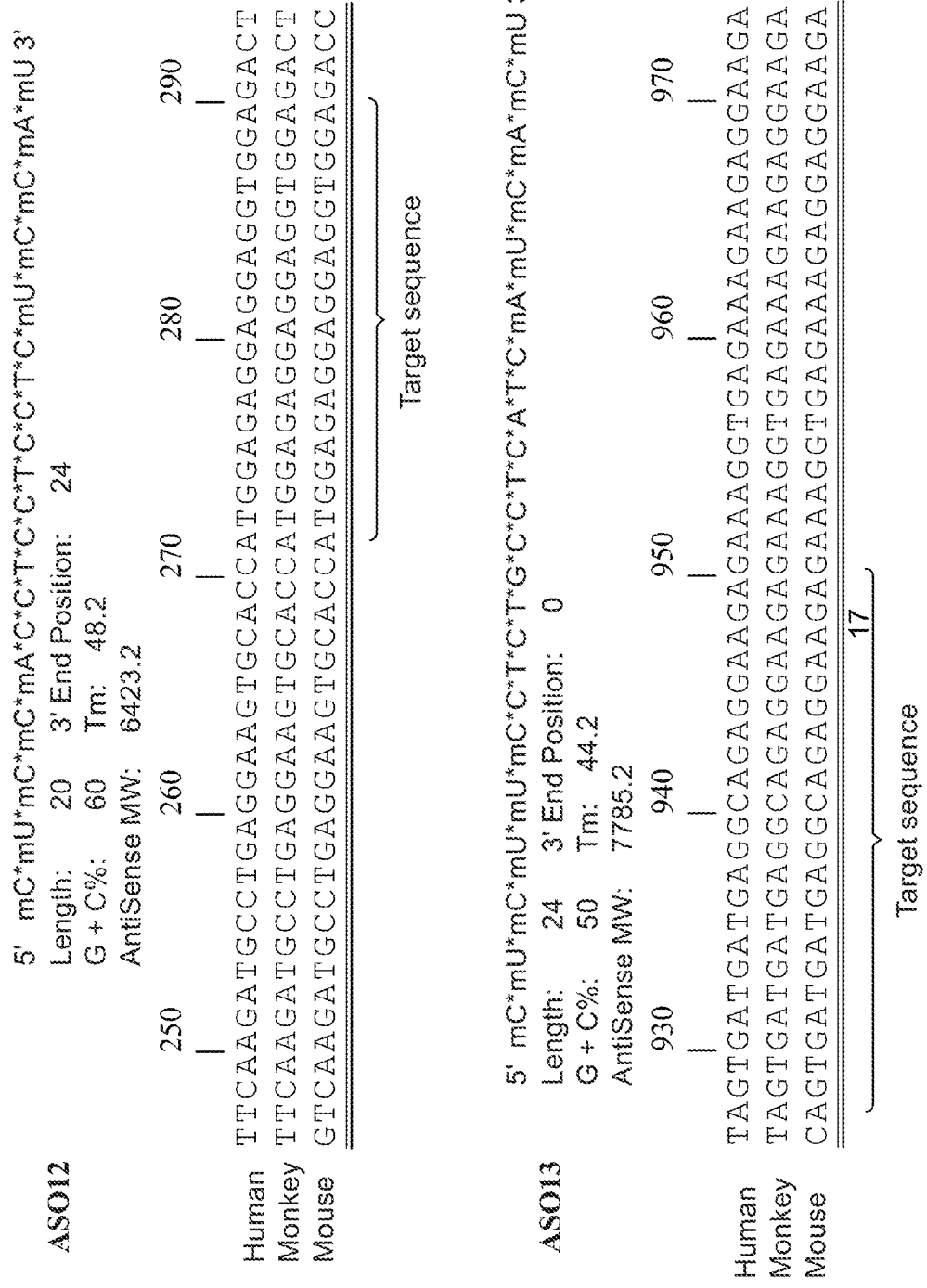
Figure 31:
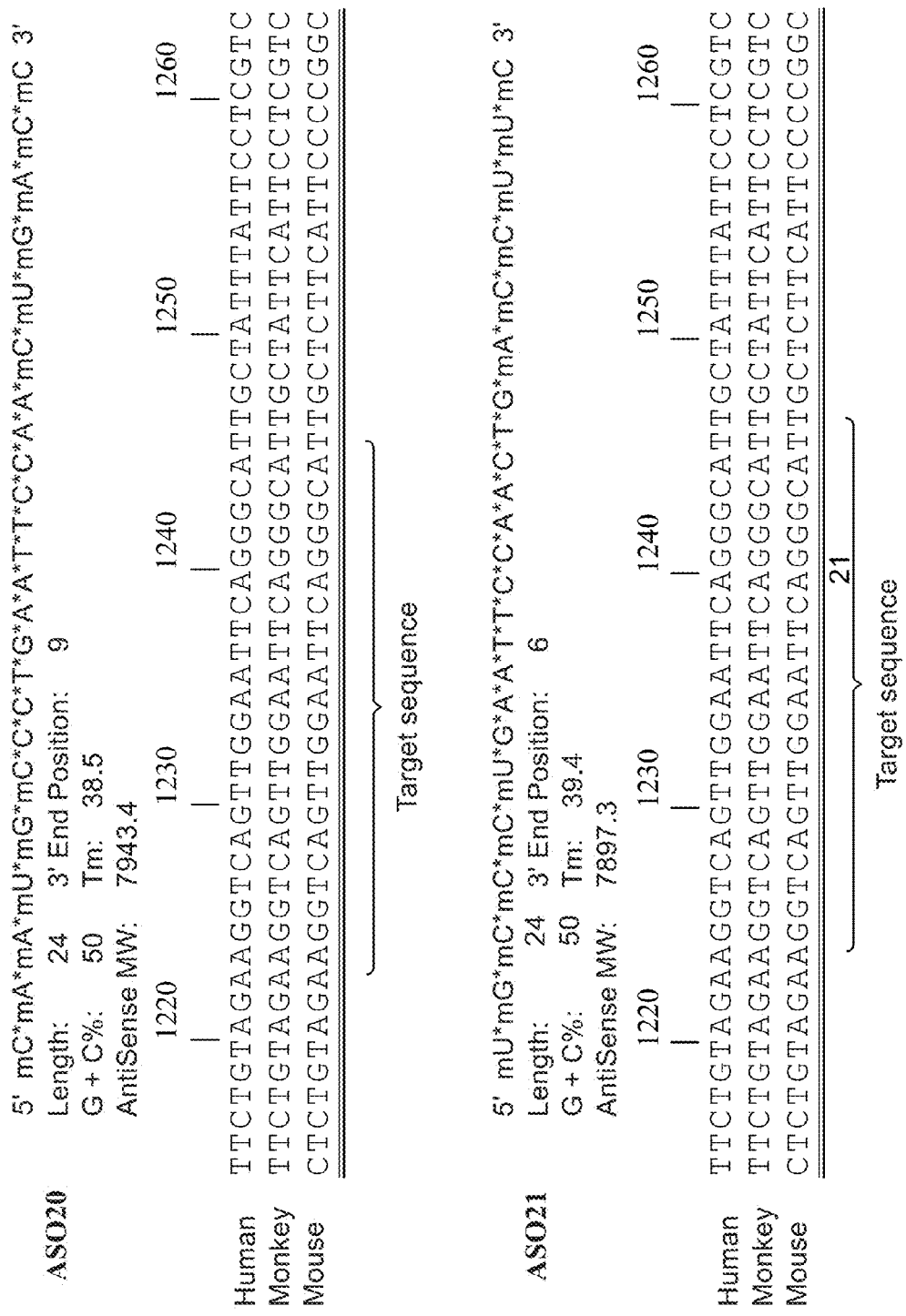

Example 20—Additional ASOs Targeting Human Hsp90ab1 are Effective for Knocking Down Hsp90ab1 Levels and Improving Glucose Tolerance ASOs 10-23 shown in FIG. 31 are directed to the human Hsp90ab1 gene. These ASOs have been designed based on regions of shared homology among the mouse, monkey and human HSP90ab1 genes, i.e. ASO10-ASO23 have 100% sequence identity to the mouse, monkey and human HSP90AB1 gene sequences. See FIG. 31. ASO10-ASO23 contain phosphorothioate linkages as indicated by an asterisk (*) in the sequences shown in FIG. 31. In addition, ASO10-ASO23 contain 2'-O-methyl ribonucleotides, as indicated by an "m" before a nucleotide in the ASO sequence shown in FIG. 31. Nucleotides in the ASO sequences in FIG. 31 that are not preceded by an "m" are deoxyribonucleotides. Thus ASO10-ASO23 contain both DNA and RNA.

Figure 25C:
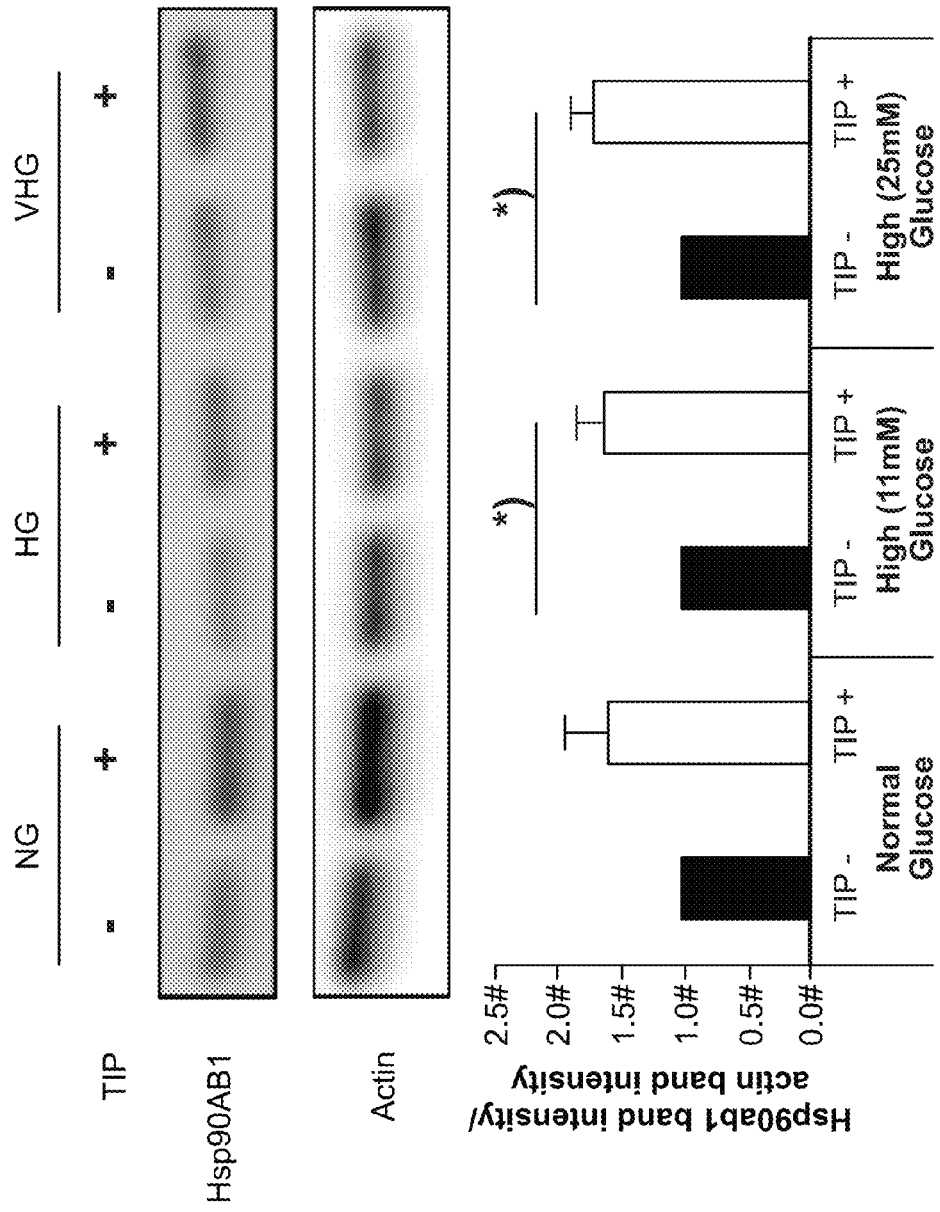
FIG. 25C upper and lower panels show quantitation of the levels of HSP90ab1 protein in human skeletal muscle myotubes treated or not treated with the inflammatory stimulus, TIP, under normoglycemic (NG), hyperglycemic (HG; 11 mM), and very hyperglycemic (VHG; 25 mM) conditions. A correlation was observed between the level of glucose and the level of HSP90ab1 protein in the presence of an inflammatory stimulus, indicating that in HSMM, inflammation induced insulin resistance is associated with increase in the expression of HSP90ab1 protein.

These ASOs are tested for their ability to reduce/knock down the levels of Hsp90ab1 in HSMM myotobes as well as in the skeletal muscles of DIO mice by carrying out experiments using the experimental protocols as described in the foregoing examples (e.g., as used to obtain the data in FIGS. 19, 20, and 25C). They are additionally tested for their ability to knock down Hsp90ab1 gene in human cells. The ASOs are shown to be effective in knocking down the levels of the Hsp90ab1 gene in both mouse cells in vitro, in the mouse in vivo, and in human cells.

These oligonucleotides directed to the human gene are also tested for their ability to improve glucose tolerance by carrying out experiments according to the experimental protocols described in the foregoing examples, or similar protocols designed to test their efficacy in human in vitro models. These ASOs directed to the human gene are also found to lead to improvement in glucose tolerance and to attain other benchmark results as were observed with ASO5 and/or ASO6. Further, similar to the results shown in FIGS. 30A and 30B, these antisense oligonucleotides are tested for and found to be effective in significantly increasing the expression of key genes involved in the regulation of glycolysis and lipid oxidation in skeletal muscles.

Example 21—Heat Shock Protein 90 β (hsp90β) Isoform Regulates Skeletal Muscle and Systemic Energy Metabolism As noted in the above examples, Hsp90ab1 was identified as a critical node in Bayesian metabolic disease network derived by the interrogation of the biology underlying diabetes in a data driven manner. This was achieved by using a proprietary platform integrating pan-omic data, mitochondrial-centric metabolic fingerprint and phenotypic assays capturing metabolic dysregulation reminiscent of obesity/diabetes sequale. Hsp90ab1 is an ATPase targeting multiple clients including vital components of insulin signaling and mitochondrial membrane proteins. However the role of Hsp90ab1 in metabolism remains unknown. Here, as described above in Example 18, we demonstrated that knock-down of Hsp90ab1 in primary human skeletal muscle myotubes, using siRNA, induced a significant increase in glycolysis, beta-oxidation and mitochondrial respiration, associated with a decrease in PDH E1α phosphorylation. These results indicated a pivotal role of Hsp90ab1 in the regulation of skeletal muscle substrate metabolism. In addition, as described above in Examples 17 and 19, the knockdown of Hsp90ab1, using an Anti-Sense Oligonucleotide (ASO) technology (ASO6), in high fat diet (HFD) fed C57B/6 mice, significantly improved glucose tolerance and suppressed fed glucose levels, after 4 weeks treatment. This was accompanied by decreased muscle PDH E1a phosphorylation, reflecting an increased insulin sensitivity and carbohydrate substrate metabolism. We also observed significant alteration in the lipidomic profile in these DIO mice treated with ASO6. For example ASO6-mediated knockdown of Hsp90ab1 in DIO mice increased 18:2 enriched species of cardiolipin in muscle. See FIG. 33A. In addition, ASO6-mediated knockdown of Hsp90ab1 decreased steric, oleic, and linoleic free fatty acids (FFA) as well as selectively decreased 18:0 and 18:0-OH acylcarnitines in the muscle of DIO mice. See FIG. 33B. Thus, cardiolipin molecular species were significantly increased while selective free fatty acids and acyl carnitines were decreased in muscle of Hsp90ab1 ASO6 treated DIO (HFD fed) mice compared to control, suggesting an increase in mitochondria activity reengaging bioenergetics capacity. Taken together, our data provides novel evidence that Hsp90ab1 isoform is a key regulator of skeletal muscle cell metabolism and systemic metabolism, and represents a target for treatment of diabetes.

In conclusion, Hsp90ab1 knockdown in HSMM increased substrate metabolism and oxidative respiration. Hsp90ab1 ASO mediated knockdown improved glucose tolerance and lowered fed glucose in HFD fed C57B/6 mice associated with decreased PDK4 expression and PDH activation. Hsp90ab1 ASO mediated knockdown influences structural lipidomic profile in muscle suggesting increased lipid oxidation.

Example 22—Evaluation of Antisense Oligonucleotides ASO5, ASO13 and ASO18 for Reducing HSP90β Protein Expression The ASO oligonucleotides ASO5, ASO13 and ASO18 were tested for their ability to reduce expression of human Hsp90AB1 protein in human skeletal muscle myotubes (HSMM) and C2C12 mouse myoblasts by Western blotting.

ASO5 was derived from the mouse HSP90ab1 gene, while ASO13 and ASO18 were directed to the human HSP90ab1 gene. The oligonucleotide NC1 was used as a negative control. HSP90AB1protein levels were normalized to the levels of actin. ASO13 and ASO18 significantly reduced Hsp90AB1 protein expression in HSMM and C2C12 myoblasts, while ASO5 did not significantly reduce Hsp90AB1 protein expression in either cell type. See FIGS. 34 and 35.

Example 23—Conjugation of HSP90AB1 Antisense Oligonucleotides

Antisense oligonucleotides (ASOs) specific to HSP90Ab1 described herein (e.g. alone or in combination with a muscle targeting moiety) are conjugated to one or more additional molecules to improve PK/PD properties. Exemplary molecules for conjugation to an ASO of the invention include creatine and PAMAM dendrimers. In certain experiments, the conjugate includes a linker for linking the HSP90ab1 ASO to the one or more additional molecules. The linker may be a covalent linker, a non-covalent linkage, or a reversible linker, where each type of linker is tested independently and/or compared with others to determine the optimal linker. In certain experiments, disulphide and maleimide are evaluated as suitable linkers for conjugation to the ASOs of the invention.

In certain experiments, the conjugate includes a pharmaceutically acceptable dendrimer. In some experiments the dendrimer is a PAMAM dendrimer. In some experiments the dendrimer is a G1, G2, G3, G4 or G5 dendrimer. In certain experiments, the dendrimer is an uncharged dendrimer or an acylated dendrimer. In additional experiments, the ASO-MTP conjugate is part of a liposome. It will be understood that in certain cases, the conjugate is formed in situ. All of these additional ASO-MTP conjugates are tested for their ability to deliver the ASO to skeletal muscle, to effect knockdown of HSP90AB1, and to effect parameters such as IPGTT, fed glucose and blood glucose levels using the DIO mouse model by carrying out experiments as described in Examples 11 and 13 above.

For example in certain experiments, creatine is conjugated to ASOs via disulfide linkages for targeted delivery of the ASOs. Several molecules of creatine per ASO are used to allow polyvalent creatine interaction with its receptors. The ASOs are derivatized at the 5' position with thiol linkers according to methods known in the art. Next, Boc protected creatine (Boc 2-creatine) is reacted with cystamine core PAMAM dendrimer (generation 1 or 2) to provide 2 or 4 targeting groups per ASO. The Boc-creatine surface modified dendrimer is deprotected with trifluoroacetic acid to yield creatine-decorated cystamine core PAMAM dendrimers. These dendrimers are reduced with DTT to yield a reactive thiol core, creatine surface modified PAMAM dendron, which in turn is reacted with thiol modified ASOs to give creatine targeted ASO with a reductively cleavable linker.

These ASO conjugates are tested for their ability to deliver the ASO to particular tissues and to effect knockdown of HSP90AB1, using routine methods in the art. Further, the effects of such conjugated ASOs on parameters such as IPGTT, fed glucose, and blood glucose level are observed using the DIO mouse model by carrying out experiments as described in Examples 11 and 13 above.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

INCORPORATION BY REFERENCE

Each reference, patent, patent application, and GenBank number referred to in the instant application is hereby incorporated by reference as if each reference were noted to be incorporated individually.

The invention claimed is:

1. A pharmaceutical composition comprising an HSP90β specific inhibitor and a pharmaceutically acceptable carrier, wherein:
   a) the inhibitor comprises a modified antisense oligonucleotide;
   b) the HSP90β specific inhibitor has a greater inhibitory activity against HSP90β compared to another HSP90 isoform; and
   c) the modified antisense oligonucleotide comprises a nucleic acid sequence selected from the group consisting of SEQ ID NO: 80 and SEQ ID NO: 104.

2. The pharmaceutical composition of claim 1, wherein the antisense oligonucleotide comprises one or more phosphorothioate linkages.

3. The pharmaceutical composition of claim 1, wherein the antisense oligonucleotide comprises one or more 2'-O-methyl ribonucleotides.

4. The pharmaceutical composition of claim 1, wherein the modified antisense oligonucleotide comprises the nucleic acid sequence mU*mC*mC*mU*mC*mC*T*C*T*T*T*C*T*C*A*C*C*T*mU*mU*mC*mU*mC*mU (ASO6, SEQ ID NO: 17) or mU*mC*mC*mU*mC*mU*T*C*T*T*T*C*T*C*A*C*C*T*mU*mU*mC*mU*mC*mU (AS06 variant 1, SEQ ID NO: 41),
   wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

5. The pharmaceutical composition of claim 1, wherein the modified antisense oligonucleotide is targeted to a muscle cell.

6. The pharmaceutical composition of claim 1, wherein the HSP90β specific inhibitor further comprises a muscle targeting moiety, and wherein the muscle targeting moiety and the antisense oligonucleotide are in a complex.

7. The pharmaceutical composition of claim 6, wherein the muscle targeting moiety comprises a muscle targeting peptide (MTP).

8. The pharmaceutical composition of claim 7, wherein the MTP comprises an amino acid sequence selected from the group consisting of: ASSLNIA (SEQ ID NO: 57); WDANGKT (SEQ ID NO: 58); GETRAPL (SEQ ID NO: 58); CGHHPVYAC (SEQ ID NO: 59); and HAIYPRH (SEQ ID NO: 60).

9. The pharmaceutical composition of claim 6, wherein the muscle targeting moiety comprises creatine.

10. The pharmaceutical composition of claim 6, wherein the complex further comprises a linker.

11. The pharmaceutical composition of claim 10, wherein the linker is selected from the group consisting of a covalent linker, a non-covalent linkage, and a reversible linker.

12. The pharmaceutical composition of claim 6, wherein the complex further comprises a pharmaceutically acceptable dendrimer.

13. The pharmaceutical composition of claim 12, wherein the pharmaceutically acceptable dendrimer is a PAMAM dendrimer.

14. The pharmaceutical composition of claim 12, wherein the pharmaceutically acceptable dendrimer is one or more of a G5 dendrimer, an uncharged dendrimer, and an acylated dendrimer.

15. The pharmaceutical composition of, claim 1, wherein the inhibitor further comprises one or more of a liposome, a microparticle and an in situ forming composition.

16. The pharmaceutical composition of claim 6, wherein the antisense oligonucleotide is released from the complex upon delivery to a muscle cell.

17. A method of treating a metabolic syndrome in a subject, comprising administering to a subject in need thereof the pharmaceutical composition of claim 1, thereby treating the metabolic syndrome in the subject, wherein the metabolic syndrome comprises one or more of type 2 diabetes, type 1 diabetes, insulin resistance, insulin insufficiency, obesity, hyperinsulinemia, and impaired glucose tolerance (IGT).

18. The method of claim 17, wherein the modified antisense oligonucleotide comprises one or more phosphorothioate linkages.

19. The method of claim 17, wherein the modified antisense oligonucleotide comprises one or more 2'-O-methyl ribonucleotides.

20. The method of claim 17, wherein the modified antisense oligonucleotide has the sequence mU*mC*mC*mU*mC*mC*T*C*T*T*T*T*C*T*C*A*C*C*T*mU*mU*mC*mU*mC*mU (ASO6, SEQ ID NO: 17) or mU*mC*mC*mU*mC*mU*T*C*T*T*T*C*T*C*A*C*C*T*mU*mU*mC*mU*mC*mU (AS06 variant 1, SEQ ID NO: 41),
wherein an asterisk (*) indicates a phosphorothioate linkage, an "m" immediately preceding a nucleotide indicates that the nucleotide is a 2'-O-methyl ribonucleotide, and a nucleotide that is not immediately preceded by an "m" is a deoxyribonucleotide.

21. The method of claim 17, wherein the subject with metabolic syndrome exhibits three or more of the following signs:
   a) Blood pressure equal to or higher than 130/85 mmHg;
   b) Fasting blood glucose equal to or higher than 100 mg/dL;
   c) Large waist circumference wherein a large waist circumference is 40 inches or more for men and 35 inches or more for women;
   d) Low HDL cholesterol wherein low HDL cholesterol is under 40 mg/dL for men and under 50 mg/dL for women; and
   e) Triglycerides equal to or higher than 150 mg/dL.

22. The method of claim 17, wherein treating the metabolic syndrome comprises one or more of normalizing a blood glucose level in the subject, normalizing an Hb1Ac level in the subject, prevention of at least one complication of diabetes associated with poor circulation, amelioration of at least one sign or symptom of type 2 diabetes, amelioration of at least one sign or symptom of type 1 diabetes, amelioration of at least one sign or symptom of insulin resistance, amelioration of at least one sign or symptom of insulin insufficiency, amelioration of at least one sign or symptom of hyperinsulinemia, amelioration of at least one sign or symptom of impaired glucose tolerance (IGT), amelioration of at least one sign or symptom of obesity, amelioration of fatty liver, modulation of fat deposition, and an altered lipidomic profile in muscle of the subject relative to a control subject.

23. The method of claim 17, wherein treating the metabolic syndrome comprises amelioration of at least one of
   a) Blood pressure equal to or higher than 130/85 mmHg;
   b) Fasting blood glucose equal to or higher than 100 mg/dL;
   c) Large waist circumference wherein a large waist circumference is 40 inches or more for men and 35 inches or more for women;
   d) Low HDL cholesterol wherein low HDL cholesterol is under 40 mg/dL for men and under 50 mg/dL for women; and
   e) Triglycerides equal to or higher than 150 mg/dL.

24. The method of claim 17, wherein treating metabolic syndrome comprises one or more of decreased expression of pyruvate dehydrogenase kinase isoenzyme 4 (PDK4), decreased phosphorylation of PDH-E1α, modulated expression of adipose triglyceride lipase (ATGL), modulated expression of PFKM (phosphofructokinase, muscle), modulated expression of ALDOA (aldolase A), modulated expression of GYS1 (glycogen synthase 1) ACCA (Acetyl-CoA carboxylase), modulated expression of HSL (Hormone sensitive lipase), SCD1 (Stearoyl-CoA desaturase), modulated expression of ACADL (Acyl-CoA Dehydrogenase), and modulated expression of CPT1b (Carnitine palmitoyltransferase I) in the subject relative to a control.

25. The method of claim 22, wherein the altered lipidomic profile comprises one or more of increased 18:2 enriched species of cardiolipin in muscle, decreased steric free fatty acids (FFA), decreased oleic free fatty acids (FFA), decreased linoleic free fatty acids (FFA), and decreased 18:0 and/or 18:0-OH acylcarnitines in the subject relative to a control.

26. The method of claim 17, wherein the modified antisense oligonucleotide is targeted to a muscle cell.

27. The method of claim 17, wherein the HSP90β specific inhibitor further comprises a muscle targeting moiety, and wherein the muscle targeting moiety and the modified antisense oligonucleotide are in a complex.

28. The method of claim 27, wherein the muscle targeting moiety comprises a muscle targeting peptide (MTP).

29. The method of claim 28, wherein the MTP comprises an amino acid sequence selected from the group consisting of: ASSLNIA (SEQ ID NO: 57); WDANGKT (SEQ ID NO: 58); GETRAPL (SEQ ID NO: 58); CGHHPVYAC (SEQ ID NO: 59); and HAIYPRH (SEQ ID NO: 60).

30. The method of claim 27, wherein the muscle targeting moiety comprises creatine.

31. The method of claim 27, wherein the complex further comprises a linker.

32. The method of claim 31, wherein the linker is selected from the group consisting of a covalent linker, a non-covalent linkage, and a reversible linker.

33. The method of claim 27, wherein the complex further comprises a pharmaceutically acceptable dendrimer.

34. The method of claim 33, wherein the pharmaceutically acceptable dendrimer is a PAMAM dendrimer.

35. The method of claim 33, wherein the pharmaceutically acceptable dendrimer is one or more of a G5 dendrimer, an uncharged dendrimer, and an acylated dendrimer.

36. The method of claim 27, wherein the inhibitor further comprises one or more of a liposome, a microparticle and an in situ forming composition.

37. The method of claim 27, wherein the antisense oligonucleotide is released from the complex upon delivery to a muscle cell.

* * * * *